US011702676B2

(12) United States Patent
Li et al.

(10) Patent No.: US 11,702,676 B2
(45) Date of Patent: Jul. 18, 2023

(54) RATIONAL POLYPLOID ADENO-ASSOCIATED VIRUS VECTORS FOR THE TREATMENT OF DISEASE

(71) Applicant: The University of North Carolina at Chapel Hill, Chapel Hill, NC (US)

(72) Inventors: Chengwen Li, Chapel Hill, NC (US); Richard Jude Samulski, Hillsborough, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 260 days.

(21) Appl. No.: 16/951,004

(22) Filed: Nov. 18, 2020

(65) Prior Publication Data

US 2021/0147877 A1 May 20, 2021

Related U.S. Application Data

(63) Continuation of application No. 16/598,779, filed on Oct. 10, 2019, now Pat. No. 10,934,560, which is a continuation of application No. 16/051,110, filed on Jul. 31, 2018, now Pat. No. 10,550,405, which is a continuation-in-part of application No. PCT/US2018/022725, filed on Mar. 15, 2018.

(60) Provisional application No. 62/678,675, filed on May 31, 2018, provisional application No. 62/668,056, filed on May 7, 2018, provisional application No. 62/630,558, filed on Feb. 14, 2018, provisional application No. 62/520,901, filed on Jun. 16, 2017, provisional application No. 62/471,762, filed on Mar. 15, 2017.

(51) Int. Cl.

| | |
|---|---|
| ***C12N 15/864*** | (2006.01) |
| ***C07K 14/005*** | (2006.01) |
| ***C12N 15/86*** | (2006.01) |
| ***A61K 48/00*** | (2006.01) |
| ***A61P 3/00*** | (2006.01) |

(52) U.S. Cl.

CPC ...... *C12N 15/8645* (2013.01); *A61K 48/0025* (2013.01); *A61P 3/00* (2018.01); *C07K 14/005* (2013.01); *C12N 15/86* (2013.01); *C07K 2317/24* (2013.01); *C12N 2750/14121* (2013.01); *C12N 2750/14122* (2013.01); *C12N 2750/14143* (2013.01); *C12N 2750/14145* (2013.01); *C12N 2750/14151* (2013.01)

(58) Field of Classification Search

None

See application file for complete search history.

(56) References Cited

U.S. PATENT DOCUMENTS

| | | | |
|---|---|---|---|
| 8,632,765 | B2 | 1/2014 | Samulski |
| 9,834,788 | B2 | 12/2017 | Maclaren et al. |
| 2002/0045264 | A1 | 4/2002 | During et al. |
| 2006/0088936 | A1 | 4/2006 | Warrington et al. |
| 2010/0098666 | A1 | 4/2010 | Wright |
| 2013/0296409 | A1 | 11/2013 | Miller et al. |
| 2015/0023924 | A1 | 1/2015 | High et al. |
| 2016/0375110 | A1 | 12/2016 | High et al. |
| 2018/0169273 | A1 | 6/2018 | Ferreira |

FOREIGN PATENT DOCUMENTS

| | | | |
|---|---|---|---|
| EP | 0766569 | | 1/2006 |
| EP | 1496944 | | 8/2008 |
| EP | 2412387 | B1 | 11/2014 |
| JP | H10502526 | A | 3/1998 |
| JP | 2009535339 | A | 10/2009 |
| JP | 2012521750 | A | 9/2012 |
| JP | 2015517301 | A | 6/2015 |
| WO | 9600587 | A1 | 1/1996 |
| WO | 2004099423 | A1 | 11/2004 |
| WO | 2005021033 | | 3/2005 |
| WO | 2008027084 | A2 | 3/2008 |
| WO | 2012112578 | | 8/2012 |
| WO | 2013158879 | | 10/2013 |
| WO | 2013164793 | A2 | 11/2013 |
| WO | 2018170310 | A1 | 9/2018 |

OTHER PUBLICATIONS

Extended European Search Report corresponding to European Patent Application No. 18907477.6 (8 pages) (dated Nov. 2, 2021).

Chai et al. "Chimeric Capsid Proteins Impact Transduction Efficiency of Haploid Adeno-Associated Virus Vectors" Viruses, 11(1138):1-13(2019).

De Backer, Maria W. A. "Optimization of viral vector technology to study gene function in the hypothalamus" Doctoral Thesis (176 pages) (Jun. 3, 2010).

Extended European Search Report corresponding to European Patent Application No. 18768025.1 (6 pages) (dated Dec. 18, 2020).

Kohlbrenner et al. "Successful Production of Pseudotyped rAAV Vectors Using a Modified Baculovirus Expression System" Molecular Therapy, 12(6):1217-1225 (2005).

Becerra et al. "Synthesis of Adeno-Associated Virus Structural Proteins Requires Both Alternative mRNA Splicing and Alternative Initiations from a Single Transcript" Journal of Virology, 62(8):2745-2754 (1988).

Agbandje-McKenna et al. "AAV Capsid Structure and Cell Interactions" Methods in Molecular Biology, 807:47-92 (2011).

(Continued)

*Primary Examiner* — Nicole Kinsey White

(74) *Attorney, Agent, or Firm* — Myers Bigel, P.A.

(57) ABSTRACT

The present invention provides a polyploid adeno-associated virus (AAV) capsid, wherein the capsid comprises capsid protein VP1, wherein said capsid protein VP1 is from one or more than one first AAV serotype, wherein said capsid protein VP2 is from one or more than one first AAV serotype and capsid protein VP3, wherein said capsid protein VP3 is from one or more than one second AAV serotype and wherein at least one of said first AAV serotype is different from at least one of said second AAV serotype and is different from at least one of said third AAV serotype, in any combination.

19 Claims, 31 Drawing Sheets

Specification includes a Sequence Listing.

(56) References Cited

OTHER PUBLICATIONS

Ambagala et al. "Viral interference with MHC class I antigen presentation pathway: the battle continues" Veterinary Immunology and Immunopathology, 107:1-15 (2005) (Abstract only).
Andre et al. "Hepatitis C virus particles and lipoprotein metabolism" Seminars in Liver Disease, 25(1):93-104 (2005) (Abstract only).
Arbetman et al. "Novel caprine adeno-associated virus (AAV) capsid (AAV-Go.1) is closely related to the primate AAV-5 and has unique tropism and neutralization properties" Journal of Virology, 79(24):15238-15245 (2005).
Asokan et al. "Reengineering a receptor footprint of adeno-associated virus enables selective and systemic gene transfer to muscle" Nature Biotechnology, 28(1):79-82 (2010).
Asokan et al. "The AAV Vector Toolkit: Poised at the Clinical Crossroads" Molecular Therapy, 20:699-708 (2012).
Asuri et al. "Directed Evolution of Adeno-associated Virus for Enhanced Gene Delivery and Gene Targeting in Human Pluripotent Stem Cells" Molecular Therapy, 20(2):329-338 (2012).
Bartlett et al. "Infectious Entry Pathway of Adeno-Associated Virus and Adeno-Associated Virus Vectors" Journal of Virology, 74:2777-2785 (2000).
Bell et al. "Identification of the Galactose Binding Domain of the Adeno-Associated Virus Serotype 9 Capsid" Journal of Virology, 86:7326-7333 (2012).
Bello et al. "Novel Adeno-associated Viruses Derived From Pig Tissues Transduce Most Major Organs in Mice" Scientific Reports, 4(6644):1-11 (2014).
Bern et al. "The role of albumin receptors in regulation of albumin homeostasis: Implications for drug delivery" Journal of Controlled Release, 211:144-162 (2015) (Abstract only).
Bertholet et al. "Leishmania Antigens Are Presented to CD8+ T Cells by a Transporter Associated with Antigen Processing—Independent Pathway In Vitro and In Vivo" Journal of Immunology, 177:3525-3533 (2006).
Blacklow et al. "Epidemiology of adenovirus-associated virus infection in a nursery population" American Journal of Epidemiology, 88:368-378 (1968) (Abstract only).
Bossis et al. "Cloning of an Avian Adeno-Associated Virus (AAAV) and Generation of Recombinant AAAV Particles" Journal of Virology, 77(12):6799-6810 (2003).
Boutin et al. "Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors" Human Gene Therapy, 21:704-712 (2010).
Bowles et al. "Phase 1 Gene Therapy for Duchenne Muscular Dystrophy Using a Translational Optimized AAV Vector" Molecular Therapy, 20(2):443-455 (2012).
Boye et al. "A Comprehensive Review of Retinal Gene Therapy" Molecular Therapy, 21:509-519 (2013).
Calcedo et al. "Worldwide Epidemiology of Neutralizing Antibodies to Adeno-Associated Viruses" Journal of Infectious Diseases, 199:381-390 (2009).
Carlisle et al. "Coating of adeno-associated virus with reactive polymers can ablate virus tropism, enable retargeting and provide resistance to neutralising antisera" The Journal of Gene Medicine, 10:400-411 (2008) (Abstract only).
Carlon et al. "Efficient Gene Transfer Into the Mouse Lung by Fetal Intratracheal Injection of rAAV2/6.2" Molecular Therapy, 18(12):2130-2138 (2010).
Carter et al. "Three-Dimensional Structure of Human Serum Albumin" Science, 244:1195-1198 (1989).
Cesbron et al. "TAT and HA2 Facilitate Cellular Uptake of Gold Nanoparticies but Do Not Lead to Cystolic Localization" PLoS One, 10:e0121683 (2015).
Chai et al. "Application of polyploid adeno-associated virus vectors for transduction enhancement and neutralizing antibody evasion" Journal of Controlled Release, 262:348-356 (2017).
Chang et al. "Human Apolipoprotein E Is Required for Infectivity and Production of Hepatitis C Virus in Cell Culture" Journal of Virology, 81(24):13783-13793 (2007).
Chaudhury et al. "The Major Histocompatibility Complex-related Fc Receptor for IgG (FcRn) Binds Albumin and Prolongs Its Lifespan" The Journal of Experimental Medicine, 197(3):315-322 (2003).
Chen et al. "Molecular Characterization of Adeno-Associated Viruses Infecting Children" Journal of Virology, 79 (23):14781-14792 (2005).
Chirmule et al. "Immune responses to adenovirus and adeno-associated virus in humans" Gene Therapy, 6:1574-1583 (1999).
Choi et al. "AAV Hybrid Serotypes: Improved Vectors for Gene Delivery" Current Gene Therapy, 5(3):299-310 (2005).
Choudhury et al. "In Vivo Selection Yields AAV-B1 Capsid for Central Nervous System and Muscle Gene Therapy" Molecular Therapy, 24(7):1247-1257 (2016).
Cronin et al. "Efficient transduction and optogenetic stimulation of retinal bipolar cells by a synthetic adeno-associated virus capsid and promoter" EMBO Molecular Medicine, 6:1175-1190 (2014).
Dalkara et al. "In vivo-directed evolution of a new adeno-associated virus for therapeutic outer retinal gene delivery from the vitreous" Science Translational Medicine. 5(189):189ra76 (2013) (Abstract only).
Davidoff et al. "Comparison of the Ability of Adeno-associated Viral Vectors Pseudotyped with Serotype 2, 5, and 8 Capsid Proteins to Mediate Efficient Transduction of the Liver in Murine and Nonhuman Primate Models" Molecular Therapy, 11(6):875-888 (2005).
Denard et al. "C-Reactive Protein (CRP) Is Essential for Efficient Systemic Transduction of Recombinant Adeno-Associated Virus Vector 1 (rAAV-1) and rAAV-6 in Mice" Journal of Virology, 87(19):10784-10791 (2013).
Denard et al. "Human Galectin 3 Binding Protein Interacts with Recombinant Adeno-Associated Virus Type 6" Journal of Virology, 86(12):6620-6631 (2012).
Deverman et al. "Cre-dependent selection yields AAV variants for widespread gene transfer to the adult brain" Nature Biotechnology, 34(2):204-209 (2016).
Ding et al. "Intracellular trafficking of adeno-associated viral vectors" Gene Therapy, 12:873-880 (2005).
Ding et al. "rAAV2 Traffics through both the Late and the Recycling Endosomes in a Dose-Dependent Fashion" Molecular Therapy, 13:671-682 (2006).
Douar et al. "Intracellular Trafficking of Adeno-Associated Virus Vectors: Routing to the Late Endosomal Compartment and Proteasome Degradation" Journal of Virology, 75(4):1824-1833 (2001).
Duan et al. "Endosomal processing limits gene transfer to polarized airway epithelia by adeno-associated virus" The Journal of Clinical Investigation, 105(11):1573-1587 (2000).
Duan, Dongsheng "Systemic delivery of adeno-associated viral vectors" Current Opinion in Virology, 21:16-25 (2016).
Elsadek et al. "Impact of albumin on drug delivery—new applications on the horizon" Journal of Controlled Release, 157(1):4-28 (2012) (Abstract only).
Elzoghby et al. "Albumin-based nanoparticles as potential controlled release drug delivery systems" Journal of Controlled Release, 157(2):168-182 (2012).
Erles et al. "Update on the prevalence of serum antibodies (IgG and IgM) to adeno-associated virus (AAV)" Journal of Medical Virology, 59:406-411 (1999) (Abstract only).
Excoffon et al. "Directed evolution of adeno-associated virus to an infectious respiratory virus" Proceedings of the National Academy of Sciences USA, 106(10):3865-3870 (2009).
Ferrari et al. "Second-Strand Synthesis Is a Rate-Limiting Step for Efficient Transduction by Recombinant Adeno-Associated Virus Vectors" Journal of Virology, 70(5):3227-3234 (1996).
Fiume et al. "Albumin-drug conjugates in the treatment of hepatic disorders" Expert Opinion on Drug Delivery, 11 (8):1203-1217 (2014) (Abstract only).
Gabriel et al. "Bioengineering of AAV2 Capsid at Specific Serine, Threonine, or Lysine Residues Improves Its Transduction Efficiency in Vitro and in Vivo" Human Gene Therapy Methods, 24(2):80-93 (2013).

(56) References Cited

OTHER PUBLICATIONS

Gao et al. "Clades of Adeno-Associated Viruses Are Widely Disseminated in Human Tissues" Journal of Virology, 78 (12):6381-6388 (2004).
Gao et al. "Empty virions in AAV8 vector preparations reduce transduction efficiency and may cause total viral particle dose-limiting side-effects" Molecular Therapy—Methods & Clinical Development, 1(9):1-8 (2014).
Gao et al. "Novel adeno-associated viruses from rhesus monkeys as vectors for human gene therapy" Proceedings of the National Academy of Sciences, 99:11854-11859 (2002).
Geoghegan et al. "Chondroitin Sulfate is the Primary Receptor for a Peptide-Modified AVV That Targets Brain Vascular Endothelium in Vivo" Molecular Therapy—Nucleic Acids, 3(e202):1-13 (2014).
Georg-Fries et al. "Analysis of proteins, helper dependence, and seroepidemiology of a new human parvovirus" Virology, 134:64-71 (1984) (Abstract only).
Girod et al. "Genetic capsid modifications allow efficient re-targeting of adeno-associated virus type 2" Nature Medicine, 5(9):1052-1056 (1999).
Govindasamy et al. "Structurally Mapping the Diverse Phenotype of Adeno-Associated Virus Serotype 4" Journal of Virology, 80:11556-11570 (2006).
Gray et al. "Directed Evolution of a Novel Adeno-associated Virus (AAV) Vector That Crosses the Seizure-compromised Blood-Brain Barrier (BBB)" Molecular Therapy, 18(3):570-578 (2010).
Grieger et al. "Separate Basic Region Motifs within the Adeno-Associated Virus Capsid Proteins Are Essential for Infectivity and Assembly" Journal of Virology, 80(11):5199-5210 (2006).
Grieger et al. "Surface-Exposed Adeno-Associated Virus Vp1-NLS Capsid Fusion Protein Rescues Infectivity of Noninfectious Wild-Type Vp2/Vp3 and Vp3-Only Capsids but Not That of Fivefold Pore Mutant Virions" Journal of Virology, 81(15):7833-7843 (2007).
Grieger et al. "Production and characterization of adeno-associated viral vectors" Nature Protocols, 1:1412-1428 (2006).
Grifman et al. "Incorporation of Tumor-Targeting Peptides into Recombinant Adeno-associated Virus Capsids" Molecular Therapy, 3(6):964-975 (2001).
Grimm et al. "In Vitro and in Vivo Gene Therapy Vector Evolution via Multispecies Interbreeding and Retargeting of Adeno-Associated Viruses" Journal of Virology, 82(12):5887-5911 (2008).
Gurda et al. "Mapping a Neutralizing Epitope onto the Capsid of Adeno-Associated Virus Serotype 8" Journal of Virology 86:7739-7751 (2012).
Halbert et al. "Repeat Transduction in the Mouse Lung by Using Adeno-Associated Virus Vectors with Different Serotypes" Journal of Virology, 74(3):1524-1532 (2000).
He et al. "Kinetics of Adeno-Associated Virus Serotype 2 (AAV2) and AAV8 Capsid Antigen Presentation in Vivo Are Identical" Human Gene Therapy, 24:545-553 (2013).
Hewitt et al. "The human cytomegalovirus gene product US6 inhibits ATP binding by TAP" The EMBO Journal, 20 (3):387-396 (2001).
Hildinger et al. "Hybrid Vectors Based on Adeno-Associated Virus Serotypes 2 and 5 for Muscle-Directed Gene Transfer" Journal of Virology, 75(13):6199-8203 (2001).
Huang et al. "Genetic Manipulation of Brown Fat Via Oral Administration of an Engineered Recombinant Adeno-associated Viral Serotype Vector" Molecular Therapy, 24(6):1062-1060 (2016).
Huang et al. "Hepatitis C virus production by human hepatocytes dependent on assembly and secretion of very low-density lipoproteins" Proceedings of the National Academy of Sciences, USA, 104(14):5848-5853 (2007).
Huttner et al. "Genetic modifications of the adeno-associated virus type 2 capsid reduce the affinity and the neutralizing effects of human serum antibodies" Gene Therapy, 10:2139-2147 (2003).
International Search Report and the Written Opinion of the International Searching Authority corresponding to International Patent Application No. PCT/US2018/022725 (9 pages) (dated Jul. 5, 2018).
International Search Report and the Written Opinion of the International Searching Authority corresponding to International Patent Application No. PCT/US2018/044632 (11 pages) (dated Jan. 31, 2019).
Issa et al. "Assessment of tropism and effectiveness of new primate-derived hybrid recombinant AAV serotypes in the mouse and primate retina" PLoS One, 8:e60361 (2013).
Jang et al. "An Evolved Adeno-associated Viral Variant Enhances Gene Delivery and Gene Targeting in Neural Stem Cells" Molecular Therapy, 19(4):667-675 (2011).
Jiang et al. "Effects of transient immunosuppression on adenoassociated, virus-mediated, liver-directed gene transfer in rhesus macaques and implications for human gene therapy" Blood, 108:3321-3328 (2006).
Jiang et al. "Recombinant Adenovirus Vectors Activate the Alternative Complement Pathway, Leading to the Binding of Human Complement Protein C3 Independent of Anti-Ad Antibodies" Molecular Therapy, 10(6):1140-1142 (2004).
Johnson et al. "Enhancement of Adeno-Associated Virus Infection by Mobilizing Capsids into and Out of the Nucleolus" Journal of Virology, 83(6)2632-2844 (2009).
Ju et al. "Effect of hydroxyurea and etoposide on transduction of human bone marrow mesenchymal stem and progenitor cell by adeno-associated virus vectors" Acta Pharmacologica Sinica, 25(2):196-202 (2004).
Kaludov et al. "Adeno-Associated Virus Serotype 4 (AAV4) and AAV5 Both Require Sialic Acid Binding for Hemagglutination and Efficient Transduction but Differ in Sialic Acid Linkage Specificity" Journal of Virology, 75:6884-6893 (2001).
Klimczak et al. "A Novel Adeno-Associated Viral Variant for Efficient and Selective Intravitreal Transduction of Rat Müller Cells" PLoS One, 4(10):e7467 (2009).
Koerber et al. "Molecular Evolution of Adeno-associated Virus for Enhanced Glial Gene Delivery" Molecular Therapy, 17(12):2088-2095 (2009).
Korbelin et al. "Pulmonary Targeting of Adeno-associated Viral Vectors by Next-generation Sequencing-guided Screening of Random Capsid Displayed Peptide Libraries" Molecular Therapy, 24(6):1050-1061 (2016).
Kotterman et al. "Antibody Neutralization Poses a Barrier to Intravitreal Adeno-Associated Viral Vector Gene Delivery to Non-Human Primates" Gene Therapy, 22(2):116-126 (2015).
Kotterman et al. "Engineering adeno-associated viruses for clinical gene therapy" Nature Reviews Genetics, 15 (7):445-451 (2014).
Kratz, Felix "Albumin as a drug carrier: design of prodrugs, drug conjugates and nanoparticles" Journal of Controlled Release, 132(3):171-183 (2008) (Abstract only).
Lambot et al. "Evidence for a Clathrin-Mediated Recycling of Albumin in Human Term Placenta" Biology of Reproduction, 74:90-97 (2006).
Le et al. "Utility of PEGylated recombinant adeno-associated viruses for gene transfer" Journal of Controlled Release, 108:161-177 (2005) (Abstract only).
Lee et al. "PEG Conjugation Moderately Protects Adeno-Associated Viral Vectors Against Antibody Neutralization" Biotechnology and Bioengineering, 92(1):24-34 (2005).
Li et al. "Adeno-associated virus capsid antigen presentation is dependent on endosomal escape" The Journal of Clinical Investigation, 123(3):1390-1401 (2013).
Li et al. "Cytotoxic-T-Lymphocyte-Mediated Elimination of Target Cells Transduced with Engineered Adeno-Associated Virus Type 2 Vector in Vivo" Journal of Virology, 83(13):6817-6824 (2009).
Li et al. "Development of Patient-specific AAV Vectors After Neutralizing Antibody Selection for Enhanced Muscle Gene Transfer" Molecular Therapy, 24:53-65 (2016).
Li et al. "Engineering and Selection of Shuffled AAV Genomes: A New Strategy for Producing Targeted Biological Nanoparticles" Molecular Therapy, 16(7):1252-1260 (2008).
Li et al. "Generation of Novel AAV Variants by Directed Evolution for Improved CFTR Delivery to Human Ciliated Airway Epithelium" Molecular Therapy, 17(12):2067-2077 (2009).

(56) References Cited

OTHER PUBLICATIONS

Li et al. "Neutralizing antibodies against adeno-associated virus examined prospectively in pediatric patients with hemophilia" Gene Therapy, 19:288-294 (2012).
Li et al. "Single Amino Acid Modification of Adeno-Associated Virus Capsid Changes Transduction and Humoral Immune Profiles" Journal of Virology, 86(15):7752-7759 (2012).
Li et al. "Site-Directed Mutagenesis of Surface-Exposed Lysine Residues Leads to Improved Transduction by AAV2, But Not AAV8, Vectors in Murine Hepatocytes in Vivo" Human Gene Therapy Methods, 26(6):211-220 (2015).
Lilley et al. "Viral modulation of antigen presentation: manipulation of cellular targets in the ER and beyond" Immunological Reviews, 207:126-144 (2005).
Liou et al. "Protein transduction in human cells in enhanced by cell-penetrating peptides fused with an endosomolytic HA2 sequence" Peptides, 37(2):273-284 (2012) (Abstract only).
Lisowski et al. "Adeno-associated virus serotypes for gene therapeutics" Current Opinion in Pharmacology, 24:59-67 (2015) (Abstract only).
Lisowski et al. "Selection and evaluation of clinically relevant AAV variants in a xenograft liver model" Nature, 506 (7488):382-386 (2014).
Lilt et al. "Enhancing gene delivery of adeno-associated viruses by cell-permeable peptides" Molecular Therapy, 1 (12):1-13 (2014).
Lochrie et al. "Adeno-associated virus (AAV) capsid genes isolated from rat and mouse liver genomic DNA define two new AAV species distantly related to AAV-5" Virology, 353:68-82 (2006).
Lochrie et al. "Mutations on the External Surfaces of Adeno-Associated Virus Type 2 Capsids That Affect Transduction and Neutralization" Journal of Virology, 80(2):821-634 (2006).
Lybarger et al. "Viral immune evasion molecules attack the ER peptide-loading complex and exploit ER-associated degradation pathways" Current Opinion in Immunology, 17:71-78 (2005) (Abstract only).
Ma et al. "Expression of liver-targeting peptide modified recombinant human endostatin and preliminary study of its biological activities" Applied Microbiology and Biotechnology, 98:7923-7933 (2014).
Machida et al. "A hepatitis B surface antigen polypeptide (P31) with the receptor for polymerized human as well chimpanzee albumins" Gastroenterology, 85(2):268-274 (1983) (Abstract only).
Maersch et al. "Optimization of stealth adeno-associated virus vectors by randomization of immunogenic epitopes" Virology, 397:167-175 (2010).
Maguire et al. "Age-dependent effects of RPE65 gene therapy for Leber's congenital amaurosis: a phase 1 dose-escalation trial" Lancet, 374(9701):1597-1605 (2009).
Maguire et al. "Directed evolution of adeno-associated virus for glioma cell transduction" J Neuro-Oncology, 96 (3):337-347 (2010).
Maheshri et al. "Directed evolution of adeno-associated virus yields enhanced gene delivery vectors" Nature Biotechnology, 24:198-204 (2006).
Manno et al. "Successful transduction of liver in hemophilia by AAV-Factor IX and limitations imposed by the host immune response" Nature Medicine, 12(3):342-347 (2006).
Marsic et al. "Vector Design Tour de Force: Integrating Combinatorial and Rational Approaches to Derive Novel Adeno-associated Virus Variants" Molecular Therapy, 22(11):1900-1909 (2014).
McCarty et al. "Adeno-associated virus terminal repeat (TR) mutant generates self-complementary vectors to overcome the rate-limiting step to transduction in vivo" Gene Therapy, 10(26):2112-2118 (2003).
McCarty et al. "Self-complementary recombinant adeno-associated virus (scAAV) vectors promote efficient transduction independently of DNA synthesis" Gene Therapy, 8(16):1248-1254 (2001).
McCraw et al. "StructurE of adeno-associated virus-2 in Complex with Neutralizing Monoclonal antibodY A20" Virology, 431(1-2):40-49 (2012).
Meeks et al. "Non-Classical Anti-Factor VIII C2 Domain Antibodies Are Pathogenic in a Murine in vivo Bleeding Model" Journal of Thrombosis and Haemostasis, 7(4):658-664 (2009).
Mehdi et al. "Hepatitis B Virus Surface Antigen Binds to Apolipoprotein H" Journal of Virology, 68(4):2415-2424 (1994).
Messina et al. "Adeno-Associated Viral Vectors Based on Serotype 3b Use Components of the Fibroblast Growth Factor Receptor Signaling Complex for Efficient Transduction" Human Gene Therapy, 23(10):1031-1042 (2012).
Michelfelder et al. "Peptide Ligands Incorporated into the Threefold Spike Capsid Domain to Re-Direct Gene Transduction of AAV8 and AAV9 in Vivo" PLoS One, 6(8):e23101 (2011).
Michelfelder et al. "Vectors selected from adeno-associated viral display peptide libraries for leukemia cell-targeted cytotoxic gene therapy" Experimental Hematology, 35(12):1786-1776 (2007) (Abstract only).
Mingozzi et al. "Overcoming Preexisting Humoral Immunity to AAV Using Capsid Decoys" Science Translational Medicine, 5(194):1-20 (2013).
Mingozzi et al. "Prevalence and pharmacological modulation of humoral immunity to AAV vectors in gene transfer to synovial tissue" Gene Therapy, 20:417-424 (2013).
Mingozzi et al. "Therapeutic in vivo gene transfer for genetic disease using AAV: progress and challenges" Nature Reviews Genetics, 12:341-355 (2011).
Mitchell et al. "Arsenic Trioxide Stabilizes Accumulations of Adeno-Associated Virus Virions at the Perinuclear Region, Increasing Transduction in Vitro and in Vivo" Journal of Virology, 87(8):4571-4583 (2013).
Mitchell et al. "Mechanistic Insights into the Enhancement of Adeno-Associated Virus Transduction by Proteasorne Inhibitors" Journal of Virology, 87(23):13035-13041 (2013).
Monahan et al. "Employing a Gain-of-Function Factor IX Variant R338L to Advance the Efficacy and Safety of Hemophilia B Human Gene Therapy: Preclinical Evaluation Supporting an Ongoing Adeno-Associated Virus Clinical Trial" Human Gene Therapy, 26(2):69-81 (2015).
Monahan et al. "Proteasome Inhibitors Enhance Gene Delivery by AAV Virus Vectors Expressing Large Genomes in Hemophilia Mouse and Dog Models: A Strategy for Broad Clinical Application" Molecular Therapy, 18(11):1907-1916 (2010).
Monteilhet et al. "A 10 Patient Case Report on the Impact of Plasmapheresis Upon Neutralizing Factors Against Adeno-associated Virus (AAV) Types 1, 2, 6, and 8" Molecular Therapy, 19(11):2084-2091 (2011).
Montoyo et al. "Conditional deletion of the MHC class I-related receptor FcRn reveals the sites of IgG homeostasis in mice" Proceedings of the National Academy of Sciences USA, 106(8):2788-2793 (2009).
Moriyama et al. "Caveolae may enable albumin to enter human renal glomerular endothelial cells" Journal of Cellular Biochemistry, 116(6):1060-1069 (2015) (Abstract only).
Moskalenko et al. "Epitope Mapping of Human Anti-Adeno-Associated Virus Type 2 Neutralizing Antibodies: Implications for Gene Therapy and Virus Structure" Journal of Virology, 74:1761-1766 (2000).
Muller et al. "Improved cardiac gene transfer by transcriptional and transductional targeting of adeno-associated viral vectors" Cardiovascular Research, 70:70-78 (2006).
Muller et al. "Random peptide libraries displayed on adeno-associated virus to select for targeted gene therapy vectors" Nature Biotechnology, 21(9):1040-1046 (2003) (Abstract only).
Murata et al. "Liver cell specific targeting by the preS1 domain of hepatitis B virus surface antigen displayed on protein nanocages" International Journal of Nanomedicine, 7:4353-4362 (2012).
Nakase et al. "Endosome-disruptive peptides for improving cytosolic delivery of bioactive macromolecules" Biopolymers, 94:763-770 (2010) (Abstract only).
Nathwani et al. "Adenovirus-Associated Virus Vector—Mediated Gene Transfer in Hemophilia B" The New England Journal of Medicine, 365:2357-2365 (2011).

(56) References Cited

OTHER PUBLICATIONS

Nathwani et al. "Long-Term Safety and Efficacy of Factor IX Gene Therapy in Hemophilia B" The New England Journal of Medicine, 371(21):1994-2004 (2014).
Nathwani et al. "Safe and efficient transduction of the liver after peripheral vein infusion of self-complementary AAV vector results in stable therapeutic expression of human FIX in nonhuman primates" Blood, 109(4):1414-1421 (2007).
Nathwani et al. "Self-complementary adeno-associated virus vectors containing a novel liver-specific human factor IX expression cassette enable highly efficient transduction of murine and nonhuman primate liver" Blood, 107:2653-2661 (2006).
Nietupski et al. "Systemic Administration of AAV8-a-galactosidase A Induces Humoral Tolerance in Nonhuman Primates Despite Low Hepatic Expression" Molecular Therapy. 19(11):1999-2011 (2011).
Nonnenmacher et al. "Intracellular Transport of Recombinant Adeno-Associated Virus Vectors" Gene Therapy, 19 (6):649-658 (2012).
Parker et al. "Multiple vitamin K-dependent coagulation zymogens promote adenovirus-mediated gene delivery to hepatocytes" Blood, 108(8):2554-2561 (2006).
Pei et al. "AAV6 virions hijack serum proteins to increase hepatocyte binding for transduction enhancement" Virology, 518:95-102 (2018).
Perabo et al. "Combinatorial engineering of a gene therapy vector: directed evolution of adeno-associated virus" The Journal of Gene Medicine, 8:155-162 (2006) (Abstract only).
Petrs-Silva et al. "High-efficiency Transduction of the Mouse Retina by Tyrosine-mutant AAV Serotype Vectors" Molecular Therapy, 17(3):463-471 (2009).
Pontisso et al. "Human Liver Plasma Membranes Contain Receptors for the Hepatitis B Virus Pre-S1 Region and, via Polymerized Human Serum Albumin, for the Pre-S2 Region" Journal of Virology, 63(5):1981-1988 (1989).
Powell et al. "Characterization of a novel adeno-associated viral vector with preferential oligodendrocyte tropism" Gene Therapy, 23(11):807-814 (2016).
Prasad et al. "Topoisomerase Inhibition Accelerates Gene Expression After Adeno-associated Virus-mediated Gene Transfer to the Mammalian Heart" Molecular Therapy, 15(4):764-771 (2007).
Pulicherla et al. "Engineering Liver-detargeted AAV9 Vectors for Cardiac and Musculoskeletal Gene Transfer" Molecular Therapy, 19(6):1070-1078 (2011).
Qiao et al. "Adeno-Associated Virus Serotype 6 Capsid Tyrosine-to-Phenylalanine Mutations Improve Gene Transfer to Skeletal Muscle" Human Gene Therapy, 21(10):1343-1348 (2010).
Qing et al. "Human fibroblast growth factor receptor 1 is a co-receptor for infection by adeno-associated virus 2" Nature Medicine, 5(1):71-77 (1999) (Abstract only).
Rabinovvitz et al. "Cross-Dressing the Virion: the Transcapsidation of Adeno-Associated Virus Serotypes Functionally Defines Subgroups" Journal of Virology, 78(9):4421-4432 (2004).
Rabinowitz et al. "Cross-Packaging of a Single Adeno-Associated Virus (AAV) Type 2 Vector Genome into Multiple AAV Serotypes Enables Transduction with Broad Specificity" Journal of Virology, 76(2):791-801 (2002).
Rhaese et al. "Human serum albumin-polyethylenimine nanoparticles for gene delivery" Journal of Controlled Release, 92:199-208 (2003).
Riviere et al. "Long-term expression and repeated administration of AAV type 1, 2 and 5 vectors in skeletal muscle of immunocompetent adult mice" Gene Therapy, 13:1300-1308 (2006).
Russell et al. "DNA synthesis and topoisomerase inhibitors increase transduction by adeno-associated virus vectors" Proceedings of the National Academy of Sciences USA, 92(12):5719-5723 (1995).
Sallach et al. "Tropism-modified AAV Vectors Overcome Barriers to Successful Cutaneous Therapy" Molecular Therapy, 22(6):929-939 (2014).
Sand et al. "Unraveling the interaction between FcRn and albumin: opportunities for design of albumin-based therapeutics" Frontiers in Immunology, 5(682):1-21 (2014).
Sarkar et al. "Total correction of hemophilia A mice with canine FVIII using an AAV 8 serotype" Blood, 103 (4):1253-1260 (2004).
Scallan et al. "Human immunoglobulin inhibits liver transduction by AAV vectors at low AAV2 neutralizing titers in SCID mice" Blood, 107(5)1810-1817 (2006).
Schmidt et al. "Cloning and Characterization of a Bovine Adeno-Associated Virus" Journal of Virology, 78(12):6509-6516 (2004).
Schuettrumpf et al. "Factor IX variant improve gene therapy efficacy for hemophilia B" Blood, 105(6):2316-2323 (2005).
Seliger et al. "Molecular mechanisms of HLA class I antigen abnormalities following viral infection and transformation" International Journal of Cancer, 118:129-138 (2006).
Sellner et al. "Generation of efficient human blood progenitor-targeted recombinant adeno-associated viral vectors (AAV) by applying an AAV random peptide library on primary human hematopoietic progenitor cells" Experimental Hematology, 36(8):957-964 (2008) (Abstract only).
Sen et al. "Targeted Modifications in Adeno-Associated Virus Serotype 8 Capsid Improves Its Hepatic Gene Transfer Efficiency in Vivo" Human Gene Therapy Methods, 24(2):104-116 (2013).
Shen et al. "Engraftment of a Galactose Receptor Footprint onto Adeno-associated Viral Capsids Improves Transduction Efficiency" The Journal of Biological Chemistry, 288(40):28814-28823 (2013).
Simoes et al. "Human serum albumin enhances DNA transfection by lipoplexes and confers resistance to inhibition by serum" Biochimica et Biophysica Acta, 1463:459-469 (2000).
Simonelli et al. "Gene Therapy for Leber's Congenital Amaurosis is Safe and Effective Through 1.5 Years After Vector Administration" Molecular Therapy, 18(3):643-650 (2010).
Sleep, Darrell "Albumin and its application in drug delivery" Expert Opinion on Drug Delivery, 12(5):793-812 (2015) (Abstract only).
Sonntag et al. "The Assembly-Activating Protein Promotes Capsid Assembly of Different Adeno-Associated Virus Serotypes" Journal of Virology, 85(23):12686-12697 (2011).
Summerford et al. "AlphaVbeta5 integrins a co-receptor for adeno-associated virus type 2 infection" Nature Medicine, 5(1):78-82 (1999).
Summerford et al. "Membrane-Associated Heparan Sulfate Proteoglycan is a Receptor for Adeno-Associated Virus Type 2 Virions" Journal of Virology, 72:1438-1445 (1998).
Sun et al. "Intraarticular factor IX protein or gene replacement protects against development of hemophilic synovitis in the absence of circulating factor IX" Blood, 112(12):4532-4541 (2008).
Tervo et al. "A designer AAV variant permits efficient retrograde access to projection neurons" Neuron, 92 (2):372-382 (2016).
Tseng et al. "Mapping the AAV capsid host antibody response toward the development of second generation gene delivery vectors" Fronteirs in Immunology, 5(9):1-11 (2014).
Vance et al. "AAV Gene Therapy for MPS1-associated Corneal Blindness" Scientific Reports, 6(22131):1-10 (2016).
Varadi et al. "Novel random peptide libraries displayed on AAV serotype 9 for selection of endothelial cell-directed gene transfer vectors" Gene Therapy, 19(8):800-809 (2012) (Abstract only).
Varkouhi et al. "Endosomal escape pathways for delivery of biologicals" Journal of Controlled Release, 151:220-228 (2011).
Wang et al. "Direct Interaction of Human Serum Proteins with AAV Virions to Enhance AAV Transduction: Immediate Impact on Clinical Applications" Gene Therapy, 24:49-59 (2017).
Wang et al. "Prediction of adeno-associated virus neutralizing antibody activity for clinical application" Gene Therapy, 22:984-992 (2015).
Wang et al. "Syngeneic AAV Pseudo-particles Potentiate Gene Transduction of AAV Vectors" Molecular Therapy: Methods & Clinical Development, 4:149-158 (2017).
Wang et al. "Recent procress of cell-penetrating peptides as new carriers for intracellular cargo delivery" Journal of Controlled Release, 174:126-136 (2014) (Abstract only).
Ward et al. "Current and future prospects for hemophilia gene therapy" Expert Review of Hematology, 9:649-659 (2016) (Abstract only).
Warrington et al. "Adeno-Associated Virus Type 2 VP2 Capsid Protein Is Nonessential and Can Tolerate Large Peptide Insertions at Its N Terminus" Journal of Virology, 78(12):6595-6609 (2004).

(56) References Cited

OTHER PUBLICATIONS

Wong et al. "Hepatocyte Targeting of Nucleic Acid Complexes and Liposomes by a T7 Phage p17 Peptide" Molecular Pharmaceutics, 3(4):386-397 (2006).
Wu et al. "Mutational Analysis of the Adeno-Associated Virus Type 2 (AAV2) Capsid Gene and Construction of AAV2 Vectors with Altered Tropism" Journal of Virology, 74:8635-8647 (2000).
Wu et al. "Optimization of Self-complementary AVV Vectors for Liver-directed Expression Results in Sustained Correction of Hemophilia B at Low Vector Dose" Molecular Therapy, 16(2):280-289 (2003).
Wu et al. "Single Amino Acid Changes Can Influence Titer, Heparin Binding, and Tissue Tropism in Different Adeno-Associated Virus Serotypes" Journal of Virology, 80:11393-11397 (2006).
Xiao et al. "Cytoplasmic Trafficking, Endosomal Escape, and Perinuclear Accumulation of Adeno-Associated Virus Type 2 Particles Are Facilitated by Microtubule Network" Journal of Virology, 86(19):10462-10473 (2012).
Xiao et al. "Gene Therapy Vectors Based on Adeno-Associated Virus Type 1" Journal of Virology, 73:3994-4003 (1999).
Xiao et al. "Production of High-Titer Recombinant Adeno-Associated Virus Vectors in the Absence of Helper Adenovirus" Journal of Virology, 72(3):2224-2232 (1998).
Xiao et al. "Quantitative 3D tracing of Gene-delivery Viral Vectors in Human Cells and Animal Tissues" Molecular Therapy, 20(2):317-328 (2012).
Xie et al. "The atomic structure of adeno-associated virus (AAV-2), a vector for human gene therapy" Proceedings of the National Academy of Sciences USA, 99:10405-10410 (2002).
Yan et al. "Ubiquitination of both Adeno-Associated Virus Type 2 and 5 Capsid Proteins Affects the Transduction Efficiency of Recombinant Vectors" Journal of Virology, 76(5):2043-2053 (2002).
Yang et al. "A myocardium tropic adeno-associated virus (AAV) evolved by DNA shuffling and in vivo selection" Proceedings of the National Academy of Sciences USA, 106(10):3946-3951 (2009).
Yu et al. "A muscle-targeting peptide displayed on AAV2 improves muscle tropism on systemic delivery" Gene Therapy, 16(8):953-962 (2009).
Yumoto et al. "Clathrin-mediated endocytosis of FITC-albumin in alveolar type II epithelial cell line RLE-6TN" American Journal of Physiology Lung Cellular and Molecular Physiology, 290(5):L946-I955 (2006).
Zahid et al. "Cell-Type Specific Penetrating Peptides: Therapeutic Promises and Challenges" Molecules, 20:13055-13070 (2015).
Zaiss al. "Complement Is an Essential Component of the Immune Response to Adeno-Associated Virus Vectors" Journal of Virology, 82(6):2727-2740 (2006).
Zhong et al. "Next generation of adeno-associated virus 2 vectors: point mutations in tyrosines lead to high-efficiency transduction at lower doses" Proceedings of the National Academy of Sciences USA; 105(22):7827-7632 (2008).
Zinn et al. "Bioluminescence imaging reveals a significant role for complement in liver transduction following intravenous delivery of adenovirus" Gene Therapy, 11(19):1452-1486 (2004).
Zinn et al. "In Silico Reconstruction of the Viral Evolutionary Lineage Yields a Potent Gene Therapy Vector" Cell Reports, 12(6):1056-1066 (2015).
Zloza et al. "High-Dose IL-2 Induces Rapid Albumin Uptake by Endothelial Cells Through Src-Dependent Caveolae-Mediated Endocytosis" Journal of Interferon & Cytokine Research, 34(11):915-919 (2014).

Haploid Design by combining mutations at start codons of capsid proteins and splice acceptor sites D = Splice Donor Site
A1 = Splice Acceptor Site 1 for VP1
A2 = Splice Acceptor Site 2 for VP2/3

VP1 capsid protein is made
VP2 and VP3 capsid proteins are not made due to A2 splice site and their respective start codons are mutated

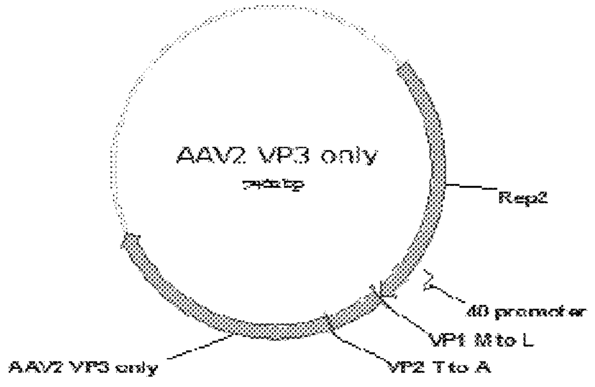

ctggctgccgatggttatcttccagattggctcgaggacactctctctgaaggaataagacagtggtggaagctcaaacctggcccaccaccaccaaa
gcccgcagagcggcataaggacgacagcaggggtcttgtgcttcctgggtacaagtacctcggacccttcaacggactcgacaagggagagccggtc
aacgaggcagacgccgcggccctcgagcacgacaaagcctacgaccggcagctcgacagcggagacaacccgtacctcaagtacaaccacgccga
cgcggagtttcaggagcgccttaaagaagatacgtcttttgggggcaacctcggacgagcagtcttccaggcgaaaaagagggttcttgaacctctgg
gcctggttgaggaacctgttaaggcggctccgggaaaaaagaggccggtagagcactctcctgtggagccagactcctcctcgggaaccggaaagg
cgggccagcagcctgcaagaaaaagattgaattttggtcagactggagacgcagactcagtacctgacccccagcctctcggacagccaccagcagc
ccctctggtctgggaactaatacgatggctacaggcagtggcgcaccaatggcagacaataacgagggcgccgacggagtgggtaattcctcggga
aattggcattgcgattccacatggatgggcgacagagtcatcaccaccagcacccgaacctgggccctgcccacctacaacaaccacctctacaaac
aaatttccagccaatcaggagcctcgaacgacaatcactactttggctacagcaccccttgggggtattttgacttcaacagattccactgccacttttc
accacgtgactggcaaagactcatcaacaacaactggggattccgacccaagagactcaacttcaagctctttaacattcaagtcaaagaggtcacg
cagaatgacggtacgacgacgattgccaataaccttaccagcacggttcaggtgtttactgactcggagtaccagctcccgtacgtcctcggctcggcg
catcaaggatgcctcccgccgttcccagcagacgtcttcatggtgccacagtatggatacctcaccctgaacaacgggagtcaggcagtaggacgctc
ttcattttactgcctggagtactttccttctcagatgctgcgtaccggaaacaactttaccttcagctacacttttgaggacgttcctttccacagcagcta
cgctcacagccagagtctggaccgtctcatgaatcctctcatcgaccagtacctgtattacttgagcagaacaaacactccaagtggaaccaccacgc
agtcaaggcttcagttttctcaggccggagcgagtgacattcgggaccagtctaggaactggcttcctggaccctgttaccgccagcagcgagtatcaa
agacatctgcggataacaacaacagtgaatactcgtggactggagctaccaagtaccacctcaatggcagagactctctggtgaatccgggcccggc
catggcaagccacaaggacgatgaagaaaagttttttcctcagagcggggttctcatctttgggaagcaaggctcagagaaaacaaatgtggacatt
gaaaaggtcatgattacagacgaagaggaaatcaggacaaccaatcccgtggctacggagcagtatggttctgtatctaccaacctccagagaggc
aacagacaagcagctaccgcagatgtcaacacacaaggcgttcttccaggcatggtctggcaggacagagatgtgtaccttcaggggcccatctggg
caaagattccacacacggacggacattttcacccctctcccctcatgggtggattcggacttaaacaccctcctccacagattctcatcaagaacaccc
cggtacctgcgaatccttcgaccaccttcagtgcggcaaagtttgcttccttcatcacacagtactccacgggacaggtcagcgtggagatcgagtggg
agctgcagaaggaaaacagcaaacgctggaatcccgaaattcagtacacttccaactacaacaagtctgttaatgtggactttactgtggacactaat
ggcgtgtattcagagcctcgccccattggcaccagatacctgactcgtaatctg

FIG. 17

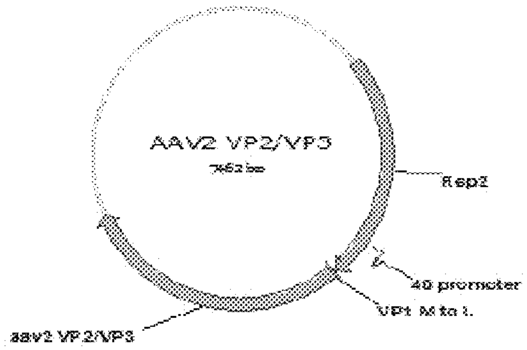

ttggctgccgatggttatcttccagattggctcgaggacactctctctgaaggaataagacagtggtggaagctcaaacctggcccaccaccaccaaa
gcccgcagagcggcataaggacgacagcaggggtcttgtgcttcctgggtacaagtacctcggacccttcaacggactcgacaagggagagccggtc
aacgaggcagacgccgcggccctcgagcacgacaaagcctacgaccggcagctcgacagcggagacaacccgtacctcaagtacaaccacgccga
cgcggagtttcaggagcgccttaaagaagatacgtcttttgggggcaacctcggacgagcagtcttccaggcgaaaaagagggttcttgaacctctgg
gcctggttgaggaacctgttaagacggctccgggaaaaaagaggccggtagagcactctcctgtggagccagactcctcctcgggaaccggaaagg
cgggccagcagcctgcaagaaaaagattgaattttggtcagactggagacgcagactcagtacctgacccccagcctctcggacagccaccagcagc
cccctctggtctgggaactaatacgatggctacaggcagtggcgcaccaatggcagacaataacgagggcgccgacggagtgggtaattcctcggga
aattggcattgcgattccacatggatgggcgacagagtcatcaccaccagcacccgaacctgggccctgcccacctacaacaaccacctctacaaac
aaatttccagccaatcaggagcctcgaacgacaatcactactttggctacagcaccccttgggggtattttgacttcaacagattccactgccacttttc
accacgtgactggcaaagactcatcaacaacaactggggattccgacccaagagactcaacttcaagctctttaacattcaagtcaaagaggtcacg
cagaatgacggtacgacgacgattgccaataaccttaccagcacggttcaggtgtttactgactcggagtaccagctcccgtacgtcctcggctcggcg
catcaaggatgcctcccgccgttcccagcagacgtcttcatggtgccacagtatggatacctcaccctgaacaacgggagtcaggcagtaggacgctc
ttcattttactgcctggagtactttccttctcagatgctgcgtaccggaaacaactttaccttcagctacacttttgaggacgttcctttccacagcagcta
cgctcacagccagagtctggaccgtctcatgaatcctctcatcgaccagtacctgtattacttgagcagaacaaacactccaagtggaaccaccacgc
agtcaaggcttcagttttctcaggccggagcgagtgacattcgggaccagtctaggaactggcttcctggaccctgttaccgccagcagcgagtatcaa
agacatctgcggataacaacaacagtgaatactcgtggactggagctaccaagtaccacctcaatggcagagactctctggtgaatccgggcccggc
catggcaagccacaaggacgatgaagaaaagttttttcctcagagcggggttctcatctttgggaagcaaggctcagagaaaacaaatgtggacatt
gaaaaggtcatgattacagacgaagaggaaatcaggacaaccaatcccgtggctacggagcagtatggttctgtatctaccaacctccagagaggc
aacagacaagcagctaccgcagatgtcaacacacaaggcgttcttccaggcatggtctggcaggacagagatgtgtaccttcaggggcccatctggg
caaagattccacacacggacggacattttcacccctctcccctcatgggtggattcggacttaaacaccctcctccacagattctcatcaagaacaccc
cggtacctgcgaatccttcgaccaccttcagtgcggcaaagtttgcttccttcatcacacagtactccacgggacaggtcagcgtggagatcgagtggg
agctgcagaaggaaaacagcaaacgctggaatcccgaaattcagtacacttccaactacaacaagtctgttaatgtggactttactgtggacactaat
ggcgtgtattcagagcctcgccccattggcaccagatacctgactcgtaatctg

FIG. 18

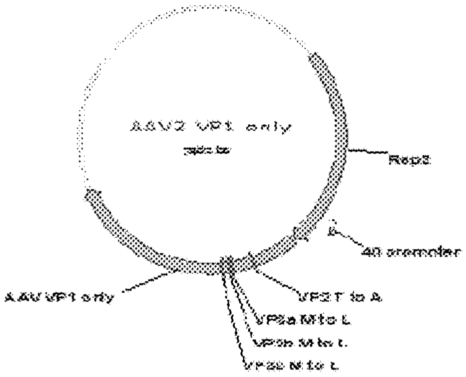

atggctgccgatggttatcttccagattggctcgaggacactctctctgaaggaataagacagtggtggaagctcaaacctggcccaccaccaccaaa
gcccgcagagcggcataaggacgacagcaggggtcttgtgcttcctgggtacaagtacctcggacccttcaacggactcgacaagggagagccggtc
aacgaggcagacgccgcggccctcgagcacgacaaagcctacgaccggcagctcgacagcggagacaacccgtacctcaagtacaaccacgccga
cgcggagtttcaggagcgccttaaagaagatacgtcttttgggggcaacctcggacgagcagtcttccaggcgaaaaagagggttcttgaacctctgg
gcctggttgaggaacctgttaaggcggctccgggaaaaaagaggccggtagagcactctcctgtggagccagactcctcctcgggaaccggaaagg
cgggccagcagcctgcaagaaaaagattgaattttggtcagactggagacgcagactcagtacctgacccccagcctctcggacagccaccagcagc
cccctctggtctgggaactaatacgctggctacaggcagtggcgcaccactggcagacaataacgagggcgccgacggagtgggtaattcctcggga
aattggcattgcgattccacatggctgggcgacagagtcatcaccaccagcacccgaacctgggccctgcccacctacaacaaccacctctacaaac
aaatttccagccaatcaggagcctcgaacgacaatcactactttggctacagcaccccttgggggtattttgacttcaacagattccactgccacttttc
accacgtgactggcaaagactcatcaacaacaactggggattccgacccaagagactcaacttcaagctctttaacattcaagtcaaagaggtcacg
cagaatgacggtacgacgacgattgccaataaccttaccagcacggttcaggtgtttactgactcggagtaccagctcccgtacgtcctcggctcggcg
catcaaggatgcctcccgccgttcccagcagacgtcttcatggtgccacagtatggatacctcaccctgaacaacgggagtcaggcagtaggacgctc
ttcattttactgcctggagtactttccttctcagatgctgcgtaccggaaacaactttaccttcagctacacttttgaggacgttcctttccacagcagcta
cgctcacagccagagtctggaccgtctcatgaatcctctcatcgaccagtacctgtattacttgagcagaacaaacactccaagtggaaccaccacgc
agtcaaggcttcagttttctcaggccggagcgagtgacattcgggaccagtctaggaactggcttcctggaccctgttaccgccagcagcgagtatcaa
agacatctgcggataacaacaacagtgaatactcgtggactggagctaccaagtaccacctcaatggcagagactctctggtgaatccgggcccggc
catggcaagccacaaggacgatgaagaaaagtttttttcctcagagcggggttctcatctttgggaagcaaggctcagagaaaacaaatgtggacatt
gaaaaggtcatgattacagacgaagaggaaatcaggacaaccaatcccgtggctacggagcagtatggttctgtatctaccaacctccagagaggc
aacagacaagcagctaccgcagatgtcaacacacaaggcgttcttccaggcatggtctggcaggacagagatgtgtaccttcaggggcccatctggg
caaagattccacacacggacggacattttcacccctctcccctcatgggtggattcggacttaaacaccctcctccacagattctcatcaagaacaccc
cggtacctgcgaatccttcgaccaccttcagtgcggcaaagtttgcttccttcatcacacagtactccacgggacaggtcagcgtggagatcgagtggg
agctgcagaaggaaaacagcaaacgctggaatcccgaaattcagtacacttccaactacaacaagtctgttaatgtggactttactgtggacactaat
ggcgtgtattcagagcctcgccccattggcaccagatacctgactcgtaatctg

FIG. 19

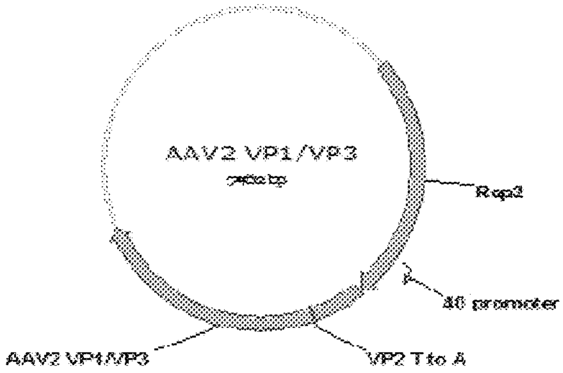

atggctgccgatggttatcttccagattggctcgaggacactctctctgaaggaataagacagtggtggaagctcaaacctggcccaccaccaccaaa
gcccgcagagcggcataaggacgacagcaggggtcttgtgcttcctgggtacaagtacctcggacccttcaacggactcgacaagggagagccggtc
aacgaggcagacgccgcggccctcgagcacgacaaagcctacgaccggcagctcgacagcggagacaacccgtacctcaagtacaaccacgccga
cgcggagtttcaggagcgccttaaagaagatacgtcttttgggggcaacctcggacgagcagtcttccaggcgaaaaagagggttcttgaacctctgg
gcctggttgaggaacctgttaaggcggctccgggaaaaaagaggccggtagagcactctcctgtggagccagactcctcctcgggaaccggaaagg
cgggccagcagcctgcaagaaaaagattgaattttggtcagactggagacgcagactcagtacctgacccccagcctctcggacagccaccagcagc
ccccctctggtctgggaactaatacgatggctacaggcagtggcgcaccaatggcagacaataacgagggcgccgacggagtgggtaattcctcggga
aaatttccagccaatcaggagcctcgaacgacaatcactactttggctacagcaccccttgggggtattttgacttcaacagattccactgccacttttc
accacgtgactggcaaagactcatcaacaacaactggggattccgacccaagagactcaacttcaagctctttaacattcaagtcaaagaggtcacg
cagaatgacggtacgacgacgattgccaataaccttaccagcacggttcaggtgtttactgactcggagtaccagctcccgtacgtcctcggctcggcg
catcaaggatgcctcccgccgttcccagcagacgtcttcatggtgccacagtatggatacctcaccctgaacaacgggagtcaggcagtaggacgctc
ttcattttactgcctggagtactttccttctcagatgctgcgtaccggaaacaactttaccttcagctacacttttgaggacgttcctttccacagcagcta
cgctcacagccagagtctggaccgtctcatgaatcctctcatcgaccagtacctgtattacttgagcagaacaaacactccaagtggaaccaccacgc
agtcaaggcttcagttttctcaggccggagcgagtgacattcgggaccagtctaggaactggcttcctggaccctgttaccgccagcagcgagtatcaa
agacatctgcggataacaacaacagtgaatactcgtggactggagctaccaagtaccacctcaatggcagagactctctggtgaatccgggcccggc
catggcaagccacaaggacgatgaagaaaagttttttcctcagagcggggttctcatctttgggaagcaaggctcagagaaaacaaatgtggacatt
gaaaaggtcatgattacagacgaagaggaaatcaggacaaccaatcccgtggctacggagcagtatggttctgtatctaccaacctccagagaggc
aacagacaagcagctaccgcagatgtcaacacacaaggcgttcttccaggcatggtctggcaggacagagatgtgtaccttcaggggcccatctggg
caaagattccacacacggacggacattttcacccctctcccctcatgggtggattcggacttaaacaccctcctccacagattctcatcaagaacaccc
cggtacctgcgaatccttcgaccaccttcagtgcggcaaagtttgcttccttcatcacacagtactccacgggacaggtcagcgtggagatcgagtggg
agctgcagaaggaaaacagcaaacgctggaatcccgaaattcagtacacttccaactacaacaagtctgttaatgtggactttactgtggacactaat
ggcgtgtattcagagcctcgccccattggcaccagatacctgactcgtaatctg

FIG. 20

RATIONAL POLYPLOID ADENO-ASSOCIATED VIRUS VECTORS FOR THE TREATMENT OF DISEASE

CROSS-REFERENCE TO RELATED APPLICATIONS

This application is a continuation application of, and claims priority to, U.S. patent application Ser. No. 16/598,779, filed Oct. 10, 2019 (allowed), which is a continuation application of the U.S. patent application Ser. No. 16/051,110, filed Jul. 31, 2018, now U.S. Pat. No. 10,550,405, issued Feb. 4, 2020, which claims the benefit under 35 U.S.C. § 119(e) of U.S. Provisional Application Nos. 62/668,056 filed May 7, 2018; and 62/678,675 filed May 31, 2018, and is a continuation-in-part of International Application No. PCT/US2018/022725, filed Mar. 15, 2018, for which benefit is claimed under 35 USC § 120, and which claims benefit under 35 U.S.C. § 119(e) of U.S. Provisional Application Nos. 62/471,762 filed Mar. 15, 2017; 62/520,901 filed Jun. 16, 2017; and 62/630,558 filed Feb. 14, 2018, the contents of each of which are incorporated herein by reference in their entireties.

STATEMENT OF GOVERNMENT SUPPORT

This invention was made with government support under Grant Numbers DK084033, AI117408, A1072176, CA016086, CA151652, HL125749, and HL112761 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-786IPCT2_ST25.txt, 111,849 bytes in size, generated on Nov. 16, 2020 and filed via EFS-Web, is provided in lieu of a paper copy. This Sequence Listing is hereby incorporated herein by reference into the specification for its disclosures.

TECHNICAL FIELD

The present invention is directed to methods for production of rational polyploid virions with desired properties, the virions, substantially homogenous populations of such virions, methods of producing substantially homogenous populations, and uses thereof.

BACKGROUND OF THE INVENTION

Adeno-associated virus (AAV) vector has been used in over 100 clinical trials with promising results, in particular, for the treatment of blindness and hemophilia B. AAV is non-pathogenic, has a broad tissue tropism, and can infect dividing or non-dividing cells. More importantly, AAV vector transduction has induced long-term therapeutic transgene expression in pre-clinical and clinical trials. Currently there are 12 serotypes of AAV isolated for gene delivery. Among them, AAV8 has been shown to be the best for mouse liver targeting. Extensive studies in pre-clinical animals with FIX deficiency and Phase I/II clinical trials have been carried out using AAV2 and AAV8 in patients with hemophilia B. The results from these trials are very promising; however, the FIX expression from patients receiving AAV/FIX was not proportional to what has been achieved in animal models even though the same vector dosage/kg was used. When $1\times10^{11}$ particles of AAV8 encoding FIX were used in FIX knock out mice for systemic administration, 160% of normal level FIX was detected in blood. However, when $2\times10^{11}$ particles of AAV8/FIX were administered, only 40% of FIX was achieved in primates and less than 1% of FIX was found in human. The inconsistent FIX expression following AAV vector transduction among these species may be due to altered hepatocyte tropism in different species. Another interesting finding from AAV FIX clinical trials is the capsid specific cytotoxic T lymphocyte (CTL) response that eradicates AAV transduced hepatocytes, resulting in therapeutic failure. This phenomenon has not been seen in animal models following AAV delivery, which points out another variation between preclinical and clinical studies. When a much higher dose of AAV/FIX vector was used, FIX expression was detected in both clinical trials using either AAV2 or AAV8; however the blood FIX level decreased at week 4 or 9 post injection, respectively. Further studies suggested that AAV vector infection elicited a capsid specific CTL response, which appeared to eliminate AAV transduced hepatocytes. Therefore, the results from these clinical trials highlight the necessity to explore effective approaches for enhancement of AAV transduction without increasing vector capsid burden. Any vector improvement that reduces AAV capsid antigen effect will also impact the daunting vector production concerns and be a welcome addition to viable gene therapy drug development.

Adeno-associated virus (AAV), a non-pathogenic-dependent parvovirus that needs helper viruses for efficient replication, is utilized as a virus vector for gene therapy because of its safety and simplicity. AAV has a broad host and cell type tropism capable of transducing both dividing and non-dividing cells. To date, 12 AAV serotypes and more than 100 variants have been identified. Different serotype capsids have different infectivity in tissues or culture cells, which depend on the primary receptor and co-receptors on the cell surface or the intracellular trafficking pathway itself. The primary receptors of some serotypes of AAV have been determined, such as heparin sulfate proteoglycan (HSPG) for AAV2 and AAV3, and N-linked sialic acid for AAV5, while the primary receptor of AAV7 and AAV8 has not been identified. Interestingly, AAV vector transduction efficiency in cultured cells may not always be translated into that in animals. For instance, AAV8 induces much higher transgene expression than other serotypes in mouse liver, but not in culture cell lines.

Of the above-mentioned 12 serotypes, several AAV serotypes and variants have been used in clinical trials. As the first characterized capsid, AAV2 has been most widely used in gene delivery such as RPE 65 for Leber congenital amaurosis and Factor IX (FIX) for hemophilia B. Although the application of AAV vectors has been proven safe and therapeutic effect has been achieved in these clinical trials, one of the major challenges of AAV vector is its low infectivity that requires relatively huge numbers of virus genomes. AAV8 vector is another vector which has been used in several clinical trials in patients with hemophilia B. The results from AAV8/FIX liver-targeted delivery have demonstrated that there are distinct species-specific differences in transgene expression between mice, non-human primates and humans. While $10^{10}$ vg of AAV8 with FIX gene could reach supra-physiologic levels (>100%) of FIX expression in FIX knock-out mice, only high doses ($2\times10^{12}$ vg/kg of body weight) could induce detectable FIX expression in humans. Based on these results described above, the development of effective strategies to enhance AAV transduction is still necessary.

The majority of people have been naturally exposed to AAVs. As a result, a large portion of the population has developed neutralizing antibodies (Nabs) in the blood and other bodily fluids against certain serotype AAVs. The presence of Nabs poses another major challenge for broader AAV applications in future clinical trials. Many approaches have been explored to enhance AAV transduction or evade Nab activity, especially genetic modification of the AAV capsid based on rational design and directed evolution. Although several AAV mutants have demonstrated high transduction in vitro or in animal models, along with the capacity to escape Nabs, the modification of the capsid composition provides an ability to alter the cell tropisms of parental AAVs.

The present invention addresses a need in the art for AAV vectors with combined desirable features.

SUMMARY OF THE INVENTION

Our previous studies have shown that the capsids from different AAV serotypes (AAV1 to AAV5) were compatible to assemble AAV virions (the terms virions, capsids, viral particles, and particles are used interchangeably in this application) and most isolated AAV monoclonal antibodies recognized several sites located on different AAV subunits. Additionally, the studies from chimeric AAV capsids demonstrated that higher transduction can be achieved with introduction of a domain for a primary receptor or tissue-specific domain from other serotypes. Introduction of AAV9 glycan receptor into AAV2 capsid enhances AAV2 transduction. Substitution of a 100 aa domain from AAV6 into AAV2 capsid increases muscle tropism. We discovered that polyploid AAV vectors which are composed of capsids from two or more AAV serotypes might take advantages from individual serotypes for higher transduction but not in certain embodiments eliminate the tropism from the parents. Moreover, these polyploid viruses might have the ability to escape the neutralization by Nabs since the majority of Nab recognize conformational epitopes and polyploid virions can have changed its surface structure.

One approach for generating rAAV with mixed or mosaic capsid shells has been to add AAV helper plasmids encoding the capsid proteins (VP1, VP2, and VP3) from a mixture of AAV serotypes. This methodology is sometimes referred to as cross-dressing. In certain embodiments it can change the antigenic patterns of certain virions. However, a wide range of virions are produced. Moreover, the virions produced are mosaics that have a mixture of serotypes. Accordingly, the population of virions produced retains some particles that will elicit an antigen response. Thus, obtaining a substantially homogenous population of predetermined virions would be desirable.

We have now discovered methodology that permits the rational design and production of such chimeric or shuffled virions. The resultant virions are sometimes referred to as polyploid, haploid, or triploid to refer to the fact that the capsid proteins VP1, VP2, and VP3 come from at least two different serotypes. The capsids can be from any of the AAV serotype, including the 12 serotypes of AAV isolated for gene therapy, other species, mutant serotypes, shuffled serotypes of such genes, e.g., AAV2, VP1.5 and AAV4 VP2, AAV4 VP3, or any other AAV serotype desired. This method permits production of infectious virus of only the virion desired which results in substantially homogenous populations of the virion.

The AAV virion has T=1 icosahedral symmetry and is composed of the three structural viral proteins, VP1, VP2, and VP3. 60 copies of the three viral proteins in a ratio of 1:1:8 to 10 (VP1:VP2:VP3, respectively) form the virion (Rayaprolu, V., et al., J. Virol. 87(24): 13150-13160 (2013).

In one embodiment, the AAV virion is an isolated virion that has at least one of the viral structural proteins, VP1, VP2, and VP3 from a different serotype than the other VPs, and each VP is only from one serotype. For example, the VP1 is only from AAV2, the VP2 is only from AAV4, and the VP3 is only from AAV8.

In an alternative embodiment, a virion particle can be constructed wherein at least one viral protein from the group consisting of AAV capsid proteins, VP1, VP2 and VP3, is different from at least one of the other viral proteins, required to form the virion particle capable of encapsidating an AAV genome. For each viral protein present (VP1, VP2, and/or VP3), that protein is the same type (e.g., all AAV2 VP1). In one instance, at least one of the viral proteins is a chimeric viral protein and at least one of the other two viral proteins is not a chimeric. In one embodiment VP1 and VP2 are chimeric and only VP3 is non-chimeric. For example, only the viral particle composed of VP1/VP2 from the chimeric AAV2/8 (the N-terminus of AAV2 and the C-terminus of AAV8) paired with only VP3 from AAV2; or only the chimeric VP1/VP2 28m-2P3 (the N-terminal from AAV8 and the C-terminal from AAV2 without mutation of VP3 start codon) paired with only VP3 from AAV2. In another embodiment only VP3 is chimeric and VP1 and VP2 are non-chimeric. In another embodiment at least one of the viral proteins is from a completely different serotype. For example, only the chimeric VP1/VP2 28m-2P3 paired with VP3 from only AAV3. In another example, no chimeric is present.

In one embodiment an AAV virion that encapsidates an AAV genome (including a heterologous gene between 2 AAV ITRs) can be formed with only two of the viral structural proteins, VP1 and VP3. In one embodiment this virion is conformationally correct, i.e., has T=1 icosahedral symmetry. In one embodiment the virions are infectious.

The population is at least $10^1$ virions, at least $10^2$ virions, at least $10^3$ virions, at least $10^4$ virions, at least $10^5$ virions, . . . at least $10^{10}$ virions, at least $10^{11}$ virions, at least $10^{12}$ virions, at least $10^{15}$ virions, at least $10^{17}$ virions. In one embodiment, the population is at least 100 viral particles. In one embodiment, the population is from $10^9$ to $10^{12}$ virions In one embodiment, the population is at least $1\times10^4$ viral genomes (vg)/ml, is at least $1\times10^5$ viral genomes (vg)/ml, is at least $1\times10^6$ viral genomes (vg)/ml, at least $1\times10^7$ viral genomes (vg)/ml, at least $1\times10^8$ viral genomes (vg)/ml, at least $1\times10^9$ viral genomes (vg)/ml, at least $1\times10^{10}$ vg/per ml, at least $1\times10^{11}$ vg/per ml, at least $1\times10^{12}$ vg/per ml. In one embodiment, the population ranges from about $1\times10^5$ vg/ml to about $1\times10^{13}$ vg/ml.

A substantially homogenous population is at least 90% of only the desired virion, at least 91%, at least 93%, at least 95%, at least 97%, at least 99%, at least 99.5%, or at least 99.9%. In one embodiment, the population is completely homogenous.

AAV2 and AAV8 have been used for clinical application. In one embodiment, we first characterized the haploid AAV virus from AAV2 and AAV8 for transduction efficiency in vitro and in vivo, as well as Nab escape ability, i.e., the immune response such as an antigenic response. In that study, we found that the virus yield of the haploid vector was not compromised and the heparin binding profile was related to the incorporation of AAV2 capsid subunit proteins. The haploid vectors AAV2/8 initiated a higher transduction in mouse muscle and liver. When applied to a mouse model with FIX deficiency, higher FIX expression and improved bleeding phenotypic correction were observed in haploid vector-treated mice compared to AAV8 group. Importantly, the haploid virus AAV2/8 had low binding affinity to A20 and was able to escape the neutralization from anti-AAV2 serum. The next polyploid virus AAV2/8/9 was made from capsids of three serotypes (AAV2, 8 and 9). It was demonstrated that the neutralizing antibody escape ability of haploid AAV2/8/9 was significantly improved against sera immunized with parental serotypes.

Thus, in one embodiment, the present invention provides an adeno-associated virus (AAV) capsid, wherein the capsid comprises capsid protein VP1, wherein said capsid protein VP1 is from one or more than one first AAV serotype and capsid protein VP3, wherein said capsid protein VP3 is from one or more than one second AAV serotype and wherein at least one of said first AAV serotype is different from at least one of said second AAV serotype, in any combination. Preferably such population is substantially homogenous. In some embodiments, the capsid of this invention comprises capsid protein VP2, wherein said capsid protein VP2 is from one or more than one third AAV serotype, wherein at least one of said one or more than one third AAV serotype is different from said first AAV serotype and/or said second AAV serotype, in any combination.

In some embodiments the AAV virion can be formed by more than the typical 3 viral structural proteins, VP1, VP2, and VP3 (see e.g., Wang, Q. et al., "Syngeneic AAV Pseudo-particles Potentiate Gene Transduction of AAV Vectors," Molecular Therapy: Methods and Clinical Development, Vol. 4, 149-158 (2017)). Such viral capsids also fall within the present invention. For example, an isolated AAV virion having viral capsid structural proteins sufficient to form an AAV virion that encapsidates an AAV genome, wherein at least one of the viral capsid structural proteins is different from the other viral capsid structural proteins, and wherein each viral capsid structural protein is only of the same type. In a further embodiment the isolated AAV virion has at least two viral structural proteins from the group consisting of AAV capsid proteins, VP1, VP2, VP1.5 and VP3, wherein the two viral proteins are sufficient to form an AAV virion that encapsidates an AAV genome, and wherein at least one of the viral structural proteins present is from a different serotype than the other viral structural protein, and wherein the VP1 is only from one serotype, the VP2 is only from one serotype, the VP1.5 is only from one serotype, and the VP3 is only from one serotype. For example, the VP1.5 can be from AAV serotype 2 and the VP3 can be from AAV serotype 8.

In some embodiments, the capsid of this invention comprises capsid protein VP1.5, wherein said capsid protein VP1.5 is from one or more than one fourth AAV serotype, wherein at least one of said one or more than one fourth AAV serotype is different from said first AAV serotype and/or said second AAV serotype, in any combination. In some embodiments, the AAV capsid protein described herein can comprise capsid protein VP2.

Thus, in certain embodiments the at least one of the viral structural proteins can be a chimeric viral structural protein, i.e., can contain segments from more than one protein. In one embodiment the chimeric viral structural protein is all from the same serotype. In another embodiment, the chimeric viral structural protein is made up of components from a more than one serotype, but these serotypes are different from at least one other serotype. In one embodiment, the viral structural proteins are not chimeric. In one embodiment, the chimeric AAV structural protein does not comprise structural amino acids from canine parvovirus. In one embodiment, the chimeric AAV structural protein does not comprise structural amino acids from b19 parvovirus. In one embodiment, the chimeric AAV structural protein does not comprise structural amino acids from canine parvovirus or b19 parvovirus. In one embodiment, the chimeric AAV structural protein only comprises structural amino acids from AAV.

In some embodiments only virions that contain at least one viral protein that is different than the other viral proteins is produced. For example, VP1 and VP2 from the same serotype and VP3 from an alternative serotype, only. In other embodiments, the VP1 is from one serotype and the VP2 and VP3 are from another serotype, only. In another embodiment, only particles where VP1 is from one serotype, VP2 is from a second serotype, and VP3 is from yet another serotype are produced.

This can be done by, for example, site specific deletions, and/or additions, changing splice donor sites, splice acceptor sites, start codons and combinations thereof.

Using AAV serotype 2 as an exemplary virus, M11 is the VP1 start codon, M138 is the VP2 start codon, and M203 is the VP3 start codon. While deletion of the start codon, typically by a substitution of M11 and M138 will render expression of VP1 and VP2 inoperative, a similar deletion of the VP3 start codon is not sufficient. This is because the viral capsid ORF contains numerous ATG codons with varying strengths as initiation codons. Thus, in designing a construct that will not express VP3 care must be taken to insure that an alternative VP3 species is not produced. With respect to VP3 either elimination of M138 is necessary or if VP2 is desired, but not VP3, then deletion of M211 and 235 in addition to M203 is typically the best approach (Warrington, K. H. Jr., et al., J. of Virol. 78(12): 6595-6609 (June 2004)). This can be done by mutations such as substitution or other means known in the art. The corresponding start codons in other serotypes can readily be determined as well as whether additional ATG sequences such as in VP3 can serve as alternative initiation codons.

This permits methods for producing populations of substantially homogenous populations of the polyploid virions—such as the haploid or triploid viral particles.

The present invention also provides an AAV capsid wherein the capsid comprises capsid protein VP1, wherein said capsid protein VP1 is from one or more than one first AAV serotype, and capsid protein VP2, wherein said capsid protein VP2 is from one or more than one second AAV serotype, and wherein at least one of said first AAV serotype is different from at least one of said second AAV serotype, in any combination.

In some embodiments, the capsid comprises capsid protein VP3, wherein said capsid protein VP3 is from one or more than one third AAV serotype, wherein at least one of said one or more than one third AAV serotype is different from said first AAV serotype and/or said second AAV serotype, in any combination. In some embodiments, the AAV capsid described herein can comprise capsid protein VP1.5.

The present invention further provides an adeno-associated virus (AAV) capsid, wherein the capsid comprises capsid protein VP1, wherein said capsid protein VP1 is from one or more than one first AAV serotype, and capsid protein VP1.5, wherein said capsid protein VP1.5 is from one or more than one second AAV serotype, and wherein at least one of said first AAV serotype is different from at least one of said second AAV serotype, in any combination.

In additional embodiments, the present invention provides a virus vector comprising: (a) an AAV capsid of this invention; and (b) a nucleic acid comprising at least one terminal repeat sequence, wherein the nucleic acid is encapsidated by the AAV capsid. The virus vector can be an AAV particle and the capsid protein, capsid, virus vector and/or AAV particle of this invention can be present in a composition that further comprises a pharmaceutically acceptable carrier.

Further provided herein is a method of making an AAV particle comprising the AAV capsid of any preceding claim, comprising: (a) transfecting a host cell with one or more plasmids that provide, in combination all functions and genes needed to assemble AAV particles; (b) introducing one or more nucleic acid constructs into a packaging cell line or producer cell line to provide, in combination all functions and genes needed to assemble AAV particles; (c) introducing into a host cell one or more recombinant baculovirus vectors that provide in combination all functions and genes needed to assemble AAV particles; and/or (d) introducing into a host cell one or more recombinant herpesvirus vectors that provide in combination all functions and genes needed to assemble AAV particles.

In further embodiments, the present invention provides a method of administering a nucleic acid to a cell, the method comprising contacting the cell with the virus vector of this invention and/or a composition of this invention.

Also provided herein is a method of delivering a nucleic acid to a subject, the method comprising administering to the subject the virus vector and/or a composition of this invention.

Additionally, provided herein is the capsid protein, capsid, virus vector, AAV particle and/or composition of this invention for use as a medicament in the beneficial treatment of a disorder or disease.

These and other aspects of the invention are addressed in more detail in the description of the invention set forth below.

BRIEF DESCRIPTION OF THE DRAWINGS

FIG. 17: Plasmid including DNA sequence (SEQ ID NO:139) for AAV2 capsid proteins wherein the start codons for VP1 and VP2 have been mutated.

FIG. 18: Plasmid including DNA sequence (SEQ ID NO:140) for AAV2 capsid proteins wherein the start codon for VP1 has been mutated.

FIG. 19: Plasmid including DNA sequence (SEQ ID NO:141) for AAV2 capsid proteins wherein the start codons for VP2 and VP3 have been mutated.

FIG. 20: Plasmid including DNA sequence (SEQ ID NO:142) for AAV2 capsid proteins wherein the start codon for VP2 has been mutated.

DETAILED DESCRIPTION OF THE INVENTION

Figure 1:
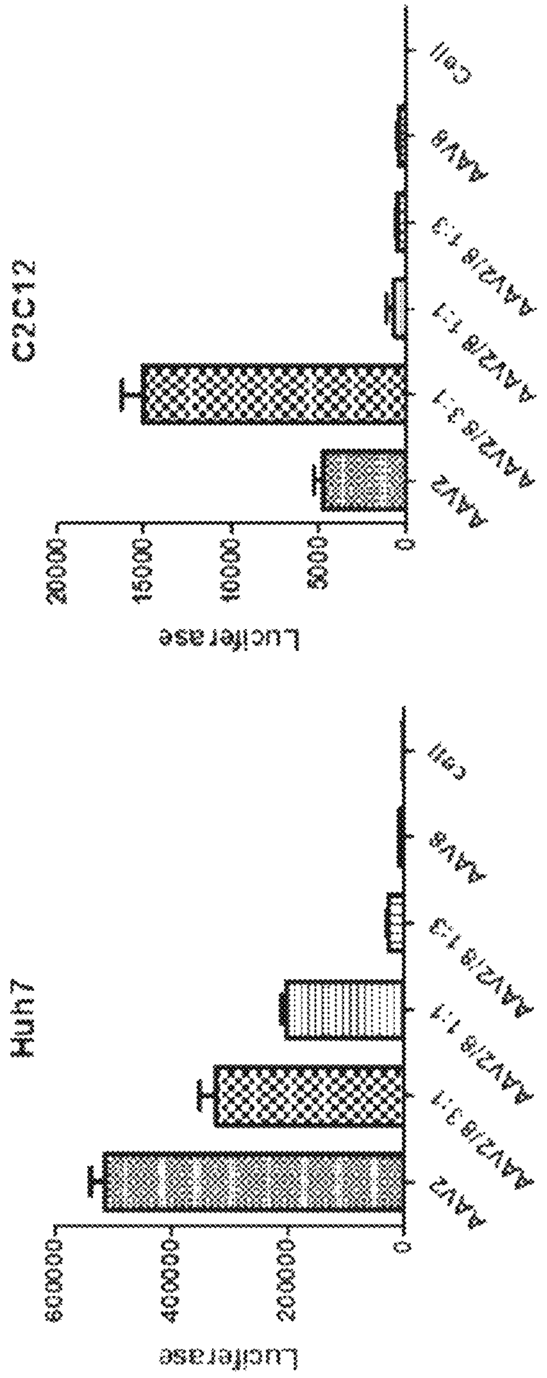
FIG. 1: Transduction profiles of the haploid viruses in vitro. Haploid or parental viruses were added to Huh7 or C2C12 cells at $10^4$ vg/cell. Cells were lysed for luciferase assay at 48 h post-transduction. The data represent an average of three separate infections, with the standard deviation indicated by an error bar.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, accession numbers and other references mentioned herein are incorporated by reference herein in their entirety.

The designation of all amino acid positions in the AAV capsid viral structural proteins in the description of the invention and the appended claims is with respect to VP1 capsid subunit numbering (native AAV2 VP1 capsid protein: GenBank Accession No. AAC03780 or YP680426). It will be understood by those skilled in the art that the modifications described herein if inserted into the AAV cap gene may result in modifications in the structural viral proteins VP1, VP2 and/or VP3 which make up the capsid subunits. Alternatively, the capsid subunits can be expressed independently to achieve modification in only one or two of the capsid subunits (VP1, VP2, VP3, VP1+VP2, VP1+VP3, or VP2+VP3).

Definitions

The following terms are used in the description herein and the appended claims:

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461,463 (CCPA 1976) (emphasis in the original); see also MPEP § 2111.03. Thus, the term "consisting essentially of" when used in a claim of this invention is not intended to be interpreted to be equivalent to "comprising." Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed (e.g., by negative proviso). For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 25%, 35%, 50%, 75%, 80%, 85%, 90%, 95%, 97% or more.

As used herein, the terms "enhance," "enhances," "enhancement" and similar terms indicate an increase of at least about 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, Muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al., (2004) *J. Virology* 78:6381-6388; Moris et al., (2004) Virology 33-:375-383; and Table 3).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) *J. Virology* 45:555; Chiarini et al., (1998) *J. Virology* 71:6823; Chiarini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci. USA* 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) *Proc. Nat. Acad. Sci.* 99:10405-10), AAV4 (Padron et al., (2005) *J. Virol.* 79: 5047-58), AAV5 (Walters et al., (2004) *J. Virol.* 78: 3361-71) and CPV (Xie et al., (1996) *J. Mol. Biol.* 6:497-520 and Tsao et al., (1991) *Science* 251: 1456-64).

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

As used here, "systemic tropism" and "systemic transduction" (and equivalent terms) indicate that the virus capsid or virus vector of the invention exhibits tropism for and/or transduces tissues throughout the body (e.g., brain, lung, skeletal muscle, heart, liver, kidney and/or pancreas). In embodiments of the invention, systemic transduction of the central nervous system (e.g., brain, neuronal cells, etc.) is observed. In other embodiments, systemic transduction of cardiac muscle tissues is achieved.

As used herein, "selective tropism" or "specific tropism" means delivery of virus vectors to and/or specific transduction of certain target cells and/or certain tissues.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 125%, 150%, 175%, 200%, 250%, 300%, 350%, 400%, 500% or more of the transduction or tropism, respectively, of the control). In particular embodiments, the virus vector efficiently transduces or has efficient tropism for neuronal cells and cardiomyocytes. Suitable controls will depend on a variety of factors including the desired tropism and/or transduction profile.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, transduction (e.g., undesirable transduction) of tissue(s) (e.g., liver) is 20% or less, 10% or less, 5% or less, 1% or less, 0.1% or less of the level of transduction of the desired target tissue(s) (e.g., skeletal muscle, diaphragm muscle, cardiac muscle and/or cells of the central nervous system).

In some embodiments of this invention, an AAV particle comprising a capsid of this invention can demonstrate multiple phenotypes of efficient transduction of certain tissues/cells and very low levels of transduction (e.g., reduced transduction) for certain tissues/cells, the transduction of which is not desirable.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

An "isolated cell" refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

A population of virions can be generated by any of the methods described herein. In one embodiment, the population is at least $10^1$ virions. In one embodiment, the population is at least $10^2$ virions, at least $10^3$, virions, at least $10^4$ virions, at least $10^5$ virions, at least $10^6$ virions, at least $10^7$ virions, at least $10^8$ virions, at least $10^9$ virions, at least $10^{10}$ virions, at least $10^{11}$ virions, at least $10^{12}$ virions, at least $10^{13}$ virions, at least $10^{14}$ virions, at least $10^{15}$ virions, at least $10^{16}$ virions, or at least $10^{17}$ virions. A population of virions can be heterogeneous or can be homogeneous (e.g., substantially homogeneous or completely homogeneous).

A "substantially homogeneous population" as the term is used herein, refers to a population of virions that are mostly identical, with few to no contaminant virions (those that are not identical) therein. A substantially homogeneous population is at least 90% of identical virions (e.g., the desired virion), and can be at least 91%, at least 92%, at least 93%, at least 94%, at least 95%, at least 96%, at least 97%, at least 98%, at least 99%, at least 99.5%, at least 99.9% of identical virions.

A population of virions that is completely homogeneous contains only identical virions.

As used herein, by "isolate" or "purify" (or grammatical equivalents) a virus vector or virus particle or population of virus particles, it is meant that the virus vector or virus particle or population of virus particles is at least partially separated from at least some of the other components in the starting material. In representative embodiments an "isolated" or "purified" virus vector or virus particle or population of virus particles is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability or induction of an immune response.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is substantially less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some preventative benefit is provided to the subject.

The terms "heterologous nucleotide sequence" and "heterologous nucleic acid molecule" are used interchangeably herein and refer to a nucleic acid sequence that is not naturally occurring in the virus. Generally, the heterologous nucleic acid molecule or heterologous nucleotide sequence comprises an open reading frame that encodes a polypeptide and/or nontranslated RNA of interest (e.g., for delivery to a cell and/or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) *Curr. Topics Microbiol. Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11 or 12 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

AAV proteins VP1, VP2 and VP3 are capsid proteins that interact together to form an AAV capsid of an icosahedral symmetry. VP1.5 is an AAV capsid protein described in US Publication No. 2014/0037585.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) Molecular Therapy 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

A "chimeric" viral structural protein as used herein means an AAV viral structural protein (capsid) that has been modified by substitutions in one or more (e.g., 2, 3, 4, 5, 6, 7, 8, 9, 10, etc.) amino acid residues in the amino acid sequence of the capsid protein relative to wild type, as well as insertions and/or deletions of one or more (e.g., 2, 3, 4, 5, 6, 7, 8, 9, 10, etc.) amino acid residues in the amino acid sequence relative to wild type. In some embodiments, complete or partial domains, functional regions, epitopes, etc., from one AAV serotype can replace the corresponding wild type domain, functional region, epitope, etc. of a different AAV serotype, in any combination, to produce a chimeric capsid protein of this invention. In other embodiments the substitutions are all from the same serotype. In other embodiments the substitutions are all from AAV or synthetic. Production of a chimeric capsid protein can be carried out according to protocols well known in the art and a large number of chimeric capsid proteins are described in the literature as well as herein that can be included in the capsid of this invention.

In an alternative embodiment, a virion particle can be constructed wherein at least one viral protein from the group consisting of AAV capsid proteins, VP1, VP2 and VP3, is different from at least one of the other viral proteins, required to form the virion particle capable of encapsidating an AAV genome. For each viral protein present (VP1, VP2, and/or VP3), that protein is the same type (e.g., all AAV2 VP1). In one instance, at least one of the viral proteins is a chimeric viral protein and at least one of the other two viral proteins is not a chimeric. In one embodiment VP1 and VP2 are chimeric and only VP3 is non-chimeric. For example, only the viral particle composed of VP1/VP2 from the chimeric AAV2/8 (the N-terminus of AAV2 and the C-terminus of AAV8) paired with only VP3 from AAV2; or only the chimeric VP1/VP2 28m-2P3 (the N-terminal from AAV8 and the C-terminal from AAV2 without mutation of VP3 start codon) paired with only VP3 from AAV2. In another embodiment only VP3 is chimeric and VP1 and VP2 are non-chimeric. In another embodiment at least one of the viral proteins is from a completely different serotype. For example, only the chimeric VP1/VP2 28m-2P3 paired with VP3 from only AAV3. In another example, no chimeric is present.

As used herein, the term "amino acid" encompasses any naturally occurring amino acid, modified forms thereof, and synthetic amino acids.

Naturally occurring, levorotatory (L-) amino acids are shown in Table 2.

Alternatively, the amino acid can be a modified amino acid residue (nonlimiting examples are shown in Table 4) and/or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described by Wang et al., *Annu Rev Biophys Biomol Struct.* 35:225-49 (2006). These unnatural amino acids can advantageously be used to chemically link molecules of interest to the AAV capsid protein.

As used herein, the term "homologous recombination" means a type of genetic recombination in which nucleotide sequences are exchanged between two similar or identical molecules of DNA. Homologous recombination also produces new combinations of DNA sequences. These new combinations of DNA represent genetic variation. Homologous recombination is also used in horizontal gene transfer to exchange genetic material between different strains and species of viruses.

As used herein, the term "gene editing," "Genome editing," or "genome engineering" means a type of genetic engineering in which DNA is inserted, deleted or replaced in the genome of a living organism using engineered nucleases, or "molecular scissors." These nucleases create site-specific double-strand breaks (DSBs) at desired locations in the genome.

As used herein, the term "gene delivery" means a process by which foreign DNA is transferred to host cells for applications of gene therapy.

As used herein, the term "CRISPR" stands for Clustered Regularly Interspaced Short Palindromic Repeats, which are the hallmark of a bacterial defense system that forms the basis for CRISPR-Cas9 genome editing technology.

As used herein, the term "zinc finger" means a small protein structural motif that is characterized by the coordination of one or more zinc ions, in order to stabilize the fold.

In some embodiments, the AAV particle of this invention can be synthetic viral vector designed to display a range of desirable phenotypes that are suitable for different in vitro and in vivo applications. Thus, in one embodiment, the present invention provides an AAV particle comprising an adeno-associated virus (AAV).

The present invention provides an array of synthetic viral vectors displaying a range of desirable phenotypes that are suitable for different in vitro and in vivo applications. In particular, the present invention is based on the unexpected discovery that combining capsid proteins from different AAV serotypes in an individual capsid allows for the development of improved AAV capsids that have multiple desirable phenotypes in each individual capsid. Such chimeric or shuffled virions are sometimes referred to as polyploid, haploid, or triploid to refer to the fact that the capsid proteins VP1, VP2, and VP3 come from at least two different serotypes. New methods for producing such virions are described herein. By preventing the translation of undesired open reading frames these methods result in the production of homogeneous populations of the generated virions.

The ability to generate a homogeneous (e.g., substantially or completely) population of recombinant virions dramatically reduces or eliminates carryover of properties of undesired/contaminating virions (e.g., transduction specificity or antigenicity).

The AAV virion has T=1 icosahedral symmetry and is composed of the three structural viral proteins, VP1, VP2, and VP3. 60 copies of the three viral proteins in a ratio of 1:1:8 to 10 (VP1:VP2:VP3, respectively) form the virion (Rayaprolu, V., et al., J. Virol. 87(24): 13150-13160 (2013).

In one embodiment, the AAV virion is an isolated virion that has at least one of the viral structural proteins, VP1, VP2, and VP3 from a different serotype than the other VPs, and each VP is only from one serotype. For example, the VP1 is only from AAV2, the VP2 is only from AAV4, and the VP3 is only from AAV8.

In one embodiment an AAV virion that encapsidates an AAV genome including a heterologous gene between 2 AAV ITRs can be formed with only two of the viral structural proteins, VP1 and VP3. In one embodiment this virion is conformationally correct, i.e., has T=1 icosahedral symmetry. In one embodiment the virions are infectious.

Infectious virions include VP1/VP3 VP1/VP2/VP3. Typically VP2/VP3 and VP3 only virions are not infectious.

The viral structural proteins used to generate these populations of virions can be from any of the 12 serotypes of AAV isolated for gene therapy, other species, mutant serotypes, shuffled serotypes of such genes, e.g., AAV2, VP1.5 and AAV4 VP2, AAV4 VP3, or any other AAV serotype desired.

For example, triploid AAV2/8/9 vector described herein, which is produced by co-transfection of AAV helper plasmids from serotypes 2, 8 and 9, has a much higher mouse liver transduction than AAV2, similar to AAV8. Importantly, triploid AAV2/8/9 vector has an improved ability to escape neutralizing antibodies from sera immunized with parental serotypes. Although AAV3 is less efficient in transducing the whole mouse body after systemic administration, the haploid vectors H-AAV83 or H-AAV93 or H-rh10-3 described herein, in which VP3 is from AAV3 and VP1/VP2 from AAV8, 9 or rh10, induce whole body transduction, as well as much higher transduction in the liver and other tissues, compared to AAV3.

Thus, in one embodiment, the present invention provides an adeno-associated virus (AAV) with a viral capsid, wherein the capsid comprises the protein VP1, wherein said VP1 is from one or more than one first AAV serotype and capsid protein VP3, wherein said capsid protein VP3 is from one or more than one second AAV serotype and wherein at least one of said first AAV serotype is different from at least one of said second AAV serotype, in any combination. When at least one viral structural protein is from more than one serotype we are referring to the phenomenon sometimes referred to as crossdressing, which results in a mosaic capsid. On the other hand when the viral capsid proteins are each from the same serotype, even though at least one of the viral proteins is from a different serotype, a mosaic capsid does not result. For example VP1 from AAV2, VP2 from AAV6, and VP3 from AAV8.

In some embodiments, the capsid of this invention comprises capsid protein VP2, wherein said capsid protein VP2 is from one or more than one third AAV serotype, wherein at least one of said one or more than one third AAV serotype is different from said first AAV serotype and/or said second AAV serotype, in any combination. In some embodiments, the AAV capsid described herein can comprise capsid protein VP1.5. VP1.5 is described in U.S. Patent Publication No. 2014/0037585 and the amino acid sequence of VP1.5 is provided herein.

In some embodiments only virions that contain at least one viral protein that is different than the other viral proteins are produced. For example, VP1 and VP2 from the same serotype and VP3 from an alternative serotype, only. In other embodiments, the VP1 is from one serotype and the VP2 and VP3 are from another serotype, only. In another embodiment, only particles where VP1 is from one serotype, VP2 is from a second serotype, and VP3 is from yet another serotype are produced.

This can be done by, for example, site specific deletions, and/or additions, changing splice donor sites, splice acceptor sites, start codons and combinations thereof.

This permits methods for producing populations of substantially homogenous populations of the polyploid virions—such as the haploid or triploid viral particles.

In some embodiments the AAV virion can be formed by more than the typical 3 viral structural proteins, VP1, VP2, and VP3 (see e.g., Wang, Q. et al., "Syngeneic AAV Pseudo-particles Potentiate Gene Transduction of AAV Vectors," Molecular Therapy: Methods and Clinical Development, Vol. 4, 149-158 (2017)). Such viral capsids also fall within the present invention. For example, an isolated AAV virion having viral capsid structural proteins sufficient to form an AAV virion that encapsidates an AAV genome, wherein at least one of the viral capsid structural proteins is different from the other viral capsid structural proteins, and wherein each viral capsid structural protein is only of the same type. In a further embodiment the isolated AAV virion has at least two viral structural proteins from the group consisting of AAV capsid proteins, VP1, VP2, VP1.5 and VP3, wherein the two viral proteins are sufficient to form an AAV virion that encapsidates an AAV genome, and wherein at least one of the viral structural proteins present is from a different serotype than the other viral structural protein, and wherein the VP1 is only from one serotype, the VP2 is only from one serotype, the VP1.5 is only from one serotype, and the VP3 is only from one serotype. For example, the VP1.5 can be from AAV serotype 2 and the VP3 can be from AAV serotype 8.

In some embodiments, the capsid of this invention comprises capsid protein VP1.5, wherein said capsid protein VP1.5 is from one or more than one fourth AAV serotype, wherein at least one of said one or more than one fourth AAV serotype is different from said first AAV serotype and/or said second AAV serotype, in any combination. In some embodiments, the AAV viral structural protein described herein can comprise viral structural protein VP2.

The present invention also provides an AAV capsid wherein the capsid comprises capsid protein VP1, wherein said capsid protein VP1 is from one or more than one first AAV serotype and capsid protein VP2, wherein said capsid protein VP2 is from one or more than one second AAV serotype and wherein at least one of said first AAV serotype is different from at least one of said second AAV serotype, in any combination. In some embodiments no chimeric viral structural protein is present in the virion.

In some embodiments, the AAV particle of this invention can comprise a capsid that comprises capsid protein VP3, wherein said capsid protein VP3 is from one or more than one third AAV serotype, wherein at least one of said one or more than one third AAV serotype is different from said first AAV serotype and/or said second AAV serotype, in any combination. In some embodiments, the AAV capsid described herein can comprise capsid protein VP1.5.

The present invention further provides an AAV particle that comprises an adeno-associated virus (AAV) capsid, wherein the capsid comprises capsid protein VP1, wherein said capsid protein VP1 is from one or more than one first AAV serotype and capsid protein VP1.5, wherein said capsid protein VP1.5 is from one or more than one second AAV serotype and wherein at least one of said first AAV serotype is different from at least one of said second AAV serotype, in any combination.

In some embodiments, the capsid comprises capsid protein VP3, wherein said capsid protein VP3 is from one or more than one third AAV serotype, wherein at least one of said one or more than one third AAV serotype is different from said first AAV serotype and/or said second AAV serotype, in any combination. In some embodiments, the AAV capsid described herein can comprise capsid protein VP1.5.

The present invention further provides an adeno-associated virus (AAV) capsid, wherein the capsid comprises capsid protein VP1, wherein said capsid protein VP1 is from one or more than one first AAV serotype and capsid protein VP1.5, wherein said capsid protein VP1.5 is from one or more than one second AAV serotype and wherein at least one of said first AAV serotype is different from at least one of said second AAV serotype, in any combination.

In some embodiments, the AAV capsid of this invention comprises capsid protein VP3, wherein said capsid protein VP3 is from one or more than one third AAV serotype, wherein at least one of said one or more than one third AAV serotype is different from said first AAV serotype and/or said second AAV serotype, in any combination. In some embodiments, the AAV capsid protein described herein can comprise capsid protein VP2.

In some embodiments of the capsid of this invention, said one or more than one first AAV serotype, said one or more than one second AAV serotype, said one or more than one third AAV serotype and said one or more than one fourth AAV serotype are selected from the group consisting of the AAV serotypes listed in Table 1, in any combination.

In some embodiments of this invention, the AAV capsid described herein lacks capsid protein VP2.

In some embodiments of the capsid of this invention comprises a chimeric capsid VP1 protein, a chimeric capsid VP2 protein, a chimeric capsid VP3 protein and/or a chimeric capsid VP1.5 protein.

In some embodiments, the AAV capsid of this invention can be AAV AAV2/8/9, H-AAV82, H-AAV92, H-AAV82G9, AAV2/8 3:1, AAV2/8 1:1, AAV2/8 1:3, or AAV8/9, all of which are described in the EXAMPLES section provided herein.

Nonlimiting examples of AAV capsid proteins that can be included in the capsid of this invention in any combination with other capsid proteins described herein and/or with other capsid proteins now known or later developed, include LK3, LK01-19, AAV-DJ, Olig001, rAAV2-retro, AAV-LiC, AAV0Kera1, AAV-Kera2, AAV-Kera3, AAV 7m8, AAV1,9, AAVr3.45, AAV clone 32, AAV clone 83, AAV-U87R7-05, AAV ShH13, AAV ShH19, AAV L1-12, AAV HAE-1, AAV HAE-2, AAV variant ShH10, AAV2.5T, AAV LS1-4, AAV Lsm, AAV1289, AAVHSC 1-17, AAV2 Rec 1-4, AAV8BP2, AAV-B1, AAV-PHP.B, AAV9.45, AAV9.61, AAV9.47, AAVM41, AAV2 displayed peptides, AAV2-GMN, AAV9-peptide displayed, AAV8 and AAV9 peptide displayed, AAVpo2.1, AAVpo4, AAVpo5, AAVpo6, AAV rh, AAV Hu, AAV-Go.1, AAV-mo.1, BAAV, AAAV, AAV8 K137R, AAV Anc80L65, AAV2G9, AAV2 265 insertion-AAV2/265D, AAV2.5, AAV3 SASTG, AAV2i8, AAV8G9, AAV2 tyrosine mutants AAV2 Y-F, AAV8 Y-F, AAV9 Y-F, AAV6 Y-F, AAV6.2 and any combination thereof.

As a nonlimiting example, the AAV capsid proteins and virus capsids of this invention can be chimeric in that they can comprise all or a portion of a capsid subunit from another virus, optionally another parvovirus or AAV, e.g., as described in international patent publication WO 00/28004.

The following publications describe chimeric or variant capsid proteins that can be incorporated into the AAV capsid of this invention in any combination with wild type capsid proteins and/or other chimeric or variant capsid proteins now known or later identified.

L Lisowski, A P Dane, K Chu, Y Zhang, S C Cunninghamm, E M Wilson, et al. Selection and evaluation of clinically relevant AAV variants in a xenograft liver model. Nature, 506 (2014), pp. 382-386 (LK03 and others LK01-19).

Grimm D, Lee J S, Wang L, Desai T, Akache B, Storm T A, Kay M A. In vitro and in vivo gene therapy vector evolution via multispecies interbreeding and retargeting of adeno-associated viruses. *J. Virol.* 2008 June: 82(12):5887-911. (AAV-D J).

Powell S K, Khan N, Parker C L, Samulski R J, Matsushima G, Gray S J, McCown T J. Characterization of a novel adeno-associated viral vector with preferential oligodendrocyte tropism. *Gene Ther.* 2016 November: 23(11):807-814. (Olig001).

Tervo D G, Hwang B Y, Viswanathan S, Gaj T, Lavzin M, Ritola K D, Lindo S, Michael S, Kuleshova E, Ojala D, Huang C C, Gerfen C R, Schiller J, Dudman J T, Hantman A W, Looger L L, Schaffer D V, Karpova A Y. A Designer AAV Variant Permits Efficient Retrograde Access to Projection Neurons. *Neuron.* 2016 Oct. 19: 92(2):372-382. (rAAV2-retro).

Marsic D, Govindasamy L, Currlin S, Markusic D M, Tseng Y S, Herzog R W, Agbandje-McKenna M, Zolotukhin S. Vector design Tour de Force: integrating combinatorial and rational approaches to derive novel adeno-associated virus variants. *Mol Ther.* 2014 November: 22(11): 1900-9. (AAV-LiC).

Sallach J, Di Pasquale G, Larcher F, Niehoff N, RUbsam M, Huber A, Chiorini J, Almarza D, Eming S A, Ulus H, Nishimura S, Hacker U T, Hallek M, Niessen C M, Bulling H. Tropism-modified AAV vectors overcome barriers to successful cutaneous therapy. *Mol Ther.* 2014 May: 22(5): 929-39. (AAV-Kera1, AAV-Kera2, and AAV-Kera3).

Dalkara D, Byrne L C, Klimczak R R, Visel M, Yin L, Merigan W H, Flannery J G, Schaffer D V. In vivo-directed evolution of a new adeno-associated virus for therapeutic outer retinal gene delivery from the vitreous. *Sci Transl Med.* 2013 Jun. 12: 5(189):189ra76. (AAV 7m8).

Asuri P, Bartel M A, Vazin T, Jang J H, Wong T B, Schaffer D V. Directed evolution of adeno-associated virus for enhanced gene delivery and gene targeting in human pluripotent stem cells. *Mol Ther.* 2012 February: 20(2):329-38. (AAV1.9).

Jang J H, Koerber J T, Kim J S, Asuri P, Vazin T, Bartel M, Keung A, Kwon I, Park K I, Schaffer D V. An evolved adeno-associated viral variant enhances gene delivery and gene targeting in neural stem cells. *Mol Ther.* 2011 April: 19(4):667-75. doi: 10.1038/mt.2010.287. (AAV r3.45).

Gray S J, Blake B L, Criswell H E, Nicolson S C, Samulski R J, McCown T J, Li W. Directed evolution of a novel adeno-associated virus (AAV) vector that crosses the seizure-compromised blood-brain barrier (BBB). *Mol Ther.* 2010 March: 18(3):570-8. (AAV clone 32 and 83).

Maguire C A, Gianni D, Meijer D H, Shaket L A, Wakimoto H, Rabkin S D, Gao G, Sena-Esteves M. Directed evolution of adeno-associated virus for glioma cell transduction. *J. Neurooncol.* 2010 February: 96(3):337-47. (AAV-U87R7-05).

Koerber J T, Klimczak R, Jang J H, Dalkara D, Flannery J G, Schaffer D V. Molecular evolution of adeno-associated virus for enhanced glial gene delivery. *Mol Ther.* 2009 December: 17(12):2088-95. (AAV ShH13, AAV ShH19, AAV L1-12)

Li W, Zhang L, Johnson J S, Zhijian W, Grieger J C, Ping-Jie X, Drouin L M, Agbandje-McKenna M, Pickles R J, Samulski R J. Generation of novel AAV variants by directed evolution for improved CFTR delivery to human ciliated airway epithelium. *Mol Ther.* 2009 December: 17(12):2067-77. (AAV HAE-1, AAV HAE-2).

Klimczak R R, Koerber J T, Dalkara D, Flannery J G, Schaffer D V. A novel adeno-associated viral variant for efficient and selective intravitreal transduction of rat Müller cells. *PLoS One.* 2009 Oct. 14: 4(10):e7467. (AAV variant ShH10).

Excoffon K J, Koerber J T, Dickey D D, Murtha M, Keshavjee S, Kaspar B K, Zabner J, Schaffer D V. Directed evolution of adeno-associated virus to an infectious respiratory virus. *Proc Natl Acad Sci USA.* 2009 Mar. 10: 106(10):3865-70. (AAV2.5T).

Sellner L, Stiefelhagen M, Kleinschmidt J A, Laufs S, Wenz F, Fruehauf S, Zeller W J, Veldwijk M R. Generation of efficient human blood progenitor-targeted recombinant adeno-associated viral vectors (AAV) by applying an AAV random peptide library on primary human hematopoietic progenitor cells. *Exp Hematol.* 2008 August: 36(8):957-64. (AAV LS1-4, AAV Lsm).

Li W, Asokan A, Wu Z, Van Dyke T, DiPrimio N, Johnson J S, Govindaswamy L, Agbandje-McKenna M, Leichtle S, Redmond D E Jr, McCown T J, Petermann K B, Sharpless N E, Samulski R J. Engineering and selection of shuffled AAV genomes: a new strategy for producing targeted biological nanoparticles. *Mol Ther.* 2008 July: 16(7):1252-60. (AAV1289).

Charbel Issa P, De Silva S R, Lipinski D M, Singh M S, Mouravlev A, You Q. Assessment of tropism and effectiveness of new primate-derived hybrid recombinant AAV serotypes in the mouse and primate retina. *PLoS ONE.* 2013: 8: e60361. (AAVHSC 1-17).

Huang W, McMurphy T, Liu X, Wang C, Cao L. Genetic Manipulation of Brown Fat Via Oral Administration of an Engineered Recombinant Adeno-associated Viral Serotype Vector. *Mol. Ther.* 2016 June: 24(6):1062-9. (AAV2 Rec 1-4).

Cronin T, Vandenberghe L H, Hantz P, et al. Efficient transduction and optogenetic stimulation of retinal bipolar cells by a synthetic adeno-associated virus capsid and promoter. *EMBO Mol. Med.* 2014: 6:1175-1190. (AAV8BP2).

Choudhury S R, Fitzpatrick Z, Harris A F, Maitland S A, Ferreira J S, Zhang Y, Ma S, Sharma R B, Gray-Edwards H L, Johnson J A, Johnson A K, Alonso L C, Punzo C, Wagner K R, Maguire C A, Kotin R M, Martin D R, Sena-Esteves M. In Vivo Selection Yields AAV-B1 Capsid for Central Nervous System and Muscle Gene Therapy. *Mol Ther.* 2016 August: 24(7): 1247-57. (AAV-B1).

Deverman B E, Pravdo P L, Simpson B P, Kumar S R, Chan K Y, Banerjee A, Wu W L, Yang B, Huber N, Pasca S P, Gradinaru V. Cre-dependent selection yields AAV variants for widespread gene transfer to the adult brain. *Nat Biotechnol.* 2016 February: 34(2):204-9. doi: 10.1038/nbt.3440. (AAV-PHP.B).

Pulicherla N, Shen S, Yadav S, Debbink K, Govindasamy L, Agbandje-McKenna M, Asokan A. Engineering liver-detargeted AAV9 vectors for cardiac and musculoskeletal gene transfer. *Mol Ther.* 2011 June: 19(6):1070-8. (AAV9 derived mutants-AAV9.45, AAV9.61, and AAV9.47).

Yang L, Jiang J, Drouin L M, Agbandje-McKenna M, Chen C, Qiao C, Pu D, Hu X, Wang D Z, Li J, Xiao X. A myocardium tropic adeno-associated virus (AAV) evolved by DNA shuffling and in vivo selection. *Proc Natl Acad Sci USA.* 2009 Mar. 10: 106(10):3946-51. (AAVM41).

Körbelin J, Sieber T, Michelfelder S, Lunding L, Spies E, Hunger A, Alawi M, Rapti K, Indenbirken D, Müller O J, Pasqualini R, Arap W, Kleinschmidt J A, Trepel M. Pulmonary Targeting of Adeno-associated Viral Vectors by Next-generation Sequencing-guided Screening of Random Capsid Displayed Peptide Libraries. *Mol Ther.* 2016 June: 24(6): 1050-61. (AAV2 displayed peptides).

Geoghegan J C, Keiser N W, Okulist A, Martins I, Wilson M S, Davidson B L. Chondroitin Sulfate is the Primary Receptor for a Peptide-Modified AAV That Targets Brain Vascular Endothelium *In Vivo. Mol Ther Nucleic Acids.* 2014 Oct. 14: 3:e202. (AAV2-GMN). Varadi K, Michelfelder S, Korff T, Hecker M, Trepel M, Katus H A, Kleinschmidt J A, Müller O J. Novel random peptide libraries displayed on AAV serotype 9 for selection of endothelial cell-directed gene transfer vectors. *Gene Ther.* 2012 August: 19(8):800-9. (AAV9-peptide displayed).

Michelfelder S, Varadi K, Raupp C, Hunger A, Korbelin J, Pahrmann C, Schrepfer S, Müller O J, Kleinschmidt J A, Trepel M. Peptide ligands incorporated into the threefold spike capsid domain to re-direct gene transduction of AAV8 and AAV9 in vivo. *PLoS One.* 2011: 6(8):e23101. (AAV8 and AAV9 peptide displayed).

Yu C Y, Yuan Z, Cao Z, Wang B, Qiao C, Li J, Xiao X. A muscle-targeting peptide displayed on AAV2 improves muscle tropism on systemic delivery. Gene Ther. 2009 August: 16(8):953-62.

Michelfelder S, Lee M K, deLima-Hahn E, Wilmes T, Kaul F, Müller O, Kleinschmidt J A, Trepel M. Vectors selected from adeno-associated viral display peptide libraries for leukemia cell-targeted cytotoxic gene therapy. Exp Hematol. 2007 December: 35(12): 1766-76.

Müller O J, Kaul F, Weitzman M D, Pasqualini R, Arap W, Kleinschmidt J A, Trepel M. Random peptide libraries displayed on adeno-associated virus to select for targeted gene therapy vectors. Nat Biotechnol. 2003 September: 21(9):1040-6.

Grifman M, Trepel M, Speece P, Gilbert L B, Arap W, Pasqualini R, Weitzman M D. Incorporation of tumor-targeting peptides into recombinant adeno-associated virus capsids. *Mol Ther.* 2001 June: 3(6):964-75.

Anne Girod, Martin Ried, Christiane Wobus, Harald Lahm, Kristin Leike, Jurgen Kleinschmidt, Gilbert Deleage and Michael Hallek. Genetic capsid modifications allow efficient re-targeting of adeno-associated virus type 2. *Nature Medicine,* 1052-1056 (1999).

Bello A, Chand A, Aviles J, Soule G, Auricchio A, Kobinger G P. Novel adeno-associated viruses derived from pig tissues transduce most major organs in mice. *Sci Rep.* 2014 Oct. 22: 4:6644. (AAVpo2.1, -po4, -po5, and -po6).

Gao G, Vandenberghe L H, Alvira M R, Lu Y, Calcedo R, Zhou X, Wilson J M. Clades of Adeno-associated viruses are widely disseminated in human tissues. *J. Virol.* 2004 June: 78(12):6381-8. (AAV rh and AAV Hu).

Arbetman A E, Lochrie M, Zhou S, Wellman J, Scallan C, Doroudchi M M, et al. Novel caprine adeno-associated virus (AAV) capsid (AAV-Go.1) is closely related to the primate AAV-5 and has unique tropism and neutralization properties. *J. Virol.* 2005: 79:15238-15245. (AAV-Go.1).

Lochrie M A, Tatsuno G P, Arbetman A E, Jones K, Pater C, Smith P H, et al. Adeno-associated virus (AAV) capsid genes isolated from rat and mouse liver genomic DNA define two new AAV species distantly related to AAV-5. *Virology.* 2006: 353:68-82. (AAV-mo.1).

Schmidt M, Katano H, Bossis I, Chiorini J A. Cloning and characterization of a bovine adeno-associated virus. *J. Virol.* 2004: 78:6509-6516. (BAAV).

Bossis I, Chiorini J A. Cloning of an avian adeno-associated virus (AAAV) and generation of recombinant AAAV particles. *J. Virol.* 2003: 77:6799-6810. (AAAV).

Chen C L, Jensen R L, Schnepp B C, Connell M J, Shell R, Sferra T J, Bartlett J S, Clark K R, Johnson P R. Molecular characterization of adeno-associated viruses infecting children. *J. Virol.* 2005 December: 79(23):14781-92. (AAV variants).

Sen D, Gadkari R A, Sudha G, Gabriel N, Kumar Y S, Selot R, Samuel R, Rajalingam S, Ramya V, Nair S C, Srinivasan N, Srivastava A, Jayandharan G R. Targeted modifications in adeno-associated virus serotype 8 capsid improves its hepatic gene transfer efficiency in vivo. *Hum Gene Ther Methods.* 2013 April: 24(2):104-16. (AAV8 K137R).

Li B, Ma W, Ling C, Van Vliet K, Huang L Y, Agbandje-McKenna M, Srivastava A, Aslanidi G V. Site-Directed Mutagenesis of Surface-Exposed Lysine Residues Leads to Improved Transduction by AAV2, But Not AAV8, Vectors in Murine Hepatocytes In Vivo. *Hum Gene Ther Methods.* 2015 December: 26(6):211-20.

Gabriel N, Hareendran S, Sen D, Gadkari R A, Sudha G, Selot R, Hussain M, Dhaksnamoorthy R, Samuel R, Srinivasan N, et al. Bioengineering of AAV2 capsid at specific serine, threonine, or lysine residues improves its transduction efficiency in vitro and in vivo. *Hum Gene Ther Methods.* 2013 April: 24(2):80-93.

Zinn E, Pacouret S, Khaychuk V, Turunen H T, Carvalho L S, Andres-Mateos E, Shah S, Shelke R, Maurer A C, Plovie E, Xiao R, Vandenberghe L H. In Silico Reconstruction of the Viral Evolutionary Lineage Yields a Potent Gene Therapy Vector. *Cell Rep.* 2015 Aug. 11: 12(6): 1056-68. (AAV Anc80L65).

Shen S, Horowitz E D, Troupes A N, Brown S M, Pulicherla N, Samulski R J, Agbandje-McKenna M, Asokan A. Engraftment of a galactose receptor footprint onto adeno-associated viral capsids improves transduction efficiency. *J. Biol Chem.* 2013 Oct. 4: 288(40):28814-23. (AAV2G9).

Li C, Diprimio N, Bowles D E, Hirsch M L, Monahan P E, Asokan A, Rabinowitz J, Agbandje-McKenna M, Samulski R J. Single amino acid modification of adeno-associated virus capsid changes transduction and humoral immune profiles. *J. Virol.* 2012 August: 86(15): 7752-9. (AAV2 265 insertion-AAV2/265D).

Bowles D E, McPhee S W, Li C, Gray S J, Samulski J J, Camp A S, Li J, Wang B, Monahan P E, Rabinowitz J E, et al. Phase 1 gene therapy for Duchenne muscular dystrophy using a translational optimized AAV vector. *Mol. Ther.* 2012 February: 20(2):443-55. (AAV2.5).

Messina E L, Nienaber J, Daneshmand M, Villamizar N, Samulski J, Milano C, Bowles D E. Adeno-associated viral vectors based on serotype 3b use components of the fibroblast growth factor receptor signaling complex for efficient transduction. *Hum. Gene Ther.* 2012 October: 23(10):1031-42. (AAV3 SASTG).

Asokan A, Conway J C, Phillips J L, Li C, Hegge J, Sinnott R, Yadav S, DiPrimio N, Nam H J, Agbandje-McKenna M, McPhee S, Wolff J, Samulski R J. Reengineering a receptor footprint of adeno-associated virus enables selective and systemic gene transfer to muscle. *Nat Biotechnol.* 2010 January: 28(1):79-82. (AAV2i8).

Vance M, Llanga T, Bennett W, Woodard K, Murlidharan G, Chungfat N, Asokan A, Gilger B, Kurtzberg J, Samulski R J, Hirsch M L. AAV Gene Therapy for MPS1-associated Corneal Blindness. *Sci Rep.* 2016 Feb. 22: 6:22131. (AAV8G9).

Zhong L, Li B, Mah C S, Govindasamy L, Agbandje-McKenna M, Cooper M, Herzog R W, Zolotukhin I, Warrington K H Jr, Weigel-Van Aken K A, Hobbs J A, Zolotukhin S, Muzyczka N, Srivastava A. Next generation of adeno-associated virus 2 vectors: point mutations in tyrosines lead to high-efficiency transduction at lower doses. *Proc Natl Acad Sci USA.* 2008 Jun. 3: 105(22):7827-32. (AAV2 tyrosine mutants AAV2 Y-F).

Petrs-Silva H, Dinculescu A, Li Q, Min S H, Chiodo V, Pang J J, Zhong L, Zolotukhin S, Srivastava A, Lewin A S, Hauswirth W W. High-efficiency transduction of the mouse retina by tyrosine-mutant AAV serotype vectors. *Mol. Ther.* 2009 March: 17(3):463-71. (AAV8 Y-F and AAV9 Y-F).

Qiao C, Zhang W, Yuan Z, Shin J H, Li J, Jayandharan G R, Zhong L, Srivastava A, Xiao X, Duan D. Adeno-associated virus serotype 6 capsid tyrosine-to-phenylalanine mutations improve gene transfer to skeletal muscle. *Hum Gene Ther.* 2010 October: 21(10):1343-8 (AAV6 Y-F).

Carlon M, Toelen J, Van der Perren A, Vandenberghe L H, Reumers V, Sbragia L, Gijsbers R, Baekelandt V, Himmelreich U, Wilson J M, Deprest J, Debyser Z. Efficient gene transfer into the mouse lung by fetal intratracheal injection of rAAV2/6.2. *Mol. Ther.* 2010 December: 18(12):2130-8. (AAV6.2).

PCT Publication No. WO2013158879A1. (lysine mutants).

The following biological sequence files listed in the file wrappers of USPTO issued patents and published applications describe chimeric or variant capsid proteins that can be incorporated into the AAV capsid of this invention in any combination with wild type capsid proteins and/or other chimeric or variant capsid proteins now known or later identified (for demonstrative purposes, U.S. patent application Ser. No. 11/486,254 corresponds to U.S. patent application Ser. No. 11/486,254): 11486254.raw, 11932017.raw, 12172121.raw, 12302206.raw, 12308959.raw, 12679144.raw, 13036343.raw, 13121532.raw, 13172915.raw, 13583920.raw, 13668120.raw, 13673351.raw, 13679684.raw, 14006954.raw, 14149953.raw, 14192101.raw, 14194538.raw, 14225821.raw, 14468108.raw, 14516544.raw, 14603469.raw, 14680836.raw, 14695644.raw, 14878703.raw, 14956934.raw, 15191357.raw, 15284164.raw, 15368570.raw, 15371188.raw, 15493744.raw, 15503120.raw, 15660906.raw, and 15675677.raw.

It would be understood that any combination of VP1 and VP3, and when present, VP1.5 and VP2 from any combination of AAV serotypes can be employed to produce the AAV capsids of this invention. For example, a VP1 protein from any combination of AAV serotypes can be combined with a VP3 protein from any combination of AAV serotypes and the respective VP1 proteins can be present in any ratio of different serotypes and the respective VP3 proteins can be present in any ratio of different serotypes and the VP1 and VP3 proteins can be present in any ratio of different serotypes. It would be further understood that, when present, a VP1.5 and/or VP2 protein from any combination of AAV serotypes can be combined with VP1 and VP3 protein from any combination of AAV serotypes and the respective VP1 0.5 proteins can be present in any ratio of different serotypes and the respective VP2 proteins can be present in any ratio of different serotypes and the respective VP1 proteins can be present in any ratio of different serotypes and the respective VP3 proteins can be present in any ratio of different serotypes and the VP1.5 and/or VP2 proteins can be present in combination with VP1 and VP3 proteins in any ratio of different serotypes.

For example, the respective viral proteins and/or the respective AAV serotypes can be combined in any ratio, which can be a ratio of A:B, A:B:C, A:B:C:D, A:B:C:D:E, A:B:C:D:E:F, A:B:C:D:E:F:G, A:B:C:D:E:F:G:H, A:B:C:D:E:F:G:H:I or A:B:C:D:E:F:G:H:I:J, wherein A can be 1, 2, 3, 4, 5, 6, 7, 8, 9, 10, 11, 12, 13, 14, 15, 20, 25, 30, 35, 40, 50, 60, 70, 80, 90, 100, etc.; B can be 1, 2, 3, 4, 5, 6, 7, 8, 9, 10, 11, 12, 13, 14, 15, 20, 25, 30, 35, 40, 50, 60, 70, 80, 90, 100, etc.; C can be 1, 2, 3, 4, 5, 6, 7, 8, 9, 10, 11, 12, 13, 14, 15, 20, 25, 30, 35, 40, 50, 60, 70, 80, 90, 100, etc.; D can be 1, 2, 3, 4, 5, 6, 7, 8, 9, 10, 11, 12, 13, 14, 15, 20, 25, 30, 35, 40, 50, 60, 70, 80, 90, 100, etc.; E can be 1, 2, 3, 4, 5, 6, 7, 8, 9, 10, 11, 12, 13, 14, 15, 20, 25, 30, 35, 40, 50, 60, 70, 80, 90, 100, etc.; F can be 1, 2, 3, 4, 5, 6, 7, 8, 9, 10, 11, 12, 13, 14, 15, 20, 25, 30, 35, 40, 50, 60, 70, 80, 90, 100, etc.; G can be 1, 2, 3, 4, 5, 6, 7, 8, 9, 10, 11, 12, 13, 14, 15, 20, 25, 30, 35, 40, 50, 60, 70, 80, 90, 100, etc.; H can be 1, 2, 3, 4, 5, 6, 7, 8, 9, 10, 11, 12, 13, 14, 15, 20, 25, 30, 35, 40, 50, 60, 70, 80, 90, 100, etc.; I can be 1, 2, 3, 4, 5, 6, 7, 8, 9, 10, 11, 12, 13, 14, 15, 20, 25, 30, 35, 40, 50, 60, 70, 80, 90, 100, etc.; and J can be 1, 2, 3, 4, 5, 6, 7, 8, 9, 10, 11, 12, 13, 14, 15, 20, 25, 30, 35, 40, 50, 60, 70, 80, 90, 100, etc.

It would also be understood that any of the VP1, VP1.5, VP2 and/or VP3 capsid proteins can be present in a capsid of this invention as a chimeric capsid protein, in any combination and ratio relative to the same protein type and/or relative to the different capsid proteins.

In further embodiments, the present invention further provides a virus vector comprising, consisting essentially of and/or consisting of (a) the AAV capsid of this invention; and (b) a nucleic acid molecule comprising at least one terminal repeat sequence, wherein the nucleic acid molecule is encapsidated by the AAV capsid. In some embodiments, the virus vector can be an AAV particle.

In some embodiments, the virus vector of this invention can have systemic or selective tropism for skeletal muscle, cardiac muscle and/or diaphragm muscle. In some embodiments, the virus vector of this invention can have reduced tropism for liver.

The present invention further provides a composition, which can be a pharmaceutical formulation, comprising the capsid protein, capsid, virus vector, AAV particle composition and/or pharmaceutical formulation of this invention and a pharmaceutically acceptable carrier.

In some nonlimiting examples, the present invention provides AAV capsid proteins (VP1, VP1.5, VP2 and/or VP3) comprising a modification in the amino acid sequence in the three-fold axis loop 4 (Opie et al., *J. Viral.* 77: 6995-7006 (2003)) and virus capsids and virus vectors comprising the modified AAV capsid protein. The inventors have discovered that modifications in this loop can confer one or more desirable properties to virus vectors comprising the modified AAV capsid protein including without limitation (i) reduced transduction of liver, (ii) enhanced movement across endothelial cells, (iii) systemic transduction; (iv) enhanced transduction of muscle tissue (e.g., skeletal muscle, cardiac muscle and/or diaphragm muscle), and/or (v) reduced transduction of brain tissues (e.g., neurons). Thus, the present invention addresses some of the limitations associated with conventional AAV vectors. For example, vectors based on AAV8 and rAAV9 vectors are attractive for systemic nucleic acid delivery because they readily cross the endothelial cell barrier; however, systemic administration of rAAV8 or rAAV9 results in most of the vector being delivered to the liver, thereby reducing transduction of other important target tissues such as skeletal muscle.

In an embodiment, the modified AAV capsid can be comprised of a VP1, a VP2 and/or a VP3 that is created through DNA shuffling to develop cell type specific vectors through directed evolution. DNA shuffling with AAV is generally descried in Li, W. et al., Mol. Ther. 16(7): 1252-12260 (2008), which is incorporated herein by reference. In an embodiment, DNA shuffling can be used to create a VP1, a VP2 and/or a VP3 using the DNA sequence for the capsid genes from two or more different AAV serotypes, AAV chimerics or other AAV. In an embodiment, a haploid AAV can be comprised of a VP1 created by DNA shuffling, a VP2 created by DNA shuffling and/or a VP3 created by DNA shuffling.

In an embodiment, a VP1 from a haploid AAV could be created by randomly fragmenting the capsid genomes of AAV2, AAV8 and AAV9 using a restriction enzyme and/or DNase to generate a VP1 capsid protein library comprised of portions of AAV2/8/9. In this embodiment, the AAV2/8/9 VP1 capsid protein created by DNA shuffling could be combined with a VP2 and/or a VP3 protein from a different serotype, in an embodiment, from AAV3. This would result in a haploid AAV wherein the capsid is comprised of a VP1 that includes amino acids from AAV2, AAV8 and AAV9 that are joined together randomly through DNA shuffling and the VP2 and/or VP3 comprise only amino acids from a native, AAV3 VP2 and/or VP3. In an embodiment, the donor to create a VP1, VP2 and/or a VP3 can be any AAV, including, AAV1, AAV2, AAV3, AAV4, AAV5, AAV6, AAV7, AAV8, AAV9, AAV10, AAV11, AAV chimerics or other AAV, or those selected from Table 1 or Table 3. In certain embodiments, the shuffled VP1 expresses e.g., only VP1, or only VP1/VP2, or only VP3.

In another embodiment, the nucleic acid encoding VP1, VP2 and/or VP3 can be created through DNA shuffling. In one embodiment, a first nucleic acid created by DNA shuffling would encode VP1. In this same embodiment, a second nucleic acid created by DNA shuffling would encode VP2 and VP3. In another embodiment, a first nucleic acid created by DNA shuffling would encode VP1. In this same embodiment, a second nucleic acid created by DNA shuffling would encode VP2 and a third nucleic acid would encode VP3. In a further embodiment, a first nucleic acid created by DNA shuffling would encode VP1 and VP2 and a second nucleic acid created by DNA shuffling would encode VP3. In an additional embodiment, a first nucleic acid created by DNA shuffling would encode VP1 and VP3 and a second nucleic acid created by DNA shuffling would encode VP2.

In embodiments of the invention, transduction of cardiac muscle and/or skeletal muscle (determined on the basis of an individual skeletal muscle, multiple skeletal muscles, or the whole range of skeletal muscles) is at least about five-fold, ten-fold, 50-fold, 100-fold, 1000-fold or higher than transduction levels in liver.

In particular embodiments, the modified AAV capsid protein of the invention comprises one or more modifications in the amino acid sequence of the three-fold axis loop 4 (e.g., amino acid positions 575 to 600 [inclusive] of the native AAV2 VP1 capsid protein or the corresponding region of a capsid protein from another AAV). As used herein, a "modification" in an amino acid sequence includes substitutions, insertions and/or deletions, each of which can involve one, two, three, four, five, six, seven, eight, nine, ten or more amino acids. In particular embodiments, the modification is a substitution. For example, in particular embodiments, 1, 2, 3, 4, 5, 6, 7, 8, 9, 10, 11, 12, 13, 14, 15, 16, 17, 18, 19, 20, 21, 22, 23, 24, 25 or more amino acids from the three-fold axis loop 4 from one AAV can be substituted into amino acid positions 575-600 of the native AAV2 capsid protein or the corresponding positions of the capsid protein from another AAV. However, the modified virus capsids of the invention are not limited to AAV capsids in which amino acids from one AAV capsid are substituted into another AAV capsid, and the substituted and/or inserted amino acids can be from any source, and can further be naturally occurring or partially or completely synthetic.

As described herein, the nucleic acid and amino acid sequences of the capsid proteins from a number of AAV are known in the art. Thus, the amino acids "corresponding" to amino acid positions 575 to 600 (inclusive) or amino acid positions 585 to 590 (inclusive) of the native AAV2 capsid protein can be readily determined for any other AAV (e.g., by using sequence alignments).

In some embodiments, the invention contemplates that the modified capsid proteins of the invention can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10, AAV11, or AAV12 capsid protein or any of the AAV shown in Table 3) but is not so limited. Those skilled in the art will understand that a variety of manipulations to the AAV capsid proteins are known in the art and the invention is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11 and/or AAV12 or any other AAV now known or later discovered). Such AAV capsid proteins are also within the scope of the present invention.

For example, in some embodiments, the AAV capsid protein to be modified can comprise an amino acid insertion directly following amino acid 264 of the native AAV2 capsid protein sequence (see, e.g., PCT Publication WO 2006/066066) and/or can be an AAV with an altered HI loop as described in PCT Publication WO 2009/108274 and/or can be an AAV that is modified to contain a poly-His sequence to facilitate purification. As another illustrative example, the AAV capsid protein can have a peptide targeting sequence incorporated therein as an insertion or substitution. Further, the AAV capsid protein can comprise a large domain from another AAV that has been substituted and/or inserted into the capsid protein.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10, AAV11 or AAV12 capsid protein or a capsid protein from any of the AAV shown in Table 1, etc.), it is intended to encompass the native capsid protein as well as capsid proteins that have alterations other than the modifications of the invention. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present invention) as compared with the native AAV capsid protein sequence. In embodiments of the invention, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments of the invention, the capsid protein comprises a deletion of 1, 2, 3, 4, 5, 6, 7, 8, 9, 10, 11, 12, 13, 14, 15, 16, 17, 18, 19 or 20, more than 20, more than 30, more than 40, more than 50, more than 60, or more than 70 amino acids (other than the amino acid deletions of the invention) as compared with the native AAV capsid protein sequence.

Using AAV serotype 2 as an exemplary virus, M11 is the VP1 start codon, M138 is the VP2 start codon, and M203 is the VP3 start codon. While deletion of the start codon, typically by a substitution of M11 and M138 will render expression of VP1 and VP2 inoperative, a similar deletion of the VP3 start codon is not sufficient. This is because the viral capsid ORF contains numerous ATG codons with varying strengths as initiation codons. Thus, in designing a construct that will not express VP3 care must be taken to insure that an alternative VP3 species is not produced. With respect to VP3 either elimination of M138 is necessary or if VP2 is desired, but not VP3, then deletion of M211 and 235 in addition to M203 is typically the best approach (Warrington, K. H. Jr., et al., J. of Virol. 78(12): 6595-6609 (June 2004)). This can be done by mutations such as substitution or other means known in the art. The corresponding start codons in other serotypes can readily be determined as well as whether additional ATG sequences such as in VP3 can serve as alternative initiation codons.

Thus, for example, the term "AAV2 capsid protein" includes AAV capsid proteins having the native AAV2 capsid protein sequence (see GenBank Accession No. AAC03780) as well as those comprising substitutions, insertions and/or deletions (as described in the preceding paragraph) in the native AAV2 capsid protein sequence.

In particular embodiments, the AAV capsid protein has the native AAV capsid protein sequence or has an amino acid sequence that is at least about 70%, 75%, 80%, 85%, 90%, 95%, 97%, 98% or 99% similar or identical to a native AAV capsid protein sequence. For example, in particular embodiments, an "AAV2" capsid protein encompasses the native AAV2 capsid protein sequence as well as sequences that are at least about 75%, 80%<85%, 90%, 95%, 97%, 98% or 99% similar or identical to the native AAV2 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2,482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

In some embodiments of the invention, a modification can be made in the region of amino acid positions 585 to 590 (inclusive) of the native AAV2 capsid protein (using VP1 numbering) or the corresponding positions of other AAV (native AAV2 VP1 capsid protein: GenBank Accession No. AAC03780 or YP680426), i.e., at the amino acids corresponding to amino acid positions 585 to 590 (VP1 numbering) of the native AAV2 capsid protein. The amino acid positions in other AAV serotypes or modified AAV capsids that "correspond to" positions 585 to 590 of the native AAV2 capsid protein will be apparent to those skilled in the art and can be readily determined using sequence alignment techniques (see, e.g., FIG. 7 of WO 2006/066066) and/or crystal structure analysis (Padron et al., (2005) *J. Virol.* 79: 5047-58).

To illustrate, the modification can be introduced into an AAV capsid protein that already contains insertions and/or deletions such that the position of all downstream sequences is shifted. In this situation, the amino acid positions corresponding to amino acid positions 585 to 590 in the AAV2 capsid protein would still be readily identifiable to those skilled in the art. To illustrate, the capsid protein can be an AAV2 capsid protein that contains an insertion following amino acid position 264 (see, e.g., WO 2006/066066). The amino acids found at positions 585 through 590 (e.g., RGNRQA (SEQ ID NO:1) in the native AAV2 capsid protein) would now be at positions 586 through 591 but would still be identifiable to those skilled in the art.

The invention also provides a virus capsid comprising, consisting essentially of, or consisting of the modified AAV capsid proteins of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11, AAV12, or any other AAV shown in Table 1 or otherwise known or later discovered, and/or is derived from any of the foregoing by one or more insertions, substitutions and/or deletions.

In embodiments of the present invention, the isolated AAV virion or substantially homogenous population of AAV virions is not a product of expression of a mixture of one nucleic acid helper plasmid that express VP1, VP2 and VP3 of one serotype with another nucleic acid helper plasmid that express VP1, VP2 and VP3 of another serotype, such expression being termed "cross-dressing."

In embodiments of the present invention, the isolated AAV virion does not comprise a mosaic capsid and the substantially homogenous population of AAV virions does not comprise a substantially homogenous population of mosaic capsids.

To the extent that any disclosure in PCT/US18/22725 filed Mar. 15, 2018 falls within the invention as defined in any one or more of the claims of this application, or within any invention to be defined in amended claims that may in the future be filed in this application or in any patent derived therefrom, and to the extent that the laws of any relevant country or countries to which that or those claims apply provide that the disclosure of PCT/US18/22725 is part of the state of the art against that or those claims in or for that or those countries, we hereby reserve the right to disclaim the said disclosure from the claims of the present application or any patent derived therefrom to the extent necessary to prevent invalidation of the present application or any patent derived therefrom.

For example, and without limitation, we reserve the right to disclaim any one or more of the following subject-matters from any claim of the present application, now or as amended in the future, or any patent derived therefrom:

A. any subject-matter disclosed in Example 9 of PCT/US18/22725; or

B. vector virions, termed polyploid vector virions, which are produced or producible by transfection of two AAV helper plasmids or three plasmids to produce individual polyploid vector virions composed of different capsid subunits from different serotypes; or C. vector virions, termed polyploid vector virions, which are produced or producible by transfection of two AAV helper plasmids which are AAV2 and AAV8 or AAV9 to produce individual polyploid vector virions composed of different capsid subunits from different serotypes; or D. vector virions, termed polyploid vector virions, which are produced or producible by transfection of three AAV helper plasmids which are AAV2, AAV8 and AAV9 to produce individual polyploid vector virions composed of different capsid subunits from different serotypes; or E. vector virions, termed haploid vectors, with VP1/VP2 from one AAV vector capsid or AAV serotype and VP3 from an alternative one, for example VP1/VP2 from (the capsid of) only one AAV serotype and VP3 from only one alternative AAV serotype; or F. any one or more AAV vector virion(s) selected from:

a vector which is generated by transfection of AAV2 helper and AAV8 helper plasmids (termed haploid AAV2/8) and which has VP1 capsid subunit from AAV8 and VP2/VP3 capsid subunits from AAV2; or a vector which is generated by transfection of AAV2 helper and AAV8 helper plasmids (termed haploid AAV2/8 or haploid AAV8/2 or haploid AAV82 or H-AAV82) and which has VP1/VP2 capsid subunits from AAV8 and VP3 capsid subunit from AAV2; or a vector in which VP1/VP2 is derived from different serotypes; or a vector (termed haploid AAV92 or H-AAV92) which has VP1/VP2 capsid subunits from AAV9 and VP3 capsid subunit from AAV2; or a vector (termed haploid AAV2G9 or H-AAV2G9) which has VP1/VP2 capsid subunits from AAV8 and VP3 capsid subunit from AAV2G9, in which AAV9 glycan receptor binding site was engrafted into AAV2; or a vector (termed haploid AAV83 or H-AAV83) which has VP1/VP2 capsid subunits from AAV8 and VP3 capsid subunit from AAV3; or a vector (termed haploid AAV93 or H-AAV93) which has VP1/VP2 capsid subunits from AAV9 and VP3 capsid subunit from AAV3; or a vector (termed haploid AAVrh10-3 or H-AAVrh10-3) which has VP1/VP2 capsid subunits from AAVrh10 and VP3 capsid subunit from AAV3; or a vector which is generated by transfection of AAV2 helper and AAV8 helper plasmids (termed haploid AAV2/8) and which has VP1 capsid subunit from AAV2 and VP2/VP3 capsid subunits from AAV8; or a vector which is generated by transfection of AAV2 helper and AAV8 helper plasmids (termed haploid AAV2/8) and which has VP1/VP2 capsid subunit from AAV2 and VP3 capsid subunits from AAV8; or a vector which is generated by transfection of AAV2 helper and AAV8 helper plasmids (termed haploid AAV2/8) and which has VP1 capsid subunit from AAV8 and VP3 capsid subunit from AAV2; or a vector which is generated by transfection of AAV2 helper and AAV8 helper plasmids (termed haploid AAV2/8) and which has VP1 capsid subunit from AAV2 and VP3 capsid subunits from AAV8; or a vector which is generated by transfection of AAV2 helper and AAV8 helper plasmids (termed haploid AAV2/8) and which has VP1/VP2/VP3 capsid subunits from AAV2; or a vector which is generated by transfection of AAV2 helper and AAV8 helper plasmids (termed haploid AAV2/8) and which has VP1/VP2/VP3 capsid subunits from AAV8; or a vector termed 28m-2VP3 or haploid 2m-2VP3 or haploid vector 28m-2VP3 in which chimeric VP1/VP2 capsid subunits have N-terminal from AAV2 and C-terminal from AAV8, and the VP3 capsid subunit is from AAV2; or a vector termed chimeric AAV8/2 or chimeric AAV82 in which chimeric VP1/VP2 capsid subunits have N-terminal from AAV8 and C-terminal from AAV2 without mutation of the VP3 start codon, and the VP3 capsid subunit is from AAV2; or a vector in which chimeric VP1/VP2 capsid subunits have N-terminal from AAV2 and C-terminal from AAV8; or G. a population, for example a substantially homogenous population, for example a population of 1010 particles, for example a substantially homogenous population of 1010 particles, of any one of the vectors of F; or H. a method of producing any one of the vectors or populations of vectors of A and/or B and/or C and/or D and/or E and/or F and/or G; or I. any combination thereof.

Without limitation, we state that the above reservation of a right of disclaimer applies at least to the original claims as appended to this application and paragraphs 1-83 as set forth herein. The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the virus capsid for transfer of the molecules into host target cells. Such associated molecules can include DNA, RNA, small organic molecules, metals, carbohydrates, lipids and/or polypeptides. In one embodiment of the invention, the therapeutically useful molecule is covalently linked (i.e., conjugated or chemically coupled) to the capsid proteins. Methods of covalently linking molecules are known by those skilled in the art.

The modified virus capsids of the invention also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, the virus capsids can be administered to block certain cellular sites prior to and/or concurrently with (e.g., within minutes or hours of each other) administration of a virus vector delivering a nucleic acid encoding a polypeptide or functional RNA of interest. For example, the inventive capsids can be delivered to block cellular receptors on liver cells and a delivery vector can be administered subsequently or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a modified virus vector according to the present invention. Further, the invention provides compositions and pharmaceutical formulations comprising the inventive modified virus capsids; optionally, the composition also comprises a modified virus vector of the invention.

The invention also provides nucleic acid molecules (optionally, isolated nucleic acid molecules) encoding the modified virus capsids and capsid proteins of the invention. Further provided are vectors, comprising the nucleic acid molecules and cells (in vivo or in culture), comprising the nucleic acid molecules and/or vectors of the invention. Suitable vectors include without limitation viral vectors (e.g., adenovirus, AAV, herpesvirus, alphaviruses, vaccinia, poxviruses, baculoviruses, and the like), plasmids, phage, YACs, BACs, and the like. Such nucleic acid molecules, vectors and cells can be used, for example, as reagents (e.g., helper packaging constructs or packaging cells) for the production of modified virus capsids or virus vectors as described herein.

Virus capsids according to the invention can be produced using any method known in the art, e.g., by expression from a baculovirus (Brown et al., (1994) Virology 198:477-488).

In some embodiments, the modifications to the AAV capsid protein of this invention are "selective" modifications. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" modification results in the insertion and/or substitution and/or deletion of less than about 20, 18, 15, 12, 10, 9, 8, 7, 6, 5, 4, 3 or 2 contiguous amino acids.

The modified capsid proteins and capsids of the invention can further comprise any other modification, now known or later identified.

The virus capsid can be a targeted virus capsid comprising a targeting sequence (e.g., substituted or inserted in the viral capsid) that directs the virus capsid to interact with cell-surface molecules present on a desired target tissue(s) (see, e.g., International Patent Publication No. WO 00/28004 and Hauck et al., (2003) *J. Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588 described by Grifman et al., *Molecular Therapy* 3:964-975 (2001)).

For example, some of the virus capsids of the invention have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids as described by Wang et al., *Annu Rev Biophys Biomol Struct.* 35:225-49 (2006)) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques,* 1$^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV 4, AAV5) to confer heparin binding to the resulting mutant.

B19 infects primary erythroid progenitor cells using globoside as its receptor (Brown et al., (1993) *Science* 262:114). The structure of B19 has been determined to 8 Å resolutions (Agbandje-McKenna et al., (1994) *Virology* 203:106). The region of the B19 capsid that binds to globoside has been mapped between amino acids 399-406 (Chapman et al., (1993) *Virology* 194:419), a looped out region between β-barrel structures E and F. (Chipman et al., (1996) *Proc. Nat. Acad. Sci. USA* 93:7502). Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV that otherwise does not bind to HS or heparin). It is known in the art that HS/heparin binding is mediated by a "basic patch" that is rich in arginines and/or lysines. In exemplary embodiments, a sequence following the motif BXXB, where "B" is a basic residue and X is neutral and/or hydrophobic. As one nonlimiting example, BXXB is RGNR. In particular embodiments, BXXB is substituted for amino acid positions 262 through 265 in the native AAV2 capsid protein or the corresponding position in the capsid protein of another AAV.

Other nonlimiting examples of suitable targeting sequences include the peptides targeting coronary artery endothelial cells identified by Müller et al., *Nature Biotechnology* 21:1040-1046 (2003) (consensus sequences NSVRDLG/S (SEQ ID NO:2), PRSVTVP (SEQ ID NO:3), NSVSSXS/A (SEQ ID NO:4)); tumor-targeting peptides as described by Grifman et al., *Molecular Therapy* 3:964-975 (2001) (e.g., NGR, NGRAHA (SEQ ID NO:5)); lung or brain targeting sequences as described by Work et al., *Molecular Therapy* 13:683-693 (2006) (QPEHSST (SEQ ID NO:6), VNTANST (SEQ ID NO:7), I-IGPMQKS (SEQ ID NO:8), PHKPPLA (SEQ ID NO:9), IKNNEMW (SEQ ID NO:10), RNLDTPM (SEQ ID NO:11), VDSHRQS (SEQ ID NO:12), YDSKTKT (SEQ ID NO:13), SQLPHQK (SEQ ID NO:14), STMQQNT (SEQ ID NO:15), TERYMTQ (SEQ ID NO:16), QPEHSST (SEQ ID NO:6), DASLSTS (SEQ ID NO:17). DLPNKKT (SEQ ID NO:18), DLTAARL (SEQ ID NO:19), EPHQFNY (SEQ ID NO:20), EPQSNHT (SEQ ID NO:21), MSSWPSQ (SEQ ID NO:22), NPKI-INAT (SEQ ID NO:23), PDGMRTT (SEQ ID NO:24), PNNNKTT (SEQ ID NO:25), QSTTHDS (SEQ ID NO:26), TGSKQKQ (SEQ ID NO:27), SLKHQAL (SEQ ID NO:28) and SPIDGEQ (SEQ ID NO:29)); vascular targeting sequences described by Hajitou et al., TCM 16:80-88 (2006) (WIFPWIQL (SEQ ID NO:30), CDCRGDCFC (SEQ ID NO:31), CNGRC (SEQ ID NO:32), CPRECES (SEQ ID NO:33), GSL, CTTHWGFTLC (SEQ ID NO:34), CGRRAGGSC (SEQ ID NO:35). CKGGRAKDC (SEQ ID NO:36), and CVPELGHEC (SEQ ID NO:37)); targeting peptides as described by Koivunen et al., *J. Nucl. Med.* 40:883-888 (1999) (CRRETAWAK (SEQ ID NO:38), KGD, VSWFSHRYSPFAVS (SEQ ID NO:39), GYRDGYAGPILYN (SEQ ID NO:40), XXXY*XXX [where Y* is phospho-Tyr] (SEQ ID NO:41), Y*E/MNW (SEQ ID NO:42), RPLPPLP (SEQ ID NO:43), APPLPPR (SEQ ID NO:44), DVFYPYPY ASGS (SEQ ID NO:45), MYWYPY (SEQ ID NO:46), DITWDQL WDLMK (SEQ ID NO:47), CWDDG/L WLC (SEQ ID NO:48), EWCEYLGGYLRCY A (SEQ ID NO:49), YXCXXGPXTWXCXP (SEQ ID NO:50), IEGPTLRQWLAARA (SEQ ID NO:51), LWXXY/W/F/H (SEQ ID NO:52), XFXXYLW (SEQ ID NO:53), SSIISHFRWGLCD (SEQ ID NO:54), MSRPACPPNDKYE (SEQ ID NO:55), CLRSGRGC (SEQ ID NO:56), CHWMFSPWC (SEQ ID NO:57), WXXF (SEQ ID NO:58), CSSRLDAC (SEQ ID NO:59), CLPVASC (SEQ ID NO:60), CGFECVRQCPERC (SEQ ID NO:61), CVALCREACGEGC (SEQ ID NO:62), SWCEPGWCR (SEQ ID NO:63), YSGKWGW (SEQ ID NO:64), GLSGGRS (SEQ ID NO:65), LMLPRAD (SEQ ID NO:66), CSCFRDVCC (SEQ ID NO:67), CRDVVSVIC (SEQ ID NO:68), CNGRC (SEQ ID NO:32), and GSL); and tumor targeting peptides as described by Newton & Deutscher, Phage Peptide Display in Handbook of Experimental Pharmacology, pages 145-163, Springer-Verlag, Berlin (2008) (MARSGL (SEQ ID NO:69), MARAKE (SEQ ID NO:70), MSRTMS (SEQ ID NO:71), KCCYSL (SEQ ID NO:72), WRR, WKR, WVR, WVK, WIK, WTR, WVL, WLL, WRT, WRG, WVS, WVA, MYWGDSHWLQYWYE (SEQ ID NO:73), MQLPLAT (SEQ ID NO:74), EWLS (SEQ ID NO:75), SNEW (SEQ ID NO:76), TNYL (SEQ ID NO:77), WIFPWIQL (SEQ ID NO:30), WDLAWMFRLPVG (SEQ ID NO:78), CTVALPGGYVRVC (SEQ ID NO:79), CVPELGHEC (SEQ ID NO:37), CGRRAGGSC (SEQ ID NO:35), CVAYCIEHHCWTC (SEQ ID NO:80), CVFAHNYDYL VC (SEQ ID NO:81), and CVFTSNYAFC (SEQ ID NO:82), VHSPNKK (SEQ ID NO:83), CDCRGDCFC (SEQ ID NO:31), CRGDGWC (SEQ ID NO:84), XRGCDX (SEQ ID NO:85), P:XXS/T (SEQ ID NO:86), CTTHWGFTLC (SEQ ID NO:34), SGKGPRQITAL (SEQ ID NO:87), A9A/Q)(N/A)(L/Y)(TN/M/R)(R/K) (SEQ ID NO:88), VYMSPF (SEQ ID NO:89), MQLPLAT (SEQ ID NO:74), ATWLPPR (SEQ ID NO:90), HTMYYHHYQHHL (SEQ ID NO:91), SEVGCRAGPLQWLCEKYFG (SEQ ID NO:92), CGLLPVGRPDRNVWRWLC (SEQ ID NO:93), CKGQCDRFKGLPWEC (SEQ ID NO:94), SGRSA (SEQ ID NO:95), WGFP (SEQ ID NO:96), LWXXAr [Ar=Y, W, F, H) (SEQ ID NO:97), XF:XXYLW (SEQ ID NO:98), AEPMPHSLNFSQYLWYT (SEQ ID NO:99), WAY(W/F) SP (SEQ ID NO:100), IELLQAR (SEQ ID NO:101), DITWDQLWDLMK (SEQ ID NO:102), AYTKCSRQWRTCMTTH (SEQ ID NO:103), PQNSKIPGPTFLDPH (SEQ ID NO:104), SMEPALPDWWWKMFK (SEQ ID NO:105), ANTPCGPYTHDCPVKR (SEQ ID NO:106), TACHQHVRMVRP (SEQ ID NO:107), VPWMEPAYQRFL (SEQ ID NO:108), DPRATPGS (SEQ ID NO:109), FRPNRAQDYNTN (SEQ ID NO:110), CTKNSYLMC (SEQ ID NO:111), C(R/Q)L/RT(G/N)XXG(AN) GC (SEQ ID NO:112), CPIEDRPMC (SEQ ID NO:113), HEWSYLAPYPWF (SEQ ID NO:114), MCPKHPLGC (SEQ ID NO:115), RMWPSSTVNLSAGRR (SEQ ID NO:116), SAKTAVSQRVWLPSHRGGEP (SEQ ID NO:117), KSREHVNNSACPSKRITAAL (SEQ ID NO:118), EGFR (SEQ ID NO:119), RVS, AGS, AGLGVR (SEQ ID NO:120), GGR, GGL, GSV, GVS, GTRQGHTMRLGVSDG (SEQ ID NO:121), IAGLATPGWSHWLAL (SEQ ID NO:122), SMSIARL (SEQ ID NO:123), HTFEPGV (SEQ ID NO:124), NTSLKRISNKRIRRK (SEQ ID NO:125), LRIKRKRRKRKKTRK (SEQ ID NO:126), GGG, GFS, LWS, EGG, LLV, LSP, LBS, AGG, GRR, GGH and GTV).

As yet a further alternative, the targeting sequence may be a peptide that can be used for chemical coupling (e.g., can comprise arginine and/or lysine residues that can be chemically coupled through their R groups) to another molecule that targets entry into a cell.

As another option, the AAV capsid protein or virus capsid of the invention can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV. Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.). The foregoing embodiments of the invention can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA: α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV2, the specific amino acid position(s) may be different than the position in AAV2 (see, e.g., Table 3). As discussed elsewhere herein, the corresponding amino acid position(s) will be readily apparent to those skilled in the art using well-known techniques.

In representative embodiments, the insertion and/or substitution and/or deletion in the capsid protein(s) results in the insertion, substitution and/or repositioning of an amino acid that (i) maintains the hydrophilic loop structure in that region; (ii) an amino acid that alters the configuration of the loop structure; (iii) a charged amino acid; and/or (iv) an amino acid that can be phosphorylated or sulfated or otherwise acquire a charge by post-translational modification (e.g., glycosylation) following 264 in an AAV2 capsid protein or a corresponding change in a capsid protein of another AAV. Suitable amino acids for insertion/substitution include aspartic acid, glutamic acid, valine, leucine, lysine, arginine, threonine, serine, tyrosine, glycine, alanine, proline, asparagine, phenylalanine, tyrosine or glutamine. In particular embodiments, a threonine is inserted or substituted into the capsid subunit. Nonlimiting examples of corresponding positions in a number of other AAV are shown in Table 3 (Position 2). In particular embodiments, the amino acid insertion or substitution is a threonine, aspartic acid, glutamic acid or phenylalanine (excepting AAV that have a threonine, glutamic acid or phenylalanine, respectively, at this position).

According to this aspect of the invention, in some embodiments the AAV capsid protein comprises an amino acid insertion following amino acid position 264 in an AAV2, AAV3a or AAV3b capsid protein(s) or in the corresponding position in an AAV2, AAV3a or AAV3b capsid protein that has been modified to comprise non-AAV2, AAV3a or AAV3b sequences, respectively, and/or has been modified by deletion of one or more amino acids (i.e., is derived from AAV2, AAV3a or AAV3b). The amino acid corresponding to position 264 in an AAV2 (or AAV3a or AAV3b) capsid subunit(s) will be readily identifiable in the starting virus that has been derived from AAV2 (or AAV3a or AAV3b), which can then be further modified according to the present invention. Suitable amino acids for insertion include aspartic acid, glutamic acid, valine, leucine, lysine, arginine, threonine, serine, tyrosine, glycine, alanine, proline, asparagine, phenylalanine, tyrosine or glutamine.

In other embodiments, the AAV capsid protein comprises an amino acid substitution at amino acid position 265 in an AAV1 capsid protein(s), at amino acid position 266 in an AAV8 capsid protein, or an amino acid substitution at amino acid position 265 in an AAV9 capsid protein or in the corresponding position in an AAV1, AAV8 or AAV9 capsid protein that has been modified to comprise non-AAV1, non-AAV8 or non-AAV9 sequences, respectively, and/or has been modified by deletion of one or more amino acids (i.e., is derived from AAV1, AAV8 or AAV9). The amino acid corresponding to position 265 in an AAV1 and AAV9 capsid subunit(s) and position 266 in the AAV8 capsid subunit(s) will be readily identifiable in the starting virus that has been derived from AAV1, AAV8 or AAV9, which can then be further modified according to the present invention. Suitable amino acids for insertion include aspartic acid, glutamic acid, valine, leucine, lysine, arginine, threonine, serine, tyrosine, glycine, alanine, proline, asparagine, phenylalanine, tyrosine or glutamine.

In representative embodiments of the invention, the capsid protein comprises a threonine, aspartic acid, glutamic acid, or phenylalanine following amino acid position 264 of the AAV2 capsid protein (i.e., an insertion) or the corresponding position of another capsid protein.

In other representative embodiments, the modified capsid proteins or virus capsids of the invention further comprise one or more mutations as described in WO 2007/089632 (e.g., an E7K mutation at amino acid position 531 of the AAV2 capsid protein or the corresponding position of the capsid protein from another AAV).

In further embodiments, the modified capsid protein or capsid can comprise a mutation as described in WO 2009/108274.

As another, possibility, the AAV capsid protein can comprise a mutation as described by Zhong et al. (*Virology* 381: 194-202 (2008); *Proc. Nat. Acad. Sci.* 105: 7827-32 (2008)). For example, the AAV capsid protein can comprise an YF mutation at amino acid position 730.

The modifications described above can be incorporated into the capsid proteins or capsids of the invention in combination with each other and/or with any other modification now known or later discovered.

The invention also encompasses virus vectors comprising the modified capsid proteins and capsids of the invention. In particular embodiments, the virus vector is a parvovirus vector (e.g., comprising a parvovirus capsid and/or vector genome), for example, an AAV vector (e.g., comprising an AAV capsid and/or vector genome). In representative embodiments, the virus vector comprises a modified AA V capsid comprising a modified capsid protein subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid encoding a polypeptide or functional RNA of interest. Recombinant virus vectors are described in more detail below.

In some embodiments, the virus vectors of the invention (i) have reduced transduction of liver as compared with the level of transduction by a virus vector without the modified capsid proteins of this invention; (ii) exhibit enhanced systemic transduction by the virus vector in an animal subject as compared with the level observed by a virus vector without the modified capsid proteins of this invention; (iii) demonstrate enhanced movement across endothelial cells as compared with the level of movement by a virus vector without the modified capsid proteins of this invention, and/or (iv) exhibit a selective enhancement in transduction of muscle tissue (e.g., skeletal muscle, cardiac muscle and/or diaphragm muscle), and/or (v) reduced transduction of brain tissues (e.g., neurons) as compared with the level of transduction by a virus vector without the modified capsid proteins of this invention. In some embodiments, the virus vector has systemic transduction toward muscle, e.g., it transduces multiple skeletal muscle groups throughout the body and optionally transduces cardiac muscle and/or diaphragm muscle.

Further, in some embodiments of the invention, the modified virus vectors demonstrate efficient transduction of target tissues.

It will be understood by those skilled in the art that the modified capsid proteins, virus capsids, virus vectors and AAV particles of the invention exclude those capsid proteins, capsids, virus vectors and AAV particles as they would be present or found in their native state.

Methods of Producing Virus Vectors

The present invention further provides methods of producing the inventive virus vectors of this invention as AAV particles. Thus, the present invention provides a method of making an AAV particle comprising the AAV capsid of this invention, comprising: (a) transfecting a host cell with one or more plasmids that provide, in combination all functions and genes needed to assemble AAV particles; (b) introducing one or more nucleic acid constructs into a packaging cell line or producer cell line to provide, in combination, all functions and genes needed to assemble AAV particles; (c) introducing into a host cell one or more recombinant baculovirus vectors that provide in combination all functions and genes needed to assemble AAV particles; and/or (d) introducing into a host cell one or more recombinant herpesvirus vectors that provide in combination all functions and genes needed to assemble AAV particles. The conditions for formation of an AAV virion are the standard conditions for production of AAV vectors in cells (e.g., mammalian or insect cells), which includes as a nonlimiting example transfection of cells in the presence of an Ad helper plasmid, or other helper virus such as HSV.

Nonlimiting examples of various methods of making the virus vectors of this invention are described in Clement and Grieger ("Manufacturing of recombinant adeno-associated viral vectors for clinical trials" *Mol. Ther. Methods Clin Dev.* 3:16002 (2016)) and in Grieger et al. ("Production of recombinant adeno-associated virus vectors using suspension HEK293 cells and continuous harvest of vector from the culture media for GMP FIX and FLT1 clinical vector" *Mol Ther* 24(2):287-297 (2016)), the entire contents of which are incorporated by reference herein.

In one representative embodiment, the present invention provides a method of producing a virus vector, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

In one embodiment, the nucleic acid template is altered so that the cap sequences cannot express all three viral structural proteins, VP1, VP2, and VP3 from a nucleic acid sequence only from one serotype (first nucleic acid sequence). This alteration can be by, for example, eliminating start codons for at least one of the viral structural proteins. The template will also contain at least one additional nucleic acid sequence (second nucleic acid sequence) from a different serotype encoding and capable of expressing the viral structural protein not capable of being expressed by the first nucleic acid sequence, wherein the second nucleic acid sequence is not capable of expressing the viral structural protein capable of expression by the first nucleic acid sequence. In one embodiment, the first nucleic acid sequence is capable of expressing two of the viral structural proteins whereas the second nucleic acid sequence is capable of expressing only the remaining viral sequence. For example, the first nucleic acid sequence is capable of expression of VP1 and VP2 but not VP3 from one serotype and the second nucleic acid sequence is capable of expression of VP3 from an alternative serotype, but not VP1 or VP2. The template is not capable of expressing any other of the three viral structural proteins. In one embodiment the first nucleic acid sequence is only capable of expressing one of the three viral structural proteins, the second nucleic acid sequence is capable of expressing only the other two viral structural proteins, but not the first.

In another embodiment there is a third nucleic acid sequence from a third serotype. In this embodiment each of the three nucleic acid sequences is only capable of expressing one of the three capsid viral structural proteins, VP1, VP2, and VP3, and each does not express a viral structural protein expressed by another of the sequences so that collectively a capsid is produced containing VP1, VP2, and VP3, wherein each of the viral structural proteins in the capsid are all from the same serotype only and in this embodiment VP1, VP2, and VP3 are all from different serotypes.

The alteration to prevent expression can be by any means known in the art. For example, eliminating start codons, splice acceptors, splice donors, and combinations thereof. Deletions and additions can be use as well as site specific changes to change reading frames. Nucleic acid sequences can also be synthetically produced. These helper templates typically do not contain ITRs.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other Ela trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158: 67).

As a further alternative, the rep/cap sequences may be stably incorporated into a cell. Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the Ela or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper viruses sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the Ela or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al., ((2001) *Gene Ther.* 18:704-12) describe a chimeric helper comprising both adenovirus and the AAV rep and cap genes.

Herpesvirus may also be used as a helper virus in AAV packaging methods.

Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Therapy* 6:986 and WO 00/17377.

As a further alternative, the virus vectors of the invention can be produced in insect cells using baculovirus vectors to deliver the rep/cap genes and rAAV template as described, for example, by Urabe et al., (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The present invention provides a method of administering a nucleic acid molecule to a cell, the method comprising contacting the cell with the virus vector, the AAV particle and/or the composition or pharmaceutical formulation of this invention.

The present invention further provides a method of delivering a nucleic acid to a subject, the method comprising administering to the subject the virus vector, the AAV particle and/or the composition or pharmaceutical formulation of this invention.

In particular embodiments, the subject is human, and in some embodiments, the subject has or is at risk for a disorder that can be treated by gene therapy protocols. Nonlimiting examples of such disorders include a muscular dystrophy including Duchenne or Becker muscular dystrophy, hemophilia A, hemophilia B, multiple sclerosis, diabetes mellitus, Gaucher disease, Fabry disease, Pompe disease, cancer, arthritis, muscle wasting, heart disease including congestive heart failure or peripheral artery disease, intimal hyperplasia, a neurological disorder including: epilepsy, Huntington's disease, Parkinson's disease or Alzheimer's disease, an autoimmune disease, cystic fibrosis, thalassemia, Hurler's Syndrome, Sly syndrome, Scheie Syndrome, Hurler-Scheie Syndrome, Hunter's Syndrome, Sanfilippo Syndrome A, B, C, D, Morquio Syndrome, Maroteaux-Lamy Syndrome, Krabbe's disease, phenylketonuria, Batten's disease, spinal cerebral ataxia, LDL receptor deficiency, hyperammonemia, anemia, arthritis, a retinal degenerative disorder including macular degeneration, adenosine deaminase deficiency, a metabolic disorder, and cancer including tumor-forming cancers.

In some embodiments of the methods of this invention, the virus vector, the AAV particle and/or the composition or pharmaceutical formulation of this invention can be administered to skeletal muscle, cardiac muscle and/or diaphragm muscle.

In the methods described herein, the virus vector, the AAV particle and/or the composition or pharmaceutical formulation of this invention can be administered/delivered to a subject of this invention via a systemic route (e.g., intravenously, intraarterially, intraperitoneally, etc.). In some embodiments, the virus vector and/or composition can be administered to the subject via an intracerebroventrical, intracisternal, intraparenchymal, intracranial and/or intrathecal route. In particular embodiments, the virus vector and/or pharmaceutical formulation of this invention are administered intravenously.

The virus vectors of the present invention are useful for the delivery of nucleic acid molecules to cells in vitro, ex vivo, and in vivo. In particular, the virus vectors can be advantageously employed to deliver or transfer nucleic acid molecules to animal cells, including mammalian cells.

Any heterologous nucleic acid sequence(s) of interest may be delivered in the virus vectors of the present invention. Nucleic acid molecules of interest include nucleic acid molecules encoding polypeptides, including therapeutic (e.g., for medical or veterinary uses) and/or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g., Vincent et al., (1993) *Nature Genetics* 5:130; U.S. Patent Publication No. 2003/017131; International Patent Publication No. WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) Nature 384:349), mini-utrophin, dotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, α-globin, spectrin, $\alpha_1$-antitrypsin, adenosine deaminase, hypoxanthine guanine phosphoribosyl transferase, glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factor-α soluble receptor), S100A1, parvalbumin, adenylyl cyclase type 6, a molecule that modulates calcium handling (e.g., SERCA2A, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein (GFP), luciferase, β-galactosidase, alkaline phosphatase, luciferase, and chloramphenicol acetyltransferase gene.

Optionally, the heterologous nucleic acid molecule encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid molecule may encode an antisense nucleic acid molecule, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn)

RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid molecule that shares homology with and recombines with a locus on a host cell chromosome. This approach can be utilized, for example, to correct a genetic defect in the host cell.

The present invention also provides virus vectors that express an immunogenic polypeptide, peptide and/or epitope, e.g., for vaccination. The nucleic acid molecule may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882,652, and 5,863,541 to Samulski et al.). The antigen may be presented in the parvovirus capsid. Alternatively, the immunogen or antigen may be expressed from a heterologous nucleic acid molecule introduced into a recombinant vector genome. Any immunogen or antigen of interest as described herein and/or as is known in the art can be provided by the virus vector of the present invention.

An immunogenic polypeptide can be any polypeptide, peptide, and/or epitope suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env gene products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.,* 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid molecule can encode any polypeptide, peptide and/or epitope that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid molecule(s) of interest can be operably associated with appropriate control sequences. For example, the heterologous nucleic acid molecule can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid molecule(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence.

The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acid molecules into a broad range of cells, including dividing and non-dividing cells. The virus vectors can be employed to deliver a nucleic acid molecule of interest to a cell in vitro, e.g., to produce a polypeptide in vitro or for ex vivo or in vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide.

Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid molecule encoding a polypeptide or functional RNA to treat and/or prevent any disorder or disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO 2003/095647], antisense against U7 snRNAs to induce exon skipping [see, e.g., WO 2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (al-antitrypsin), Lesch-Nyhan Syndrome (hypoxanthine guanine phosphoribosyl transferase), Niemann-Pick disease (sphingomyelinase), Tay-Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, and interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid molecule can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers.

Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector expressing a cancer cell antigen according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin-5, interleukin-6, interleukin-7, interleukin-8, interleukin-9, interleukin-10, interleukin-11, interleukin-12, interleukin-1β, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors, AAV particles and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc.

Human subjects include neonates, infants, juveniles, adults and geriatric subjects.

In representative embodiments, the subject is "in need of" the methods of the invention.

In particular embodiments, the present invention provides a pharmaceutical composition comprising a virus vector and/or capsid and/or AAV particle of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form. For administration to a subject or for other pharmaceutical uses, the carrier will be sterile and/or physiologically compatible.

By "pharmaceutically acceptable" it is meant a material that is not toxic or otherwise undesirable, i.e., the material may be administered to a subject without causing any undesirable biological effects.

One aspect of the present invention is a method of transferring a nucleic acid molecule to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above).

The degree of protection conferred need not be complete or permanent, as long as the benefits of administering the immunogenic polypeptide outweigh any disadvantages thereof.

A further aspect of the invention is a method of administering the virus vector and/or virus capsid to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$ to about $10^{13}$ transducing units.

In particular embodiments, more than one administration (e.g., two, three, four, five, six, seven, eight, nine, ten, etc., or more administrations) may be employed to achieve the desired level of gene expression over a period of various intervals, e.g., hourly, daily, weekly, monthly, yearly, etc. Dosing can be single dosage or cumulative (serial dosing), and can be readily determined by one skilled in the art. For instance, treatment of a disease or disorder may comprise a one-time administration of an effective dose of a pharmaceutical composition virus vector disclosed herein. Alternatively, treatment of a disease or disorder may comprise multiple administrations of an effective dose of a virus vector carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a virus vector disclosed herein can be administered to an individual once every six months for an indefinite period of time, or until the individual no longer requires therapy. A person of ordinary skill in the art will recognize that the condition of the individual can be monitored throughout the course of treatment and that the effective amount of a virus vector disclosed herein that is administered can be adjusted accordingly.

In an embodiment, the period of administration of a virus vector is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or capsid can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or capsid. In representative embodiments, a depot comprising the virus vector and/or capsid is implanted into skeletal, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector and/or virus capsid according to the present invention is administered to skeletal muscle, diaphragm muscle and/or cardiac muscle (e.g., to treat and/or prevent muscular dystrophy, heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-$\alpha 2$, $\alpha$-sarcoglycan, $\beta$-sarcoglycan, $\gamma$-sarcoglycan, $\delta$-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [α-galactosidase A] or a glycogen storage disorder such as Pompe disease [lysosomal acid α glucosidase]). Other suitable proteins for treating and/or preventing metabolic disorders are described herein. The use of muscle as a platform to express a nucleic acid of interest is described in U.S. Patent publication US 2002/0192189.

Thus, as one aspect, the invention further encompasses a method of treating and/or preventing a metabolic disorder in a subject in need thereof, the method comprising: administering a treatment or prevention effective amount of a virus vector of the invention to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1 and fragments thereof (e.g., I1C), S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US2004/0013645. The virus vectors and/or virus capsids disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors and virus capsids can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay-Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector.

The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye may be by topical application of liquid droplets. As a further alternative, the virus vector and/or capsid may be administered as a solid, slow-release formulation (see, e.g., U.S. Pat. No. 7,201, 898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

In other aspects of this embodiment, a virus vector reduces the severity of a disease or disorder by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a virus vector reduces the severity of a disease or disorder from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A virus vector disclosed herein may comprise a solvent, emulsion or other diluent in an amount sufficient to dissolve a virus vector disclosed herein. In other aspects of this embodiment, a virus vector disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, a virus vector disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20%

(v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

Aspects of the present specification disclose, in part, treating an individual suffering from a disease or disorder. As used herein, the term "treating," refers to reducing or eliminating in an individual a clinical symptom of the disease or disorder; or delaying or preventing in an individual the onset of a clinical symptom of a disease or disorder. For example, the term "treating" can mean reducing a symptom of a condition characterized by a disease or disorder, by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with a specific disease or disorder are well known and can be determined by a person of ordinary skill in the art by taking into account factors, including, without limitation, the location of the disease or disorder, the cause of the disease or disorder, the severity of the disease or disorder, and/or the tissue or organ affected by the disease or disorder. Those of skill in the art will know the appropriate symptoms or indicators associated with a specific type of disease or disorder and will know how to determine if an individual is a candidate for treatment as disclosed herein.

In aspects of this embodiment, a therapeutically effective amount of a virus vector disclosed herein reduces a symptom associated with a disease or disorder by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a virus vector disclosed herein reduces a symptom associated with a disease or disorder by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a virus vector disclosed herein reduces a symptom associated with disease or disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In one embodiment, a virus vector disclosed herein is capable of increasing the level and/or amount of a protein encoded in the virus vector that is administered to a patient by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, virus vector is capable of reducing the severity of a disease or disorder in an individual suffering from the disease or disorder by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In aspects of this embodiment, a therapeutically effective amount of a virus vector disclosed herein increases the amount of protein that is encoded within the virus vector in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100% as compared to an individual not receiving the same treatment. In other aspects of this embodiment, a therapeutically effective amount of a virus vector disclosed herein reduces the severity of a disease or disorder or maintains the severity of a disease or disorder in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a virus vector disclosed herein reduces or maintains the severity of a disease or disorder in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

A virus vector is administered to an individual or a patient. An individual or a patient is typically a human being, but can be an animal, including, but not limited to, dogs, cats, birds, cattle, horses, sheep, goats, reptiles and other animals, whether domesticated or not.

In an embodiment, a virus vector of the present invention can be used to create an AAV that targets a specific tissue including, but not limited to, the central nervous system, retina, heart, lung, skeletal muscle and liver. These targeted virus vectors can be used to treat diseases that are tissue specific, or for the production of proteins that are endogenously produced in a specific normal tissue, such as a Factor IX (FIX), Factor VIII, FVIII and other proteins known in the art.

Diseases of the Central Nervous System

In an embodiment, diseases of the central nervous system can be treated using an AAV, wherein the AAV comprises a recipient AAV that can be any AAV serotype and a donor capsid that is selected from one or more of AAV1, AAV2, AAV3, AAV4, AAV5, AAV7, AAV8, AAV9 or AAV10. In one embodiment, the recipient AAV is an AAV2 and the donor capsid that is selected from one or more of AAV1, AAV2, AAV3, AAV4, AAV5, AAV7, AAV8, AAV9 or AAV10. In another embodiment, the recipient AAV is AAV3 and the donor capsid that is selected from one or more of AAV1, AAV2, AAV3, AAV4, AAV5, AAV7, AAV8, AAV9 or AAV10.

Diseases of the Retina

In an embodiment, diseases of the retina can be treated using an AAV, wherein the AAV comprises a recipient AAV that can be any AAV serotype and a donor capsid that is selected from one or more of AAV1, AAV2, AAV3, AAV4, AAV5, AAV7, AAV8, AAV9 or AAV10. In one embodiment, the recipient AAV is an AAV2 and the donor capsid that is selected from one or more of AAV1, AAV2, AAV3, AAV4, AAV5, AAV7, AAV8, AAV9 or AAV10. In another embodiment, the recipient AAV is AAV3 and the donor capsid is selected from AAV1, AAV2, AAV3, AAV4, AAV5, AAV7, AAV8, AAV9 or AAV10.

Diseases of the Heart

In a further embodiment, diseases of the heart can be treated using an AAV, wherein the AAV comprises a recipient AAV that can be any AAV serotype and the donor capsid that is selected from one or more of AAV1, AAV3, AAV4, AAV6 or AAV9. In an additional embodiment, the recipient AAV is an AAV2 and the donor capsid that is selected from one or more of AAV1, AAV3, AAV4, AAV6 or AAV9. In another embodiment, the recipient AAV is an AAV3, and the donor capsid that is selected from one or more of AAV1, AAV3, AAV4, AAV6 or AAV9.

Diseases of the Lung

In an embodiment, diseases of the lung can be treated using an AAV, wherein the AAV serotype comprises a recipient AAV that can be any AAV serotype and the donor capsid that is selected from one or more of AAV1, AAV5, AAV6, AAV9 or AAV10. In another embodiment, the recipient AAV is AAV2 and the donor capsid that is selected from one or more of AAV1, AAV5, AAV6, AAV9 or AAV10. In a further embodiment, the recipient AAV is AAV3 and the donor capsid is selected from that is selected from one or more of AAV1, AAV5, AAV6, AAV9 or AAV10.

Diseases of the Skeletal Muscle

In a further embodiment, diseases of the skeletal muscles can be treated using an AAV, wherein the AAV serotype comprises a recipient AAV that can be any AAV serotype and the donor capsid that is selected from one or more of AAV1, AAV2, AAV6, AAV7, AAV8, or AAV9. In another embodiment, the recipient AAV is AAV2 and the donor capsid that is selected from one or more of AAV1, AAV2, AAV6, AAV7, AAV8, or AAV9. In an embodiment, the recipient AAV is AAV3 and the donor capsid that is selected from one or more of AAV1, AAV2, AAV6, AAV7, AAV8, or AAV9.

Diseases of the Liver

In an embodiment, diseases of the liver can be treated using an AAV, wherein the AAV serotype comprises a recipient AAV that can be any AAV and the donor capsid that is selected from one or more of AAV2, AAV3, AAV6, AAV7, AAV8, or AAV9. In an additional embodiment, the recipient AAV is AAV2 and the donor capsid that is selected from one or more of AAV2, AAV3, AAV6, AAV7, AAV8, or AAV9. In a further embodiment, the recipient AAV is AAV3 and the donor capsid that is selected from one or more of AAV2, AAV3, AAV6, AAV7, AAV8, or AAV9.

In some embodiments, the present application may be defined in any of the following paragraphs:

1. An isolated AAV virion having at least two viral structural proteins from the group consisting of AAV capsid proteins, VP1, VP2, and VP3, wherein the two viral proteins are sufficient to form an AAV virion that encapsidates an AAV genome, and wherein at least one of the viral structural proteins present is from a different serotype than the other viral structural protein, and wherein the VP1 is only from one serotype, the VP2 is only from one serotype and the VP3 is only from one serotype.

2. The isolated AAV virion of paragraph 1, wherein all three viral structural proteins are present.

3. The isolated AAV virion of paragraph 2, wherein all three viral structural proteins are from different serotypes.

4. The isolated AAV virion of paragraph 2, wherein only one of the three structural proteins is from a different serotype.

5. The isolated AAV virion of paragraph 4, wherein the one viral structural protein different from the other two viral structural proteins is VP1.

6. The isolated AAV virion of paragraph 4, wherein the one viral structural protein different from the other two viral structural proteins is VP2.

7. The isolated AAV virion of paragraph 4, wherein the one viral structural protein different from the other two viral structural proteins is VP3.

8. A substantially homogenous population of virions of paragraphs 1-7, wherein the population is at least $10^1$ virions.

9. The substantially homogenous population of virions of paragraph 8, wherein the population is at least $10^7$ virions.

10. The substantially homogenous population of virions of paragraph 8, wherein the population is at least $10^7$ to $10^{15}$ virions.

11. The substantially homogenous population of virions of paragraph 8, wherein the population is at least $10^9$ virions.

12. The substantially homogenous population of virions of paragraph 8, wherein the population is at least $10^{10}$ virions.

13. The substantially homogenous population of virions of paragraph 8, wherein the population is at least $10^{11}$ virions.

14. The substantially homogenous population of virions of paragraph 10, where population of virions is at least 95% homogenous.

15. The substantially homogenous population of virions of paragraph 10, where population of virions is at least 99% homogenous.

16. A method to create an adeno-associated virus (AAV) virion comprising contacting cells, under conditions for formation of AAV virions, with a first nucleic acid sequence and a second nucleic acid sequence, wherein the AAV virion is formed from at least VP1, and VP3 viral structural proteins, wherein the first nucleic acid encodes VP1 from a first AAV serotype only but is not capable of expressing VP3 and the second nucleic acid sequence encodes VP3 from a second AAV serotype only that is different than the first AAV serotype and further is not capable of expressing VP1, and wherein, the AAV virion comprises VP1 from the first serotype only and VP3 from the second serotype only, and wherein if VP2 is expressed, it is only from one serotype.

17. The method of paragraph 16, wherein the first nucleic acid has mutations in the start codons of VP2 and VP3 that prevent translation of VP2 and VP3 from an RNA transcribed from the first nucleic acid and further wherein, the second nucleic acid has mutations in the start codon of VP1 that prevent translation of VP1 from an RNA transcribed from the second nucleic acid.

18. The method of paragraph 16, wherein VP2 from only one serotype is expressed. 19. The method of paragraph 18, wherein VP2 is from a different serotype than VP1 and a different serotype than VP3.

20. The method of paragraph 18, wherein VP2 is from the same serotype as VP1.

21. The method of paragraph 18, wherein VP2 is from the same serotype as VP3.

22. The method of paragraph 16, wherein the first AAV serotype is AAV1, AAV2, AAV3, AAV4, AAV5, AAV6, AAV7, AAV8, AAV9, AAV10, AAV11, or an AAV selected from Table 1 or Table 3, or any chimeric of each AAV.

23. The method of paragraph 16, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

24. The method of paragraph 18 wherein an AAV virion is formed from VP1, VP2 and VP3 capsid proteins, wherein the viral structural proteins are encoded in the first nucleic acid from a first AAV serotype only and a second nucleic acid from a second AAV serotype only that is different than the first AAV serotype and further wherein, the first nucleic acid has mutations in the A2 Splice Acceptor Site and further wherein, the second nucleic acid has mutations in the A1 Splice Acceptor Site, and wherein, the polyploid AAV virion comprises VP1 from the first serotype only and VP2 and VP3 from the second serotype only.

25. The method of paragraph 24, wherein the first AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

26. The method of paragraph 24, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

27. The method of paragraph 18, wherein the viral structural proteins are encoded in the first nucleic acid sequence from a first AAV serotype only, that is different from the second and third serotypes, the second nucleic acid sequence from a second AAV serotype only that is different than the first and third AAV serotypes and the third nucleic acid sequence from a third AAV serotype only that is different from the first and second AAV serotypes and further wherein, the first nucleic acid sequence has mutations in the start codons of VP2 and VP3 that prevent translation of VP2 and VP3 from an RNA transcribed from the first nucleic acid and further wherein, the second nucleic acid sequence has mutations in the start codons of VP1 and VP3 that prevent translation of VP1 and VP3 from an RNA transcribed from the second nucleic acid sequence and further wherein, the third nucleic acid sequence has mutations in the start codons of VP1 and VP2 that prevent translation of VP1 and VP2 form an RNA transcribed from the third nucleic acid, and wherein, the AAV virion comprises VP1 form the first serotype only, VP2 from the second serotype only, and VP3 from the third serotype only.

28. The method of paragraph 27, wherein the first AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

29. The method of paragraph 27, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

30. The method of paragraph 27, wherein the third AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

31. The method of paragraph 18 wherein, the first nucleic acid sequence has mutations in the start codons of VP2 and VP3 that prevent translation of VP2 and VP3 from an RNA transcribed from the first nucleic acid sequence and a mutation in the A2 Splice Acceptor Site and further wherein, the second nucleic acid sequence has mutations in the start codon of VP1 that prevent translation of VP1 from an RNA transcribed from the second nucleic acid sequence and a mutation in the A1 Splice Acceptor Site, and wherein, the AAV polyploid capsid comprises VP1 form the first serotype only and VP2 and VP3 from the second serotype only.

32. The method of paragraph 31, wherein the first AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

33. The method of paragraph 31, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

34. The method of paragraph 18, wherein the viral structural proteins are encoded in the first nucleic acid sequence are created through DNA shuffling of two or more different AAV serotypes and further wherein, the start codons for VP2 and VP3 are mutated such that VP2 and VP3 cannot be translated from an RNA transcribed from the first nucleic acid sequence, and further wherein, the capsid proteins are encoded in the second nucleic acid from a single AAV serotype only, wherein the second nucleic acid has mutations in the start codon of VP1 that prevent translation of VP1 from an RNA transcribed from the second nucleic acid, and wherein, the polyploid AAV capsid comprises VP1 form the first nucleic acid sequence created through DNA shuffling and VP2 and VP3 from the second serotype only.

35. The method of paragraph 18, wherein the viral structural proteins are encoded in the first nucleic acid sequence are created through DNA shuffling of two or more different AAV serotypes and further wherein, the start codons for VP2 and VP3 are mutated such that VP2 and VP3 cannot be translated from an RNA transcribed from the first nucleic acid and the A2 Splice Acceptor Site of the first nucleic acid is mutated, and further wherein, the capsid proteins are encoded in the second nucleic acid sequence from a single AAV serotype only, wherein the second nucleic action has mutations in the start codon of VP1 that prevent translation of VP1 from an RNA transcribed from the second nucleic acid and a mutation in the A1 Splice Acceptor Site, and wherein, the polyploid AAV capsid comprises VP1 form the first nucleic acid created through DNA shuffling and VP2 and VP3 from the second serotype only.

36. The virion of paragraph 15, wherein the AAV serotype is selected from the group consisting of AAV1, AAV2, AAV3, AAV4, AAV5, AAV6, AAV7, AAV8, AAV9, AAV10, AAV11, an AAV selected from Table 1 or Table 3, and any chimeric of each AAV.

37. A substantially homogenous population of virions produced by the method of paragraph 16.

38. A substantially homogenous population of virions produced by the method of paragraph 18.

39. The AAV virion of paragraph 38, wherein the heterologous gene encodes a protein to treat a disease.

40. The AAV virion of paragraph 39, wherein the disease is selected from a lysosomal storage disorder such as a mucopolysaccharidosis disorder (e.g., Sly syndrome[-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

41. The isolated AAV virion of paragraphs 1-7, wherein at least one of the viral structural proteins is a chimeric viral structural protein.

42. The isolated AAV virion of paragraph 41, wherein the chimeric viral structural protein is from AAV serotypes, but different from the other viral structural proteins.

43. The isolate AAV virion of paragraphs 1-7, wherein none of the viral structural proteins are chimeric viral structural proteins.

44. The isolated AAV virion of paragraph 41, wherein there is no overlap in serotypes between the chimeric viral structural protein and at least one other viral structural protein.

45. A method of modulating transduction using the method of paragraphs 16-35.

46. The method of paragraph 45, wherein the method enhances transduction.

47. A method of changing tropism of an AAV virion comprising using the method of paragraphs 16-35.

48. A method of changing immunogenicity of an AAV virion comprising using the method of paragraphs 16-35.

49. A method of increasing vector genome copy number in tissues comprising using the method of paragraphs 16-35.

50. A method for increasing transgene expression comprising using the method of paragraphs 16-35.

51. A method of treating a disease comprising administering an effective amount of the virion of paragraphs 1-7, 36, 43, and 44, the substantially homogenous population of virions of paragraphs 8-15, 37-42, and 44, or the virions made by the method of paragraphs 16-35, wherein the heterologous gene encodes a protein to treat a disease suitable for treatment by gene therapy to a subject having the disease.

52. The method of paragraph 51, wherein the disease is selected from genetic disorders, cancers, immunological diseases, inflammation, autoimmune diseases and degenerative diseases.

53. The method of paragraphs 51 and 52, wherein multiple administrations are made.

54. The method of paragraph 53, wherein different polyploid virions are used to evade neutralizing antibodies formed in response to a prior administration.

55. A method of increasing at least one of transduction, copy number, and transgene expression over an AAV vector having a particle having all its viral structural proteins from only one serotype comprising administering the AAV virion of paragraphs 1-15 and 36-44.

56. An isolated AAV virion having viral capsid structural proteins sufficient to form an AAV virion that encapsidates an AAV genome, wherein at least one of the viral capsid structural proteins is different from the other viral capsid structural proteins, and wherein the virion only contains the same type of each of the structural proteins.

57. The isolated AAV virion of paragraph 56 having at least two viral structural proteins from the group consisting of AAV capsid proteins, VP1, VP2, and VP3, wherein the two viral proteins are sufficient to form an AAV virion that encapsidates an AAV genome, and wherein at least one of the other viral structural proteins present is different than the other viral structural protein, and wherein the virion contains only the same type of each structural protein.

58. The isolated AAV virion of paragraph 57, wherein all three viral structural proteins are present.

59. The isolated AAV virion of paragraph 58, further comprising a fourth AAV structural protein.

60. The isolated AAV virion of paragraph 56 having at least two viral structural proteins from the group consisting of AAV capsid proteins, VP1, VP2, VP1.5 and VP3, wherein the two viral proteins are sufficient to form an AAV virion that encapsidates an AAV genome, and wherein at least one of the viral structural proteins present is from a different serotype than the other viral structural protein, and wherein the VP1 is only from one serotype, the VP2 is only from one serotype, the VP1.5 is only from one serotype, and the VP3 is only from one serotype.

61. The isolated AAV virion of paragraphs 57-60, wherein at least one of the viral structural proteins is a chimeric protein that is different from at least one of the other viral structural proteins.

62. The virion of paragraph 61, wherein only VP3 is chimeric and VP1 and VP2 are non-chimeric.

63. The virion of paragraph 61, wherein only VP1 and VP2 are chimeric and only VP3 is non-chimeric.

64. The virion of paragraph 63 wherein the chimeric is comprised of subunits from AAV serotypes 2 and 8 and VP3 is from AAV serotype 2.

65. The isolated AAV virion of paragraphs 56-64, wherein all the viral structural proteins are from different serotypes.

66. The isolated AAV virion of paragraphs 56-64, wherein only one of the structural proteins is from a different serotype.

67. A substantially homogenous population of virions of paragraphs 56-66, wherein the population is at least $10^7$ virions.

68. The substantially homogenous population of virions of paragraph 67, wherein the population is at least $10^7$ to $10^{15}$ virions.

69. The substantially homogenous population of virions of paragraph 67, wherein the population is at least $10^9$ virions.

70. The substantially homogenous population of virions of paragraph 67, wherein the population is at least $10^{10}$ virions.

71. The substantially homogenous population of virions of paragraph 67, wherein the population is at least $10^{11}$ virions.

72. The substantially homogenous population of virions of paragraphs 67-71, where population of virions is at least 95% homogenous.

73. The substantially homogenous population of virions of paragraph 72, where population of virions is at least 99% homogenous.

74. The virion of paragraphs 56-73, wherein the AAV serotype is selected from the group consisting of AAV1, AAV2, AAV3, AAV4, AAV5, AAV6, AAV7, AAV8, AAV9, AAV10, AAV11, an AAV selected from Table 1 or Table 3, and any chimeric of each AAV.

75. A substantially homogenous population of virions of paragraph 73.

76. The AAV virion of paragraphs 56-74, wherein the heterologous gene encodes a protein to treat a disease.

77. The AAV virion of paragraph 76, wherein the disease is selected from a lysosomal storage disorder such as a mucopolysaccharidosis disorder (e.g., Sly syndrome[-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

78. The isolated AAV virion of paragraphs 56-60 and 66-77, wherein none of the viral structural proteins are chimeric viral structural proteins.

79. The isolated AAV virion of paragraphs 57-78, wherein there is no overlap in serotypes between the chimeric viral structural protein and at least one other viral structural protein.

80. A method of treating a disease comprising administering an effective amount of the virion of paragraphs 56-66, 74, 76-79, or the substantially homogenous population of virions of paragraphs 67-73 and 75, wherein the heterologous gene encodes a protein to treat a disease suitable for treatment by gene therapy to a subject having the disease.

81. The method of paragraph 80, wherein the disease is selected from genetic disorders, cancers, immunological diseases, inflammation, autoimmune diseases and degenerative diseases.

82. The method of paragraphs 80 and 81, wherein multiple administrations are made. 83. The method of paragraph 82, wherein different polyploid virions are used to evade neutralizing antibodies formed in response to a prior administration.

84. The isolated AAV virion of paragraphs 1-7, 36, 39-44, 56-66, 74, 76-79, the substantially homogenous population of paragraphs 8-15, 37-38, 67-73, 75 and methods of 16-35, 45-55, and 80-83, wherein applicants disclaim as follows: To the extent that any disclosure in PCT/US18/22725 filed Mar. 15, 2018 falls within the invention as defined in any one or more of the claims of this application, or within any invention to be defined in amended claims that may in the future be filed in this application or in any patent derived therefrom, and to the extent that the laws of any relevant country or countries to which that or those claims apply provide that the disclosure of PCT/US18/22725 is part of the state of the art against that or those claims in or for that or those countries, we hereby reserve the right to disclaim the said disclosure from the claims of the present application or any patent derived therefrom to the extent necessary to prevent invalidation of the present application or any patent derived therefrom.

For example, and without limitation, we reserve the right to disclaim any one or more of the following subject-matters from any claim of the present application, now or as amended in the future, or any patent derived therefrom:

A. any subject-matter disclosed in Example 9 of PCT/US18/22725; or

B. vector virions, termed polyploid vector virions, which are produced or producible by transfection of two AAV helper plasmids or three plasmids to produce individual polyploid vector virions composed of different capsid subunits from different serotypes; or C. vector virions, termed polyploid vector virions, which are produced or producible by transfection of two AAV helper plasmids which are AAV2 and AAV8 or AAV9 to produce individual polyploid vector virions composed of different capsid subunits from different serotypes; or D. vector virions, termed polyploid vector virions, which are produced or producible by transfection of three AAV helper plasmids which are AAV2, AAV8 and AAV9 to produce individual polyploid vector virions composed of different capsid subunits from different serotypes; or E. vector virions, termed haploid vectors, with VP1/VP2 from one AAV vector capsid or AAV serotype and VP3 from an alternative one, for example VP1/VP2 from (the capsid of) only one AAV serotype and VP3 from only one alternative AAV serotype; or F. any one or more AAV vector virion(s) selected from:

a vector which is generated by transfection of AAV2 helper and AAV8 helper plasmids (termed haploid AAV2/8) and which has VP1 capsid subunit from AAV8 and VP2/VP3 capsid subunits from AAV2; or a vector which is generated by transfection of AAV2 helper and AAV8 helper plasmids (termed haploid AAV2/8 or haploid AAV8/2 or haploid AAV82 or H-AAV82) and which has VP1/VP2 capsid subunits from AAV8 and VP3 capsid subunit from AAV2; or a vector in which VP1/VP2 is derived from different serotypes; or a vector (termed haploid AAV92 or H-AAV92) which has VP1/VP2 capsid subunits from AAV9 and VP3 capsid subunit from AAV2; or a vector (termed haploid AAV2G9 or H-AAV2G9) which has VP1/VP2 capsid subunits from AAV8 and VP3 capsid subunit from AAV2G9, in which AAV9 glycan receptor binding site was engrafted into AAV2; or a vector (termed haploid AAV83 or H-AAV83) which has VP1/VP2 capsid subunits from AAV8 and VP3 capsid subunit from AAV3; or a vector (termed haploid AAV93 or H-AAV93) which has VP1/VP2 capsid subunits from AAV9 and VP3 capsid subunit from AAV3; or a vector (termed haploid AAVrh10-3 or H-AAVrh10-3) which has VP1/VP2 capsid subunits from AAVrh10 and VP3 capsid subunit from AAV3; or a vector which is generated by transfection of AAV2 helper and AAV8 helper plasmids (termed haploid AAV2/8) and which has VP1 capsid subunit from AAV2 and VP2/VP3 capsid subunits from AAV8; or a vector which is generated by transfection of AAV2 helper and AAV8 helper plasmids (termed haploid AAV2/8) and which has VP1/VP2 capsid subunit from AAV2 and VP3 capsid subunits from AAV8; or a vector which is generated by transfection of AAV2 helper and AAV8 helper plasmids (termed haploid AAV2/8) and which has VP1 capsid subunit from AAV8 and VP3 capsid subunit from AAV2; or a vector which is generated by transfection of AAV2 helper and AAV8 helper plasmids (termed haploid AAV2/8) and which has VP1 capsid subunit from AAV2 and VP3 capsid subunits from AAV8; or a vector which is generated by transfection of AAV2 helper and AAV8 helper plasmids (termed haploid AAV2/8) and which has VP1/VP2/VP3 capsid subunits from AAV2; or a vector which is generated by transfection of AAV2 helper and AAV8 helper plasmids (termed haploid AAV2/8) and which has VP1/VP2/VP3 capsid subunits from AAV8; or a vector termed 28m-2VP3 or haploid 2m-2VP3 or haploid vector 28m-2VP3 in which chimeric VP1/VP2 capsid subunits have N-terminal from AAV2 and C-terminal from AAV8, and the VP3 capsid subunit is from AAV2; or a vector termed chimeric AAV8/2 or chimeric AAV82 in which chimeric VP1/VP2 capsid subunits have N-terminal from AAV8 and C-terminal from AAV2 without mutation of the VP3 start codon and the VP3 capsid subunit is from AAV2; or a vector in which chimeric VP1/VP2 capsid subunits have N-terminal from AAV2 and C-terminal from AAV8; or G. a population, for example a substantially homogenous population, for example a population of 1010 particles, for example a substantially homogenous population of 1010 particles, of any one of the vectors of F; or H. a method of producing any one of the vectors or populations of vectors of A and/or B and/or C and/or D and/or E and/or F and/or G; or I. any combination thereof.

Without limitation, we state that the above reservation of a right of disclaimer applies at least to the original claims as appended to this application and paragraphs 1-83 as set forth herein. The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

In some embodiments, the present application may be defined in any of the following paragraphs:

1. An isolated AAV virion having three viral structural proteins from the group consisting of AAV capsid proteins, VP1, VP2, and VP3, wherein the viral proteins are sufficient to form an AAV virion that encapsidates an AAV genome, and wherein the VP1 and VP2 viral structural proteins present are from the same serotype and the VP3 serotype is from an alternative serotype, and wherein the VP1 and VP2 are only from a single serotype, and the VP3 is only from a single serotype.

2. The isolated AAV virion of paragraph 1 wherein VP1 and VP2 are from AAV serotype 8 or 9 and VP3 is from AAV serotype 3 or 2.

3. The isolated AAV virion of paragraph 1 wherein VP1 and VP2 are from AAV serotype 8 and VP3 is from AAV serotype 2G9.

4. An isolated AAV virion having three viral structural proteins from the group consisting of AAV capsid proteins, VP1, VP2, and VP3, wherein the viral proteins are sufficient to form an AAV virion that encapsidates an AAV genome, and wherein the VP1 and VP2 viral structural proteins present are from the same chimeric serotype and the VP3 serotype is not a chimeric serotype, and wherein the VP1 and VP2 are only from a single chimeric serotype, and the VP3 is only from a single serotype, wherein VP1 and VP2 are from chimeric AAV serotype 28m and VP3 is from AAV serotype 2.

5. The isolated AAV virion of paragraph 1 wherein VP1 and VP2 are from AAV serotype AAV rh10 and VP3 is from AAV serotype 2G9.

6. A method to create an adeno-associated virus (AAV) virion comprising contacting cells, under conditions for formation of AAV virions, with a first nucleic acid sequence and a second nucleic acid sequence, wherein the AAV virion is formed from VP1, VP2, and VP3 viral structural proteins, wherein the first nucleic acid encodes VP1 and VP2 from a first AAV serotype only but is not capable of expressing VP3 and the second nucleic acid sequence encodes VP3 from an alternative AAV serotype that is different than the first AAV serotype and further is not capable of expressing VP1 or VP2, and wherein, the AAV virion comprises VP1 and VP2 only from the first serotype and VP3 only from the second serotype.

7. The AAV virion produced by the method of paragraph 6.

8. The method of paragraph 2, wherein VP1 and VP2 are from AAV serotype 8 or 9 and VP3 is from AAV serotype 3 or 2.

9. The method of paragraph 2, wherein VP1 and VP2 are from AAV serotype 8 and VP3 is from AAV serotype 2G9.

10. A method to create an adeno-associated virus (AAV) virion comprising contacting cells, under conditions for formation of AAV virions, with a first nucleic acid sequence and a second nucleic acid sequence, wherein the AAV virion is formed from VP1, VP2, and VP3 viral structural proteins, wherein the first nucleic acid encodes VP1 and VP2 from a first chimeric AAV serotype only but is not capable of expressing VP3 and the second nucleic acid sequence encodes VP3 from an alternative AAV serotype and further is not capable of expressing VP1 or VP2, wherein VP1 and VP2 are from AAV serotype 28m and VP3 is from AAV serotype 2.

11. The method of paragraph 2, wherein VP1 and VP2 are from AAV serotype AAV rh10 and VP3 is from AAV serotype 2G9.

12. A haploid vector with VP1/VP2 from one AAV vector capsid and VP3 from an alternative one.

13. A haploid vector AAV82 (H-AAV82) with VP1/VP2 from AAV8 and VP3 from AAV2.

14. A haploid vector AAV92 (H-AAV92) with VP1/VP2 from AAV9 and VP3 from AAV2.

15. A haploid vector AAV82 G9 (H-AAV82G9) in which VP1/VP2 is from AAV8 and VP3 is from AAV2G9, wherein AAV2G9 has engrafted AAV9 glycan receptor binding sites into AAV2.

16. A haploid vector AAV83 (H-AAV83), wherein VP1/VP2 is from AAV8 and VP3 is from AAV3.

17. A haploid vector AAV93 (H-AAV93), wherein VP1/VP2 is from AAV9 and VP3 is from AAV3.

18. A haploid vector AAVrh10-3 (H-AAVrh10-3), wherein VP1/VP2 is from AAVrh10 and VP3 is from AAV3.

19. A vector 28m-2VP3 (H-28m-2VP3) in which chimeric VP1/VP2 capsid subunits have N-terminal from AAV2 and C-terminal from AAV8, and the VP3 capsid subunit is from AAV2.

20. A vector termed chimeric AAV8/2 or chimeric AAV82 in which chimeric VP1/VP2 capsid subunits have N-terminal from AAV8 and C-terminal from AAV2 without mutation of the VP3 start codon and the VP3 capsid subunit is from AAV2.

In some embodiments, the present application may be defined in any of the following paragraphs:

1. A method to create a polyploid adeno-associated virus (AAV) capsid comprising contacting cells, under conditions for formation of AAV virions, with a first nucleic acid sequence and a second nucleic acid sequence, wherein an AAV capsid is formed from VP1, VP2 and VP3 capsid proteins, wherein the capsid proteins are encoded in the first nucleic acid from a first AAV serotype only and the second nucleic acid from a second AAV serotype only that is different than the first AAV serotype and further wherein, the first nucleic acid has mutations in the start codons of VP2 and VP3 that prevent translation of VP2 and VP3 from an RNA transcribed from the first nucleic acid and further wherein, the second nucleic acid has mutations in the start codon of VP1 that prevent translation of VP1 from an RNA transcribed from the second nucleic acid, and wherein, the polyploid AAV capsid comprises VP1 from the first serotype only and VP2 and VP3 from the second serotype only.

2. The method of paragraph 1, wherein the first AAV serotype is AAV1, AAV2, AAV3, AAV4, AAV5, AAV6, AAV7, AAV8, AAV9, AAV10, AAV11, or an AAV selected from Table 1 or Table 3, or any chimeric of each AAV.

3. The method of paragraph 1, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

4. A method to create a polyploid adeno-associated virus (AAV) capsid comprising contacting cells, under conditions for formation of AAV virions, with a first nucleic acid sequence, and a second nucleic acid sequence, wherein an AAV capsid is formed from VP1, VP2 and VP3 capsid proteins, wherein the capsid proteins are encoded in the first nucleic acid from a first AAV serotype only and a second nucleic acid from a second AAV serotype only that is different than the first AAV serotype and further wherein, the first nucleic acid has mutations in the A2 Splice Acceptor Site and further wherein, the second nucleic acid has mutations in the A1 Splice Acceptor Site, and wherein, the polyploid AAV capsid comprises VP1 from the first serotype only and VP2 and VP3 from the second serotype only.

5. The method of paragraph 4, wherein the first AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

6. The method of paragraph 4, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

7. A method to create a polyploid adeno-associated virus (AAV) capsid comprising contacting cells, under conditions for formation of AAV virions, with a first nucleic acid sequence, a second nucleic acid sequence, and a third nucleic acid sequence, wherein an AAV capsid is formed from VP1, VP2 and VP3 capsid proteins, wherein the capsid proteins are encoded in the first nucleic acid from a first AAV serotype only that is different from the second and third serotypes, the second nucleic acid from a second AAV serotype only that is different than the first and third AAV serotypes and the third nucleic acid from a third AAV serotype only that is different from the first and second AAV serotypes and further wherein, the first nucleic acid has mutations in the start codons of VP2 and VP3 that prevent translation of VP2 and VP3 from an RNA transcribed from the first nucleic acid and further wherein, the second nucleic acid has mutations in the start codons of VP1 and VP3 that prevent translation of VP1 and VP3 from an RNA transcribed from the second nucleic acid and further wherein, the third nucleic acid has mutations in the start codons of VP1 and VP2 that prevent translation of VP1 and VP2 form an RNA transcribed from the third nucleic acid, and wherein, the polyploid AAV capsid comprises VP1 form the first serotype only, VP2 from the second serotype only and VP3 from the third serotype only.

8. The method of paragraph 7, wherein the first AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

9. The method of paragraph 7, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

10. The method of paragraph 7, wherein the third AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

11. A method to create a polyploid adeno-associated virus (AAV) capsid comprising contacting cells, under conditions for formation of AAV virions, with a first nucleic acid sequence and a second nucleic acid sequence, wherein an AAV capsid is constructed from VP1, VP2 and VP3 capsid proteins, wherein the capsid proteins are encoded in the first nucleic acid from a first AAV serotype only and the second nucleic acid from a second AAV serotype only that is different than the first AAV serotype and further wherein, the first nucleic acid has mutations in the start codons of VP2 and VP3 that prevent translation of VP2 and VP3 from an RNA transcribed from the first nucleic acid and a mutation in the A2 Splice Acceptor Site and further wherein, the second nucleic acid has mutations in the start codon of VP1 that prevent translation of VP1 from an RNA transcribed from the second nucleic acid and a mutation in the A1 Splice Acceptor Site, and wherein, the AAV polyploid capsid comprises VP1 form the first serotype only and VP2 and VP3 from the second serotype only.

12. The method of paragraph 11, wherein the first AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

13. The method of paragraph 11, wherein the second AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

14. A method to create a polyploid adeno-associated virus (AAV) capsid, comprising contacting cells, under conditions for formation of AAV virions, with a first nucleic acid and a second nucleic acid, wherein an AAV capsid is formed from VP1, VP2 and VP3 capsid proteins, wherein the capsid proteins are encoded in the first nucleic acid that is created through DNA shuffling of two or more different AAV serotypes and further wherein, the start codons for VP2 and VP3 are mutated such that VP2 and VP3 cannot be translated from an RNA transcribed from the first nucleic acid, and further wherein, the capsid proteins are encoded in the second nucleic acid from a single AAV serotype only, wherein the second nucleic acid has mutations in the start codon of VP1 that prevent translation of VP1 from an RNA transcribed from the second nucleic acid, and wherein, the polyploid AAV capsid comprises VP1 form the first nucleic acid created through DNA shuffling and VP2 and VP3 from the second serotype only.

15. A method to create a polyploid adeno-associated virus (AAV) capsid comprising contacting cells, under conditions for formation of AAV virions, with a first nucleic acid and a second nucleic acid, wherein an AAV capsid is formed from VP1, VP2 and VP3 capsid proteins, wherein the capsid proteins are encoded in the first nucleic acid that is created through DNA shuffling of two or more different AAV serotypes and further wherein, the start codons for VP2 and VP3 are mutated such that VP2 and VP3 cannot be translated from an RNA transcribed from the first nucleic acid and the A2 Splice Acceptor Site of the first nucleic acid is mutated, and further wherein, the capsid proteins are encoded in the second nucleic acid from a single AAV serotype only, wherein the second nucleic action has mutations in the start codon of VP1 that prevent translation of VP1 from an RNA transcribed from the second nucleic acid and a mutation in the A1 Splice Acceptor Site, and wherein, the polyploid AAV capsid comprises VP1 form the first nucleic acid created through DNA shuffling and VP2 and VP3 from the second serotype only.

16. The method of paragraphs 14 and 15, wherein the AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

17. The method of any of paragraphs 1-16, wherein the AAV capsid has substantially homogenous capsid proteins.

18. The method of paragraph 17, wherein the polyploid adeno-associated virus (AAV) substantially homogenous capsid protein is VP1.

19. The method of paragraph 17, wherein the substantially homogenous capsid protein is VP2.

20. The method of paragraph 17, wherein the substantially homogenous capsid protein is VP3.

21. The method of paragraph 17, wherein the substantially homogenous capsid protein is VP1 and VP2, VP1 and VP3, VP2 and VP3, or VP1 and VP2 and VP3.

22. The method of any of paragraphs 1-21, wherein the polyploid adeno-associated virus (AAV) is in a substantially homogenous population of AAV capsids.

23. The method of paragraph 22, wherein the polyploid adeno-associated virus (AAV) is in a substantially homogenous population of AAV virions comprising capsid protein VP1 of only one serotype.

24. The method of paragraph 22, The method of paragraph 17, wherein the polyploid adeno-associated virus (AAV) is in a substantially homogenous population of AAV virions comprising capsid protein VP2 of only one serotype.

25. The method of paragraph 22, wherein the polyploid adeno-associated virus (AAV) is in a substantially homogenous population of AAV virions comprising capsid protein VP3 of only one serotype.

26. The method of paragraph 22, wherein the polyploid adeno-associated virus (AAV) is in a substantially homogenous population of AAV virions comprising capsid protein VP1 and VP2 of only one serotype, or VP1 and VP3 of only one serotype, or VP2 and VP3 of only one serotype, or VP1 of only one serotype.

27. A polyploid AAV, wherein the polyploid AAV is prepared using the method of any of paragraphs 1-26.

28. The polyploid AAV of any of paragraphs 1-27, wherein the polyploid AAV is constructed from VP1 and VP3 only.

29. A polyploid AAV, wherein the polyploid AAV is prepared using the method of any of paragraphs 1-28 and further wherein, the polyploid AAV includes a heterologous gene.

30. The polyploid AAV of paragraph 29, wherein the heterologous gene encodes a protein to treat a disease.

31. The polyploid AAV of paragraph 30, wherein the disease is selected from a lysosomal storage disorder such as a mucopolysaccharidosis disorder (e.g., Sly syndrome[-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

In some embodiments, the present application may be defined in any of the following paragraphs:

1. An isolated AAV virion having at least two viral structural proteins from the group consisting of AAV capsid proteins, VP1, VP2, and VP3, wherein the two viral proteins are sufficient to form an AAV virion that encapsidates an AAV genome, and wherein at least one of the other viral structural proteins present is different than the other viral structural protein, and wherein the virion contains only the same type of each structural protein.

2. The isolated AAV virion of paragraph 1, wherein all three viral structural proteins are present.

3. The isolated AAV virion of paragraphs 1 and 2, wherein at least one of the viral structural proteins is a chimeric protein that is different from at least one of the other viral structural proteins.

4. The virion of paragraph 3, wherein only VP3 is chimeric and VP1 and VP2 are non-chimeric.

5. The virion of paragraph 3, wherein only VP1 and VP2 are chimeric and only VP3 is non-chimeric.

6. The virion of paragraph 5 wherein the chimeric is comprised of subunits from AAV serotypes 2 and 8 and VP3 is from AAV serotype 2.

7. The isolated AAV virion of paragraphs 1-6, wherein all three viral structural proteins are from different serotypes.

8. The isolated AAV virion of paragraphs 1-6, wherein only one of the three structural proteins is from a different serotype.

9. The substantially homogenous population of virions of paragraph 8, wherein the population is at least $10^7$ virions.

10. The substantially homogenous population of virions of paragraph 8, wherein the population is at least $10^7$ to $10^{15}$ virions.

11. The substantially homogenous population of virions of paragraph 8, wherein the population is at least $10^9$ virions.

12. The substantially homogenous population of virions of paragraph 8, wherein the population is at least $10^{10}$ virions.

13. The substantially homogenous population of virions of paragraph 8, wherein the population is at least $10^{11}$ virions.

14. The substantially homogenous population of virions of paragraphs 9-13, where population of virions is at least 95% homogenous.

15. The substantially homogenous population of virions of paragraph 14, where population of virions is at least 99% homogenous.

16. The virion of paragraphs 1-15, wherein the AAV serotype is AAV1, AAV2, AAV3, AAV4, AAV5, AAV6, AAV7, AAV8, AAV9, AAV10 or AAV11, or an AAV selected from Table 1 or Table 3, or any chimeric of each AAV.

17. A substantially homogenous population of virions of paragraph 16.

18. The AAV virion of paragraphs 1-17, wherein the heterologous gene encodes a protein to treat a disease.

19. The AAV virion of paragraph 18, wherein the disease is selected from a lysosomal storage disorder such as a mucopolysaccharidosis disorder (e.g., Sly syndrome[-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

20. The isolated AAV virion of paragraphs 1-2 and 8-19, wherein none of the viral structural proteins are chimeric viral structural proteins.

21. The isolated AAV virion of paragraphs 1-19, wherein there is no overlap in serotypes between the chimeric viral structural protein and at least one other viral structural protein.

22. A method of treating a disease comprising administering an effective amount of the virion of paragraphs 1-9, 16, 18-21, or the substantially homogenous population of virions of paragraphs 10-15 and 17, wherein the heterologous gene encodes a protein to treat a disease suitable for treatment by gene therapy to a subject having the disease.

23. The method of paragraph 22, wherein the disease is selected from genetic disorders, cancers, immunological diseases, inflammation, autoimmune diseases and degenerative diseases.

24. The method of paragraphs 22 and 23, wherein multiple administrations are made.

25. The method of paragraph 24, wherein different polyploid virions are used to evade neutralizing antibodies formed in response to a prior administration.

26. The isolated AAV virion of paragraphs 1-25, wherein applicants disclaim as follows: To the extent that any disclosure in PCT/US18/22725 filed Mar. 15, 2018 falls within the invention as defined in any one or more of the claims of this application, or within any invention to be defined in amended claims that may in the future be filed in this application or in any patent derived therefrom, and to the extent that the laws of any relevant country or countries to which that or those claims apply provide that the disclosure of PCT/US18/22725 is part of the state of the art against that or those claims in or for that or those countries, we hereby reserve the right to disclaim the said disclosure from the claims of the present application or any patent derived therefrom to the extent necessary to prevent invalidation of the present application or any patent derived therefrom.

For example, and without limitation, we reserve the right to disclaim any one or more of the following subject-matters from any claim of the present application, now or as amended in the future, or any patent derived therefrom:

A. any subject-matter disclosed in Example 9 of PCT/US18/22725; or

B. vector virions, termed polyploid vector virions, which are produced or producible by transfection of two AAV helper plasmids or three plasmids to produce individual polyploid vector virions composed of different capsid subunits from different serotypes; or C. vector virions, termed polyploid vector virions, which are produced or producible by transfection of two AAV helper plasmids which are AAV2 and AAV8 or AAV9 to produce individual polyploid vector virions composed of different capsid subunits from different serotypes; or D. vector virions, termed polyploid vector virions, which are produced or producible by transfection of three AAV helper plasmids which are AAV2, AAV8 and AAV9 to produce individual polyploid vector virions composed of different capsid subunits from different serotypes; or E. vector virions, termed haploid vectors, with VP1/VP2 from one AAV vector capsid or AAV serotype and VP3 from an alternative one, for example VP1/VP2 from (the capsid of) only one AAV serotype and VP3 from only one alternative AAV serotype; or F. any one or more AAV vector virion(s) selected from:

a vector which is generated by transfection of AAV2 helper and AAV8 helper plasmids (termed haploid AAV2/8) and which has VP1 capsid subunit from AAV8 and VP2/VP3 capsid subunits from AAV2; or a vector which is generated by transfection of AAV2 helper and AAV8 helper plasmids (termed haploid AAV2/8 or haploid AAV8/2 or haploid AAV82 or H-AAV82) and which has VP1/VP2 capsid subunits from AAV8 and VP3 capsid subunit from AAV2; or a vector in which VP1/VP2 is derived from different serotypes; or a vector (termed haploid AAV92 or H-AAV92) which has VP1/VP2 capsid subunits from AAV9 and VP3 capsid subunit from AAV2; or a vector (termed haploid AAV2G9 or H-AAV2G9) which has VP1/VP2 capsid subunits from AAV8 and VP3 capsid subunit from AAV2G9, in which AAV9 glycan receptor binding site was engrafted into AAV2; or a vector (termed haploid AAV83 or H-AAV83) which has VP1/VP2 capsid subunits from AAV8 and VP3 capsid subunit from AAV3; or a vector (termed haploid AAV93 or H-AAV93) which has VP1/VP2 capsid subunits from AAV9 and VP3 capsid subunit from AAV3; or a vector (termed haploid AAVrh10-3 or H-AAVrh10-3) which has VP1/VP2 capsid subunits from AAVrh10 and VP3 capsid subunit from AAV3; or a vector which is generated by transfection of AAV2 helper and AAV8 helper plasmids (termed haploid AAV2/8) and which has VP1 capsid subunit from AAV2 and VP2/VP3 capsid subunits from AAV8; or a vector which is generated by transfection of AAV2 helper and AAV8 helper plasmids (termed haploid AAV2/8) and which has VP1/VP2 capsid subunit from AAV2 and VP3 capsid subunits from AAV8; or a vector which is generated by transfection of AAV2 helper and AAV8 helper plasmids (termed haploid AAV2/8) and which has VP1 capsid subunit from AAV8 and VP3 capsid subunit from AAV2; or a vector which is generated by transfection of AAV2 helper and AAV8 helper plasmids (termed haploid AAV2/8) and which has VP1 capsid subunit from AAV2 and VP3 capsid subunits from AAV8; or a vector which is generated by transfection of AAV2 helper and AAV8 helper plasmids (termed haploid AAV2/8) and which has VP1/VP2/VP3 capsid subunits from AAV2; or a vector which is generated by transfection of AAV2 helper and AAV8 helper plasmids (termed haploid AAV2/8) and which has VP1/VP2/VP3 capsid subunits from AAV8; or a vector termed 28m-2VP3 or haploid 2m-2VP3 or haploid vector 28m-2VP3 in which chimeric VP1/VP2 capsid subunits have N-terminal from AAV2 and C-terminal from AAV8, and the VP3 capsid subunit is from AAV2; or a vector termed chimeric AAV8/2 or chimeric AAV82 in which chimeric VP1/VP2 capsid subunits have N-terminal from AAV8 and C-terminal from AAV2 without mutation of the VP3 start codon, and the VP3 capsid subunit is from AAV2; or a vector in which chimeric VP1/VP2 capsid subunits have N-terminal from AAV2 and C-terminal from AAV8; or G. a population, for example a substantially homogenous population, for example a population of 1010 particles, for example a substantially homogenous population of 1010 particles, of any one of the vectors of F; or H. a method of producing any one of the vectors or populations of vectors of A and/or B and/or C and/or D and/or E and/or F and/or G; or I. any combination thereof.

Without limitation, we state that the above reservation of a right of disclaimer applies at least to the original claims as appended to this application and paragraphs 1-83 as set forth herein. The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

EXAMPLES

Example 1: Application of Polyploid Adeno-Associated Virus Vector for Transduction Enhancement and Neutralizing Antibody Evasion Adeno-associated virus (AAV) vectors have been successfully used in clinical trials in patients with hemophilia and blindness. Exploration of effective strategies to enhance AAV transduction and escape neutralizing antibody activity is still imperative. Previous studies have shown the compatibility of capsids from AAV serotypes and recognition sites of AAV Nab located on different capsid subunits of one virion. In this study, we co-transfected AAV2 and AAV8 helper plasmids at different ratios (3:1, 1:1 and 1:3) to assemble haploid capsids and study their transduction and Nab escape activity. The haploid virus yield was similar to the parental ones and the heparin sulfate binding ability was positively correlated with AAV2 capsid input. To determine whether the tropism of these haploid vectors was changed by mixing the capsid protein, the transduction efficacy of the haploid viruses was analyzed by transducing human Huh7 and mouse C2C12 cell lines (FIG. 1). Although the haploid vector transduction was lower than AAV2 in Huh7 cells, haploid vector AAV2/8 3:1 induced a 3-fold higher transduction that that of AAV2 in C2C12 cells.

Figure 2:
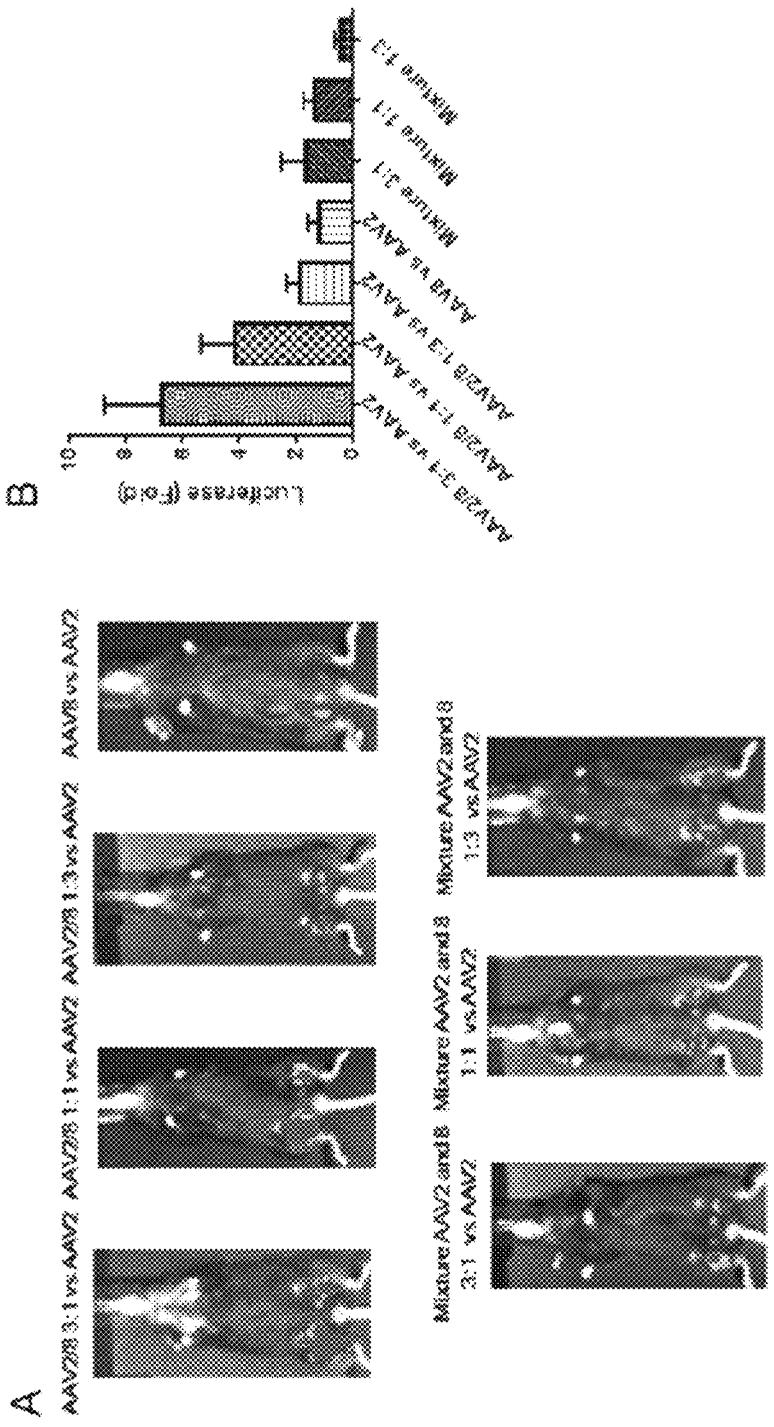
FIG. 2: Transduction of the haploid viruses in mouse muscle. $1\times10^{10}$ vg of the haploid viruses, parental viruses or viruses mixed with AAV2 and AAV8 were injected into C57BL/6 mice via direct muscular injection. Each group included 4 mice. (Panel A) After one week, luciferase gene expression was imaged by IVIS imaging system. (Panel B) The photon signal was measured and calculated. The data represent an average of luciferase gene expression values for the 4 injected mice in each group, with the standard deviation indicated by an error bar. Face up: left leg-AAV8 or haploid or mixture viruses, right leg-AAV2.

After muscular injection, all of the haploid viruses induced higher transduction than parental AAV vectors (2- to 9-fold over AAV2) with the highest of these being the haploid vector AAV2/8 1:3. After systemic administration, 4-fold higher transduction in the liver was observed with haploid AAV2/8 1:3 than that with AAV8 alone. Haploid AAV2/89 and their parental vectors were directly injected into the muscle of the hind legs in C57B16 mice. As controls, the mixtures of AAV2 and AAV8 viruses at ratios of 3:1, 1:1 and 1:3 were also investigated. For a convenient comparison, one leg was injected with AAV2 and the opposite leg with haploid vector. Compared to AAV2, a similar muscular transduction was achieved for the parental AAV8 capsid (FIG. 2). Contrary to the results in C2C12 cells, an enhanced muscular transduction was observed form all of the haploid viruses (FIG. 2). The haploid vectors AAV2/9 1:1 and AAV2/8 1:3 achieved a 4-fold and a 2-fold higher transduction than AAV2, respectively. Notably, the muscular transduction of the haploid vector AAV2/8 3:1 was over 6-fold higher than that of AAV2. All of the controls (injections that were a result of physically mixing parental vectors), however, had similar transduction efficiencies as the AAV2 vector.

Further, we packaged the therapeutic factor IX cassette into haploid AAV2/8 1:3 capsids and injected them into FIX knockout mice via tail vein. Higher FIX expression and improved phenotypic correction were achieved with haploid AAV2/8 1:3 virus vector compared to that of AAV8. Additionally, haploid virus AAV2/8 1:3 was able to escape AAV2 neutralization and had very low Nab cross-reactivity with AAV2.

To improve Nab evasion ability of polyploid virus, we produced triploid vector AAV2/8/9 vector by co-transfecting AAV2, AAV8 and AAV9 helper plasmids at the ratio of 1:1:1. After systemic administration, 2-fold higher transduction in the liver was observed with triploid vector AAV2/8/9 than that with AAV8. Neutralizing antibody analysis demonstrated that AAV2/8/9 vector was able to escape neutralizing antibody activity from mouse sera immunized with parental serotypes. These results indicate that polyploid virus might potentially acquire advantage from parental serotypes for enhancement of transduction and evasion of Nab recognition. This strategy should be explored in future clinical trials in patients with positive neutralizing antibodies.

The number of helper plasmids with different cap genes is not limited and can be mixed and matched based on the specific requirements of a particular treatment regimen.

Cell lines. HEK293 cells, Huh7 cells and C2C12 cells were maintained at 37° C. in 5% CO2 in Dulbecco's Modified Eagle's Medium with 10% fetal bovine serum and 10% penicillin-streptomycin.

Recombinant AAV virus production. Recombinant AAV was produced by a triple-plasmid transfection system. A 15-cm dish of HEK293 cells was transfected with 9 μg of AAV transgene plasmid pTR/CBA-Luc, 12 μg of AAV helper plasmid, and 15 μg of Ad helper plasmid XX680. To generate triploid AAV2/8 virions, the amount of each helper plasmid for AAV2 or AAV8 transfected was co-transfected at three different ratios of 1:1, 1:3 and 3:1. To make haploid AAV2/8/9 vectors, the ratio of helper plasmid for each serotype was 1:1:1. Sixty hours post-transfection, HEK293 cells were collected and lysed. Supernatant was subjected to CsCl gradient ultra-centrifugation. Virus titer was determined by quantitative PCR.

Western and Immune-blot. According to the virus titer, the same amount of virions were loaded in each lane, followed by electrophoresis on a NuPage 4-10% polyacrylamide Bis-Tris gel (Invitrogen, Carlsbad, Calif.) and then transferred to PVDF membrane via iBlot® 2 Dry Blotting System (Invitrogen, Carlsbad, Calif.). The membrane was incubated with the B1 antibody specific to AAV capsid proteins.

A native immunoblot assay was carried out as previously described. Briefly, purified capsids were transferred to a Hybond-ECL membrane (Amersham, Piscataway, N.J.) by using vacuum dot-blotter. The membranes were blocked for 1 h in 10% milk PBS and then incubated with monoclonal antibody A20 or ADK8. The membranes were incubated with a peroxidase-coupled goat anti-mouse antibody for 1 hr. The proteins were visualized by Amersham Imager 600 (GE Healthcare Biosciences, Pittsburgh, Pa.).

In vitro transduction assay. Huh7 and C2C12 cells were transduced by recombinant viruses with $1\times10^4$ vg/cell in a flat-bottom, 24-well plate. Forty-eight hours later, cells were harvested and evaluated by a luciferase assay system (Promega, Madison, Wis.).

Heparin inhibition assays. The ability of soluble heparin to inhibit the binding of recombinant viruses to Huh7 or C2C12 cells was assayed. Briefly, AAV2, AAV8, haploid viruses AAV2/8 1:1, AAV2/8 1:3 and AAV2/8 3:1 were incubated in DMEM in the presence, or absence, of soluble HS for 1 hat 37° C. After the pre-incubation, the mixture of recombinant viruses and soluble HS were added into Huh7 or C2C12 cells. At 48 h post-transduction, cells were harvested and evaluated by luciferase assay.

Figure 5:
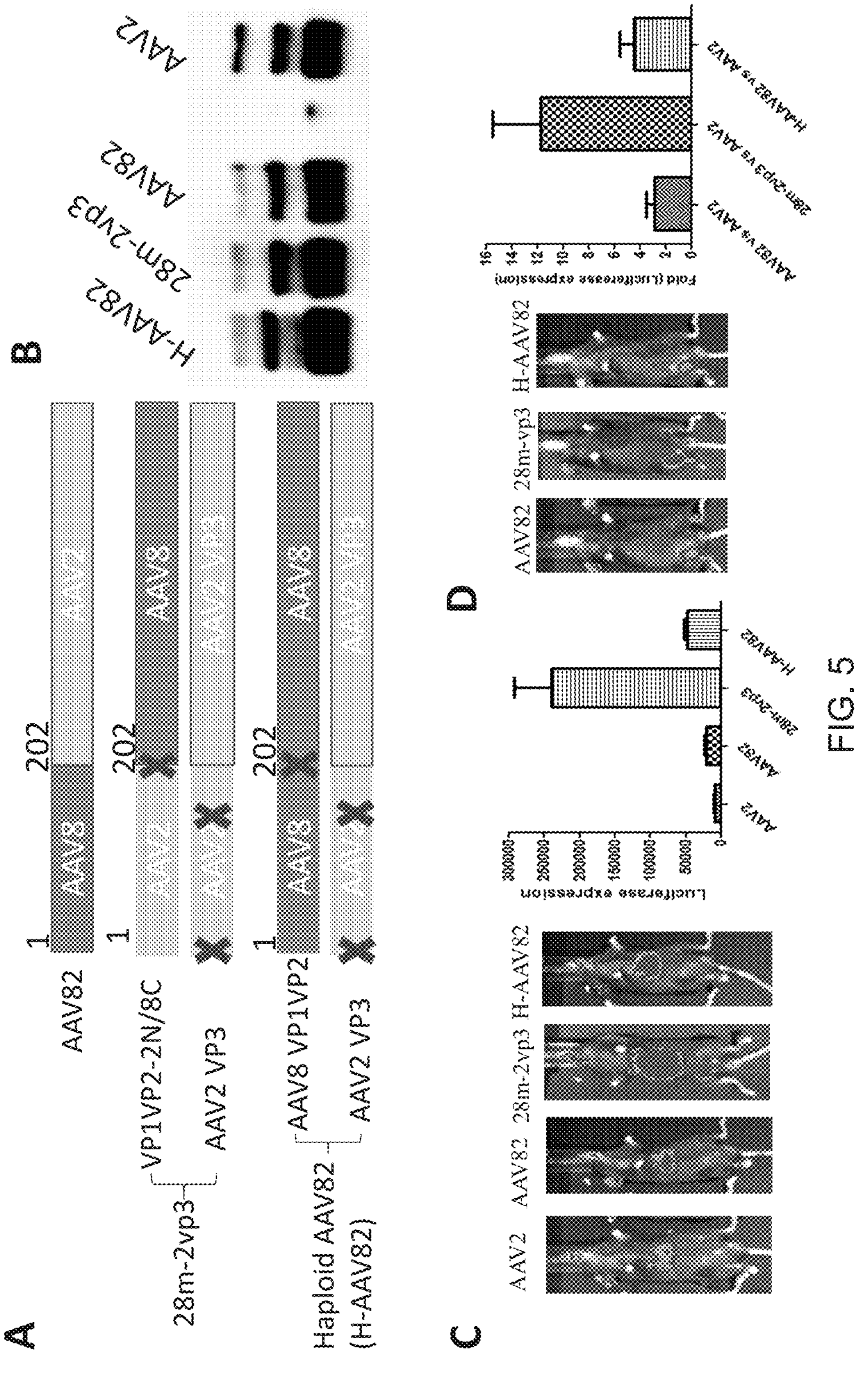
FIG. 5: Transduction of haploid AAV82 from AAV2 and AAV8. Panel A. The composition of AAV capsid subunits. Panel B. Western blot for haploid viruses. Panel. C. Representative imaging and the quantitation of liver transduction. Panel D. Representative imaging and the quantification of muscle transduction.

The antigen presentation from the haploid AAV capsid is similar to that of AAV8 in vivo. To study the efficacy of the capsid antigen presentation, we produced a haploid AAV2/8 OVA 1:3 vector by the transfection of pXR2-OVA and pXR8-OVA at the ratio of 1:3. $1\times10^{11}$ vg of AAV2/8-OVA and AAV8-OVA vectors were administered via retro-orbital injection in the C57BL/6 mice. Three days later, CFSE-labeled OT-1 mouse spleen cells were transferred into the C57BL/6 mice. At day 10 post-transferring OT-1 spleen cells, T cell proliferation was measured by flow cytometry. OT-1 T cell proliferation was significantly increased in mice receiving AAV2/8-OVA 1:3 or AAV8-OVA when compared to control mice without AAV vector administration (FIG. 5). There was no difference, however, for OT-1 cell proliferation between the AAV2/8-OVA 1:3 and AAV8-OVA groups.

Animal study. Animal experiments performed in this study were conducted with C57BL/6 mice and FIX−/− mice. The mice were maintained in accordance to NIH guidelines, as approved by the UNC Institutional Animal Care and Use Committee (IACUC). Six-week-old female C57BL/6 mice were injected with $3\times10^{10}$ vg of recombinant viruses via retro-orbital injection. Luciferase expression was imaged one week post-injection using a Xenogen IVIS Lumina (Caliper Lifesciences, Waltham, Mass.) following i.p. injection of D-luciferin substrate (Nanolight Pinetop, Ariz.). Bioluminescent images were analyzed using Living Image (PerkinElmer, Waltham, Mass.). For muscle transduction, $1\times10^{10}$ particles of AAV/Luc were injected into the gastrocnemius of 6-week-old C57BL/6 females. Mice were imaged at the indicated time points.

Figure 3:
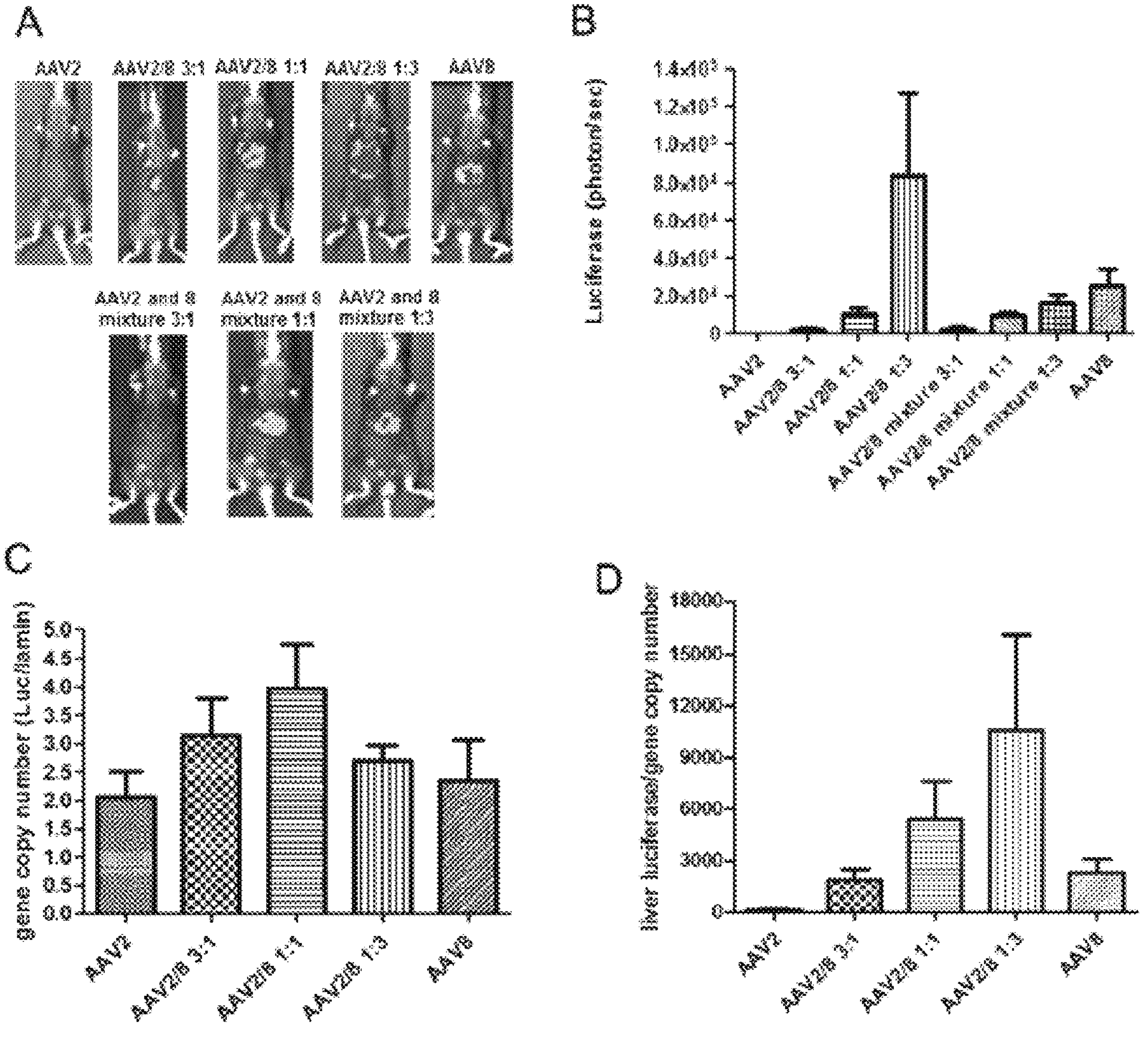
FIG. 3: Transduction of the haploid viruses in mouse liver. $3\times10^{10}$ vg of the haploid virus was administered via intravenous injection. At week 1 post-injection, luciferase expression was imaged by IVIS imaging system (Panel A), and the photon signal was measured and calculated (Panel B). At week 2 post-injection, mice were euthanized and their livers were harvested for DNA extraction AAV genome copy in the liver was measured by qPCR ((Panel C) and relatively luciferase expression per AAV genome copy number was calculated (Panel D). The data represent the average and standard deviation from 4 mice.

Next, the transduction efficiency of haploid viruses in the mouse liver was evaluated. The mixtures of AAV2 and AAV8 viruses were also injected as controls. A dose of C57BL/6 mice were injected with $3\times10^{10}$ vg of recombinant viruses via the retro-orbital vein and the imaging was carried out at day 3 post-AAV injection. The haploid virus AAV2/8 1:3 induced the highest transduction efficiency even over the other haploid combinations, the mixtures of parental viruses and the parental AAV8 in mouse livers (FIGS. 3A and 3B). The transduction efficiency of the haploid vector AAV2/8 1:3 was about 4-fold higher than that of AAV8 (FIG. 3 B). The liver transduction from the other haploid viruses was lower than that from the parental AAV8, but higher than that of AAV2 (FIGS. 3A and 3B). At day 7 post-injection, the mice were sacrificed, the livers were harvested, and the genomic DNA was isolated. The luciferase gene copy number in the liver was determined by qPCR. Different from the results for liver transduction efficiency, a similar AAV vector genome copy number was found in the liver regardless of virus composition (FIG. 3C). When transgene expression was normalized to gene copy number, the haploid vector AAV2/8 1:3 induced the highest relative transgene expression than any other haploid vector combination or parental serotypes (FIG. 3D).

FIX knockout male mice (FIX KO mice) received $1\times10^{10}$ vg via tail vein injection. At various time points after injection, blood was collected from the retro-orbital plexus. At week 6, mouse bleeding analysis was performed.

Quantitation of luciferase expression in the liver Animals utilized for imaging studies were sacrificed at week 4 after recombinant virus injection, and the livers were collected. Livers were minced and homogenized in passive lysis buffer. After the liver lysates were centrifuged, luciferase activity in supernatant was detected. Total protein concentration in tissue lysates were measured using the Bradford assay (BioRad, Hercules, Calif.).

Detection of AAV genome copy number in the liver. The minced livers were treated by Protease K. The total genome DNA was isolated by PureLink Genomic DNA mini Kit (Invitrogen, Carlsbad, Calif.). The luciferase gene was detected by qPCR assay. The mouse lamin gene served as an internal control.

Human FIX expression, function and tail-bleeding time assays. The human FIX expression, one-stage hFIX activity assay and tail-bleeding time assay were performed as previously described. Neutralization assay Huh7 cells were seeded in a 48-well plate at a density of $10^5$ cells for each well. Two-fold dilutions of the mouse antibody were incubated with AAV-Luc ($1\times10^8$ vg) for 1 hr 37° C. The mixture was added into cells and incubated for 48 hers at 37° C. Cells were lysed with passive lysis buffer (Promega, Madison, Wis.) and luciferase activity was measured. Nab titers were defined as the highest dilution for which luciferase activity was 50% lower than serum-free controls.

Statistical analysis. The data were presented as mean±SD. The Student t test was used to carry out all statistical analyses. P values<0.05 were considered a statistically significant difference.

Figure 4:
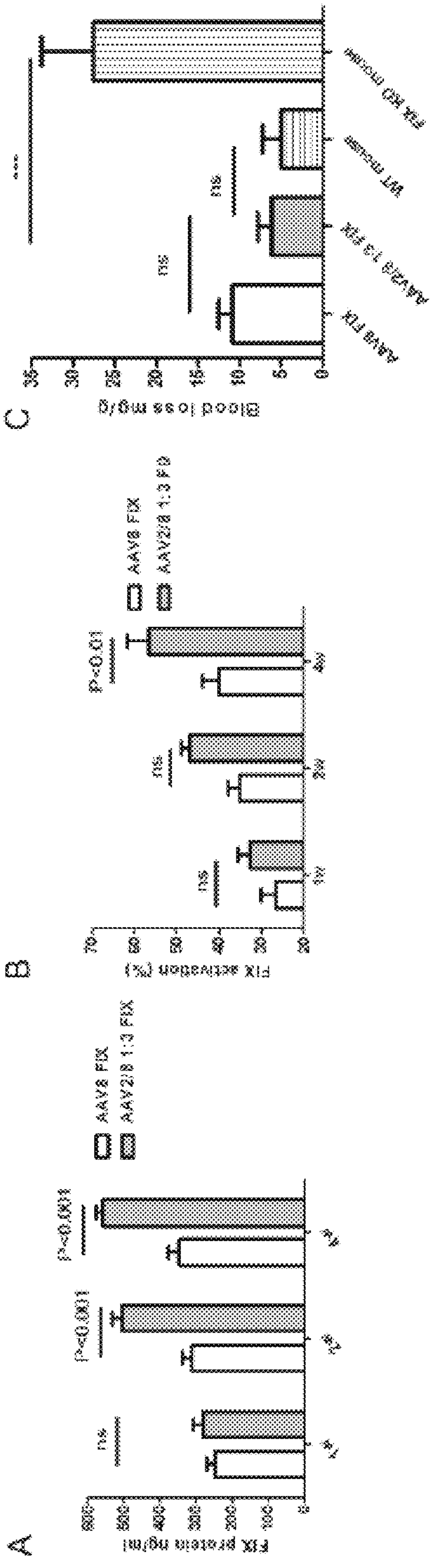
FIG. 4: Therapeutic level of fix via haploid virus delivery. FIX knockout mice were injected with $1\times10^{10}$ vg of each vector via tail vein. At 1, 2 and 4 weeks post-injection, blood samples were collected. (Panel A) hFIX protein levels were tested by enzyme-linked immunosorbent assay. (Panel B) hFIX function was tested by the hFIX-specific one stage clotting assay. At week 6 post-injection, blood loss was determined by measuring the absorbance at A575 of hemoglobin content in the saline solution (Panel C). The data represent the average and standard deviations from 5 mice (knock-out mice and normal mice, without AAV treatment, as controls) or 8 mice (AAV8 FIX or AAV2/8 1:3/FIX treated groups).

An AAV2/8 1:3 was tested to determine if it would increase the therapeutic transgene expression in an animal disease model. A human FIX (hFIX or human Factor IX) was used as a therapeutic gene and injected the haploid vector AAV2/8 1:3/hFIX into FIX knockout (KO) mice via tail vein at a dose of $1\times10^{10}$ vg/mouse. The haploid vector encodes the human-optimized FIX transgene and is driven by the liver specific promoter, TTR. At week 1, 2, and 4 post-injection, ELISA and one-stage factor activity analyzed the hFIX expression and activity in circulation, respectively. At week 6, the blood loss for in vivo hFIX function was evaluated using a tail clipping assay. Consistent with the observation of high liver transduction with the haploid AAV vectors in wild-type C57BL/6 mice, the haploid vector AAV2/8 1:3 liver targeting produced much more hFIX than an AAV8 vector after 2 weeks post-injection (FIG. 4A). The higher hFIX protein expression of AAV2/8 1:3 correlated as predicted with high FIX activity (FIG. 4B). The blood loss for the mice with AAV2/8 1:3/hFIX injection was similar to that of wild-type C57BL/6 mice, and much less than that of KO mice (FIG. 4C). Although there was no significant difference of the blood loss between the mice with AAV8 and AAV2/8 1:3/hFIX injection in statistics, the AAV8 mice had a little more blood loss that that of AAV2/8 1:3 mice (FIG. 4C).

Ability of the haploid viruses AAV2/8 to escape Nab. To study whether the haploid virus is able to escape Nabs generated in response to a parental vector, a Nab binding assay was performed using monoclonal antibodies by an immune-blot assay. Three dilutions of virus-genome-containing particles were adsorbed to a nitrocellulose membrane and probed with Nab A20 or ADK8, which recognizes intact AAV2 or AAV8 respectively. The neutralization profiles of the haploid viruses against A20 and ADK9 were similar to the data from a native immune-blot. (Table 5). The haploid AAV2/8 1:3 almost completely escaped the AAV2 serum and A20 neutralization, which suggest that this haploid virus has the potential to be used for individuals who have anti-AAV2 Nabs (Table 5).

Characterization of haploid viruses in vitro. Our previous study has demonstrated the capsid compatibility among AAV1, 2, 3 and 5 capsids. The haploid viruses were produced by transfection of AAV helper plasmids from two serotypes at the different ratios with AAV transgene and adenovirus helper 00(6-80. The enhanced transduction from haploid virus was observed in some cell lines compared to the parental vectors. AAV2 is well characterized for its biology and as a gene delivery vehicle and AAV8 has attracted a lot of attention due to high transduction in mouse liver. Both serotypes have been utilized in several clinical trials in patients with hemophilia. To investigate the possibility of AAV serotype 2 and 8 capsid to form haploid virus and their transduction profile, we transfected the helper plasmids of AAV2 and AAV8 at the ratios of 3:1, 1:1 and 1:3 to make haploid vectors. All of the haploid viruses were purified using cesium gradient and tittered by Q-PCR. There was no significant difference in virus yield between the haploid viruses and the parental AAV2 or AAV8. To determine whether the capsid proteins of haploid viruses were expressed, Western blot analysis was performed on equivalent virus genomes from purified haploid viruses using monoclonal antibody B1 which recognizes the capsid proteins of AAV2 and AAV8. In all haploid viruses, the mixture of VP2 capsids from AAV2 and AAV8 was observed, the intensity of VP2 capsid from AAV2 or AAV8 in haploid viruses was related to the ratio of two helper plasmids. These results suggested that the capsids from AAV 2 and AAV8 were compatible and able to be ensemble into AAV virions.

To determine whether the tropism of haploid virus was changed by mixing the capsid proteins, the transduction efficacy of haploid viruses was analyzed by transducing human Huh7 and mouse C2C12 cell lines. The transduction efficiency of AAV8 was much lower than AAV2 in both of the cell lines. The transduction from all haploid vectors was higher than that from AAV8, and the efficiency was positively correlated with addition of AAV2 capsid in both cell lines. Although haploid vector transduction was lower than AAV2 in Huh7 cells, haploid vector AAV2/8 3:1 induced 3-fold higher transduction than AAV2 in C2C12 cells.

This in vitro transduction data supports that the virus preparation is composed of haploid vectors but not the mixture of individual serotype vector and indicate that haploid vector may enhance AAV transduction. Heparin sulfate proteoglycan has been identified as the primary receptor of AAV2. Next, we investigated whether inhibition of heparin binding ability changed transduction of haploid viruses. Pre-incubation of AAV vectors with soluble heparin blocked AAV2 transduction by nearly 100% in both Huh7 and C2C12 cells, and blocked AAV8 transduction by 37% and 56% in Huh7 and C2C12 cells, respectively. The inhibition of haploid vector transduction by soluble heparin was dependent on the input of AAV2 capsid in both cell lines. Higher inhibition of transduction was observed with more AAV2 capsid input. This result suggests that haploid viruses may use both primary receptors from parental vectors for effective transduction [FIG. 1].

Increased muscular transduction of haploid viruses. As described above, the transduction efficiency of haploid virus AAV2/8 3:1 is higher than that of AAV2 and AAV8 in the muscle cell line C2C12. Next we studied whether the high transduction in vitro was translated into mouse muscle tissues. AAV2/8 haploid and parental vectors were directly injected into muscle of hind legs in C57BL/6 mouse. As controls, the mixtures of AAV2 and AAV8 viruses at the ratios of 3:1, 1:1 and 1:3 were also investigated. For convenient comparison, one leg was injected with AAV2 and the other one with tested vector. A total vector of $1\times10^{10}$ vg for each virus was administered. Compared to AAV2, similar muscular transduction was achieved for AAV8. Contrary to the result in C2C12 cells, enhanced muscular transduction was observed from all of the haploid viruses [FIG. 2].

Haploid vectors AAV2/8 1:1 and AAV2/8 1:3 achieved 4- and 2-fold higher transduction than AAV2, respectively. Notably, the muscular transduction of haploid vector AAV2/8 3:1 was over 6-fold higher than that of AAV2. However, all of the mixture viruses had similar transduction efficiencies to AAV2. These results suggest that haploid virus is able to increase muscular transduction and further supports that viruses produced from co-transfection of two capsid plasmids are haploid.

Enhanced liver transduction of haploid viruses. AAV2 and AAV8 have been used for liver targeting in several clinical trials in patients with hemophilia B. We also evaluated the transduction efficiency of haploid viruses in mouse liver. The viruses mixed with AAV2 and AAV8 were also injected as controls. A dose of $3\times10^{10}$ vg of AAV/luc vector was administered in C57BL mice via retro-orbital vein; the imaging was carried out at day 3 post-AAV injection. The haploid virus AAV2/8 1:3 induced the highest transduction efficiency than other haploid, mixture viruses and even parental AAV8 in mouse livers [FIGS. 3A and 3B]. The transduction efficiency of haploid vector AAV2/8 1:3 was about 4-fold higher than that of AAV8 [FIG. 3B]. The liver transduction from other haploid viruses was lower than that from the parental vector AAV8 but higher than AAV2 [FIGS. 3A and 3B]. At day 7 post-injection, the mice were sacrificed, the livers were harvested and the genomic DNA was isolated. The luciferase gene copy number in the liver was determined by qPCR. Different from the result for liver transduction efficiency, similar AAV vector genome copy number was found in the liver regardless of haploid viruses or AAV serotypes 2 and 8 [FIG. 3C]. When transgene expression was normalized to gene copy number, consistent to transgene expression in the liver, haploid vector AAV2/8 1:3 induced the highest relative transgene expression than any other haploid vectors and serotypes [FIG. 3D]. The transduction profile of haploid viruses in the liver was different from that in muscle transduction, in which all haploid viruses induced higher transgene expression than that from parental serotypes, with the best from AAV2/8 3:1.

Augmented therapeutic FIX expression and improved bleeding phenotypic correction with haploid vector in a hemophilia B mouse model Based on the above results, haploid vector AAV2/8 1:3 induced much higher liver transduction than AAV8. Next, we further tested whether the haploid vector AAV2/8 1:3 could increase the therapeutic transgene expression in an animal disease model. We used human FIX (hFIX) as a therapeutic gene and injected haploid vector AAV2/8 1:3/hFIX, which encoded human-optimized FIX transgene, and driven by the liver-specific promoter, TTR, into FIX knockout (KO) mice via tail vein at a dose of $1\times10^{10}$ vg/mouse. At week 1, 2 and 4 post-injection, the hFIX expression and activity in circulation were analyzed by ELISA and one-stage factor activity, respectively. At week 6, the blood loss for in vivo hFIX function was evaluated using a tail clipping assay. Consistent to the observation of high liver transduction with haploid AAV vector in wide-type C57BL/6 mice, haploid vector AAV2/8 1:3 liver targeting produced much more hFIX than AAV8 vector after 2 weeks post-injection [FIG. 4A]. The higher hFIX protein expression of AAV2/8 1:3 was closely related to high FIX activity [FIG. 4B]. The blood loss for the mice with AAV2/8 1:3/hFIX injection was similar to that of wild-type C57BL/6 mice and less than that of KO mice [FIG. 4C]. However, AAV8-treated mice had more blood loss than that in wild type mice [FIG. 4C}. These data show that haploid vector AAV2/8 1:3 increases therapeutic transgene expression from the liver and improves disease phenotypic correction.

The ability of haploid viruses AAV2/8 to escape neutralizing antibody. Each individual haploid virus virion is composed of 60 subunits from different AAV serotype capsids. Insertion of some capsid subunits from one serotype into other capsid subunits from a different serotype may change the virion surface structure. It is well known that most AAV monoclonal antibodies recognize residues on the different subunits of one single virion. To study whether haploid virus is able to escape Nabs generated from parental vector, first we performed Nab binding assay using monoclonal antibodies by an immune-blot assay. Three dilutions of virus-genome-containing particles were adsorbed to a nitrocellulose membrane and probed with Nab A20 or ADK8, which recognizes intact AAV2 or AAV8, respectively. All of the haploid viruses and virus with mixture of AAV2 and AAV8 were recognized by monoclonal antibody ADK8 or A20. The reactivity of haploid viruses with A20 was increased by incorporation of more AAV2 capsids into haploid virus virion. However, there was no obvious change for the recognition of anti-AAV8 Nab ADK8 among the haploid viruses, regardless of capsid ratios. Notably, the binding of haploid AAV2/8 1:3 to A20 was much weaker than those of parental AAV2 and the virus with mixture of AAV2 and 8 at the ratio 1:3, which indicated that A20 binding sites are depleted on the haploid AAV2/8 1:3 virion surface.

Next we analyzed the immunological profile of haploid viruses against sera from AAV-immunized mice. Nab titers were used to evaluate the ability of serum to inhibit vector transduction. Sera were collected from mice treated with parental viruses at week 4 post-injection. As shown in Table 5, the neutralization profiles of the haploid viruses against A20 or ADK8 were similar to the data from native immune-blot. There was no Nab cross-reactivity between AAV8 and AAV2. It is interesting to note that AAV8-immunized mouse sera had similar neutralizing activity against AAV8 virus and all of the haploid viruses, regardless of the amount of AAV8 capsid incorporation, but not the viruses mixed with AAV2 and AAV8. No inhibition of AAV8 serum on mixture viruses may be explained by the superior transduction from AAV2 to AAV8 in tested cell line. However, haploid viruses partially escaped the neutralization from AAV2 serum. The transduction of haploid AAV2/8 1:1 got a 16-fold decrease than parental AAV2 after incubation of virus and anti-AAV2 serum. The ability to escape AAV2 serum Nab for haploid viruses was much higher than that for viruses mixed with AAV2 and AAV8. Strikingly, the haploid AAV2/8 1:3 almost completely escaped the AAV2 serum and A20 neutralization, suggesting that the haploid virus has the potential to be used for the individuals who have the anti-AAV2 Nab (Table 5).

Improved neutralizing antibody evasion ability with triploid vector made from three serotypes. Our data described above demonstrated that haploid AAV2/8 viruses were not able to escape AAV8 neutralizing antibody activity, but had the capacity to evade AAV2 neutralizing antibody, which depended on the amount of capsid integration from AAV8. To study whether the polyploid virus made from more serotypes capsids improved the Nab escaping ability, we made the triploid virus AAV2/8/9 with the ratio of 1:1:1. After injection of the triploid vector AAV2/8/9 into mice, compared to AAV2, triploid virus AAV2/8/9 induced 2 fold higher transduction in the liver than AAV8. No difference in liver transduction was observed among AAV8 and haploid vectors AAV2/9 and AAV8/9 in which the triploid vector was made from two AAV helper plasmids at ratio of 1:1. It was noted that AAV9 systemic administration induced higher liver transduction than AAV8. When neutralizing antibody assay was performed, haploid AAV2/8/9 vector improved its Nab escape ability by about 20 fold, 32 fold and 8 fold, respectively when compared to AAV2, 8 and 9 (Table 6).

In this study, polyploid AAV virions were assembled from capsids of 2 serotypes or 3 serotypes. The binding ability of haploid viruses to AAV2 primary receptor heparin was dependent on the amount of AAV2 capsid input. All of the haploid viruses achieved higher transduction efficacy than parental AAV2 vector in mouse muscle and liver, while haploid virus AAV2/8 1:3 had a significant enhancement of liver transduction than parental AAV8 vector. Compared to AAV8, systemic administration of the haploid virus AAV2/8 1:3 to deliver human FIX induced much higher FIX expression and improved hemophilia phenotypic correction in FIX−/− mice. Importantly, the haploid virus AAV2/8 1:3 was able to escape the neutralization of anti-AAV2 serum. Integration of AAV9 capsid into haploid AAV2/8 virions further improved neutralizing antibody escape capacity.

The primary receptor of AAV2 is HSPG, while the primary receptor of AAV8 is still unclear. To study whether haploid viruses could use receptors from both AAV2 and AAV8, we performed heparin inhibition assay to test the ability of haploid viruses to binding heparin receptor motif. The heparin inhibition results, in Huh7 and C2C12 cell lines, support that haploid viruses use the heparin receptor motif of AAV2 capsids for effective transduction. To some extent, AAV8 also showed decreased transduction efficiency in the presence of heparin, but the transduction efficiency is still higher than that of AAV2.

One of the most challenging aspects of efficient transduction in clinical trials is broad prevalence of neutralizing antibodies to AAV vector. Nab-mediated clearance of AAV vectors has become a limited factor for repeating administration of AAV gene transfer. Several studies have explored genetically modifying AAV capsids for Nab evasion by rational mutation of neutralizing antibody recognizing sites or directed evolution approaches. Capsid mutation may change AAV tropism and transduction efficiency. Additionally, the identification of Nab binding sites on AAV virions is far behind vector application in clinical trials, and it is impossible to figure out all Nab binding sites from poly sera. Previous studies have demonstrated that the recognition sites of several AAV monoclonal antibodies are spun on the different subunits of one virion. When AAV8 capsid is introduced into AAV2 virion, the A20 binding ability and neutralizing activity from AAV2-immunized sera were dramatically decreased for haploid viruses. Integration of AAV2 capsids into AAV8 virions did not reduce the capacity to bind intact AAV8 monoclonal antibody ADK8 and did not escape the neutralizing activity of anti-AAV8 sera (Table 5). This suggests that all Nab recognition sites from poly-sera may be located on the same subunit of AAV8 virion. Also, the result suggests that the AAV8 capsids integrated into AAV2 virions may play a major role in virus intracellular trafficking.

When triploid virus was made from capsids of three serotypes AAV2, 8 and 9, different from triploid vectors AAV2/8, haploid AAV2/8/9 virus has an ability to escape neutralizing antibody activity sera from AAV2, 8 or 9 immunized mice, which suggests that AAV8 and AAV9 share the similar transduction pathway.

Several lines of evidences from this study support the polyploid virion assembly from transfection of two or three AAV helper plasmids. (1) Two VP2 bands of different sizes were displayed from haploid viruses using western blot analysis. These VP2s match the size from different serotypes. (2) The transduction profiles were different in C2C12 versus Huh7 cells. Haploid AAV2/8 3:1 vector, in particular, demonstrated lower transduction than that with AAV2 in Huh7 cells, but higher in C2C12 cells. (3) Higher muscle transduction was demonstrated with all haploid AAV2/8 viruses as compared with parental vectors AAV2 and AAV8, as well as the viruses with a mixture of AAV2 and AAV8. (4) Triploid virus AAV2/8 1:3 had enhanced liver tropism when compared to AAV8. (5) The binding pattern of haploid viruses to A20 and ADK8 is different from the viruses with a mixture of AAV2 and AAV8. (6) The profile of AAV2 serum neutralizing activity is different between haploid viruses and mixture viruses. (7) Triploid AAV2/8/9 virus evades neutralizing antibody activity of sera from mice immunized with any parental serotypes.

These polyploid viruses enhance the transduction efficiency in vitro and in vivo, and even escape neutralization from parental vector immunized sera. Application of the polyploid virus to deliver a therapeutic transgene FIX was able to increase FIX expression and improve hemophilia phenotypic correction in mice with FIX deficiency. These results indicate that haploid AAV vectors have the ability to enhance transduction and evade Nabs.

Example 2: Enhanced AAV Transduction from Haploid AAV Vectors by Assembly of AAV Virions with VP1/VP2 from One AAV Vector and VP3 from an Alternative One by Application of Rational Polyploid Methodology In above studies, we have demonstrated that increased AAV transduction has been achieved using polyploid vectors which are produced by transfection of two AAV helper plasmids (AAV2 and AAV8 or AAV9) or three plasmids (AAV2, AAV8 and AAV9). These individual polyploid vector virions may be composed of different capsid subunits from different serotypes. For example, haploid AAV2/8, which is generated by transfection of AAV2 helper and AAV8 helper plasmids, may have capsid subunits with different combinations in one virion for effective transduction: VP1 from AAV8 and VP2/VP3 from AAV2, or VP1/VP2 from AAV8 and VP3 from AAV2, or VP1 from AAV2 and VP2/VP3 from AAV8, or VP1/VP2 from AAV2 and VP3 from AAV8, or VP1 from AAV8 and VP3 from AAV2, or VP1 from AAV2 and VP3 from AAV8, or VP1/VP2/VP3 from AAV2, or VP1/VP2/VP3 from AAV8. In the following studies, we found that enhanced transduction could be achieved from haploid vectors with VP1/VP2 from one AAV vector capsid and VP3 from an alternative one.

The generation of VP1, VP2 and VP3 by different AAV serotypes offers two different strategies for producing these different proteins. Interestingly, the VP proteins are translated from a single CAP nucleotide sequence with overlapping sequences for VP1, VP2 and VP3.

Figure 31:
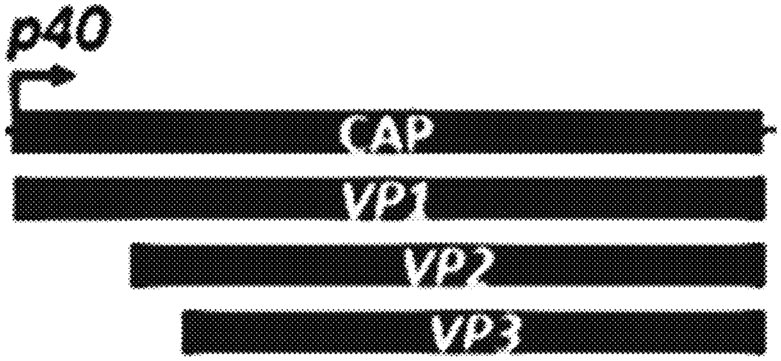
FIG. 31: Illustrates that the Cap gene encodes three proteins—VP1, VP2, and VP3.

The Cap gene encodes for 3 proteins—VP1, VP2 and VP3. As shown in FIG. 31, VP1 contains the VP2 and VP3 proteins, and VP2 contains the VP3 protein. Therefore, the Cap gene has 3 segments, start of VP1—start of VP2—start of VP3—end of all 3 VP proteins.

In the case of sourcing the Cap genes from two different AAV serotypes (designated as A and B), there are 6 possible combinations of the three Cap proteins. In one case, the VP1 identified as serotype A, which can be any serotype (or chimeric or other nonnaturally occurring AAV) is only from a first serotype A and the VP2/VP3 identified as serotype B, is only from serotype B, and is a serotype that is different from the serotype (or chimeric or other nonnaturally occurring AAV) of VP1. In one case both VP1 and VP2 are only from a first serotype A, and VP3 is only from serotype B. Methods to create a VP1 of a first serotype and VP2/VP3 of a second serotype; or VP1/VP2 from a first serotype and VP3 form a second serotype, are disclosed in the Examples set forth herein. In one case, VP1 and VP3 are only from a first serotype and VP2 is only from a second serotype.

| VP1 | VP2 | VP3 |
|---|---|---|
| A | B | B |
| A | B | A |
| A | A | B |
| B | B | A |
| B | A | B |
| B | A | A |

In the case of sourcing the Cap genes from three different AAV serotypes (designated as A, B and C), there are 6 possible combination of the three Cap proteins. In this case, the VP1 identified as serotype A, which can be any serotype (or chimeric or other nonnaturally occurring AAV) is from a first serotype that is different from the serotype of VP2 and VP3; the VP2 identified as serotype B, which is a serotype that is different from the serotype (or chimeric or other nonnaturally occurring AAV) of VP1 and VP3, is from a second serotype; and, the serotype of VP3 identified as serotype C, which is a serotype that is different from the serotype (or chimeric or other nonnaturally occurring AAV) of VP1 and the serotype of VP2, is from a third serotype. Methods to create a VP1 of a first serotype, a VP2 of a second serotype and a VP3 of a third serotype are disclosed in the Examples set forth herein.

| VP1 | VP2 | VP3 |
|---|---|---|
| A | B | C |
| A | C | B |
| B | A | C |
| B | C | A |
| C | A | B |
| C | B | A |

In an embodiment, when VP1 is identified as a first serotype A and VP2 and VP3 are identified as a second serotype B, it is understood that in one embodiment, this would mean that VP1 is only from serotype A and that VP2 and VP3 is only from serotype B. In another embodiment, when VP1 is identified as a first serotype A, VP2 as a second serotype B and VP3 as a third serotype C, it is understood that in one embodiment, this this would mean that VP1 is only from serotype A; that VP2 is only from serotype B; and VP3 is only from serotype C. As described in more detail in the Examples below, in one embodiment, to create a haploid vector using two different serotypes you could include a nucleotide sequence for VP1 from serotype A (or chimeric or other nonnaturally occurring AAV) that expresses only VP1 from serotype A and a second nucleotide sequence for VP2 and/or VP3 only from a second serotype, or alternatively VP2 only from a second serotype, and VP3 only from a third serotype (see for example, FIGS. 13-15). In one embodiment, VP1/VP2 are only from a first serotype and VP3 is only from a second serotype.

In the case of 3 different Cap genes, the helper plasmid can be generated with a full copy of the nucleotide sequence for the particular VP protein from the three AAV serotypes. The individual Cap genes will generate the VP proteins associated with that particular AAV serotype (designated as A, B and C).

| VP1 | VP2 | VP3 |
|---|---|---|
| A | B | C |
| A | C | B |
| B | A | C |
| B | C | A |
| C | A | B |
| C | B | A |

In an embodiment, when VP1 is identified as a first serotype A and VP2 is identified as a second serotype B and VP3 is identified as a third serotype C, it is understood that in one embodiment, this would mean that VP1 is only from serotype A; that VP2 is only from serotype B and VP3 is only from serotype C. As described in more detail in the Examples below, to create such a haploid vector would include a nucleotide sequence for VP1 from serotype A that expresses only VP1 from serotype A and not VP2 or VP3 from serotype A; a second nucleotide sequence that expresses VP2 of serotype B and not VP3 of serotype B; and a third nucleotide sequence that expresses VP3 of serotype C.

In certain embodiments, the haploid virions comprise only VP1 and VP3 capsid proteins. In certain embodiments, the haploid virions comprise VP1, VP2, and VP3 capsid proteins.

It should be noted that in each of these embodiments of various combinations of VP1 with VP3 to form a haploid virion; or various serotype combinations of VP1/VP2/VP3 to from a haploid virion, the nucleotide sequences that express the capsid proteins can be expressed from one or more vector, e.g., plasmid. In one embodiment, the nucleic acid sequences that express VP1, or VP2, or VP3, are codon optimized so that recombination between the nucleotide sequences is significantly reduced, particularly when expressed from one vector, e.g., plasmid etc.

Rational Haploid vector with C-terminal of VP1/VP2 from AAV8 and VP3 from AAV2 enhances AAV transduction. It has been demonstrated that haploid vectors AAV2/8 at any ratio of AAV2 capsid to AAV8 capsid induced higher liver transduction than AAV2 or the viruses with mixture of AAV2 vectors and AAV8 vectors at the same ratio. To elucidate which AAV subunits in individual haploid AAV2/8 vector contributes to higher transduction than AAV2, we made different constructs which expressed AAV8 VP1/VP2 only, AAV2 VP3 only, chimeric VP1/VP2 (28m-2VP3) with N-terminal from AAV2 and C-terminal from AAV8, or chimeric AAV8/2 with N-terminal from AAV8 and C-terminal from AAV2 without mutation of VP3 start codon. These plasmids were used to produce haploid AAV vector with different combination. After injection of $1\times10^{10}$ particles of these haploid vectors in mice via retro-orbital vein, the liver transduction efficiency was evaluated. Chimeric AAV82 vector (AAV82) induced a little higher liver transduction than AAV2. However, haploid AAV82 (H-AAV82) had much higher liver transduction than AAV2. A further increase in liver transduction with haploid vector 28m-2vp3 was observed. We also administered these haploid vectors into the muscles of mice. For easy comparison, the right leg was injected with AAV2 vector and the left leg was injected with haploid vector when the mouse was face up. At week 3 after AAV injection, the images were taken. Consistent to observation in the liver, all haploid vectors and chimeric vectors had higher muscular transduction with the best from haploid vector 28m-2vp3. This result indicates that the chimeric VP1/VP2 with N-terminal from AAV2 and C-terminal from AAV8 attributes to high liver transduction of haploid AAV82 vectors.

Enhanced AAV liver transduction from haploid vector with VP1/VP2 from other serotypes and VP3 from AAV2. We have shown that haploid vector AAV82 with VP1/VP2 from AAV8 and VP3 from AAV2 increases the liver transduction as described above. Next, we would like to examine whether other haploid virions, in which VP1/VP2 is derived from different serotypes, also increases transduction. In preclinical studies, AAV9 has been shown to efficiently transduce different tissues. We have made a haploid AAV92 vector (H-AAV92) in which VP1/VP2 was from AAV9 and VP3 from AAV2. After systemic administration, the imaging was performed at week 1. About 4-fold higher liver transduction was achieved with H-AAV92 than that with AAV2. This data indicates that VP1/VP2 from other serotypes is also capable of increasing AAV2 transduction.

Enhanced AAV liver transduction from haploid vector with VP3 from AAV2 mutant or other serotypes. AAV9 uses glycan as primary receptor for effective transduction. In our previous studies, we have engrafted AAV9 glycan receptor binding site into AAV2 to make AAV2G9 and found that AAV2G9 has higher liver tropism than AAV2. Herein we made haploid vector (H-AAV82G9) in which VP1/VP2 from AAV8 and VP3 from AAV2G9. After systemic injection into mice, compared to AAV2G9, more than 10 fold higher liver transduction was observed at both week 1 and week 2 post H-AAV82G9 application. To study haploid vectors in which VP3 from other serotypes and VP1/VP2 from different serotypes or variants, we cloned other constructs: AAV3 VP3 only, AAV rh10 VP1/VP2 only, and made different haploid vectors with various combination (H-AAV83, H-AAV93 and H-AAVrh10-3). After systemic injection into mice, the imaging was carried out at week 1. Consistent to the results obtained from other haploid vectors, higher liver transduction was achieved with haploid vectors (H-AAV83, H-AAV93 and H-AAVrh10-3) than that with AAV3. It is interesting to note that these haploid vectors also induced a whole body transduction based on imaging profile, which is different from the results from haploid vectors 5 with VP3 from AAV2, which only transduced the liver efficiently. Collectively, haploid vectors with VP1/VP2 from one serotype and VP3 from an alternative one are able to enhance transduction and perhaps change tropism.

Haploid vector with VP1/VP3 from one AAV serotype and VP2 from another AAV serotype enhances AAV transduction and escapes antibody neutralization. To study haploid vectors in which VP2 is from one serotype and VP1/VP3 from a different serotype, several constructs will be generated. A construct that expresses AAV2 VP2 only will be generated. This will be accomplished by incorporation of a mutation of the AAV2 VP1 start codon and/or a mutation of the AAV2 VP1 splice acceptor site e.g., shown in FIG. 10, combined with a mutation of the VP3 start codon. A construct that expresses AAV8 VP1/3 only will also be generated. This will be accomplished by incorporation of a mutation of the AAV8 VP2 start codon. Similarly a construct that expresses AAV2 VP1/3 only and a construct that expresses AAV8 VP2 only will be generated.

A substantially homogeneous population of haploid vectors encoding a luciferase transgene and having either AAV2VP1 and AAV8VP1/3, or having AAV8VP1 and AAV2 VP1/3, will be made from these constructs using the appropriate plasmids and helper virus. $1\times10^{10}$ particles of these haploid vectors will be injected into mice via retro-orbital vein, and the liver transduction efficiency evaluated by imaging after 1 week. It is expected that higher liver transduction will be achieved with the homogeneous population of the haploid vector than with AAV2, and that far lower Nab cross-reactivity will be seen with the haploid vector, compared to activity with AAV2 or AAV8. Further, the homogeneous haploid vector population may also induce a whole body transduction (e.g., as identified based on an imaging profile), which differs from the results using either AAV2 or AAV8.

In these examples, we demonstrate that the haploid viruses made from the VP1/VP2 and VP3s from compatible serotypes also increase transduction. After systemic injection of $2\times10^{10}$ vg of AAV vectors into mice, it was found that haploid AAV vectors composed of VP1/VP2 from serotypes 7, 8, 9, and rh10 and VP3 from AAV2 or AAV3 display a 2- to 7-fold increase in transduction across multiple tissue types, including liver, heart, and brain, when compared to AAV2-only and AAV3-only capsids. These tissues additionally had higher vector genome copy numbers in these tissues, indicating that an incorporation of non-cognate VP1/VP2 can influence AAV receptor binding and intracellular trafficking. In addition, chimeric and haploid capsids were created with either AAV2 or AAV8 VP1/VP2 combined with AAV2 or AAV8 VP3. When these haploid AAV vectors were injected into mice, the haploid AAV vectors composed of AAV8 VP1/2 and AAV2 VP3 had a 5-fold higher transduction than viruses composed solely of AAV2 VPs. Remarkably, haploid vectors composed of VP1/VP2 from the chimeric AAV2/8 (the N-terminus of AAV2 and the C-terminus of AAV8) paired with VP3 from AAV2 had a 50-fold increase in transgene expression compared to capsids composed of AAV8 VP1/VP2 paired with AAV2 VP3. Given the same proportion of the capsid coming from AAV8 VP3, the difference lies in the VP1/2 N-terminal region between AAV2 and AAV8, which may indicate a 'communication' between the VP1/2 N-terminus of AAV2 with its cognate VP3. Collectively, work presented herein provides insight into current AAV production strategies that can increase transduction across multiple tissue types.

The haploid vectors will also be injected into the muscles of mice. For easy comparison, the right leg will be injected with AAV2 vector and the left leg will be injected with haploid vector when the mouse is face up. At week 3 after AAV injection, the images will be taken. Enhanced transduction in muscle by the haploid vectors is also expected.

The ability of homogeneous population of haploid viruses to escape neutralizing antibody. To study whether haploid virus is able to escape Nabs generated from parental vector, an Nab binding assay will be performed using monoclonal antibodies by an immune-blot assay. Three dilutions of virus-genome-containing particles will be adsorbed to a nitrocellulose membrane and probed with Nab A20 or ADK8, which recognizes intact AAV2 or AAV8, respectively. It is expected that the homogeneous population of haploid viruses will have much reduced to undetectable recognition by monoclonal antibody ADK8 or A20.

Next, the immunological profile of the homogeneous population of haploid viruses using sera from AAV-immunized mice will be generated. Nab titers will be used to evaluate the ability of serum to inhibit vector transduction. Sera will be collected from mice treated with parental viruses at week 4 post-injection. The neutralization profiles of the haploid viruses against A20 or ADK8 will be compared, and are expected to be similar to the data obtained from a native immune-blot. No Nab cross-reactivity is expected to be seen between AAV8 and AAV2. The homogeneous population of haploid viruses are expected to at least partially, and perhaps completely escape the neutralization from either AV2 serum or AAV8 serum.

Figure 7:
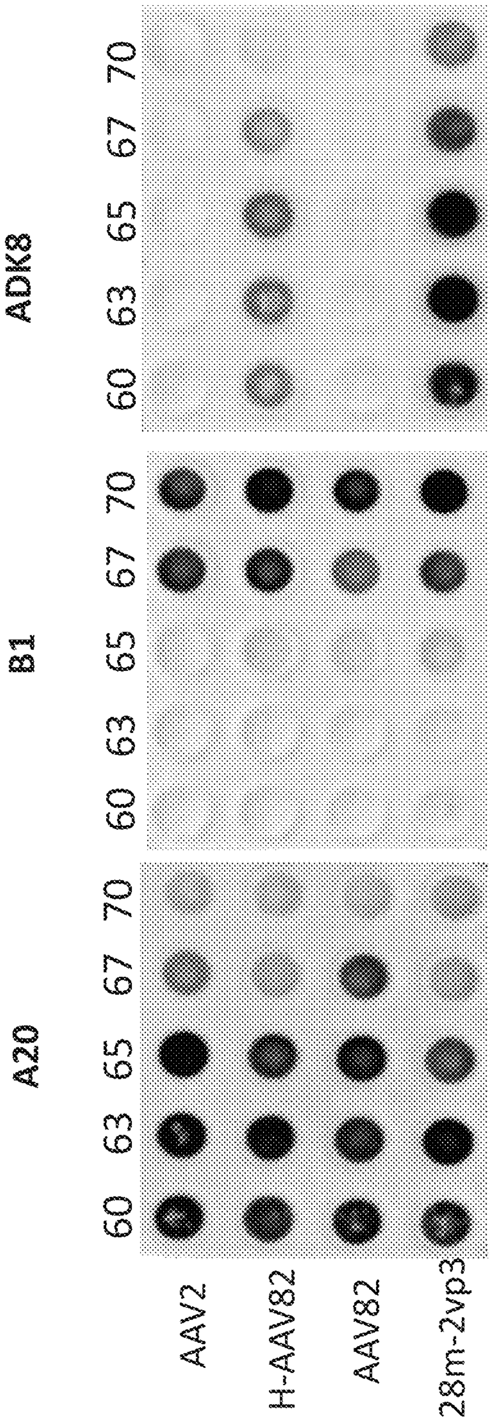
FIG. 7: AAV stability against heating.
Figure 9:
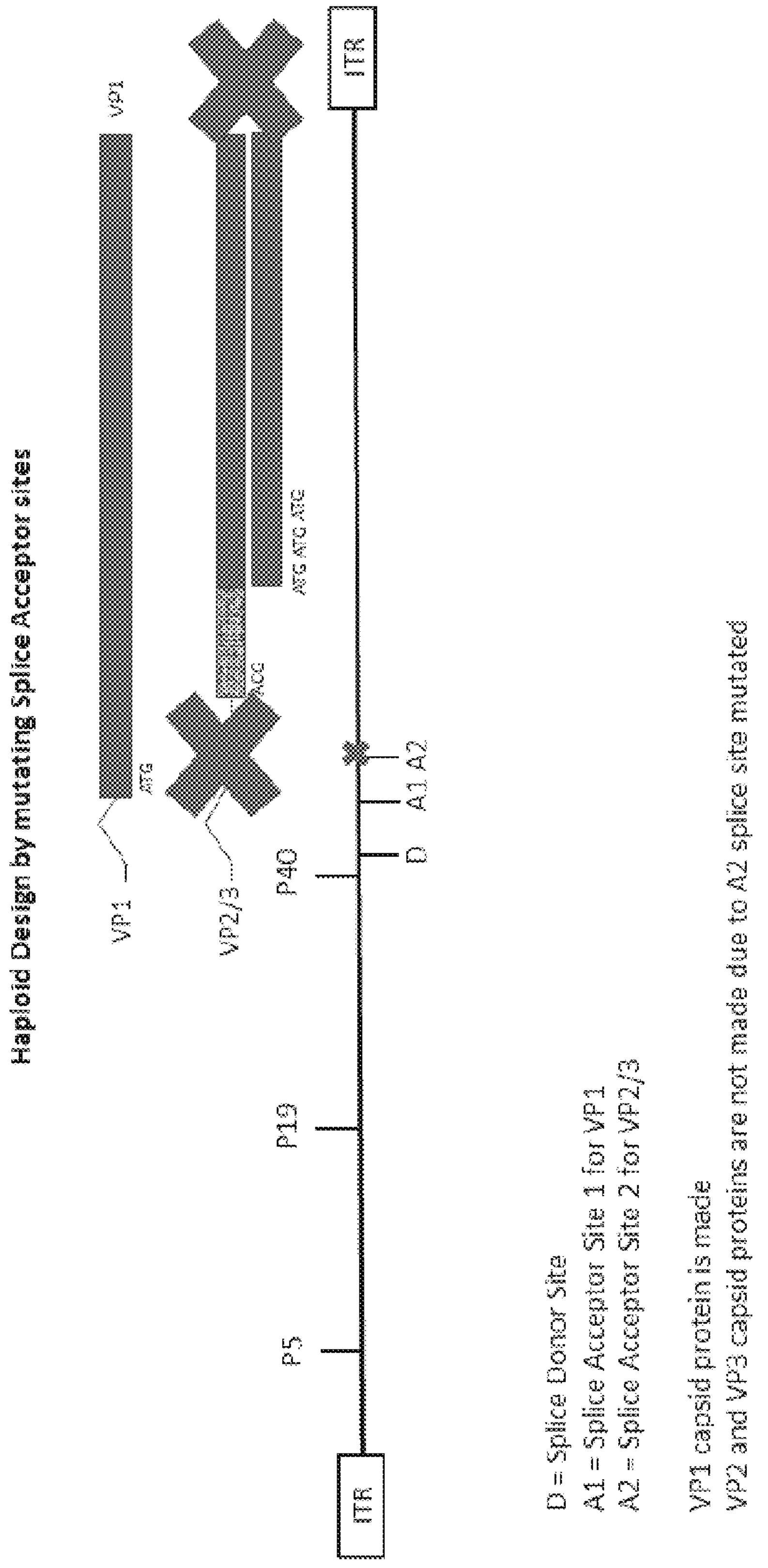
FIG. 9: Haploid design by mutating the Splice Acceptor Site A2.
Figure 11:
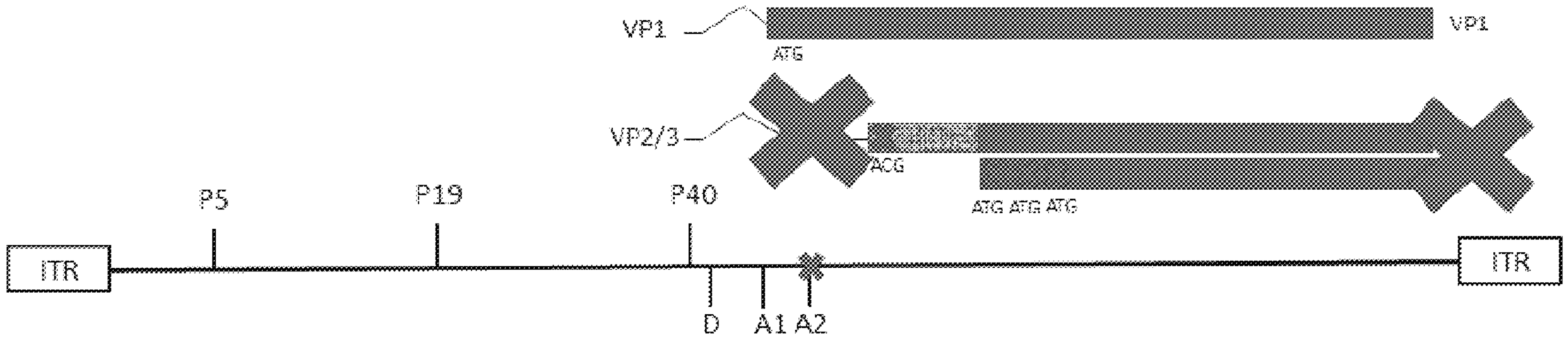
FIG. 11: Haploid design by mutating the start codons of capsid proteins for VP2/VP3 and the Splice Acceptor Site A2.
Figure 21:
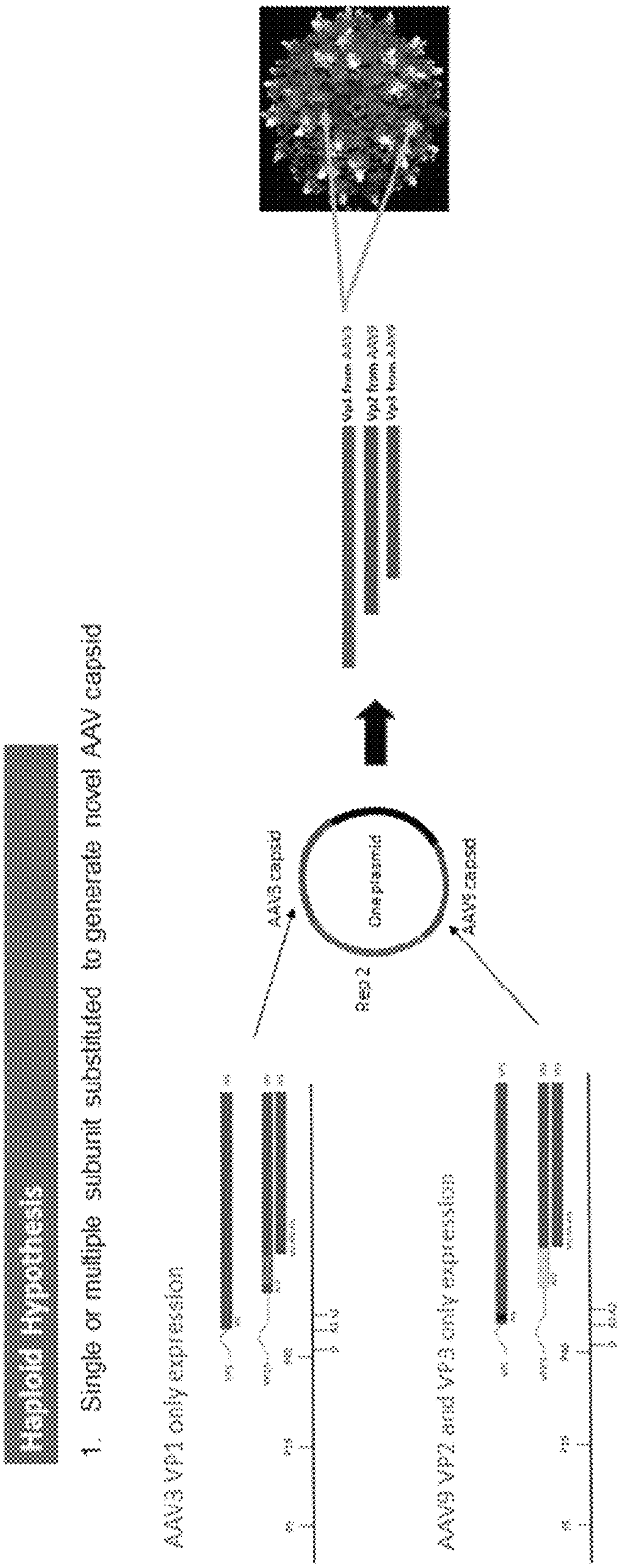
FIG. 21: Single or multiple subunits substituted to generate a novel polyploid AAV capsid.

Haploid vector with VP2/VP3 from one AAV serotype and VP1 from another AAV serotype enhances AAV transduction and escapes antibody neutralization. To study haploid vectors in which VP1 is from one serotype and VP2/VP3 from a different serotype, several constructs will be generated. A construct that expresses AAV2 VP1 only will be generated. This will be accomplished by incorporation of a mutation of the AAV2 VP2 start codon, a mutation of the AAV2 VP3 start codon e.g., as shown in FIG. 7 and FIG. 21, or a mutation of the VP2 and VP3 splice acceptor site e.g., as shown in FIG. 9, or mutation of both e.g., as shown in FIG. 11. A construct that expresses AAV8 VP2/3 only will be generated. This will be accomplished by incorporation of a mutation of the AAV8 VP1 start codon, e.g., see FIG. 21, and/or the splice acceptor site e.g., see FIG. 12. Similarly, a construct that expresses AAV2 VP2/3 only will be generated, and a construct that expresses AAV8 VP1 only will be generated.

A substantially homogeneous population of haploid vectors encoding a luciferase transgene and having either AAV2VP1 and AAV8VP2/3, or having AAV8VP1 and AAV2 VP2/3, will be made from these constructs using the appropriate plasmids and helper virus. $1\times10^{10}$ particles of these haploid vectors will be injected into mice via retro-orbital vein, and the liver transduction efficiency evaluated by imaging after 1 week. It is expected that higher liver transduction will be achieved with the homogeneous population of the haploid vector than with AAV2, and that far lower Nab cross-reactivity will be seen with the haploid vector, compared to activity with AAV2 or AAV8. Further, the homogeneous haploid vector population may also induce a whole body transduction (e.g., as identified based on an imaging profile), which differs from the results using either AAV2 or AAV8.

The haploid vectors will also be injected into the muscles of mice. For easy comparison, the right leg will be injected with AAV2 vector and the left leg will be injected with haploid vector when the mouse is face up. At week 3 after AAV injection, the images will be taken. Enhanced transduction in muscle by the haploid vectors is also expected.

The ability of homogeneous population of haploid viruses to escape neutralizing antibody. To study whether haploid virus is able to escape Nabs generated from parental vector, an Nab binding assay will be performed using monoclonal antibodies by an immune-blot assay. Three dilutions of virus-genome-containing particles will be adsorbed to a nitrocellulose membrane and probed with Nab A20 or ADK8, which recognizes intact AAV2 or AAV8, respectively. It is expected that the homogeneous population of haploid viruses will have much reduced to undetectable recognition by monoclonal antibody ADK8 or A20.

Next, the immunological profile of the homogeneous population of haploid viruses using sera from AAV-immunized mice will be generated. Nab titers will be used to evaluate the ability of serum to inhibit vector transduction. Sera will be collected from mice treated with parental viruses at week 4 post-injection. The neutralization profiles of the haploid viruses against A20 or ADK8 will be compared, and are expected to be similar to the data obtained from a native immune-blot. No Nab cross-reactivity is expected to be seen between AAV8 and AAV2. The homogeneous population of haploid viruses are expected to at least partially, and perhaps completely escape the neutralization from either AV2 serum or AAV8 serum.

Triploid Vector with VP1 from One AAV Serotype, VP2 from Another AAV Serotype, and VP3 from a Third AAV Serotype Enhances AAV Transduction and Escapes Antibody Neutralization.

To study triploid vectors in which VP1, VP2 and VP3 are each from a different AAV serotype, several constructs will be generated. A construct that expresses AAV2 VP1 only will be generated. This will be accomplished by incorporation of either a mutation of the AAV2 VP2 start codon and mutation of the VP3 start codon e.g., as shown in FIG. 7, or incorporation of a mutation of the splice acceptor site for VP2/3 e.g., as shown in FIG. 9. A construct that expresses AAV9 VP2 only will be generated. This will be accomplished by incorporation of a mutation in the AAV9 VP1 start codon and/or incorporation of a mutation in the AAV9 VP1 splice acceptor site, and mutation of the VP3 start codon. Alternatively, this will be accomplished by synthesizing a fragment of the AAV9 Cap coding sequence that omits the upstream coding sequences for VP1, and mutation of the VP3 start codon. A construct that expresses AAV8 VP3 only will be generated. This will be accomplished by incorporating of a mutation in the AAV8 VP1 start codon and/or splice acceptor site, and incorporation of a mutation in the AAV8 VP2 start codon. Alternatively, this will be accomplished by synthesizing a fragment of the AAV8 Cap coding sequence that omits the upstream coding sequences for VP1 and VP2.

Figure 13:
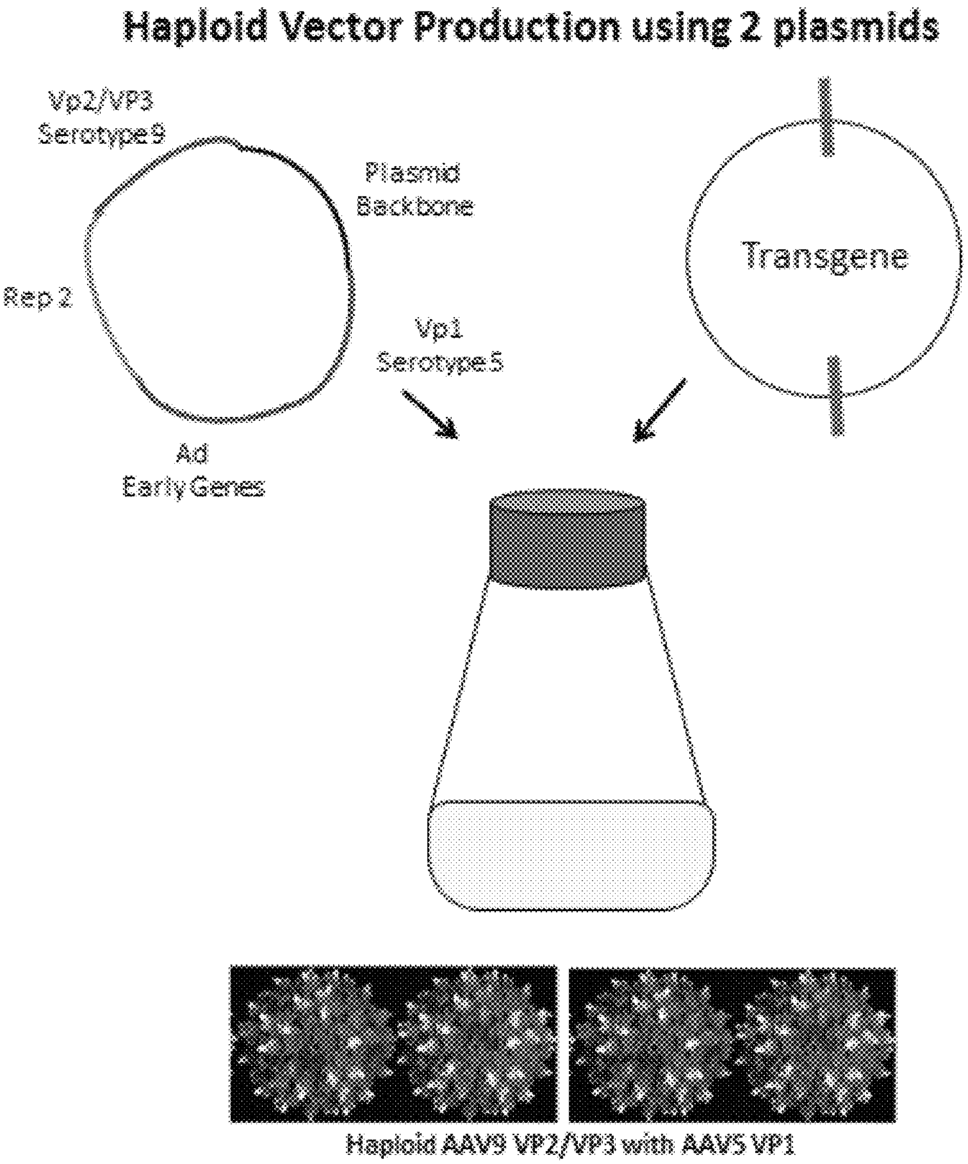
FIG. 13: Haploid vector production using two plasmids.
Figure 14:
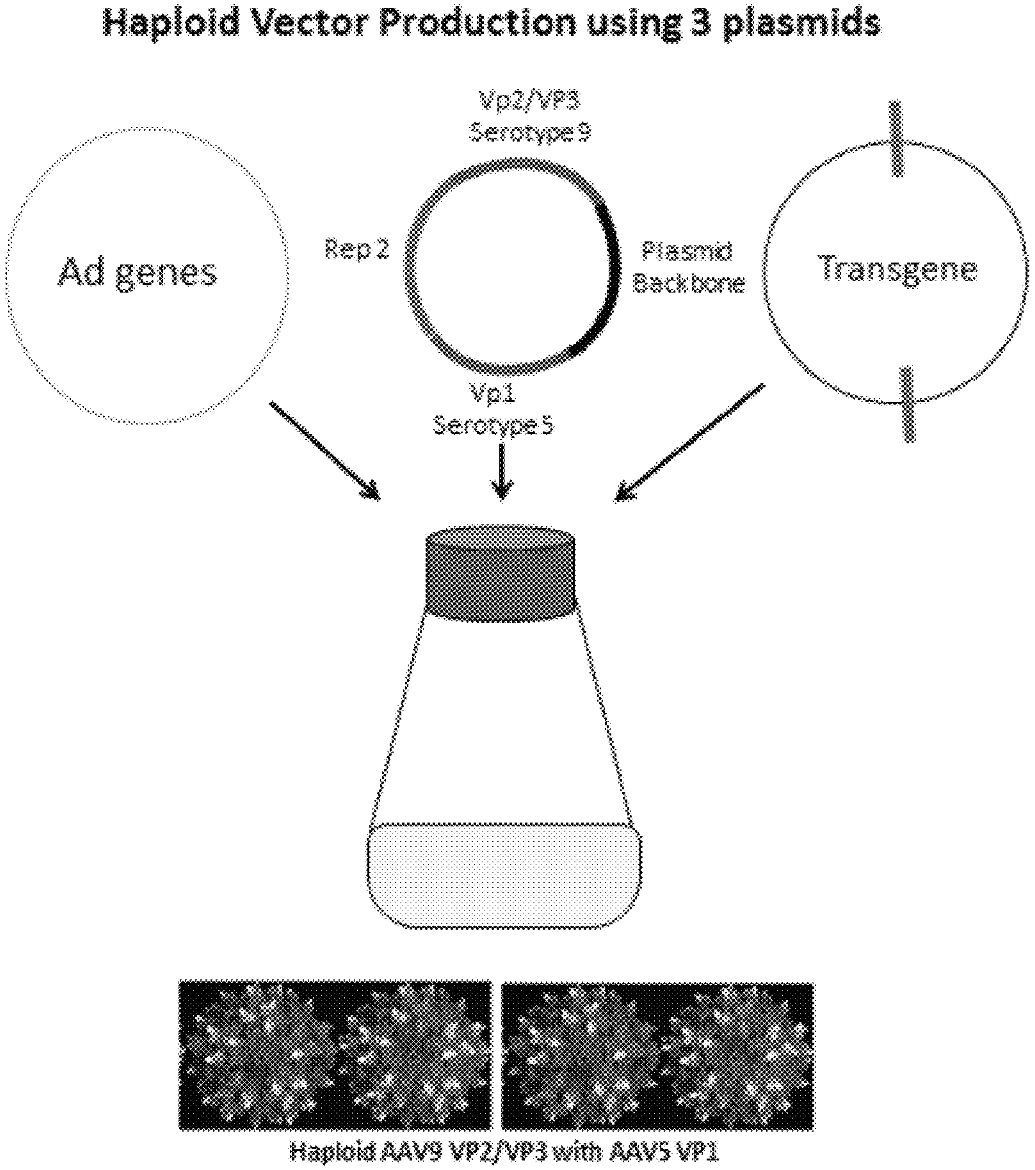
FIG. 14: Haploid vector production using three plasmids.
Figure 15:
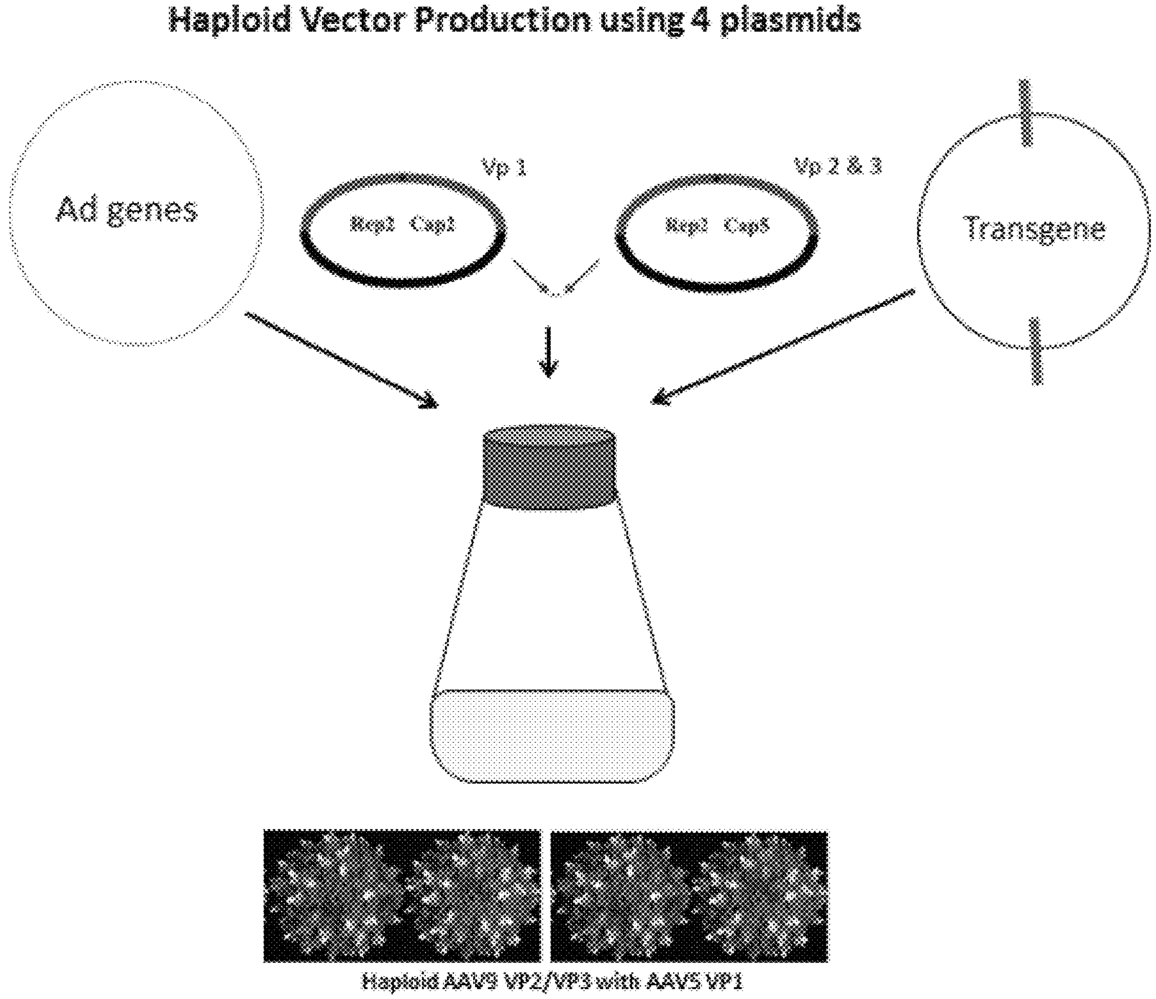
FIG. 15: Haploid vector production using four plasmids.

A substantially homogeneous population of triploid vectors encoding a luciferase transgene and having AAV2 VP1, AAV9 VP2, and AAV8 VP3, will be made from these constructs using the appropriate plasmids and helper virus (e.g., see FIGS. 13, 14, and 15). $1\times10^{10}$ particles of these triploid vectors will be injected into mice via retro-orbital vein, and the liver transduction efficiency evaluated by imaging after 1 week. It is expected that higher liver transduction will be achieved with the homogeneous population of the triploid vector than with AAV2, AAV9 or AAV8, and that far lower Nab cross-reactivity will be seen with the triploid vector, compared to activity with either AAV2, AAV8 or AAV8. Further, the homogeneous triploid vector population may also induce a whole body transduction (e.g., as identified based on an imaging profile).

The triploid vectors will also be injected into the muscles of mice. For easy comparison, the right leg will be injected with AAV2 vector, AAV9 vector or AAV8 vector, and the left leg will be injected with triploid vector when the mouse is face up. At week 3 after AAV injection, the images will be taken. Enhanced transduction in muscle by the triploid vectors is expected.

The ability of homogeneous population of triploid viruses to escape neutralizing antibody. Each individual haploid virus virion is composed of 60 subunits from the respective different AAV serotype capsids. Combining serotype capsid proteins derived from three different serotypes is expected to change the virion surface structure. It is well known that most AAV monoclonal antibodies recognize residues on the different subunits of one single virion. To study whether triploid virus is able to escape Nabs generated from parental vector, an Nab binding assay will be performed using monoclonal antibodies by an immune-blot assay. Three dilutions of virus-genome-containing particles will be adsorbed to a nitrocellulose membrane and probed with Nab A20 or ADK8, which recognizes intact AAV2 or AAV8, respectively. It is expected that the homogeneous population of triploid viruses will have much reduced to undetectable recognition by monoclonal antibody ADK8 or A20.

Next, the immunological profile of the homogeneous population of triploid viruses using sera from AAV-immunized mice will be generated. Nab titers will be used to evaluate the ability of serum to inhibit vector transduction. Sera will be collected from mice treated with parental viruses at week 4 post-injection. The neutralization profiles of the triploid viruses against A20 or ADK8 will be compared, and are expected to be similar to the data obtained from a native immune-blot. No Nab cross-reactivity is expected to be seen between AAV8 and AAV2. The homogeneous population of triploid viruses are expected to at least partially, and perhaps completely escape the neutralization from either AAV2 serum, AAV9 serum, or AAV8 serum.

Example 3: Polyploid Adeno-Associated Virus Vectors Enhance Transduction and Escape Neutralizing Antibody Adeno-associated virus (AAV) vectors have been successfully used in clinical trials in patients with hemophilia and blindness. Although the application of AAV vectors has proven safe and shown therapeutic effect in these clinical trials, one of the major challenges is its low infectivity that requires relatively large amount of virus genomes. Additionally, a large portion of the population has neutralizing antibodies (Nabs) against AAVs in the blood and other bodily fluids. The presence of Nabs poses another major challenge for broader AAV applications in future clinical trials. Effective strategies to enhance AAV transduction and escape neutralizing antibody activity are highly demanded. Previous studies have shown the compatibility of capsids from AAV serotypes and recognition sites of AAV Nab located on different capsid subunits of one virion. In this study, we propose to study whether polyploid AAV viruses produced from co-transfection of different AAV helper plasmids have the ability for enhanced AAV transduction and escape of Nabs. We co-transfected AAV2 and AAV8 helper plasmids at different ratios (3:1, 1:1 and 1:3) to assemble haploid capsids. The haploid virus yield was similar to the parental ones, suggesting that these two AAV capsids were compatible. In Huh7 and C2C12 cell lines, the transduction efficiency of AAV8 was much lower than those from AAV2;

however, the transduction from all haploid vectors was higher than that from AAV8. The transduction efficiency and the heparin sulfate binding ability for haploid vectors were positively correlated with amount of integrated AAV2 capsid. These results indicate that the haploid virus vectors retain their parental virus properties and take advantage of the parental vectors for enhanced transduction. After muscular injection, all of the haploid viruses induced higher transduction than parental AAV vectors (2- to 9-fold over AAV2) with the highest of these being the haploid vector AAV2/8 3:1.

Figure 6:
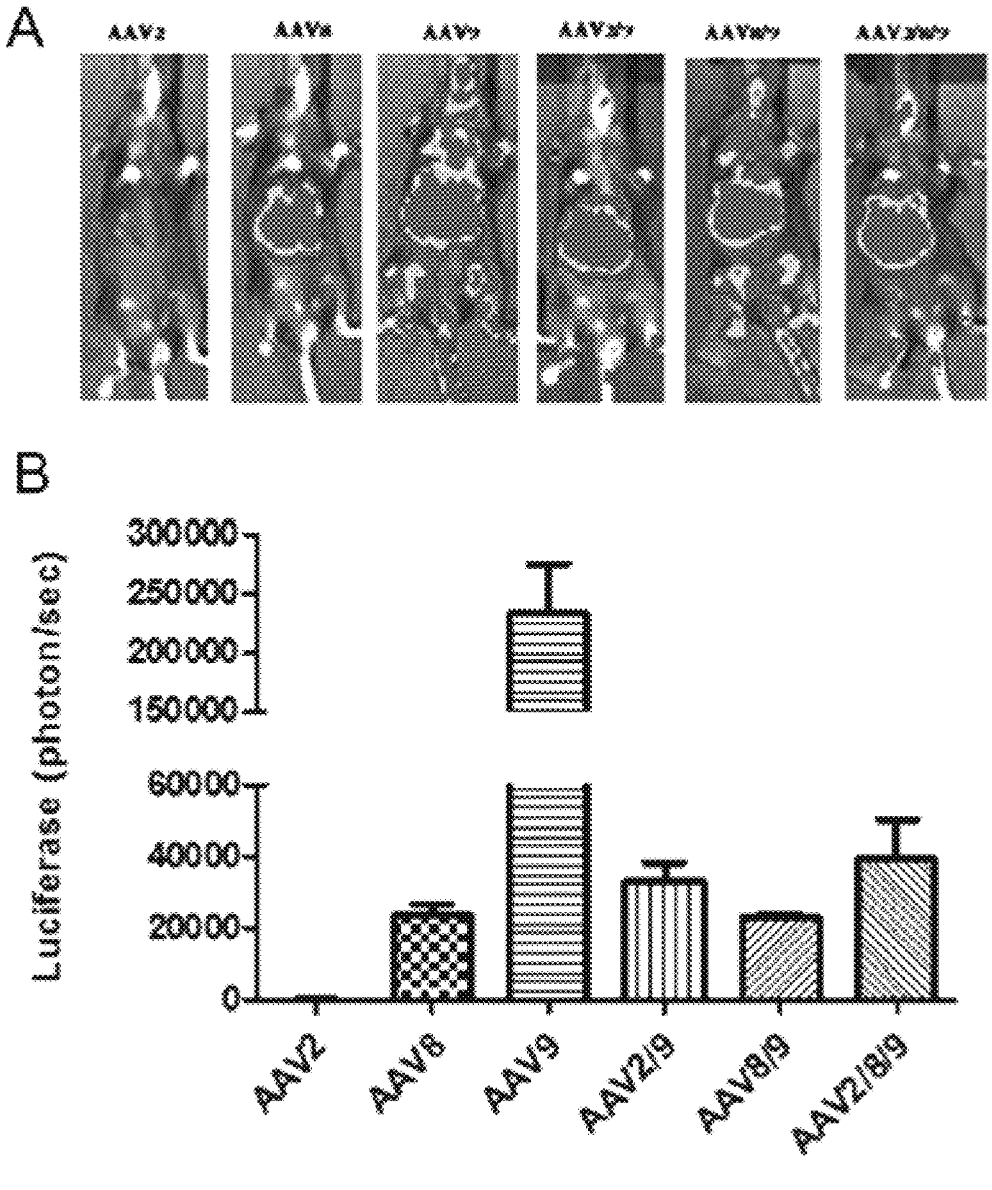
FIG. 6: Liver transduction with the triploid virus AAV2/8/9. $3\times10^{10}$ vg of the haploid viruses were injected via retro-orbital vein. At week 1 post-injection, luciferase gene expression was imaged by IVIS imaging system (Panel A), and the photon signal was measured and calculated (Panel B). The data represent the average and standard deviation from 5 mice.

After systemic administration, 4-fold higher transduction in the liver was observed with haploid vector AAV2/8 1:3 than that with AAVS alone. Importantly, we packaged the therapeutic factor IX cassette into haploid vector AAV2/8 1:3 capsids and injected them into FIX knockout mice via tail vein. Higher FIX expression and improved phenotypic correction were achieved with haploid vector AAV2/8 1:3 virus vector compared to that of AAVS. Strikingly, haploid virus AAV2/8 1:3 was able to escape AAV2 neutralization and had very low Nab cross-reactivity with AAV2. But AAVS neutralizing antibody can inhibit haploid vector AAV2/8 transduction the same efficiency as AAV8. Next, we produced triploid vector AAV2/8/9 vector by co-transfecting AAV2, AAV8 and AAV9 helper plasmids at the ratio of 1:1:1. After systemic administration, 2-fold higher transduction in the liver was observed with triploid vector AAV2/8/9 than that with AAV8 (FIG. 6). Neutralizing antibody analysis demonstrated that AAV2/8/9 vector was able to escape neutralizing antibody activity from mouse sera immunized with parental serotype, different from AAV2/8 triploid vector. The results indicate that polyploid virus might potentially acquire advantage from parental serotypes for enhancement of transduction and has ability for evasion of Nab recognition. This strategy should be explored in future clinical trials in patients with positive neutralizing antibodies.

Example 4: Substitution of AAV Capsid Subunits Enhances Transduction and Escapes Neutralizing Antibody Therapeutic effect has been achieved in clinical trials in patients with blood diseases and blind disorders using adeno-associated virus (AAV) vector. However, two concerns restrict broadening AAV vector application: AAV capsid specific cytotoxic T cell (CTL) and neutralizing antibodies (Nabs). Enhancing AAV transduction with low dose of AAV vector will potentially decrease capsid antigen load and hopefully ablate capsid CTL mediated clearance of AAV transduced target cells without compromise of transgene expression. Currently, 12 serotypes and over 100 variants or mutants have been explored for gene delivery due to their different tissue tropism and transduction efficiency. It has been demonstrated that there is compatibility of capsid among AAV serotypes, and integration of specific amino acids from one serotype into another AAV capsid enhances AAV transduction. By taking advantage of different mechanisms for effective AAV transduction from different serotypes, enhanced AAV transduction was achieved using mosaic virus in which AAV capsid subunits are derived from different serotypes in vitro and in vivo. The recent structural studies on interaction of AAV vectors with monoclonal neutralizing antibodies demonstrated that Nab binds to residues on several different subunits of one virion surface, which suggests that change of subunit assembly of AAV virion may ablate the AAV Nab binding site and then escape Nab activity. We have demonstrated that the mosaic AAV vector is able to evade Nab activity. These results indicate that substitution of AAV capsid subunits has the potential to enhance AAV transduction and the ability of neutralizing antibody evasion.

Adeno-associated virus (AAV) vector has been successfully applied in clinical trials in patients with blood diseases and blind disorders. Two concerns restrict broad AAV vector application: AAV capsid specific cytotoxic T cell (CTL) response mediated elimination of AAV transduced target cells and neutralizing antibodies (Nabs) mediated blocking of AAV transduction. It has been demonstrated that capsid antigen presentation is dose-dependent, which indicates that enhancing AAV transduction with low dose of AAV vector will potentially decrease capsid antigen load and hopefully ablate capsid CTL mediated clearance of AAV transduced target cells without compromise of transgene expression. Several approaches have been explored for this purpose including: optimization of transgene cassette, modification of AAV capsid and interference of AAV trafficking with pharmacological agents. Modification of AAV capsid may change AAV tropism; especially AAV transduction efficiency is unknown in human tissues. Though several clinical trials have been ongoing, the AAV vector was empirically chosen based on observation from animal models. Pharmacological reagents for enhancing AAV transduction usually have unwanted side effects. It is imperative to develop ideal strategies to enhance AAV transduction but without changing its tropism from modification of capsids and no side effects from pharmacological treatment. Currently, there are 12 serotypes and over 100 variants or mutants which have been explored for gene delivery. Effective AAV transduction involves following steps including: binding on the target cell surface via receptors and co-receptors, endocytosis into endosomes, escape from endosomes, nuclear entrance, AAV virion uncoating followed by transgene expression. To rationally design novel AAV vectors for enhanced transduction, we have developed chimeric viruses: AAV2.5 (in which AAV2 mutant with 5 aa substitution from AAV1) and AAV2G9 (in which galactose receptor from AAV9 is engrafted into AAV2 capsid). Both chimeric mutants induce a much higher transduction than AAV2 in mouse muscle and liver, respectively. These observations indicate that these chimeric viruses may use properties from both AAV serotypes for enhanced transduction (for example, AAV2G9 uses two primary receptors-heparin and galactose for effective cell surface binding). Based on the compatibility among capsid subunits from different AAV serotypes for virus assembly and our preliminary results, which demonstrated that integration of specific amino acids from other serotypes (1 or 9) into AAV serotype 2 enhanced AAV2 transduction in muscle and the liver, we reason that substitution of some capsid subunits from other serotypes is able to enhance AAV transduction by taking advantage of different mechanisms for effective AAV transduction from different serotypes. In addition, pre-existing antibodies to naturally occurring AAV have impacted success for hemophilia B and other AAV gene transfer studies. In the general human population, around 50% carry neutralizing antibodies. Several approaches have been considered to design NAb-evading AAV vectors, including chemical modification, different serotype of AAV vector, rational design and combinatorial mutagenesis of the capsid in situ as well as biological depletion of NAb titer (empty capsid utilization, B cell depletion and plasma-apheresis). These approaches have low efficiency or side-effect or change of AAV tropism. The recent structural studies on interaction of AAV vectors with monoclonal neutralizing antibodies demonstrated that Nab binds to residues on several different subunits of one virion surface, which suggests that change of subunit assembly of AAV virion may ablate the AAV Nab binding site and then escape Nab activity. We have results strongly supporting the notion that novel mosaic AAV vectors have potential to enhance transduction in various tissues and are able to escape neutralizing antibody activity.

Treatment of Diseases

In each of the following Examples 5-6 for treatment of diseases: e.g., of the central nervous system, heart, lung, skeletal muscle, and liver; including e.g. Parkinson's disease, Alzheimer's disease, cystic fibrosis, ALS, Duchenne Muscular Dystrophy, limb girdle muscular dystrophy, Myasthenia Gravis, and Hemophilia A or B; the capsid virion described therein that is generated using the specified AAV serotypes and mosaicism is alternatively generated using the rational polyploid method of Example 2, to generate a haploid capsid where VP1 is only from the first serotype, and VP2 and/or VP3 is only from the second serotype; or e.g., where VP1, VP2 and VP3 are each from a different serotype. Alternative methods for creating such virions are also, e.g. Described in Examples 7-15.

Example 5: Treatment of Diseases of the Central Nervous System (CNS) with VP1/VP2/VP3 from Two or More Different AAV Serotypes In a first experiment, two helper plasmids are used. The first helper plasmid has the Rep and Cap genes from AAV2 and the second helper plasmid has the Rep gene from AAV2 and the Cap gene from AAV4. A third plasmid encodes for the nucleotide sequence for Glutamic Acid Decarboxylase 65 (GAD65) and/or Glutamic Acid Decarboxylase 67 (GAD67), which nucleotide sequence is inserted between two ITRs. A polyploid virion can be used to encapsidate the therapeutic GAD65 and/or GAD67 containing nucleic acid sequence. In the following examples, the capsid can be prepared using for example the rational polyploid method of Example 2 to produce, for example, a haploid capsid where VP1 is only from one serotype, VP3 is only from an alternative serotype, and VP2 may or may not be present. When VP2 is present it is only from one serotype that may be the same as either VP1 or VP3, or can be from a third serotype or the capsid can be prepared by the cross-dressing methodology described above that results in mosaic haploid capsids. The haploid AAV generated from the three plasmids contains the nucleotide sequence for GAD65 and/or GAD67protein to treat Parkinson's disease, in part by increasing the specificity for central nervous system tissues associated with Parkinson's disease through the use of multiple AAV serotypes to source the proteins that code for VP1, VP2 and VP3 according to the methods of the present invention. In fact, the haploid virus created by this method to treat Parkinson's disease can have a higher specificity for the relevant tissue than a virus vector comprised of only AAV2 or AAV4.

In a further experiment, two helper plasmids are again used with different AAV serotypes as the source for the Rep and Cap genes. The first helper plasmid has the Rep and Cap genes from AAV3 and the second helper plasmid has the Rep gene from AAV3 and the Cap gene from AAV5. A third plasmid encodes the nucleotide sequence for CLN2 to treat Batten's disease is contained in a third plasmid and has been inserted between two ITRs. The haploid AAV generated from the three plasmids contains the nucleotide sequence to treat Batten's disease, in part by increasing the specificity for central nervous system tissues associated with Parkinson's disease through the use of multiple AAV serotypes to source the proteins that code for VP1, VP2 and VP3 according to the methods of the present invention. In fact, the haploid virus created by this method to treat Batten's disease has a higher specificity for the relevant central nervous system tissue than a virus vector comprised of only AAV3 or AAV5.

In another experiment, three helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV4. A third helper plasmid has the Rep gene from AAV3 and the Cap gene from AAV5. A fourth plasmid encodes the nucleotide sequence for Nerve Growth Factor (NGF) to treat Alzheimer's disease is contained in a third plasmid and has been inserted between two ITRs. The triploid AAV generated from the four plasmids contains the nucleotide sequence to treat Alzheimer's disease, in part by increasing the specificity for central nervous system tissues associated with Alzheimer's disease through the use of multiple AAV serotypes (e.g., AAV3, AAV4 and AAV5) to source the proteins that code for VP1, VP2 and VP3 according to the methods of the present invention. In fact, the triploid virus created by this method to treat Alzheimer's disease has a higher specificity for the relevant central nervous system tissue than a virus vector comprised of only AAV3, AAV4 or AAV5.

In another experiment, one helper plasmid is used with different AAV serotypes as the source for the Rep and Cap genes. The helper plasmid has the Rep from AAV2 and VP1 from AAV2, VP2 from AAV4 and VP3 from AAV5. A second plasmid encodes the nucleotide sequence for AAC inserted between two ITRs to treat Canavan's disease. The triploid AAV generated from the two plasmids contains the nucleotide sequence to treat Canavan's disease, in part by increasing the specificity for central nervous system tissues associated with Canavan's disease through the use of multiple AAV serotypes (e.g., AAV2, AAV4 and AAV5) to source the proteins that code for VP1, VP2 and VP3 according to the methods of the present invention. In fact, the triploid virus created by this method to treat Canavan's disease has a higher specificity for the relevant central nervous system tissue than a virus vector comprised of only AAV2, AAV4 or AAV5.

Treatment of Diseases of Heart with VP1/VP2/VP3 from Two or More Different AAV Serotypes. In an experiment, two helper plasmids are used with different AAV serotypes as the source for the Rep and Cap genes. The first helper plasmid has the Rep and Cap genes from AAV2 and the second helper plasmid has the Rep gene from AAV2 and the Cap gene from AAV6. A third plasmid encodes the nucleotide sequence for the protein to treat heart disease is contained in a third plasmid and has been inserted between two ITRs. The haploid AAV generated from the three plasmids contains the nucleotide sequence to treat heart disease, in part by increasing the specificity heart tissue associated with heart's disease through the use of multiple AAV serotypes to source the proteins that code for VP1, VP2 and VP3 according to the methods of the present invention. In fact, the haploid virus created by this method to treat heart disease has a higher specificity for the relevant heart tissue than a virus vector comprised of only AAV2 or AAV6.

In a further experiment, two helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV9. A third plasmid encodes the nucleotide sequence for the protein to treat heart disease is contained in a third plasmid and has been inserted between two ITRs. The haploid AAV generated from the three plasmids contains a nucleotide sequence encoding a protein to treat heart disease, in part by increasing the specificity heart tissue associated with heart's disease through the use of multiple AAV serotypes to source the proteins that code for VP1, VP2 and VP3 according to the methods of the present invention. In fact, the haploid virus created by this method to treat heart disease has a higher specificity for the relevant heart tissue than a virus vector comprised of only AAV3 or AAV9.

In an experiment, three helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV6. A third helper plasmid has the Rep gene from AAV3 and the Cap gene from AAV9. A fourth plasmid contains a nucleotide sequence that encodes a protein to treat heart disease is contained in a third plasmid and has been inserted between two ITRs. The triploid AAV generated from the four plasmids contains the nucleotide sequence to treat heart disease, in part by increasing the specificity for heart tissue associated with heart disease through the use of multiple AAV serotypes (e.g., AAV3, AAV6 and AAV9) to source the proteins that code for VP1, VP2 and VP3 according to the methods of the present invention. In fact, the triploid virus created by this method to treat heart disease has a higher specificity for the relevant heart tissue than a virus vector comprised of only AAV3, AAV6 or AAV9.

In another experiment, one helper plasmid is used with different AAV serotypes as the source for the Rep and Cap genes. The helper plasmid has the Rep from AAV2 and VP1 from AAV2, VP2 from AAV3 and VP3 from AAV9. A second plasmid contains a nucleotide sequence encoding a protein to treat heart disease inserted between two ITRs. The triploid AAV generated from the two plasmids encodes the nucleotide sequence to treat heart disease, in part by increasing the specificity for heart tissues associated with heart disease through the use of multiple AAV serotypes (e.g., AAV2, AAV3 and AAV9) to source the proteins that code for VP1, VP2 and VP3 according to the methods of the present invention. In fact, the triploid virus created by this method to treat heart disease has a higher specificity for the relevant heart tissue than a virus vector comprised of only AAV2, AAV3 or AAV9.

In another experiment, one helper plasmid is used with different AAV serotypes as the source for the Rep and Cap genes. The helper plasmid has the Rep from AAV3 and VP1 from AAV3, VP2 from AAV6 and VP3 from AAV6. A second plasmid contains a nucleotide sequence encoding a protein to treat heart disease inserted between two ITRs. The haploid AAV generated from the two plasmids encodes the nucleotide sequence to treat heart disease, in part by increasing the specificity for heart tissues associated with heart disease through the use of multiple AAV serotypes (e.g., AAV3 and AAV6) to source the proteins that code for VP1, VP2 and VP3 according to the methods of the present invention. In fact, the haploid virus created by this method to treat heart disease has a higher specificity for the relevant heart tissue than a virus vector comprised of only AAV2 or AAV6.

In another experiment, one helper plasmid is used with different AAV serotypes as the source for the Rep and Cap genes. The helper plasmid has the Rep from AAV3 and VP1 from AAV3, VP2 from AAV6 and VP3 from AAV9. A second plasmid contains a nucleotide sequence encoding a protein to treat heart disease inserted between two ITRs. The triploid AAV generated from the two plasmids encodes the nucleotide sequence to treat heart disease, in part by increasing the specificity for heart tissues associated with heart disease through the use of multiple AAV serotypes (e.g., AAV3, AAV6 and AAV9) to source the proteins that code for VP1, VP2 and VP3 according to the methods of the present invention. In fact, the triploid virus created by this method to treat heart disease has a higher specificity for the relevant heart tissue than a virus vector comprised of only AAV3, AAV6 or AAV9.

Treatment of Diseases of the Lung with VP1/VP2/VP3 from Two or More Different AAV Serotypes. In an experiment, two helper plasmids are again used with different AAV serotypes as the source for the Rep and Cap genes. The first helper plasmid has the Rep and Cap genes from AAV2 and the second helper plasmid has the Cap gene from AAV9. A third plasmid encodes for the nucleotide sequence for CFTR to treat Cystic Fibrosis is inserted between two ITRs. The haploid AAV generated from the three plasmids contains the nucleotide sequence for CFTR to treat Cystic Fibrosis, in part by increasing the specificity for lung tissue associated with Cystic Fibrosis through the use of multiple AAV serotypes to source the proteins that code for VP1, VP2 and VP3 according to the methods of the present invention. In fact, the haploid virus created by this method to treat Cystic Fibrosis has a higher specificity for the relevant tissue than a virus vector comprised of only AAV2 or AAV9.

In an experiment, two helper plasmids are again used with different AAV serotypes as the source for the Rep and Cap genes. The first helper plasmid has the Rep and Cap genes from AAV3 and the second helper plasmid has the Rep from AAV3 and the Cap gene from AAV10. A third plasmid encodes for the nucleotide sequence for CFTR to treat Cystic Fibrosis is inserted between two ITRs. The haploid AAV generated from the three plasmids contains the nucleotide sequence for CFTR to treat Cystic Fibrosis, in part by increasing the specificity for lung tissue associated with Cystic Fibrosis through the use of multiple AAV serotypes to source the proteins that code for VP1, VP2 and VP3 according to the methods of the present invention. In fact, the haploid virus created by this method to treat Cystic Fibrosis has a higher specificity for the relevant tissue than a virus vector comprised of only AAV3 or AAV10.

In an experiment, three helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV9. A third helper plasmid has the Rep gene from AAV3 and the Cap gene from AAV10. A fourth plasmid encodes a nucleotide sequence for CFTR to treat Cystic Fibrosis is contained in a third plasmid and has been inserted between two ITRs. The triploid AAV generated from the four plasmids contains the nucleotide sequence for CFTR to treat Cystic Fibrosis, in part by increasing the specificity for lung tissue associated with Cystic Fibrosis through the use of multiple AAV serotypes (e.g., AAV3, AAV9 and AAV10) to source the proteins that code for VP1, VP2 and VP3 according to the methods of the present invention. In fact, the triploid virus created by this method to treat Cystic Fibrosis has a higher specificity for the relevant tissue than a virus vector comprised of only AAV3, AAV9 or AAV10.

In another experiment, one helper plasmid is used with different AAV serotypes as the source for the Rep and Cap genes. The helper plasmid has the Rep from AAV2 and VP1 from AAV2, VP2 from AAV9 and VP3 from AAV9. A second plasmid encodes the nucleotide sequence for CFTR inserted between two ITRs to treat Cystic Fibrosis. The haploid AAV generated from the two plasmids contains the nucleotide sequence to treat Cystic Fibrosis, in part by increasing the specificity for central nervous system tissues associated with Cystic Fibrosis through the use of multiple AAV serotypes (e.g., AAV2 and AAV9) to source the proteins that code for VP1, VP2 and VP3 according to the methods of the present invention. In fact, the haploid virus created by this method to treat Cystic Fibrosis has a higher specificity for the relevant tissue than a virus vector comprised of only AAV2 or AAV9.

In a further experiment, one helper plasmid is used with different AAV serotypes as the source for the Rep and Cap genes. The helper plasmid has the Rep from AAV3 and VP1 from AAV2, VP2 from AAV10 and VP3 from AAV10. A second plasmid encodes the nucleotide sequence for CFTR inserted between two ITRs to treat Cystic Fibrosis. The haploid AAV generated from the two plasmids contains the nucleotide sequence to treat Cystic Fibrosis, in part by increasing the specificity for central nervous system tissues associated with Cystic Fibrosis through the use of multiple AAV serotypes (e.g., AAV3 and AAV10) to source the proteins that code for VP1, VP2 and VP3 according to the methods of the present invention. In fact, the haploid virus created by this method to treat Cystic Fibrosis has a higher specificity for the relevant tissue than a virus vector comprised of only AAV3 or AAV10.

In another experiment, one helper plasmid is used with different AAV serotypes as the source for the Rep and Cap genes. The helper plasmid has the Rep from AAV2 and VP1 from AAV2, VP2 from AAV9 and VP3 from AAV10. A second plasmid encodes the nucleotide sequence for CFTR inserted between two ITRs to treat Cystic Fibrosis. The triploid AAV generated from the two plasmids contains the nucleotide sequence to treat Cystic Fibrosis, in part by increasing the specificity for central nervous system tissues associated with Canavan's disease through the use of multiple AAV serotypes (e.g., AAV2, AAV9 and AAV10) to source the proteins that code for VP1, VP2 and VP3 according to the methods of the present invention. In fact, the triploid virus created by this method to treat Cystic Fibrosis has a higher specificity for the relevant tissue than a virus vector comprised of only AAV2, AAV9 or AAV10.

Treatment of Diseases of the Skeletal Muscle with VP1/VP2/VP3 from Two or More Different AAV Serotypes. For the following experiments, the skeletal muscle disease can be, but is not limited to, Duchene Muscular Dystrophy, Limb Girdle Muscular Dystrophy, Cerebral Palsy, Myasthenia Gravis and Amyotrophic Lateral Sclerosis (ALS).

In an experiment, two helper plasmids are again used with different AAV serotypes as the source for the Rep and Cap genes. The first helper plasmid has the Rep and Cap genes from AAV2 and the second helper plasmid has the Rep from AAV2 and the Cap gene from AAV8. A third plasmid encodes for the nucleotide sequence for a protein to treat a disease of the skeletal muscle that is inserted between two ITRs. The haploid AAV generated from the three plasmids contains the nucleotide sequence for a protein to treat a disease of the skeletal muscle, in part by increasing the specificity for skeletal muscle associated with a disease of the skeletal muscle through the use of multiple AAV serotypes to source the proteins that code for VP1, VP2 and VP3 according to the methods of the present invention. In fact, the haploid virus created by this method to treat a skeletal muscle disease has a higher specificity for the relevant skeletal muscle tissue than a virus vector comprised of only AAV2 or AAV8.

In an experiment, two helper plasmids are again used with different AAV serotypes as the source for the Rep and Cap genes. The first helper plasmid has the Rep and Cap genes from AAV3 and the second helper plasmid has the Rep from AAV3 and the Cap gene from AAV9. A third plasmid encodes for the nucleotide sequence for a protein to treat a disease of the skeletal muscle that is inserted between two ITRs. The haploid AAV generated from the three plasmids contains the nucleotide sequence for a protein to treat a disease of the skeletal muscle, in part by increasing the specificity for skeletal muscle associated with a disease of the skeletal muscle through the use of multiple AAV serotypes to source the proteins that code for VP1, VP2 and VP3 according to the methods of the present invention. In fact, the haploid virus created by this method to treat a skeletal muscle disease has a higher specificity for the relevant skeletal muscle tissue than a virus vector comprised of only AAV3 or AAV9.

In an experiment, three helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV8. A third helper plasmid has the Rep gene from AAV3 and the Cap gene from AAV9. A fourth plasmid encodes for the nucleotide sequence for a protein to treat a disease of the skeletal muscle that is inserted between two ITRs. The triploid AAV generated from the four plasmids contains the nucleotide sequence for a protein to treat a skeletal muscle disease, in part by increasing the specificity for skeletal muscle associated with a disease of the skeletal muscle through the use of multiple AAV serotypes (e.g., AAV3, AAV8 and AAV9) to source the proteins that code for VP1, VP2 and VP3 according to the methods of the present invention. In fact, the triploid virus created by this method to treat a skeletal muscle disease has a higher specificity for the relevant tissue than a virus vector comprised of only AAV3, AAV8 or AAV9.

In another experiment, one helper plasmid is used with different AAV serotypes as the source for the Rep and Cap genes. The helper plasmid has the Rep from AAV3 and VP1 from AAV3, VP2 from AAV9 and VP3 from AAV9. A second plasmid encodes for the nucleotide sequence for a protein to treat a disease of the skeletal muscle that is inserted between two ITRs. The haploid AAV generated from the two plasmids contains the nucleotide sequence to treat a disease of the skeletal muscle that, in part by increasing the specificity for skeletal muscle tissues associated with a skeletal muscle disease through the use of multiple AAV serotypes (e.g., AAV3 and AAV9) to source the proteins that code for VP1, VP2 and VP3 according to the methods of the present invention. In fact, the haploid virus created by this method to treat a skeletal muscle disease has a higher specificity for the relevant skeletal muscle tissue than a virus vector comprised of only AAV3 or AAV9.

In another experiment, one helper plasmid is used with different AAV serotypes as the source for the Rep and Cap genes. The helper plasmid has the Rep from AAV3 and VP1 from AAV3, VP2 from AAV8 and VP3 from AAV8. A second plasmid encodes for the nucleotide sequence for a protein to treat a disease of the skeletal muscle that is inserted between two ITRs. The haploid AAV generated from the two plasmids contains the nucleotide sequence to treat a disease of the skeletal muscle that, in part by increasing the specificity for skeletal muscle tissues associated with a skeletal muscle disease through the use of multiple AAV serotypes (e.g., AAV3 and AAV8) to source the proteins that code for VP1, VP2 and VP3 according to the methods of the present invention. In fact, the haploid virus created by this method to treat a skeletal muscle disease has a higher specificity for the relevant skeletal muscle tissue than a virus vector comprised of only AAV3 or AAV8.

In another experiment, one helper plasmid is used with different AAV serotypes as the source for the Rep and Cap genes. The helper plasmid has the Rep from AAV3 and VP1 from AAV3, VP2 from AAV8 and VP3 from AAV9. A second plasmid encodes for the nucleotide sequence for a protein to treat a disease of the skeletal muscle that is inserted between two ITRs. The triploid AAV generated from the two plasmids contains the nucleotide sequence to treat a disease of the skeletal muscle that, in part by increasing the specificity for skeletal muscle tissues associated with a skeletal muscle disease through the use of multiple AAV serotypes (e.g., AAV3, AAV8 and AAV9) to source the proteins that code for VP1, VP2 and VP3 according to the methods of the present invention. In fact, the triploid virus created by this method to treat a skeletal muscle disease has a higher specificity for the relevant skeletal muscle tissue than a virus vector comprised of only AAV3, AAV8 or AAV9.

Treatment of Diseases of the Liver with VP1/VP2/VP3 from Two or More Different AAV Serotypes. In an experiment, two helper plasmids are again used with different AAV serotypes as the source for the Rep and Cap genes. The first helper plasmid has the Rep and Cap genes from AAV2 and the second helper plasmid has the Rep from AAV2 and the Cap gene from AAV6. A third plasmid encodes for the nucleotide sequence for a Factor IX (FIX) to treat Hemophilia B that is inserted between two ITRs. The haploid AAV generated from the three plasmids contains the nucleotide sequence for a protein to treat a disease of the skeletal muscle, in part by increasing the specificity for FIX associated with Hemophilia B through the use of multiple AAV serotypes to source the proteins that code for VP1, VP2 and VP3 according to the methods of the present invention. In fact, the haploid virus created by this method to treat liver tissue in a patient suffering from Hemophilia B has a higher specificity for the relevant tissue than a virus vector comprised of only AAV2 or AAV6.

In an experiment, two helper plasmids are again used with different AAV serotypes as the source for the Rep and Cap genes. The first helper plasmid has the Rep and Cap genes from AAV2 and the second helper plasmid has the Rep from AAV3 and the Cap gene from AAV7. A third plasmid encodes for the nucleotide sequence for a Factor IX (FIX) to treat Hemophilia B that is inserted between two ITRs. The haploid AAV generated from the three plasmids contains the nucleotide sequence for a protein to treat a disease of the skeletal muscle, in part by increasing the specificity for FIX associated with Hemophilia B through the use of multiple AAV serotypes to source the proteins that code for VP1, VP2 and VP3 according to the methods of the present invention. In fact, the haploid virus created by this method to treat liver tissue in a patient suffering from Hemophilia B has a higher specificity for the relevant tissue than a virus vector comprised of only AAV3 or AAV7.

In an experiment, three helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV6. A third helper plasmid has the Rep gene from AAV3 and the Cap gene from AAV7. A fourth plasmid encodes for the nucleotide sequence for a Factor IX (FIX) to treat Hemophilia B that is inserted between two ITRs. The triploid AAV generated from the four plasmids contains the nucleotide sequence for a protein to treat Hemophilia B, in part by increasing the specificity for liver tissue associated with Hemophilia B through the use of multiple AAV serotypes (e.g., AAV3, AAV6 and AAV7) to source the proteins that code for VP1, VP2 and VP3 according to the methods of the present invention. In fact, the triploid virus created by this method to treat liver tissue in a patient suffering from Hemophilia B has a higher specificity for the relevant tissue than a virus vector comprised of only AAV3, AAV6 or AAV7.

In another experiment, one helper plasmid is used with different AAV serotypes as the source for the Rep and Cap genes. The helper plasmid has the Rep from AAV2 and VP1 from AAV2, VP2 from AAV6 and VP3 from AAV6. A second plasmid encodes for the nucleotide sequence for FIX to treat Hemophilia B that is inserted between two ITRs. The haploid AAV generated from the two plasmids contains the nucleotide sequence to treat Hemophilia B that, in part by increasing the specificity for liver tissues associated with Hemophilia B through the use of multiple AAV serotypes (e.g., AAV2 and AAV6) to source the proteins that code for VP1, VP2 and VP3 according to the methods of the present invention. In fact, the haploid virus created by this method to treat liver tissue in a patient suffering from Hemophilia B has a higher specificity for the relevant tissue than a virus vector comprised of only AAV2 or AAV6.

In another experiment, one helper plasmid is used with different AAV serotypes as the source for the Rep and Cap genes. The helper plasmid has the Rep from AAV2 and VP1 from AAV3, VP2 from AAV7 and VP3 from AAV7. A second plasmid encodes for the nucleotide sequence for FIX to treat Hemophilia B that is inserted between two ITRs. The haploid AAV generated from the two plasmids contains the nucleotide sequence to treat Hemophilia B that, in part by increasing the specificity for liver tissues associated with Hemophilia B through the use of multiple AAV serotypes (e.g., AAV3 and AAV7) to source the proteins that code for VP1, VP2 and VP3 according to the methods of the present invention. In fact, the haploid virus created by this method to treat liver tissue in a patient suffering from Hemophilia B has a higher specificity for the relevant tissue than a virus vector comprised of only AAV3 or AAV7.

In another experiment, one helper plasmid is used with different AAV serotypes as the source for the Rep and Cap genes. The helper plasmid has the Rep from AAV2 and VP1 from AAV3, VP2 from AAV6 and VP3 from AAV7. A second plasmid encodes for the nucleotide sequence for FIX to treat Hemophilia B that is inserted between two ITRs. The triploid AAV generated from the two plasmids contains the nucleotide sequence to treat Hemophilia B that, in part by increasing the specificity for liver tissues associated with Hemophilia B through the use of multiple AAV serotypes (e.g., AAV3, AAV6 and AAV7) to source the proteins that code for VP1, VP2 and VP3 according to the methods of the present invention. In fact, the triploid virus created by this method to treat liver tissue in a patient suffering from Hemophilia B has a higher specificity for the relevant tissue than a virus vector comprised of only AAV3, AAV6 or AAV7.

In an experiment, two helper plasmids are again used with different AAV serotypes as the source for the Rep and Cap genes. The first helper plasmid has the Rep and Cap genes from AAV2 and the second helper plasmid has the Rep from AAV2 and the Cap gene from AAV6. A third plasmid encodes for the nucleotide sequence for a Factor VIII (FVIII) to treat Hemophilia A that is inserted between two ITRs. The haploid AAV generated from the three plasmids contains the nucleotide sequence for a protein to treat a disease of the skeletal muscle, in part by increasing the specificity for FVIII associated with Hemophilia A through the use of multiple AAV serotypes to source the proteins that code for VP1, VP2 and VP3 according to the methods of the present invention. In fact, the haploid virus created by this method to treat liver tissue in a patient suffering from Hemophilia A has a higher specificity for the relevant tissue than a virus vector comprised of only AAV2 or AAV6.

In an experiment, two helper plasmids are again used with different AAV serotypes as the source for the Rep and Cap genes. The first helper plasmid has the Rep and Cap genes from AAV2 and the second helper plasmid has the Rep from AAV3 and the Cap gene from AAV7. A third plasmid encodes for the nucleotide sequence for a FVIII to treat Hemophilia A that is inserted between two ITRs. The haploid AAV generated from the three plasmids contains the nucleotide sequence for a protein to treat a disease of the skeletal muscle, in part by increasing the specificity for FVIII associated with Hemophilia A through the use of multiple AAV serotypes to source the proteins that code for VP1, VP2 and VP3 according to the methods of the present invention. In fact, the haploid virus created by this method to treat liver tissue in a patient suffering from Hemophilia A has a higher specificity for the relevant tissue than a virus vector comprised of only AAV3 or AAV7.

In an experiment, three helper plasmids are used with different AAV serotypes as the source for the Rep and Cap genes. The first helper plasmid has the Rep and Cap genes from AAV3 and the second helper plasmid has the Rep gene from AAV3 and the Cap gene from AAV6. A third helper plasmid has the Rep gene from AAV3 and the Cap gene from AAV7. A fourth plasmid encodes for the nucleotide sequence for a FVIII to treat Hemophilia A that is inserted between two ITRs. The triploid AAV generated from the four plasmids contains the nucleotide sequence for a FVIII protein to treat Hemophilia A, in part by increasing the specificity for liver tissue associated with Hemophilia B through the use of multiple AAV serotypes (e.g., AAV3, AAV6 and AAV7) to source the proteins that code for VP1, VP2 and VP3 according to the methods of the present invention. In fact, the triploid virus created by this method to treat liver tissue in a patient suffering from Hemophilia A has a higher specificity for the relevant tissue than a virus vector comprised of only AAV3, AAV6 or AAV7.

In another experiment, one helper plasmid is used with different AAV serotypes as the source for the Rep and Cap genes. The helper plasmid has the Rep from AAV2 and VP1 from AAV2, VP2 from AAV6 and VP3 from AAV6. A second plasmid encodes for the nucleotide sequence for FVIII to treat Hemophilia B that is inserted between two ITRs. The haploid AAV generated from the two plasmids contains the nucleotide sequence for FVIII to treat Hemophilia A that, in part by increasing the specificity for liver tissues associated with Hemophilia A through the use of multiple AAV serotypes (e.g., AAV2 and AAV6) to source the proteins that code for VP1, VP2 and VP3 according to the methods of the present invention. In fact, the haploid virus created by this method to treat liver tissue in a patient suffering from Hemophilia A has a higher specificity for the relevant tissue than a virus vector comprised of only AAV2 or AAV6.

In another experiment, one helper plasmid is used with different AAV serotypes as the source for the Rep and Cap genes. The helper plasmid has the Rep from AAV2 and VP1 from AAV3, VP2 from AAV7 and VP3 from AAV7. A second plasmid encodes for the nucleotide sequence for FVIII to treat Hemophilia A that is inserted between two ITRs. The haploid AAV generated from the two plasmids contains the nucleotide sequence for FVIII to treat Hemophilia A that, in part by increasing the specificity for liver tissues associated with Hemophilia B through the use of multiple AAV serotypes (e.g., AAV3 and AAV7) to source the proteins that code for VP1, VP2 and VP3 according to the methods of the present invention. In fact, the haploid virus created by this method to treat liver tissue in a patient suffering from Hemophilia A has a higher specificity for the relevant tissue than a virus vector comprised of only AAV3 or AAV7.

In another experiment, one helper plasmid is used with different AAV serotypes as the source for the Rep and Cap genes. The helper plasmid has the Rep from AAV2 and VP1 from AAV3, VP2 from AAV6 and VP3 from AAV7. A second plasmid encodes for the nucleotide sequence for FVIII to treat Hemophilia A that is inserted between two ITRs. The triploid AAV generated from the two plasmids contains the nucleotide sequence for FVIII to treat Hemophilia B that, in part by increasing the specificity for liver tissues associated with Hemophilia A through the use of multiple AAV serotypes (e.g., AAV3, AAV6 and AAV7) to source the proteins that code for VP1, VP2 and VP3 according to the methods of the present invention. In fact, the triploid virus created by this method to treat liver tissue in a patient suffering from Hemophilia A has a higher specificity for the relevant tissue than a virus vector comprised of only AAV3, AAV6 or AAV7.

Example 6: Use of AAVs of the Instant Invention to Treat a Disease

Treatment of Parkinson's Disease. A male patient of 45 years of age suffering from Parkinson's disease is treated with an AAV generated from a cell line, such as the isolated HEK293 cell line with ATCC No. PTA 13274 (see e.g., U.S. Pat. No. 9,441,206), which contains a first helper plasmid that has the Rep and Cap genes from AAV2 and a second helper plasmid that has the Rep gene from AAV2 and the Cap gene from AAV4 and a third plasmid that encodes for the nucleotide sequence for Glutamic Acid Decarboxylase 65 (GAD65) and/or Glutamic Acid Decarboxylase 67 (GAD67), which nucleotide sequence is inserted between two ITRs. The haploid AAV generated from the three plasmids contains the nucleotide sequence for GAD65 and/or GAD67 protein to treat Parkinson's disease. The AAV is administered to the patient, who shortly after administration shows a reduction in the frequency of tremors and an improvement in the patient's balance. Over time the patient also sees a reduction in the number and severity of hallucinations and delusions that the patient suffered from prior to administration of the AAV.

Treatment of Batten Disease. A male patient of 8 years of age suffering from Batten disease is treated with an AAV generated from a cell line, such as the isolated HEK293 cell line with ATCC No. PTA 13274 (see e.g., U.S. Pat. No. 9,441,206), which contains a first helper plasmid that has the Rep and Cap genes from AAV3 and a second helper plasmid that has the Rep gene from AAV3 and the Cap gene from AAV5. A third plasmid encodes the nucleotide sequence for CLN2 to treat Batten's disease, wherein the CLN 2 gene has been inserted between two ITRs. The haploid AAV generated from the three plasmids contains the nucleotide sequence to treat Batten's disease. The AAV is administered to the patient, who shortly after administration shows an increase in mental acuity. Additionally, the patient sees a reduction in seizures and improvement in sign and motor skills that the patient suffered from prior to administration of the AAV.

Treatment of Alzheimer's Disease. A female patient of 73 years suffering from Alzheimer's disease is treated with an AAV generated from a cell line, such as the isolated HEK293 cell line with ATCC No. PTA 13274 (see e.g., U.S. Pat. No. 9,441,206), which contains a first helper plasmid that has the Rep and Cap genes from AAV3; a second helper plasmid that has the Rep gene from AAV3 and the Cap gene from AAV4; and, a third helper plasmid that has the Rep gene from AAV3 and the Cap gene from AAV5. A fourth plasmid encodes the nucleotide sequence for Nerve Growth Factor (NGF) to treat Alzheimer's disease, wherein NGF has been inserted between two ITRs. The triploid AAV is administered to the patient, who shortly after administration shows an increase in mental acuity and short-term memory. The patient also is able to better communicate with others and begins to function more independently than prior to administration of the AAV.

Treatment of Heart Disease. A male patient of 63 years suffering from heart disease is treated with an AAV generated from a cell line, such as the isolated HEK293 cell line with ATCC No. PTA 13274 (see, e.g., U.S. Pat. No. 9,441,206), which contains either:

(1) a first helper plasmid that has the Rep and Cap genes from AAV2; a second helper plasmid that has the Rep gene from AAV2 and the Cap gene from AAV6; and, a third plasmid encodes the nucleotide sequence for the protein to treat heart disease that is contained in a third plasmid and has been inserted between two ITRs;

(2) a first helper plasmid that has the Rep and Cap genes from AAV3; a second helper plasmid that has the Rep gene from AAV3 and the Cap gene from AAV9; and, a third plasmid encodes the nucleotide sequence for the protein to treat heart disease that is contained in a third plasmid and has been inserted between two ITRs;

(3) a first helper plasmid that has the Rep and Cap genes from AAV3; a second helper plasmid that has the Rep gene from AAV3 and the Cap gene from AAV6; a third helper plasmid that has the Rep gene from AAV3 and the Cap gene from AAV9; and, a fourth plasmid contains a nucleotide sequence that encodes a protein to treat heart disease is contained in a third plasmid and has been inserted between two ITRs;

(4) a helper plasmid that has the Rep from AAV2 and VP1 from AAV2, VP2 from AAV3 and VP3 from AAV9; and, a second plasmid that contains a nucleotide sequence encoding a protein to treat heart disease inserted between two ITRs;

(5) a helper plasmid that has the Rep from AAV3 and VP1 from AAV3, VP2 from AAV6 and VP3 from AAV6; and, a second plasmid contains a nucleotide sequence encoding a protein to treat heart disease inserted between two ITRs; or, (6) a helper plasmid that has the Rep from AAV3 and VP1 from AAV3, VP2 from AAV6 and VP3 from AAV9; and, a second plasmid contains a nucleotide sequence encoding a protein to treat heart disease inserted between two ITRs, wherein the polyploid AAV is administered to the patient, who shortly after administration shows a reduction in the symptoms associated with heart disease and shows a commensurate improvement in the patient's heart health.

Treatment of Cystic Fibrosis. A 19 year old female suffering from Cystic Fibrosis is treated with an AAV generated from a cell line, such as the isolated HEK293 cell line with ATCC No. PTA 13274 (see e.g., U.S. Pat. No. 9,441,206), which contains either:

(1) a first helper plasmid that has the Rep and Cap genes from AAV3; a second helper plasmid that has the Rep from AAV3 and the Cap gene from AAV10; and, a third plasmid that encodes for the nucleotide sequence for CFTR that is inserted between two ITRs;

(2) a first helper plasmid that has the Rep and Cap genes from AAV3; a second helper plasmid that has the Rep gene from AAV3 and the Cap gene from AAV9; a third helper plasmid that has the Rep gene from AAV3 and the Cap gene from AAV10; and a fourth plasmid that encodes a nucleotide sequence for CFTR that has been inserted between two ITRs;

(3) a helper plasmid that has the Rep from AAV2 and VP1 from AAV2, VP2 from AAV9 and VP3 from AAV9; and a second plasmid that encodes the nucleotide sequence for CFTR inserted between two ITRs;

(4) a helper plasmid that has the Rep from AAV3 and VP1 from AAV2, VP2 from AAV10 and VP3 from AAV10; and, a second plasmid that encodes the nucleotide sequence for CFTR inserted between two ITRs; or, (7) a helper plasmid that has the Rep from AAV2 and VP1 from AAV2, VP2 from AAV9 and VP3 from AAV10; and, a second plasmid encodes the nucleotide sequence for CFTR inserted between two ITRs, wherein the AAV is administered to the patient, who shortly after administration shows a slowing in the increase of damage to the patient's lung; a reduction in the increase in the loss of lung function and a reduction in the speed by which the liver is damaged and a slowdown in the increase in the severity of liver cirrhosis. The same patient also sees a reduction in the severity of the Cystic Fibrosis-related diabetes that the patient had begun to suffer.

Treatment of Skeletal Muscle Disease—Amyotrophic Lateral Sclerosis (ALS). A male of 33 years of age who is suffering from Amyotrophic Lateral Sclerosis (ALS) is treated with an AAV generated from a cell line, such as the isolated HEK293 cell line with ATCC No. PTA 13274 (see e.g., U.S. Pat. No. 9,441,206), which contains either:

(1) a first helper plasmid that has the Rep and Cap genes from AAV2; a second helper plasmid that has the Rep from AAV2 and the Cap gene from AAV8; and, a third plasmid that encodes for the nucleotide sequence for superoxide dismutase 1 (SOD1) that is inserted between two ITRs;

(2) a first helper plasmid that has the Rep and Cap genes from AAV3; a second helper plasmid that has the Rep from AAV3 and the Cap gene from AAV9; and, a third plasmid that encodes for the nucleotide sequence for SOD1 that is inserted between two ITRs;

(3) a first helper plasmid that has the Rep and Cap genes from AAV3; a second helper plasmid that has the Rep gene from AAV3 and the Cap gene from AAV8; a third helper plasmid that has the Rep gene from AAV3 and the Cap gene from AAV9; and, a fourth plasmid that encodes for the nucleotide sequence for SOD1 that is inserted between two ITRs;

(4) a helper plasmid that has the Rep from AAV3 and VP1 from AAV3, VP2 from AAV9 and VP3 from AAV9; and, a second plasmid that encodes for the nucleotide sequence for SOD1 that is inserted between two ITRs;

(5) a helper plasmid that has the Rep from AAV3 and VP1 from AAV3, VP2 from AAV8 and VP3 from AAV8; and, a second plasmid encodes for the nucleotide sequence for SOD1 that is inserted between two ITRs; or, (6) a helper plasmid that has the Rep from AAV3 and VP1 from AAV3, VP2 from AAV8 and VP3 from AAV; and, a second plasmid encodes for the nucleotide sequence for SOD1 that is inserted between two ITRs, wherein the AAV is administered to the patient, who shortly after administration shows a reduction in the symptoms associated with ALS, including a slow down or stop in the progression of damage to motor neurons in the brain and the spinal cord and the maintenance of communication between the brain and the muscles of the patient.

Treatment of Duchenne Muscular Dystrophy. A male of 5 years of age who is suffering from Duchenne Muscular Dystrophy (DMD) is treated with an AAV generated from a cell line, such as the isolated HEK293 cell line with ATCC No. PTA 13274, which contains either:

(1) a first helper plasmid that has the Rep and Cap genes from AAV2; a second helper plasmid that has the Rep from AAV2 and the Cap gene from AAV8; and, a third plasmid that encodes for the nucleotide sequence for dystrophin that is inserted between two ITRs;

(2) a first helper plasmid that has the Rep and Cap genes from AAV3; a second helper plasmid that has the Rep from AAV3 and the Cap gene from AAV9; and, a third plasmid that encodes for the nucleotide sequence for dystrophin that is inserted between two ITRs;

(3) a first helper plasmid that has the Rep and Cap genes from AAV3; a second helper plasmid that has the Rep gene from AAV3 and the Cap gene from AAV8; a third helper plasmid that has the Rep gene from AAV3 and the Cap gene from AAV9; and, a fourth plasmid that encodes for the nucleotide sequence for dystrophin that is inserted between two ITRs;

(4) a helper plasmid that has the Rep from AAV3 and VP1 from AAV3, VP2 from AAV9 and VP3 from AAV9; and, a second plasmid that encodes for the nucleotide sequence for dystrophin that is inserted between two ITRs;

(5) a helper plasmid that has the Rep from AAV3 and VP1 from AAV3, VP2 from AAV8 and VP3 from AAV8; and, a second plasmid encodes for the nucleotide sequence for dystrophin that is inserted between two ITRs; or, (6) a helper plasmid that has the Rep from AAV3 and VP1 from AAV3, VP2 from AAV8 and VP3 from AAV; and, a second plasmid encodes for the nucleotide sequence for dystrophin that is inserted between two ITRs, wherein the AAV is administered to the patient, who shortly after administration shows a slowing in the increase of damage and wasting to the patient's skeletal muscles, as well a slowing or stoppage to the damage suffered by heart and lung as a result of Duchene Muscular Dystrophy.

Treatment of Myasthenia Gravis. A female of 33 years of age who is suffering from Myasthenia Gravis (MG) is treated with an AAV generated from a cell line, such as the isolated HEK293 cell line with ATCC No. PTA 13274, which contains either:

(1) a first helper plasmid that has the Rep and Cap genes from AAV2; a second helper plasmid that has the Rep from AAV2 and the Cap gene from AAV8; and, a third plasmid that encodes the nucleotide sequence for the gene such that the patient will no longer suffer from MG that is inserted between two ITRs;

(2) a first helper plasmid that has the Rep and Cap genes from AAV3; a second helper plasmid that has the Rep from AAV3 and the Cap gene from AAV9; and, a third plasmid that encodes for the gene such that the patient will no longer suffer from MG that is inserted between two ITRs;

(3) a first helper plasmid that has the Rep and Cap genes from AAV3; a second helper plasmid that has the Rep gene from AAV3 and the Cap gene from AAV8; a third helper plasmid that has the Rep gene from AAV3 and the Cap gene from AAV9; and, a fourth plasmid that encodes for the gene such that the patient will no longer suffer from MG that is inserted between two ITRs;

(4) a helper plasmid that has the Rep from AAV3 and VP1 from AAV3, VP2 from AAV9 and VP3 from AAV9; and, a second plasmid that encodes for the gene such that the patient will no longer suffer from MG that is inserted between two ITRs;

(5) a helper plasmid that has the Rep from AAV3 and VP1 from AAV3, VP2 from AAV8 and VP3 from AAV8; and, a second plasmid encodes for the gene such that the patient will no longer suffer from MG that is inserted between two ITRs; or, (6) a helper plasmid that has the Rep from AAV3 and VP1 from AAV3, VP2 from AAV8 and VP3 from AAV; and, a second plasmid encodes for the gene such that the patient will no longer suffer from MG that is inserted between two ITRs, wherein the AAV is administered to the patient, who shortly after administration shows a slowing in the increase breakdown in the communication between muscles and the nerves of the patient's body, resulting in a slow down or stoppage in the severity in the loss of muscle control. The patient's mobility stabilizes and no longer worsens after administration of the AAV and the patient's breathing also does not worsen after administration of the AAV.

Treatment of Limb Girdle Muscular Dystrophy. A male of 13 years of age who is suffering from Limb Girdle Muscular Dystrophy (LGMD) is treated with an AAV generated from a cell line, such as the isolated HEK293 cell line with ATCC No. PTA 13274, which contains either:

(1) a first helper plasmid that has the Rep and Cap genes from AAV2; a second helper plasmid that has the Rep from AAV2 and the Cap gene from AAV8; and, a third plasmid that encodes for the nucleotide sequence for one of the fifteen genes with a mutation associated with LGMD, including, but not limited to myotilin, telethonin, calpain-3, alpha-sarcoglycan and beta-sarcoglycan that is inserted between two ITRs;

(2) a first helper plasmid that has the Rep and Cap genes from AAV3; a second helper plasmid that has the Rep from AAV3 and the Cap gene from AAV9; and, a third plasmid that encodes for the nucleotide sequence for one of the fifteen genes with a mutation associated with LGMD, including, but not limited to myotilin, telethonin, calpain-3, alpha-sarcoglycan and beta-sarcoglycan that is inserted between two ITRs;

(3) a first helper plasmid that has the Rep and Cap genes from AAV3; a second helper plasmid that has the Rep gene from AAV3 and the Cap gene from AAV8; a third helper plasmid that has the Rep gene from AAV3 and the Cap gene from AAV9; and, a fourth plasmid that encodes for the nucleotide sequence for one of the fifteen genes with a mutation associated with LGMD, including, but not limited to myotilin, telethonin, calpain-3, alpha-sarcoglycan and beta-sarcoglycan that is inserted between two ITRs;

(4) a helper plasmid that has the Rep from AAV3 and VP1 from AAV3, VP2 from AAV9 and VP3 from AAV9; and, a second plasmid that encodes for the nucleotide sequence for one of the fifteen genes with a mutation associated with LGMD, including, but not limited to myotilin, telethonin, calpain-3, alpha-sarcoglycan and beta-sarcoglycan that is inserted between two ITRs;

(5) a helper plasmid that has the Rep from AAV3 and VP1 from AAV3, VP2 from AAV8 and VP3 from AAV8; and, a second plasmid encodes for the nucleotide sequence for one of the fifteen genes with a mutation associated with LGMD, including, but not limited to myotilin, telethonin, calpain-3, alpha-sarcoglycan and beta-sarcoglycan that is inserted between two ITRs; or, (6) a helper plasmid that has the Rep from AAV3 and VP1 from AAV3, VP2 from AAV8 and VP3 from AAV; and, a second plasmid encodes for the nucleotide sequence for one of the fifteen genes with a mutation associated with LGMD, including, but not limited to myotilin, telethonin, calpain-3, alpha-sarcoglycan and beta-sarcoglycan that is inserted between two ITRs, wherein one or more of the AAV's, each encoding one of the 15 different genes associated with LGMD is administered to the patient, who shortly after administration shows a slowing or stoppage in additional muscle wasting and atrophy.

Treatment of Diseases of the Liver—Hemophilia B. A male of 9 years of age who is suffering from a Hemophilia B resulting from a deficiency of Factor IX (FIX) is treated with an AAV generated from a cell line, such as the isolated HEK293 cell line with ATCC No. PTA 13274, which contains either:

(1) a first helper plasmid that has the Rep and Cap genes from AAV2; a second helper plasmid that has the Rep from AAV2 and the Cap gene from AAV6; and, a third plasmid that encodes for the nucleotide sequence for FIX to treat Hemophilia B that is inserted between two ITRs;

(2) a first helper plasmid that has the Rep and Cap genes from AAV2; a second helper plasmid that has the Rep from AAV3 and the Cap gene from AAV7; and a third plasmid that encodes for the nucleotide sequence for FIX to treat Hemophilia B that is inserted between two ITRs;

(3) a first helper plasmid that has the Rep and Cap genes from AAV3; a second helper plasmid that has the Rep gene from AAV3 and the Cap gene from AAV6; a third helper plasmid that has the Rep gene from AAV3 and the Cap gene from AAV7; and a fourth plasmid that encodes for the nucleotide sequence for FIX that is inserted between two ITRs;

(4) a helper plasmid that has the Rep from AAV2 and VP1 from AAV2, VP2 from AAV6 and VP3 from AAV6; and a second plasmid that encodes for the nucleotide sequence for FIX that is inserted between two ITRs;

(5) a helper plasmid that has the Rep from AAV2 and VP1 from AAV3, VP2 from AAV7 and VP3 from AAV7; and a second plasmid that encodes for the nucleotide sequence for FIX that is inserted between two ITRs; or, (6) a helper plasmid that has the Rep from AAV2 and VP1 from AAV3, VP2 from AAV6 and VP3 from AAV7' and a second plasmid encodes for the nucleotide sequence for FIX that is inserted between two ITRs, wherein the AAV is administered to the patient, who shortly after administration shows a reduction in the severity of the Hemophilia B, including a reduction in bleeding episodes.

Treatment of Hemophilia A. A male of 8 years of age who is suffering from a Hemophilia A resulting from a deficiency of Factor VIII (FVIII) is treated with an AAV generated from a cell line, such as the isolated HEK293 cell line with ATCC No. PTA 13274, which contains either:

(1) a first helper plasmid that has the Rep and Cap genes from AAV2; a second helper plasmid that has the Rep from AAV2 and the Cap gene from AAV6; and, a third plasmid that encodes for the nucleotide sequence for FVIII that is inserted between two ITRs;

(2) a first helper plasmid that has the Rep and Cap genes from AAV2; a second helper plasmid that has the Rep from AAV3 and the Cap gene from AAV7; and a third plasmid that encodes for the nucleotide sequence for FVIII that is inserted between two ITRs;

(3) a first helper plasmid that has the Rep and Cap genes from AAV3; a second helper plasmid that has the Rep gene from AAV3 and the Cap gene from AAV6; a third helper plasmid that has the Rep gene from AAV3 and the Cap gene from AAV7; and a fourth plasmid that encodes for the nucleotide sequence for FVIII that is inserted between two ITRs;

(4) a helper plasmid that has the Rep from AAV2 and VP1 from AAV2, VP2 from AAV6 and VP3 from AAV6; and a second plasmid that encodes for the nucleotide sequence for FVIII that is inserted between two ITRs;

(5) a helper plasmid that has the Rep from AAV2 and VP1 from AAV3, VP2 from AAV7 and VP3 from AAV7; and a second plasmid that encodes for the nucleotide sequence for FVIII that is inserted between two ITRs; or, (6) a helper plasmid that has the Rep from AAV2 and VP1 from AAV3, VP2 from AAV6 and VP3 from AAV7' and a second plasmid encodes for the nucleotide sequence for FVIII that is inserted between two ITRs, wherein the AAV is administered to the patient, who shortly after administration shows a reduction in the severity of the Hemophilia A, including a reduction in bleeding episodes.

Figure 8:
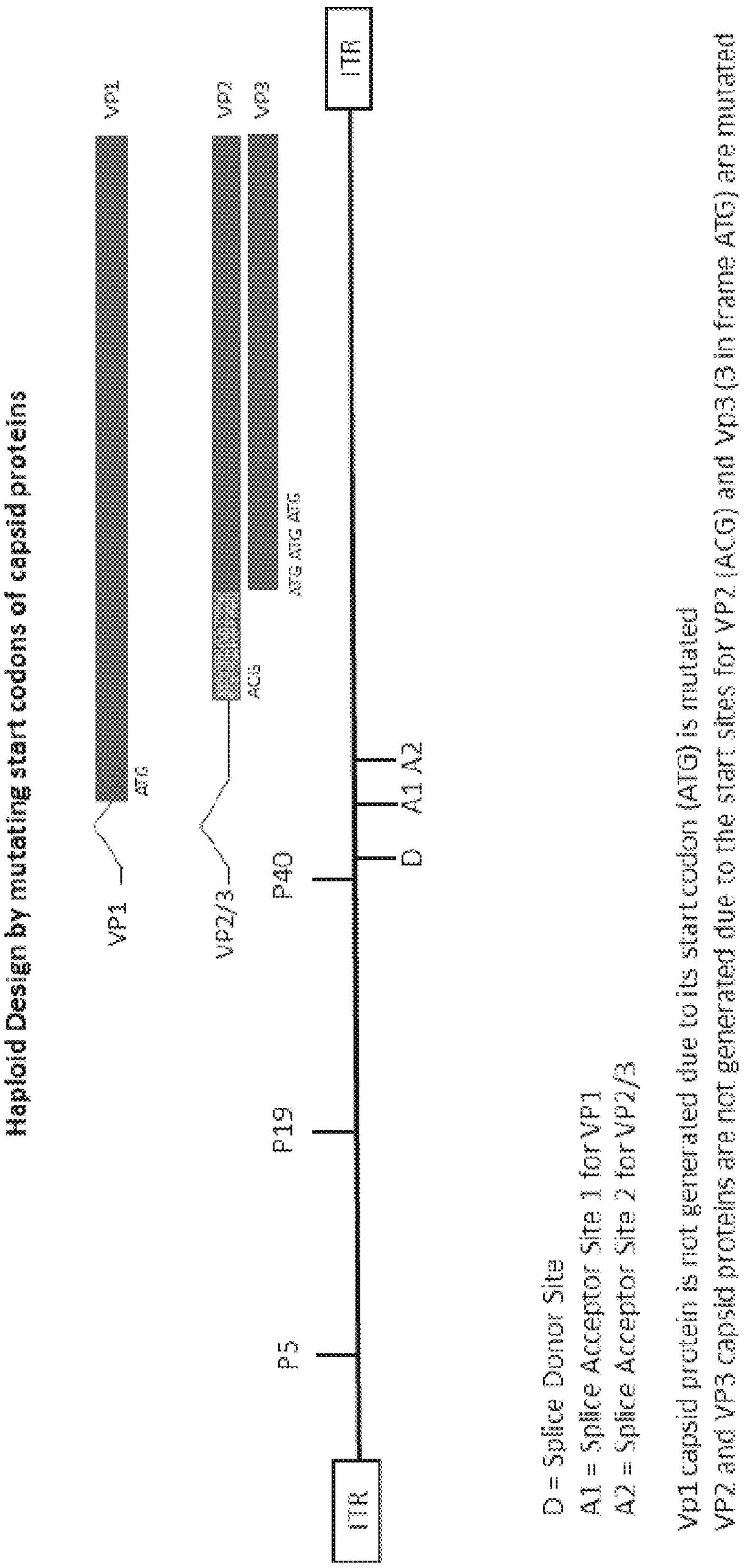
FIG. 8: Haploid design by mutating start codons of capsid protein VP1.

Example 7. Creation of Haploid Capsids from Two Different Serotypes and Mutation of Start Codons In this example, polyploid AAV virions are assembled from capsids of two different serotypes. The nucleotide sequence for VP1, VP2 and VP3 from a first AAV serotype only are ligated into a helper plasmid and the nucleotide sequence for VP1, VP2 and VP3 from a second AAV serotype only is ligated into the same or different helper plasmid, such that the helper plasmid/s include/s the nucleic acid sequences for VP1, VP2 and VP3 capsid proteins from two different serotypes. Either prior to ligation, or following ligation of the first and second serotype nucleotide sequences coding for VP1, VP2 and VP3 capsid proteins into the helper plasmid, the capsid nucleotide sequences are altered to provide a VP1 from a first serotype only and a VP2 and VP3 from a second serotype only. In this example, the VP1 nucleotide sequence of the first serotype has been altered by mutating the start codons for VP2 and VP3 capsid proteins as shown in FIG. 7. In this example, the ACG start site of VP2 and the three ATG start sites of VP3 are mutated such that these codons cannot initiate the translation of the RNA transcribed from the nucleotide sequence of the VP2 and VP3 capsid proteins from the first serotype. Similarly, as shown in FIG. 8, the ATG start site of VP1 is mutated in the nucleotide sequence coding for the capsid proteins of the second serotype such that this codon cannot initiate the translation of the RNA coding for VP1, but translation can be initiated for both VP2 and VP3. Thus, in this example, a polypoid AAV virion is created that includes a VP1, but not VP2 or VP3 from a first serotype only and a VP2 and VP3, but not a VP1 from a second serotype only.

In applying this technique of creating a polyploid AAV virion through mutation of start codons, the start codons of VP2 and VP3 of AAV2 were mutated as shown with highlights in FIG. 19, such that only VP1 is translated from an RNA transcribed from the plasmid set forth in FIG. 19. In the further application of this technique, the start codon of VP1 of AAV2 were mutated as shown with highlights in FIG. 18 such that VP2 and VP3, but not VP1 is translated from an RNA transcribed from the plasmid set forth in FIG. 19. Thus, mutation of the start codons provides a method of knocking out the expression of one or more of VP1, VP2 and VP3.

Example 8. Creation of Haploid Capsids from Two Different Serotypes and Mutation of Start Codons In this example, polyploid AAV virions are assembled from capsids of two different serotypes. The nucleotide sequence for VP1, VP2 and VP3 from a first AAV serotype only are ligated into a helper plasmid and the VP1, VP2 and VP3 from a second AAV serotype only is ligated into the same or different helper plasmid, such that the helper plasmid/s include the VP1, VP2 and VP3 capsid proteins from two different serotypes. Either prior to ligation or following ligation of the first and second serotype nucleotide sequences coding for VP1, VP2 and VP3 capsid proteins into the helper plasmid, the capsid nucleotide sequences are altered to provide a VP1 and VP3 from a first serotype only and a VP2 from a second serotype only. In this example, the ACG start site of VP2 is mutated such that this codon cannot initiate the translation of the RNA transcribed from the nucleotide sequence of the VP2 capsid protein from the first serotype. Similarly, the ATG start site of VP1 and VP3 is mutated in the nucleotide sequence coding for the capsid proteins of the second serotype such that these codons cannot initiate the translation of the RNA coding for VP1 and VP3, but translation can be initiated for both VP2. Thus, in this example, a polypoid AAV virion is created that includes VP1 and VP3, but not VP2 from a first serotype only and a VP2, but not VP1 and VP3 from a second serotype only.

In applying this technique of creating a polyploid AAV virion through mutation of start codons, the start codon of VP2 of AAV2 were mutated as shown with highlights in FIG. 20, such that VP1 and VP3 are translated from an RNA transcribed from the plasmid set forth in FIG. 20. Thus, mutation of the start codons provides a method of knocking out the expression of one or more of VP1, VP2 and VP3.

Figure 10:
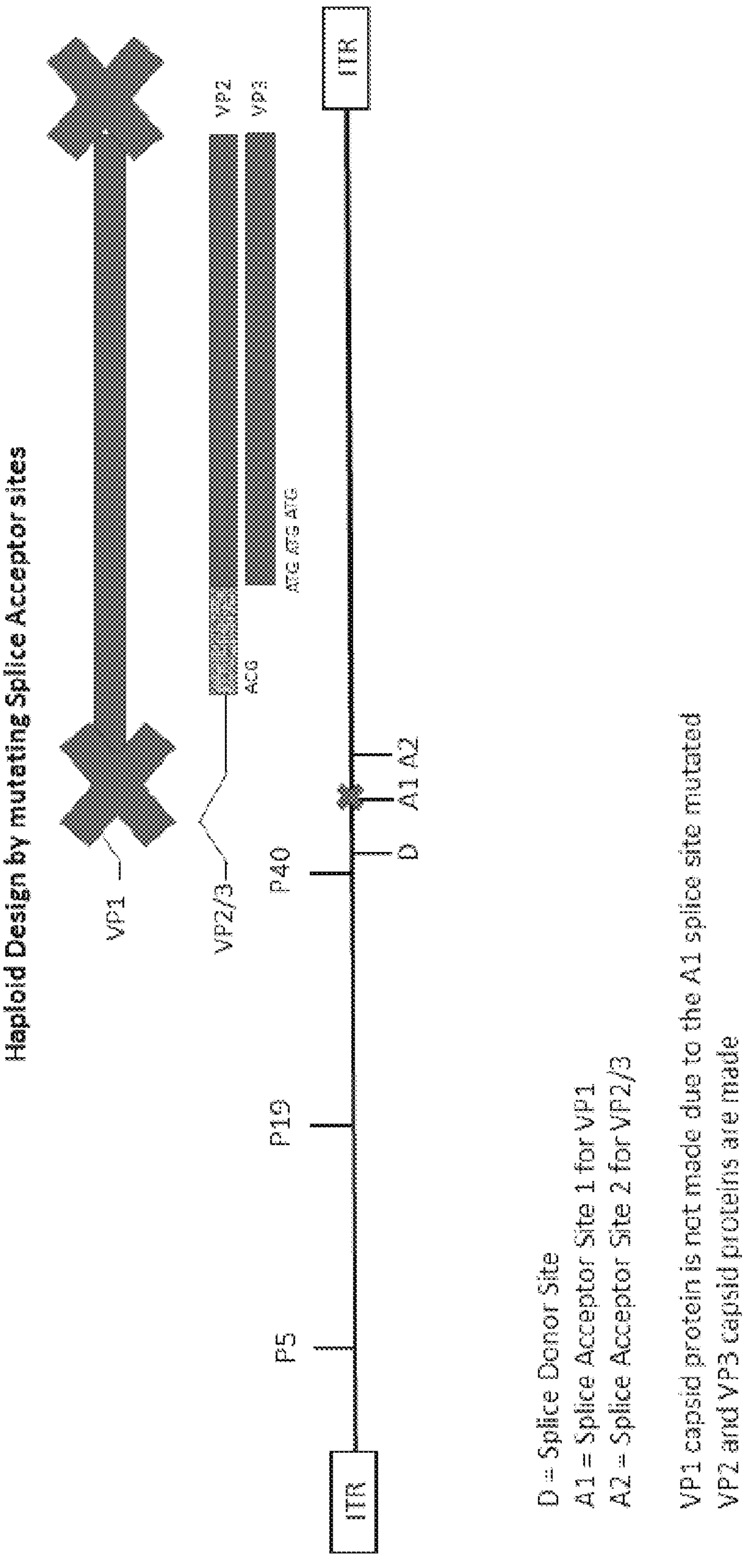
FIG. 10: Haploid design by mutating the Splice Acceptor Site A1.

Example 9. Creation of Haploid Capsids from Two Different Serotypes and Mutation of Splice Acceptor Sites In this example, polyploid AAV virions are assembled from capsids of two different serotypes. The nucleotide sequence for VP1, VP2 and VP3 from a first AAV serotype only are ligated into a helper plasmid and the VP1, VP2 and VP3 from a second AAV serotype only is ligated into the same or different helper plasmid, such that the helper plasmid/s include the VP1, VP2 and VP3 capsid proteins from two different serotypes. Either prior to ligation or following ligation of the first and second serotype nucleotide sequences coding for VP1, VP2 and VP3 capsid proteins into the helper plasmid/s, the capsid nucleotide sequences are altered to provide a VP1 from a first serotype only and a VP2 and VP3 from a second serotype only. In this example, the nucleotide sequence of the first serotype has been altered by mutating the A2 Splice Acceptor Site as shown in FIG. 9. In this example, by mutating the A2 Splice Acceptor Site, the VP2 and VP3 capsid proteins from the first serotype are not produced. Similarly, as shown in FIG. 10, by mutating the A1 Splice Acceptor Site, the VP1 capsid protein from the second serotype is not produced, while VP2 and VP3 capsid proteins are produced. Thus, in this example, a polypoid AAV virion is created that includes a VP1, but not VP2 or VP3 from a first serotype only and a VP2 and VP3, but not a VP1 from a second serotype only.

Figure 12:
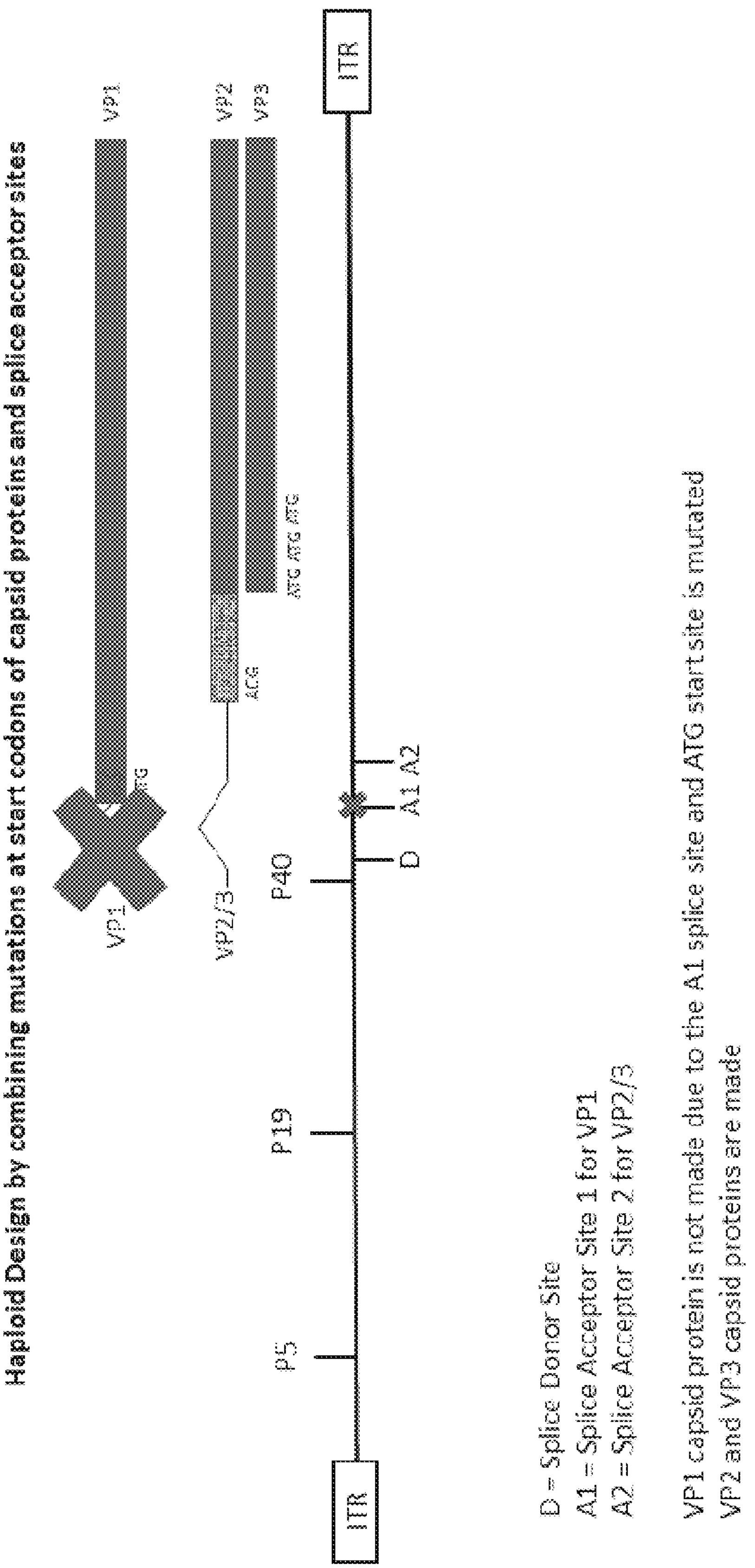
FIG. 12: Haploid design by mutating the start codon of capsid protein VP1 and the Splice Acceptor Site A1.

Example 10. Creation of Haploid Capsids from Two Different Serotypes and Mutation of Start Codons and Splice Acceptor Sites In this example, polyploid AAV virions are assembled from capsids of two different serotypes. The nucleotide sequence for VP1, VP2 and VP3 from a first AAV serotype only are ligated into a helper plasmid and the VP1, VP2 and VP3 from a second AAV serotype only are ligated into a same or different plasmid, such that the helper plasmid/s include/s the VP1, VP2 and VP3 capsid proteins from two different serotypes. Either prior to ligation or following ligation of the first and second serotype nucleotide sequences coding for VP1, VP2 and VP3 capsid proteins into the helper plasmid, the capsid nucleotide sequences are altered to provide a VP1 from a first serotype only and a VP2 and VP3 from a second serotype only. In this example, the nucleotide sequence of the first serotype has been altered by mutating the start codons for the VP2 and VP3 capsid proteins and mutating the A2 Splice Acceptor Site as shown in FIG. 11. In this example, the ACG start site of VP2 and the three ATG start sites of VP3 along with the A2 Splice Acceptor Site are mutated. As a result, only the VP1 capsid protein of the first serotype is produced. Neither the VP2 or VP3 capsid proteins from the first serotype are produced. Similarly, as shown in FIG. 12, the ATG start site of VP1 is mutated along with the A1 Splice Acceptor Site. As a result, only the VP2 and VP3 capsid proteins of the second serotype are produced. VP1 capsid protein form the second serotype is not produced. Thus, in this example, a polypoid AAV virion is created that includes VP1, but not VP2 or VP3 from a first serotype only and VP2 and VP3, but not VP1 from a second serotype only.

Example 11. Creation of Haploid Capsids from Two Different Serotypes Using Two Plasmids In this example, a haploid AAV virion comprising VP1 from AAV5 and VP2/VP3 from AAV9 is created using two plasmids. As shown in FIG. 13, a helper plasmid is created that includes a plasmid backbone along with Ad Early Genes and Rep (e.g., from AAV2). This helper plasmid has ligated into it the nucleotide sequence coding for the capsid proteins from AAV5 only and a separate nucleotide sequence coding for the capsid proteins of AAV9 only. With regard to the nucleotide sequence coding for the capsid proteins of AAV5, this nucleotide sequence has had either the start codons for VP2/VP3 mutated to prevent translation and/or the A2 Splice Acceptor Site has been mutated to prevent splicing. With regard to the nucleotide sequence coding for the capsid proteins of AAV9, this nucleotide sequence has had either the start codon for VP1 mutated to prevent translation and/or the A1 Splice Acceptor Site has been mutated to prevent splicing. The helper plasmid, along with a plasmid encoding the transgene with two ITRs are transfected into HEK293 cell line with ATCC No. PTA 13274 (see e.g., U.S. Pat. No. 9,441,206). The virus is purified from the supernatant and characterized. As shown in FIG. 13, the viral capsid includes VP2/VP3 of AA9 (shown in light grey) and VP1 of AAV5 (shown in dark grey) as seen in the virions set forth at the bottom of FIG. 13.

Example 12. Creation of Haploid Capsids from Two Different Serotypes Using Three Plasmids In this example, a haploid AAV virion comprising VP1 from AAV5 and VP2/VP3 from AAV9 is created using three plasmids. As shown in FIG. 14, a first helper plasmid is created that includes the Ad Early Genes. A second helper plasmid is created that includes a plasmid backbone along with Rep (e.g., AAV2). This second helper plasmid has ligated into it the nucleotide sequence coding for the capsid proteins from AAV5 only and a separate nucleotide sequence coding for the capsid proteins of AAV9 only. With regard to the nucleotide sequence coding for the capsid proteins of AAV5, this nucleotide sequence has had either the start codons for VP2/VP3 mutated to prevent translation and/or the A2 Splice Acceptor Site has been mutated to prevent splicing. With regard to the nucleotide sequence coding for the capsid proteins of AAV9, this nucleotide sequence has had either the start codon for VP1 mutated to prevent translation and/or the A1 Splice Acceptor Site has been mutated to prevent splicing. The helper plasmids, along with a plasmid encoding the transgene with two ITRs are transfected into HEK293 cell line with ATCC No. PTA 13274 (see e.g., U.S. Pat. No. 9,441,206). The virus is purified form the supernatant and characterized. As shown in FIG. 14, the viral capsid includes VP2/VP3 of AAV9 (shown in light grey) and VP1 of AAV5 (shown in dark grey) as seen in the virions set forth at the bottom of FIG. 13.

Example 13. Creation of Haploid Capsids from Two Different Serotypes Using Four Plasmids In this example, a haploid AAV virion comprising VP1 from AAV5 and VP2/VP3 from AAV9 is created using four plasmids. As shown in FIG. 15, a first helper plasmid is created that includes the Ad Early Genes. A second helper plasmid is created that includes a plasmid backbone along with Rep (e.g., AAV2). This second helper plasmid has ligated into it the nucleotide sequence coding for the capsid proteins from AAV5 only. A third helper plasmid is created that includes a plasmid backbone along with the Rep. This third helper plasmid has ligated into it the nucleotide sequence coding for the capsid proteins of AAV9 only. A fourth plasmid includes the transgene and two ITRs. With regard to the nucleotide sequence coding for the capsid proteins of AAV5, this nucleotide sequence has had either the start codons for VP2/VP3 mutated to prevent translation and/or the A2 Splice Acceptor Site has been mutated to prevent splicing. With regard to the nucleotide sequence coding for the capsid proteins of AAV9, this nucleotide sequence has had either the start codon for VP1 mutated to prevent translation and/or the A1 Splice Acceptor Site has been mutated to prevent splicing. The helper plasmids, along with a plasmid encoding the transgene with two ITRs are transfected into HEK293 cell line with ATCC No. PTA 13274 (see e.g., U.S. Pat. No. 9,441,206). The virus is purified form the supernatant and characterized. As shown in FIG. 14, the viral capsid includes VP2/VP3 of AA9 (shown in light grey) and VP1 of AAV5 (shown in dark grey) as seen in the virions set forth at the bottom of FIG. 13.

Example 14. Creation of Haploid Capsids from Three Different Serotypes and Mutation of Start Codons In this example, polyploid AAV virions are assembled from capsids of three different serotypes. A helper plasmid is constructed so that the nucleotide sequence for VP1, VP2 and VP3 from a first AAV serotype only, the VP1, VP2 and VP3 from a second AAV serotype only and the VP1, VP2 and VP3 from a third AAV serotype only are ligated into a helper plasmid/s, such that the helper plasmid/s include/s the nucleic acid sequences for VP1, VP2 and VP3 capsid proteins from three different serotypes. Either prior to ligation or following ligation of the nucleotide sequences coding for VP1, VP2 and VP3 capsid proteins from each of the three different serotypes into the helper plasmid, the capsid nucleotide sequences are altered to provide VP1 from the first serotype only, VP2 from the second serotype only and VP3 from the third serotype only. In this example, the VP1 nucleotide sequence of the first serotype has been altered by mutating the start codons for the VP2 and VP3 capsid proteins. In this example, the ACG start codon of VP2 and the three ATG start codons of VP3 are mutated such that these codons cannot initiate the translation of the RNA transcribed from the nucleotide sequence of the VP2 and VP3 capsid proteins from the first serotype. Similarly, the VP1 and VP3 nucleotide sequence of the second serotype have been altered by mutating the start codons for the VP1 and VP3 capsid proteins. In this example, the ATG start site of VP1 and the three ATG start codons of VP3 are mutated such that these codons cannot initiate the translation of the RNA transcribed from the nucleotide sequence of the VP1 and VP3 capsid proteins. Further, the VP1 and VP2 nucleotide sequence of the third serotype have been altered by mutating the start codons for the VP1 and VP2 capsid proteins. In this example, the ATG start codon of VP1 and the ACG start codon of VP2 are mutated such that these codons cannot initiate the translation of the RNA transcribed from the nucleotide sequence of the VP1 and VP2 capsid proteins. Thus, in this example, a polypoid AAV virion is created that includes a VP1, but not VP2, nor VP3 from a first serotype only; a VP2, but not a VP1, nor VP2 from a second serotype only; and, VP3, but not VP1, nor VP2 from a third serotype only.

Example 15. Creation of Haploid Capsids from Two Different Serotypes Using DNA Shuffling In this experiment, polyploid AAV virions are created from AAV capsid proteins from one AAV serotype only and from a nucleic acid created from DNA shuffling of three different AAV serotypes. In this example, the nucleotide capsid protein sequences for AAV1, AAV2 and AAV8 are subjected to treatment with one or more restriction enzymes and/or DNase and the DNA is cleaved into DNA fragments of 50-100 bp in length. The mixture of DNA fragments is then subject to polymerase chain reaction (PCR) without primers. The PCR is repeated multiple times or until the DNA molecules created by PCR reach the size of the nucleic acid coding for the capsid genes. At this point, another round of PCR is conducted wherein primers are added that include sequences for restriction enzyme recognition sites to allow for ligation of the newly created DNA into a helper plasmid. Prior to ligation into a helper plasmid, the AAV1/2/8 nucleotide sequence is sequenced and any start codons within the nucleotide sequence that could start translation of VP2 and VP3 capsid proteins from an RNA transcribed from this sequence are mutated to prevent translation. In this manner, the AAV1/2/8 can only produce VP1 and the AAV1/2/8 nucleotide sequence is ligated into a helper plasmid. In this experiment, the nucleotide sequence coding for the capsid proteins (VP1, VP2 and VP3) of AAV9 is also ligated into the same of different helper plasmid. To create the polyploid AAV virion with VP1 from the AAV1/2/8 nucleotide sequence created by DNA shuffling and VP2 and VP3 from AAV9 only, the ATG start codon of VP1 of AAV9 is mutated such that an RNA encoding VP1 cannot be translated. Thus, in this example, a polypoid AAV virion is created that includes VP1, but not VP2 or VP3 from a nucleotide sequence created by DNA shuffling the capsid protein nucleotide sequences of AAV1/2/8 and VP2 and VP3, but not VP1 from AAV9 only.

Figure 16:
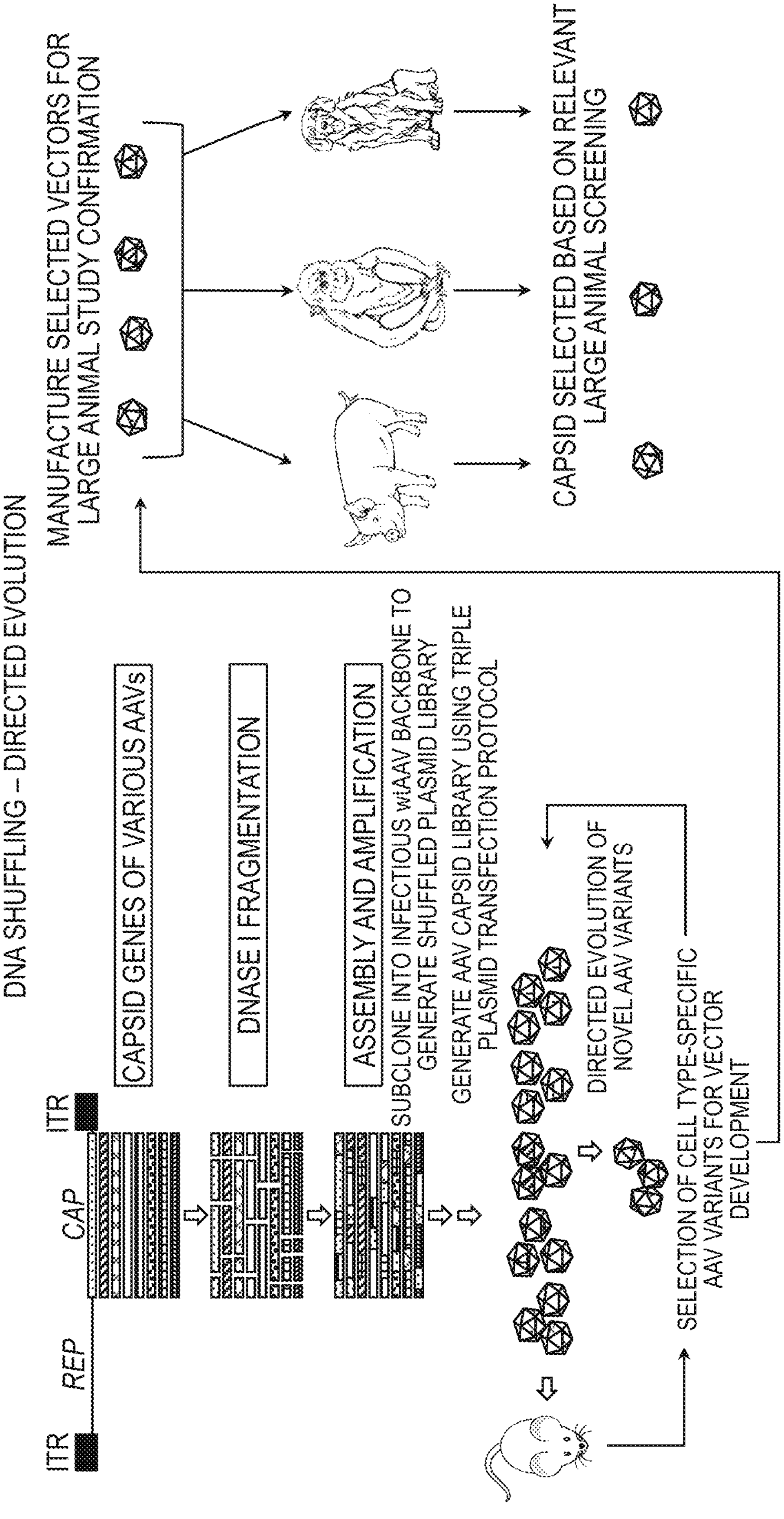
FIG. 16: A schematic showing the use of DNA shuffling to obtain virions having desired characteristics.

An example of DNA shuffling is set forth in FIG. 16, that starts with the nucleic acid coding for VP1, VP2 and VP3 from eight AAV serotypes and processes the nucleic acid, first through DNase I fragmentation, which is followed by assembly and amplification of the various fragments of the nucleic acid from eight AAVs. The DNA shuffled nucleic acids that are generated encode for the AAV capsid proteins, which are then expressed to create a library of capsids. These capsids are then tested on animals to screen for those capsids that show specific tissue tropism and/or reduced immunogenicity and those that show promise are selected for further development (FIG. 16).

Example 16. Liver Transduction of Haploid Vector H-AAV829

Figure 22A:
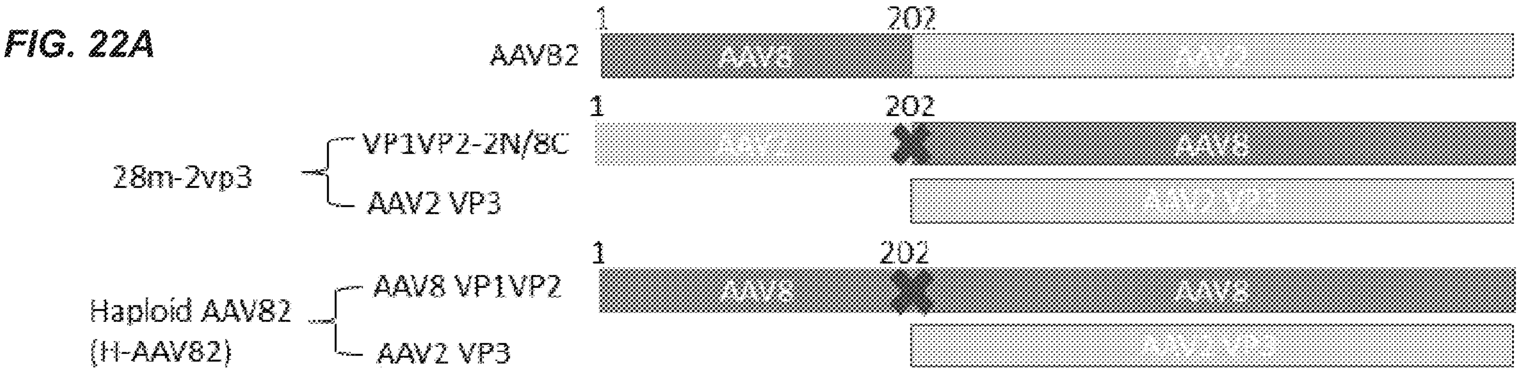
FIGS. 22A-C: Liver transduction of haploid vector H-AAV82. (22A) the composition of AAV capsid subunits. Haploid AAV viruses were produced from co-transfection of two plasmids (one encoding VP1 and VP2, another one for VP3). (22B) $3\times10^{10}$ particles of AAV vector were injected into C57BL mice via retro-orbital vein. The imaging was performed one week later. (22C) The quantitation of liver transduction. The data represented the average of 5 mice and standard deviations.
Figure 22B:
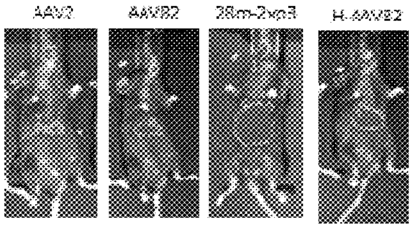
Figure 22C:
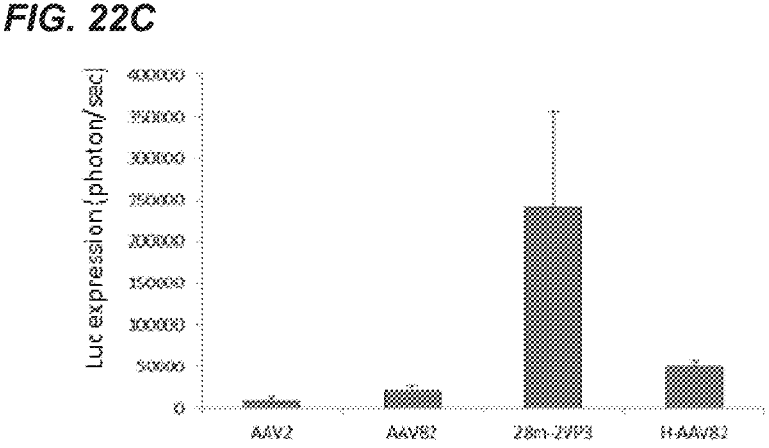

An experiment was conducted with three AAVs. In FIG. 22 A. the composition of AAV capsid subunits is shown. A hybrid AAV is shown that combines the VP1 only amino acids from AAV8 with those coding for VP2 and VP3 from AAV2 (AAV82). Two haploid AAV viruses were produced from co-transfection of two plasmids (one encoding VP1 and VP2, another one for VP3) into HEK293 cells. The three AAVs, AAV82, 28m-2vp3 and H-AAV82, along with an AAV2 parental control were injected in C57BL6 mice via the retro-orbital vein at a dose of $3\times10^{10}$ particles (FIG. 22B). The imaging was performed one week later (FIG. 22B). Liver transduction was quantitated based on data that represented the average of 5 mice and standard deviations (FIG. 22C).

Example 17. Muscle Transduction of Haploid Vector H-AAV82

Figure 23A:
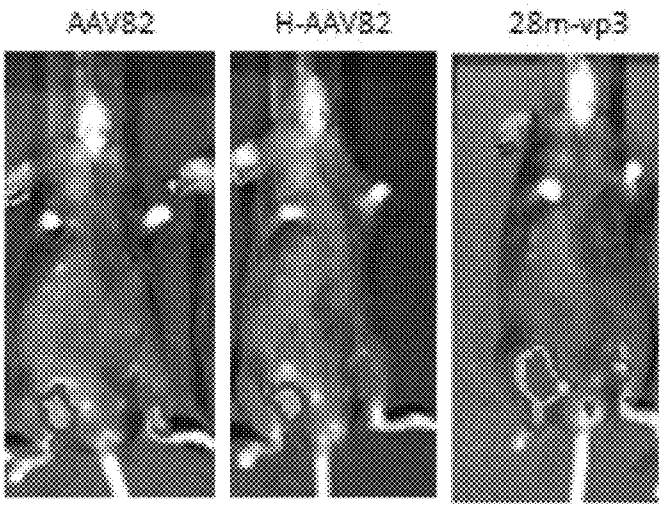
FIGS. 23A-B: Muscle transduction of haploid vector H-AAV82. $1\times10^9$ particles of AAV/luc were injected into mouse hind leg muscle. At week 3 post injection, the imaging was taken for 3 min. Face up: left leg-haploid AAV, right leg-AAV2. (23A) Representative imaging. (23B) Data from 4 mice after muscular injection. The fold increase of transduction was calculated by transduction from haploid AAV to AAV2.
Figure 23B:
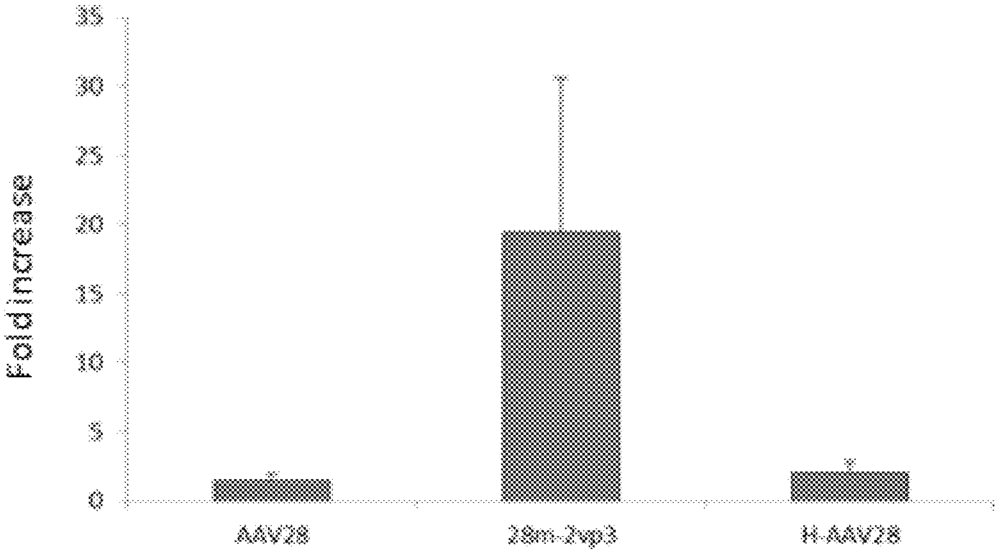

The three AAVs from Example 23 (AAV82, H-AAV82 and 28m-vp3) were next injected into mouse hind leg muscle at a dose of $1\times10^{9}$ particles of AAV/luc. At week 3 post injection, imaging was conducted for a period of 3 minutes as seen in FIG. 23A. The imaging was conducted face up: left leg-AAV82, H-AAV82 or 28m-vp3 and right leg-AAV2 parental AAV. FIG. 23B provides the data from 4 mice after the muscular injection with the fold increase of transduction calculated by transduction from AAV82, H-AAV82 or 28m-vp3 to the parental AAV2.

Example 18. Liver Transduction of Haploid Vector H-AAV92

Figure 24A:
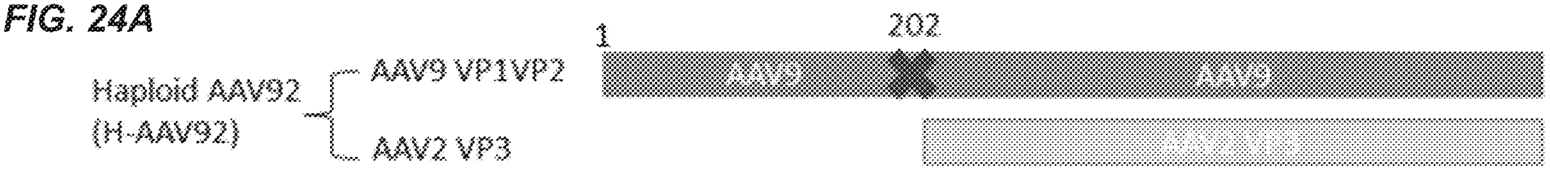
FIGS. 24A-C: Liver transduction of haploid vector H-AAV92. (24A) the composition of AAV capsid subunit. Haploid AAV viruses were produced from co-transfection of two plasmids (one encoding AAV9 VP1 and VP2, another one for AAV2 VP3). (24B) $3\times10^{10}$ particles of AAV vector were injected into C57BL mice via retro-orbital vein. The imaging was performed one week later. (24C) The quantitation of liver transduction. The data represented the average of 5 mice and standard deviations.
Figure 24B:
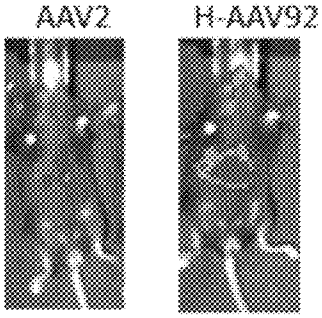
Figure 24C:
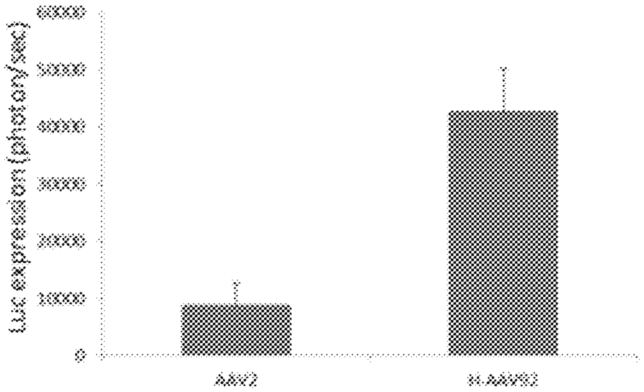

In this experiment a haploid AAV92 is created wherein the VP1 and VP2 are from AAV9 only and the VP3 is from AAV3 only (FIG. 24A). The H-AAV92 was produced from co-transfection of two plasmids (one encoding AAV9 VP1 and VP2, another one for AAV2 VP3) into HEK293 cells. H-AAV92 and parental AAV2 were injected into C57BL6 mice via the retro-orbital vein at a dose of $3\times10^{10}$ particles (FIG. 24B). Imaging was performed one week later (FIG. 24B). Liver transduction was quantitated based on data that represented the average of 5 mice and standard deviations (FIG. 24C).

Example 19. Liver Transduction of Haploid Vector H-AAV82G9

Figure 25A:
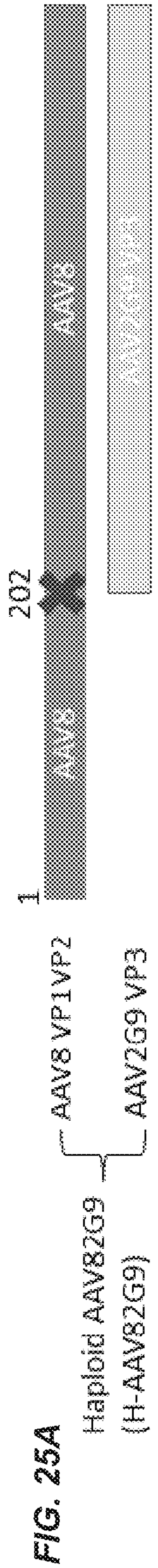
FIGS. 25A-C: Liver transduction of haploid vector H-AAV82G9. (25A) the composition of AAV capsid subunit. Haploid AAV viruses were produced from co-transfection of two plasmids (one encoding AAV8 VP1 and VP2, another one for AAV2G9 VP3). (25B) $3\times10^{10}$ particles of AAV vector were injected into C57BL mice via retro-orbital vein. At week 1 post AAV administration, the imaging was carried out. (25C) The quantitation of liver transduction. The data represented the average of 5 mice and standard deviations.
Figure 25B:
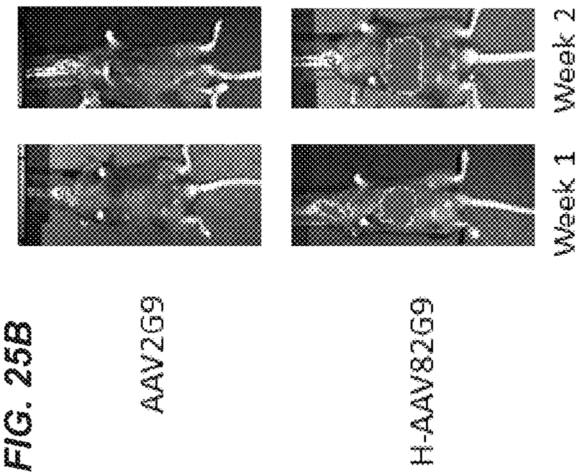
Figure 25C:
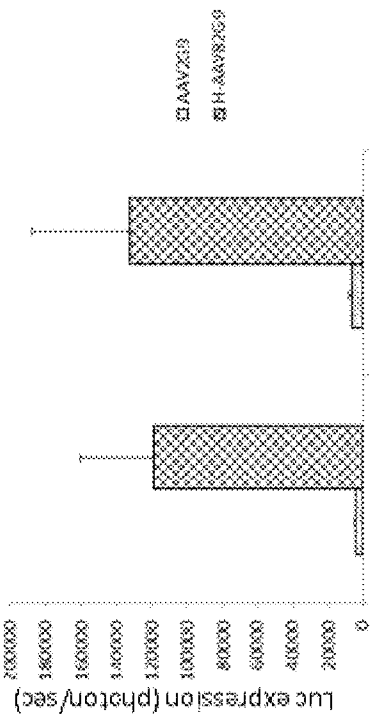

In this experiment a haploid AAV82G9 is created wherein the VP1 and VP2 are from AAV8 only and the VP3 is from AAV2G9 only (FIG. 25A). The H-AAV82G9 was produced from co-transfection of two plasmids (one encoding AAV8 VP1 and VP2, another one for AAV2G9 VP3) into HEK293 cells. H-AAV82G9 and AAV2G9 were injected into C57BL6 mice via the retro-orbital vein at a dose of $3\times10^{10}$ particles (FIG. 25B). Imaging was performed one week later (FIG. 25 B). Liver transduction was quantitated based on data that represented the average of 5 mice and standard deviations (FIG. 25C).

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term “about.” As used herein, the term “about” means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

All methods described herein can be performed in any suitable order unless otherwise indicated herein or otherwise clearly contradicted by context. The use of any and all examples, or exemplary language (e.g., “such as”) provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term “consisting of” excludes any element, step, or ingredient not specified in the claims. The transition term “consisting essentially of” limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Example 20. Chimeric Capsid Proteins and AAV Haploid Virus Vector Transduction As explained above, a series of constructs for AAV helper plasmids were made with mutants in start codes of capsid ORFs, in which only one or two viral VP proteins would be expressed. Chimeric AAV helper constructs in which VP1/2 protein was driven from two different serotypes (AAV2 and AAV8) were also made. These constructs were used to produce a bunch of haploid virus vectors and evaluate their transduction efficacy in mice. It was found that enhanced transduction was achieved from haploid vectors with VP1/VP2 from serotypes 7, 8, 9, and rh10, and VP3 from AAV2 or AAV3 when compared to AAV2-only and AAV3-only vectors. It was further shown that AAV vectors made from the chimeric VP1/VP2 capsid with N-terminus from AAV2 and C-terminus from AAV8 and VP3 from AAV2 induced much higher transduction. The data provided herein show a simple and effective method that enhances AAV transduction for further application of AAV vectors.

Haploid Vector with VP1/VP2 from Other Serotypes and VP3 from AAV2 Enhance AAV Liver Transduction.

The haploid virus was produced by co-transfecting the plasmids expressed AAV8 VP1/2 and AAV2 VP3 at the ratio of 1:1. The results showed that haploid vector AAV82 with VP1/VP2 from AAV8 and VP3 from AAV2 increased the liver transduction (FIGS. 22B and 22C).

A haploid AAV92 vector (H-AAV92) was produced using VP1/VP2 of AAV9 and VP3 of AAV2 (FIG. 24A). After systemic administration, the imaging was performed at week 1. About 4-fold higher liver transduction was achieved with H-AAV92 than that with AAV2 (FIGS. 24B and 24C). This data indicates that VP1/VP2 from other serotype is able to increase AAV2 transduction.

Enhanced AAV Liver Transduction from Haploid Vector with VP3 from AAV2 Mutant.

AAV9 vectors use glycan as primary receptor for their effective transduction. In previous studies, AAV9 glycan receptor binding site were engrafted into the AAV2 capsid to make AAV2G9 vector and it was found that AAV2G9 has higher liver tropism than AAV2. Described herein is a haploid vector (H-AAV82G9) in which VP1/VP2 from AAV8 and VP3 from AAV2G9 (FIG. 25A). After systemic injection into mice, compared to AAV2G9, more than 10 fold higher liver transduction was observed at both week 1 and week 2 post H-AAV82G9 application (FIGS. 25B and 25C). This data indicates that the integration of VP1/VP2 from other serotype into AAV2 mutant VP3 was able to increase liver transduction.

Enhanced AAV Liver Transduction from Haploid Vector with VP3 from AAV3.

Figure 26A:
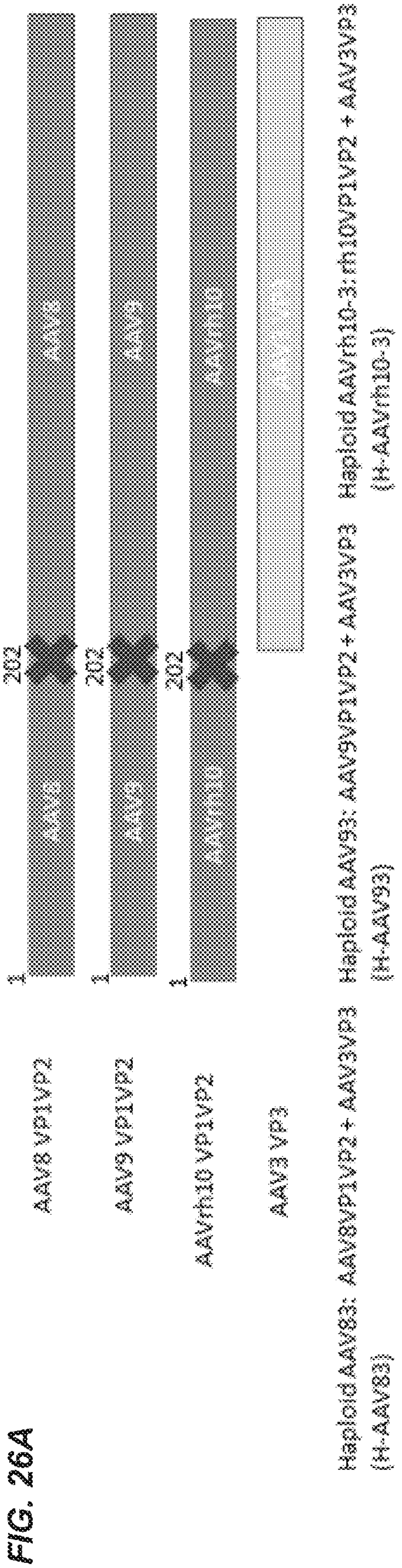
FIGS. 26A-D: Liver transduction of haploid AAV83, AAV93 and AAVrh10-3. (26A) The composition of AAV capsid subunits. (26B) Representative imaging. (26C) The quantification of liver transduction. (26D) The quantification of viral genome in the indicated organ, as compared to mouse lamin (internal control for expression levels).

Haploid vectors in which VP3 is from other serotypes and VP1/VP2 from different serotypes or variants where the start codes were mutated and the VP proteins constructs were made to express AAV3 VP3 only or AAV rh10 VP1/VP2 only. The different haploid H-AAV83 (VP1/VP2 from AAV8 and VP3 from AAV3), H-AAV93 (VP1/VP2 from AAV9 and VP3 from AAV3) and H-AAVrh10-3 (VP1/VP2 from AAV rh10 and VP3 from AAV3) vectors were produced (FIG. 26A) and injected into mice via systemic administration.

Figure 26B:
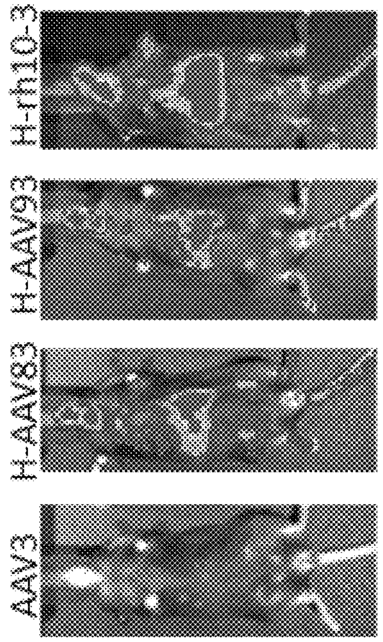
Figure 26C:
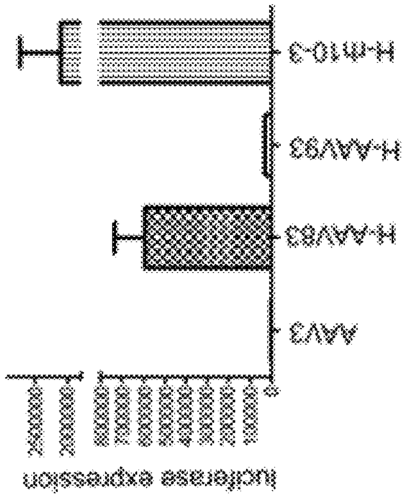
Figure 26D:
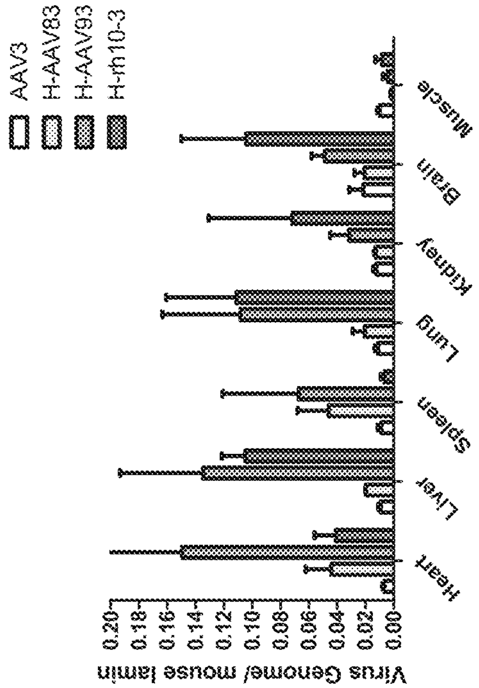

The imaging was carried out at week 1. As shown in FIGS. 26B and 26C, higher liver transduction was achieved with haploid vectors (H-AAV83, H-AAV93 and H-AAVrh10-3) than that with AAV3. This is consistent to the results obtained from other haploid vectors. Furthermore, these haploid vectors also enhanced the transduction from other tissues as shown in FIGS. 26B and 26D. Interestingly, these haploid vectors also induced a whole body transduction based on imaging profile, which is different from the results from haploid vectors with VP3 from AAV2, which only transduced the liver efficiently (FIGS. 22 and 24). Collectively, haploid vectors with VP1/VP2 from one serotype and VP3 from an alternative one were able to enhance transduction and perhaps change their tropism.

Haploid Vector with C-Terminus of VP1/VP2 from AAV8 and VP3 from AAV2 Enhances AAV Transduction.

Figure 27A:
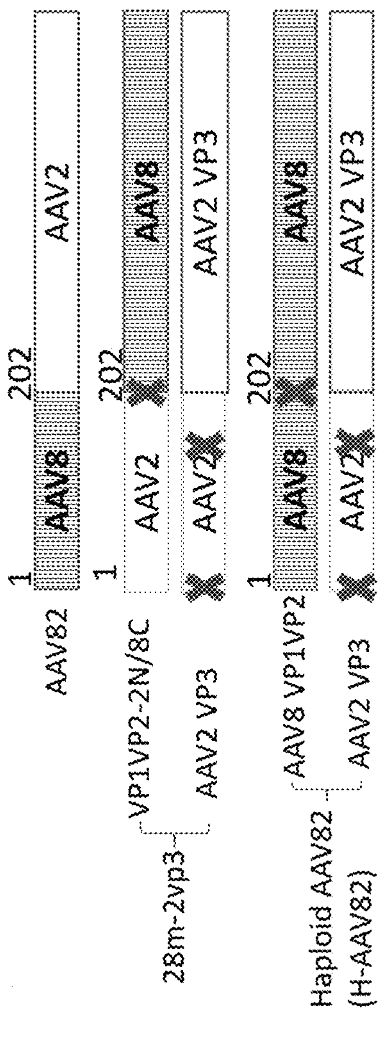
FIGS. 27A-D: Transduction of haploid AAV82 from AAV2 and AAV8. (27A) The composition of AAV capsid subunits. (27B) Western blot for haploid viruses. (27C) Representative imaging and the quantitation of liver transduction. (27D) Representative imaging and the quantitation of muscle transduction.
Figure 27B:
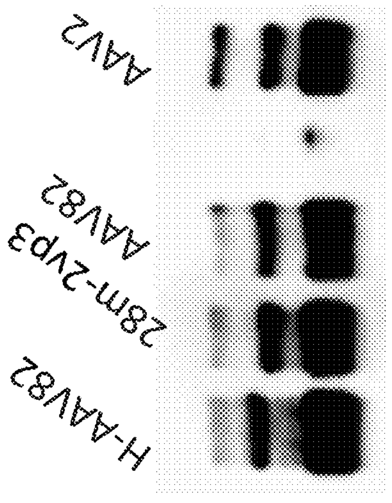
Figure 27C:
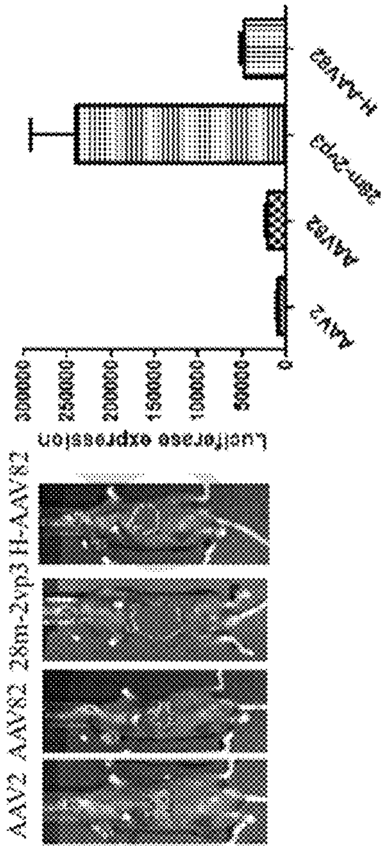
Figure 27D:
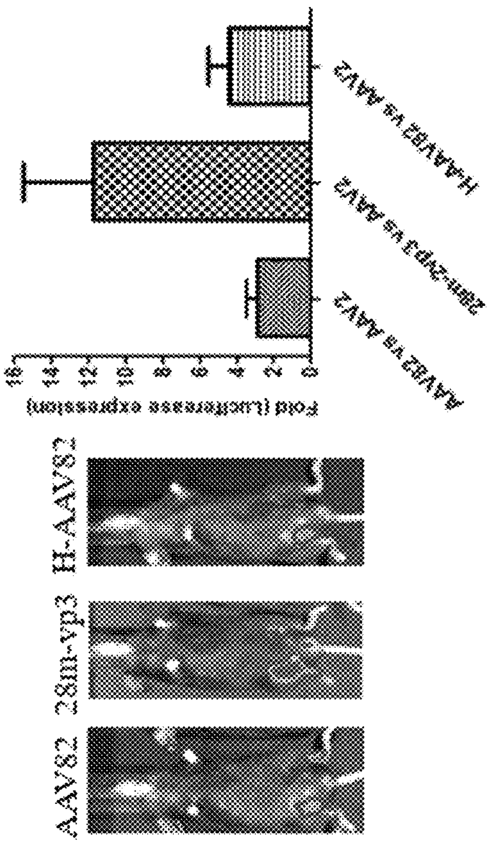

A series of constructs which expressed AAV8 VP1/VP2 only, AAV2 VP3 only, chimeric VP1/VP2 (28m-2VP3) with N-terminal from AAV2 and C-terminal from AAV8, or chimeric AAV8/2 with N-terminal from AAV8 and C-terminal from AAV2 without mutation of VP3 start codon were generated (FIG. 27A). These plasmids were used to produce haploid AAV vector with different combination at a plasmid ratio of 1:1 (FIG. 27B). After injection of $1\times10^{10}$ particles of these haploid vectors in mice via retro-orbital vein, the liver transduction efficiency was evaluated (FIG. 27C). Chimeric AAV82 vector (AAV82) induced a little higher liver transduction than AAV2. However, haploid AAV82 (H-AAV82) had much higher liver transduction than AAV2. A further increase in liver transduction with haploid vector 28m-2vp3 was observed. These haploid vectors were administered into the muscles of mice. For easy comparison, the right leg was injected with AAV2 vector and the left leg was injected with haploid vector when the mouse was face up. At week 3 after AAV injection, the images were taken. Consistent to observation in the liver, all haploid vectors and chimeric vectors had higher muscular transduction with the best from haploid vector 28m-2vp3 (FIG. 27D). This result indicates that the chimeric VP1/VP2 with N-terminal from AAV2 and C-terminal from AAV8 attributes to high liver transduction of haploid AAV82 vectors.

Increased Virion Trafficking to the Nucleus from Chimeric Haploid Vectors.

Figure 28:
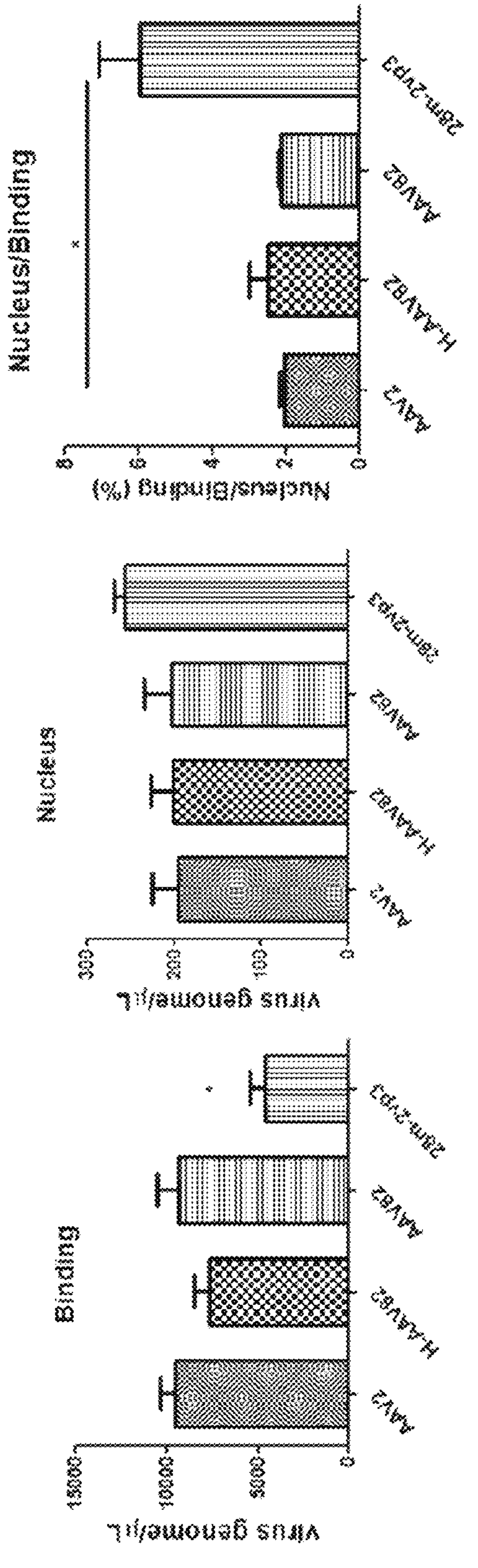
FIG. 28: Analysis of haploid abilities for binding and trafficking.

AAV transduction involves many steps. Upon binding, AAV virions are taken up into the endosome via endocytosis. After escape from the endosomes, AAV virions travel to the nucleus for transgene expression. It was determined which steps result in the high transduction from the haploid vectors. First, AAV vector binding assay was performed and less 28m-2VP3 virions was found bound to Huh7 cells than other vectors (FIG. 28). Next, the AAV genome copy number was detected in the nucleus and no difference was found between different AAV vectors. It is interesting to note, when compared the AAV genome copy number to bound virion, more AAV virions were observed in the nucleus (FIG. 28). These results indicate that AAV vector 28m-2VP3 is more efficient for trafficking.

High Transduction of Haploid AAV Vector does not Result from Virion Stability.

Figure 29:
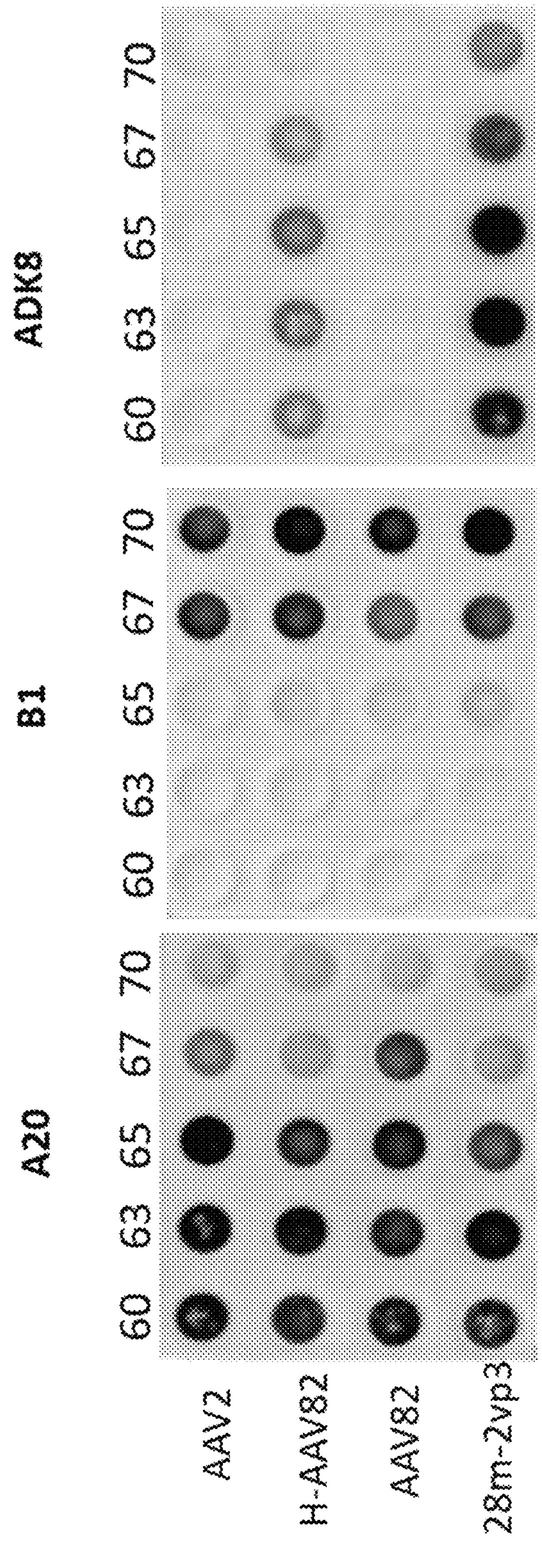
FIG. 29: AAV stability against heating.

The following experiments were performed by heating the virus virions. The viruses were heated at different temperature for half hour and then applied for western blot using the primary antibodies A20 ADK8 or B1 to recognize intact or un-intact virions. As shown in FIG. 29, when viruses were heated at 70° C., all virus virions fell apart. There was no different for stability against heating between AAV haploid vectors regardless of different temperature except for AAV82 vectors. This data indicates that the enhanced transduction may not relate to haploid virion stability.

The Effect of Acidic Condition on VP1 N-Terminus Exposure of Haploid Vector.

Figure 30:
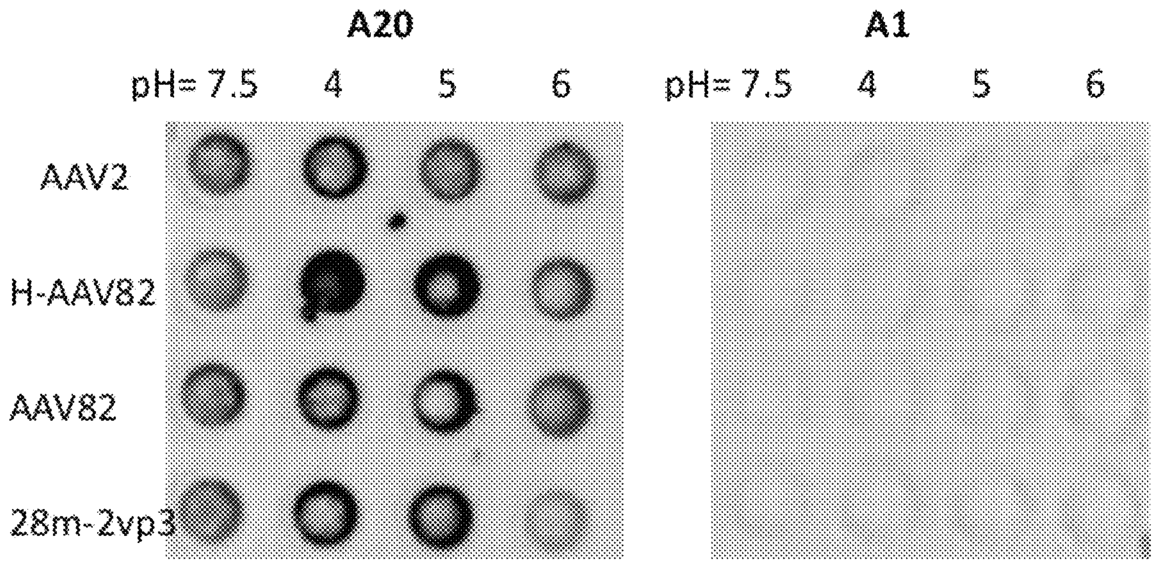
FIG. 30: Detection of N-terminus exposure under different pH.

It has been demonstrated that VP1/VP2 N-terminus is exposed on virion surface in the acidic endosome after endocytosis of AAV vectors. VP1/VP2 terminus contains the phospholipase A2 and NLS domains for AAV vector which help AAV viruses escape from the endosome and travel to the nucleus. AAV haploid vectors were incubated with PBS at different pH values for 30 minutes, then applied to Western blot analysis to detect N-terminus of VP1 using antibody A1. The result showed that no any VP1 N-terminus was exposed when virus was treated with different pH (FIG. 30).

The data presented herein show that enhanced transduction could be achieved from haploid vectors with VP1/VP2 from one AAV vector capsid and VP3 from an alternative one.

Plasmids and site-directed mutagenesis. All of the plasmids that were used to express VP12 and VP3 were made by site-directed mutagenesis. Mutagenesis was performed using QuikChange II XL Site-Directed mutagenesis Kit (Agilent) according to the manufacturer's manual. The fragment that contained the N-terminus (1201 aa) of AAV2 capsid and C-terminus of AAV8 capsid was generated by overlapping PCR. Then, the fragment was cloned into the SwaI and NotI sites of pXR. All of the mutations and constructs were verified by DNA sequencing.

Virus production. Recombinant AAV was produced by a triple-plasmid transfection system. A 15-cm dish of HEK293 cells was transfected with 9 ug of AAV transgene plasmid pTR/CBA-Luc, 12 ug of AAV helper plasmid containing AAV Rep and Cap genes, and 15 ug of Ad helper plasmid 00(6-80. Sixty hours post-transfection, HEK293 cells were collected and lysed. Supernatant was subjected to CsCl gradient ultra-centrifugation. Virus titer was determined by quantitative PCR.

In vitro transduction assay. Huh7 and C2C12 cells were transduced by recombinant viruses with $1\times10^4$ vg/cell in a flat-bottom, 24-well plate. Forty-eight hours later, cells were harvested and evaluated by a luciferase assay system (Promega, Madison, Wis.).

Animal study. Animal experiments performed in this study were conducted with C57BL/6 mice and FIX−/− mice. The mice were maintained in accordance to NIH guidelines, as approved by the UNC Institutional Animal Care and Use Committee (IACUC). Six-week-old female C57BL/6 mice were injected with $1\times10^{10}$ vg of recombinant viruses via retro-orbital injection. Luciferase expression was imaged 1 week post-injection using a Xenogen IVIS Lumina (Caliper Lifesciences, Waltham, Mass.) following i.p. injection of D-luciferin substrate (Nanolight Pinetop, Ariz.). Bioluminescent images were analyzed using Living Image (PerkinElmer, Waltham, Mass.). For muscle transduction, $5\times10^9$ particles of AAV/Luc were injected into the gastrocnemius of 6-week-old C57BL/6 females. Mice were imaged at the indicated time points.

Detection of AAV genome copy number in the liver. The minced livers were treated with Protease K and total genomic DNA was isolated by the Pure Link Genomic DNA mini Kit (Invitrogen, Carlsbad, Calif.). The luciferase gene was detected by qPCR assay. The mouse lamin gene served as an internal control.

Statistical analysis. The data were presented as mean±SD. The Student t test was used to carry out all statistical analyses. P values of <0.05 were considered a statistically significant difference.

REFERENCES

1. Srivastava A, Lusby E W, Berns K I. 1983. Nucleotide sequence and organization of the adeno-associated virus 2 genome. Journal of Virology 45:555-564.
2. Srivastava A. 2016. In vivo tissue-tropism of adeno-associated viral vectors. Current Opinion in Virology 21:75-80.
3. Manno C S, Chew A J, Hutchison S, Larson P J, Herzog R W, Arruda V R, Tai S J, Ragni M V, Thompson A, Ozelo M, Couto L B, Leonard D G B, Johnson F A, McClelland A, Scallan C, Skarsgard E, Flake A W, Kay M A, High K A, Glader B. 2003. AAV-mediated factor IX gene transfer to skeletal muscle in patients with severe hemophilia B. Blood 101:29632972.
4. Lisowski L, Tay S S, Alexander I E. 2015. Adeno-associated virus serotypes for gene therapeutics. Current Opinion in Pharmacology 24:59-67.
5. Boye S E, Boye S L, Lewin A S, Hauswirth W W. 2013. A Comprehensive Review of Retinal Gene Therapy. Mol Ther 21:509-519.
6. Smalley E. 2017. First AAV gene therapy poised for landmark approval. Nature Biotechnology 35:998.
7. Nathwani A C, Reiss U M, Tuddenham E G D, Rosales C, Chowdary P, McIntosh J, Della Peruta M, Lheriteau E, Patel N, Raj D, Riddell A, Pie J, Rangarajan S, Bevan D, Recht M, Shen Y M, Halka K G, Basner-Tschakarjan E, Mingozzi F, High K A, Allay J, Kay M A, Ng C Y C, Zhou J, Cancio M, Morton C L, Gray J T, Srivastava D, Nienhuis A W, Davidoff A M. 2014. Long-Term Safety and Efficacy of Factor IX Gene Therapy in Hemophilia B. The New England journal of medicine 371:1994-2004.
8. Nathwani A C, Tuddenham E G D, Rangarajan S, Rosales C, McIntosh J, Linch D C, Chowdary P, Riddell A, Pie A J, Harrington C, O'Beirne J, Smith K, Pasi J, Glader B, Rustagi P, Ng C Y C, Kay M A, Zhou J, Spence Y, Morton C L, Allay J, Coleman J, Sleep S, Cunningham J M, Srivastava D, Basner-Tschakarjan E, Mingozzi F, High K A, Gray J T, Reiss U M, Nienhuis A W, Davidoff A M. 2011. Adenovirus-Associated Virus Vector-Mediated Gene Transfer in Hemophilia B. New England Journal of Medicine 365:2357-2365.
9. Simioni P, Tormene D, Tognin G, Gavasso S, Bulato C, Iacobelli N P, Finn J D, Spiezia L, Radu C, Arruda V R. 2009. X-Linked Thrombophilia with a Mutant Factor IX (Factor IX Padua). New England Journal of Medicine 361:1671-1675.
10. Saraiva J, Nobre R J, Pereira de Almeida L. 2016. Gene therapy for the CNS using AAVs: The impact of systemic delivery by AAV9. Journal of Controlled Release 241:94-109.
11. Chai Z, Sun J, Rigsbee K M, Wang M, Samulski R J, Li C. 2017. Application of polyploid adeno-associated virus vectors for transduction enhancement and neutralizing antibody evasion. Journal of Controlled Release 262:348-356.

TABLE 1

|  | GenBank Accession Number |
|---|---|
| Complete Genomes |  |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_OOl829 |
| Adeno-associated virus 5 | Yl8065, AF085716 |
| Adeno-associated virus 6 | NC_001862 |
| Avian AAVA TCC VR-865 | AYl86198, AY629583, NC_004828 |
| Avian AAV strain DA-I | NC_006263, AY629583 |
| Bovine AAV | NC_005889, AY388617, AAR26465 |
| AAVIJ | AAT46339, AY631966 |
| AAV12 | AB116639, DQ813647 |
| Clade A |  |
| AAVI | NC_002077, AF063497 |
| AAV6 | NC_001862 |
| Hu.48 | AY530611 |
| Hu43 | AY530606 |
| Hu 44 | AY530607 |
| Hu 46 | AY530609 |
| Clade B |  |
| Hu19 | AY530584 |
| Hu20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hul3 | AY530578 |
| Hu56 | AY530618 |
| Hu57 | AY530619 |
| I-Iu49 | AY530612 |
| Hu58 | AY530620 |
| Hu34 | AY530598 |
| Hu35 | AY530599 |
| AAV2 | NC_00l401 |
| Hu45 | AY530608 |
| Hu47 | AY5306JO |
| Hu51 | AY530613 |
| Hu52 | AY530614 |
| HuT41 | AY695378 |
| HuS17 | AY695376 |
| HuT88 | AY695375 |
| HuT71 | AY695374 |
| HuT70 | AY695373 |
| HuT40 | AY695372 |
| Hu T32 | AY695371 |
| Hu T17 | AY695370 |
| Hu LG15 | AY695377 |
| Clade C |  |
| Hu9 | AY530629 |
| Hu JO | AY530576 |
| Hull | AY530577 |

TABLE 1-continued

| | GenBank Accession Number |
|---|---|
| Hu53 | AY530615 |
| Hu55 | AY530617 |
| Hu54 | AY530616 |
| Hu7 | AY530628 |
| Hul8 | AY530583 |
| Hu IS | AY530580 |
| Hul6 | AY530581 |
| Hu25 | AY530591 |
| Hu60 | AY530622 |
| Ch5 | AY243021 |
| Hu3 | AY530595 |
| Hui | AY530575 |
| Hu4 | AY530602 |
| Hu2 | AY530585 |
| Hu61 | AY530623 |
| Clade D | |
| Rh62 | AY530573 |
| RMB | AY530561 |
| Rh54 | AY5 30567 |
| Rh55 | AY530568 |
| Cy2 | AY243020 |
| AAV7 | AF5J3851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| RJ1(3 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bbl | AY243023 |
| Bb2 | AY243022 |
| RhlO | AY243015 |
| Hui? | AY530582 |
| Hu6 | AY530621 |
| Rh25 | AY530557 |
| Pi2 | AY530554 |
| Pil | AY530553 |
| Pi3 | AY530555 |
| Rh57 | AY530569 |
| Rh50 | AY530563 |
| RM9 | AY530562 |
| Hu39 | AY530601 |
| Rh58 | AY530570 |
| Rh61 | AY530572 |
| Rh52 | AY530565 |
| Rh53 | AY530566 |
| RhSI | AY530564 |
| Rh64 | AY530574 |
| Rh43 | AY530560 |
| AAV8 | AF513852 |
| Rh8 | AY242997 |
| Rh1 | AY530556 |
| Clade F | |
| Hul4 (AAV9) | AY530579 |
| Hu31 | AY530596 |
| Hu32 | AY530597 |
| Clonal Isolate | |
| AAVS | Yl8065, AF085716 |
| AAV3 | NC_001729 |
| AAV3B | NC_001863 |

TABLE 1-continued

| | GenBank Accession Number |
|---|---|
| AAV4 | NC_001829 |
| Rh34 | AY243001 |
| Rh33 | AY243002 |
| Rh32 | AY243003 |

TABLE 2

Amino acid residues and abbreviations

| Amino Acid Residue | Abbreviation Three-Letter Code | One-Letter Code |
|---|---|---|
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Praline | Pro | P |
| Serine | Ser | S |
| Threonine | Thr | T |
| Tryptophan | Trp | W |
| Tyrosine | Tyr | Y |
| Valine | Val | V |

TABLE 3

| Serotype | Position 1 | Position 2 |
|---|---|---|
| AAV1 | A263X | T265X |
| AAV2 | Q263X | —265X |
| AAV3a | Q263X | —265X |
| AAV3b | Q263X | —265X |
| AAV4 | S257X | —259X |
| AAV5 | G253X | V255X |
| AAV6 | A263X | T265X |
| AAV7 | E264X | A266X |
| AAV8 | G264X | S266X |
| AAV9 | S263X | S265X |

Where, (X)→ mutation to any amino acid
(—) → insertion of any amino acid
Note:
Position 2 inserts are indicated by the site of insertion

TABLE 4

| Modified Amino Acid Residue Amino Acid Residue Derivatives | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |

TABLE 4-continued

| Modified Amino Acid Residue<br>Amino Acid Residue Derivatives | Abbreviation |
|---|---|
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |

TABLE 4-continued

| Modified Amino Acid Residue<br>Amino Acid Residue Derivatives | Abbreviation |
|---|---|
| allo-Isoleucine | alle |
| Methionine sulfoxide | MSO |
| N-Methylglycine, sarcosine | MeGly |
| N-Methylisoleucine | Melle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe (4-Cl) |
| 2-Fluorophenylalanine | Phe (2-F) |
| 3-Fluorophenylalanine | Phe (3-F) |
| 4-Fluorophenylalanine | Phe (4-F) |
| Phenylglycine | Phg |
| Beta-2-thienylalanine | Thi |

TABLE 5

Neutralization antibody titer and cross-reactivity for triploid virus AAV2/8 Vector

| | | | Haploid virus AAV2/8 | | | Mixture virus AAV2 and AAV8 | | | |
|---|---|---|---|---|---|---|---|---|---|
| | | AAV2 | 3:1 | 1:1 | 1:3 | 3:1 | 1:1 | 1:3 | AAV8 |
| mAb | A20 | 512 | 2048 | 32 | <2 | ND | ND | ND | <2 |
| | ADK8 | <2 | 512 | 512 | 1024 | ND | ND | ND | 1024 |
| serum | AAV2 | 4096 | 1024 | 256 | 8 | 4096 | 2048 | 1024 | <2 |
| | AAV8 | <2 | 256 | 256 | 512 | <2 | <2 | <2 | 512 |

TABLE 6

Neutralization antibody titer and cross-reactivity for haploid virus AAV2/8/9

| | AAV2 | AAV8 | AAV9 | AAV2/9 | AAV8/9 | AAV2/8/9 |
|---|---|---|---|---|---|---|
| SerumAAV2 | >2048 | <2 | | 512 | | 128 |
| SerumAAV8 | <2 | 128 | | | 32 | 4 |
| SerumAAV9 | <2 | 16 | 2048 | 512 | | 256 |
| Serum AAV2/8/9 | 8 | 128 | 128 | 64 | 512 | 128 |

Sequences

```
AAV1 (SEQ ID NO: 127)
   1 ctctcccccc tgtcgcgttc gctcgctcgc tggctcgttt ggggggtgg cagctcaaag
  61 agctgccaga cgacggccct ctggccgtcg ccccccaaa cgagccagcg agcgagcgaa
 121 cgcgacaggg gggagagtgc cacactctca agcaaggagg ttttgtaagt ggtgatgtca
 181 tatagttgtc acgcgatagt taatgattaa cagtcaggtg atgtgtgtta tccaatagga
 241 tgaaagcgcg cgcatgagtt ctcgcgagac ttccggggta taaaggggtg agtgaacgag
 301 cccgccgcca ttctctgctc tgaactgcta gaggaccctc gctgccatgg ctaccttcta
 361 cgaagtcatt gttcgcgtcc catttgacgt ggaggaacat ctgcctggaa tttctgacag
 421 ctttgtggac tgggtaactg gtcaaatttg ggagctgcct cccgagtcag atttgaattt
 481 gactctgatt gagcagcctc agctgacggt tgctgacaga attcgccgcg tgttcctgta
 541 cgagtggaac aaattttcca agcaggaatc caaattcttt gtgcagtttg aaaagggatc
 601 tgaatatttt catctgcaca cgcttgtgga gacctccggc atctcttcca tggtcctagg
 661 ccgctacgtg agtcagattc gcgcccagct ggtgaaagtg gtcttccagg gaatcgagcc
 721 acagatcaac gactgggtcg ccatcaccaa ggtaaagaag ggcggagcca ataaggtggt
 781 ggattctggg tatattcccg cctacctgct gccgaaggtc caaccggagc ttcagtgggc
 841 gtggacaaac ctggacgagt ataaattggc cgccctgaac ctggaggagc gcaaacggct
 901 cgtcgcgcag tttctggcag aatcctcgca gcgctcgcag gaggcggctt cgcagcgtga
 961 gttctcggct gacccggtca tcaaaagcaa gacttcccag aaatacatgg cgctcgtcaa
1021 ctggctcgtg gagcacggca tcacttccga gaagcagtgg atccaggaga atcaggagag
1081 ctacctctcc ttcaactcca cgggcaactc tcggagccaa atcaaggccg cgctcgacaa
1141 cgcgaccaaa atcatgagtc tgacaaaaag cgcggtggac tacctcgtgg ggagctccgt
1201 tcccgaggac atttcaaaaa acagaatctg gcaaattttt gagatgaacg gctacgaccc
1261 ggcctacgcg ggatccatcc tctacggctg gtgtcagcgc tccttcaaca agaggaacac
1321 cgtctggctc tacggacccg ccacgaccgg caagaccaac atcgcggagg ccatcgccca
```

-continued

| Sequences |
|---|
| 1381 cactgtgccc ttttacggct gcgtgaactg gaccaatgaa aactttccct ttaatgactg |
| 1441 tgtggacaaa atgctcattt ggtgggagga gggaaagatg accaacaagg tggttgaatc |
| 1501 cgccaaggcc atcctggggg gctccaaggt gcgggtcgat cagaaatgta aatcctctgt |
| 1561 tcaaattgat tctacccccg tcattgtaac ttccaataca aacatgtgtg tggtggtgga |
| 1621 tgggaattcc acgacctttg aacaccagca gccgctggag gaccgcatgt tcaaatttga |
| 1681 actgactaag cggctcccgc cagattttgg caagattact aagcaggaag tcaaagactt |
| 1741 ttttgcttgg gcaaaggtca atcaggtgcc ggtgactcac gagtttaaag ttcccaggga |
| 1801 attggcggga actaaagggg cggagaaatc tctaaaacgc ccactgggtg acgtcaccaa |
| 1861 tactagctat aaaagtccag agaagcgggc ccggctctca tttgttcccg agacgcctcg |
| 1921 cagttcagac gtgactgtcg atcccgctcc tctgcgaccg ctcaattgga attcaaggta |
| 1981 tgattgcaaa tgtgaccatc atgctcaatt tgacaacatt tctgacaaat gtgatgaatg |
| 2041 tgaatatttg aatcggggca aaaatggatg tatctgtcac aatgtaactc actgtcaaat |
| 2101 ttgtcacggg attccccccct gggagaagga aaacttgtca gattttgggg attttgacga |
| 2161 tgccaataaa gaacagtaaa taaagcgagt agtcatgtct tttgttgatc accctccaga |
| 2221 ttggttggaa gaagttggtg aaggtcttcg cgagtttttg ggccttgaag cgggcccacc |
| 2281 gaaaccgaaa cccaatcagc agcatcaaga tcaagcccgt ggtcttgtgc tgcctggtta |
| 2341 taactatctc ggacccggaa acggtctcga tcgaggagag cctgtcaaca gggcagacga |
| 2401 ggtcgcgcga gagcacgaca tctcgtacaa cgagcagctt gaggcgggag acaacccccta |
| 2461 cctcaagtac aaccacgcgg acgccgagtt tcaggagaag ctcgccgacg acacatcctt |
| 2521 cgggggaaac ctcggaaagg cagtctttca ggccaagaaa agggttctcg aaccttttgg |
| 2581 cctggttgaa gagggtgcta agacggcccc taccggaaag cggatagacg accactttcc |
| 2641 aaaaagaaag aaggctcgga ccgaagagga ctccaagcct tccacctcgt cagacgccga |
| 2701 agctggaccc agcggatccc agcagctgca aatcccagca caaccagcct caagtttggg |
| 2761 agctgataca atgtctgcgg gaggtggcgg cccattgggc gacaataacc aaggtgccga |
| 2821 tggagtgggc aatgcctcgg gagattggca ttgcgattcc acgtggatgg gggacagagt |
| 2881 cgtcaccaag tccacccgca cctgggtgct gcccagctac aacaaccacc agtaccgaga |
| 2941 gatcaaaagc ggctccgtcg acggaagcaa cgccaacgcc tactttggat acagcacccc |
| 3001 ctgggggtac tttgacttta accgcttcca cagccactgg agcccccgag actggcaaag |
| 3061 actcatcaac aactattggg gcttcagacc ccggtctctc agagtcaaaa tcttcaacat |
| 3121 ccaagtcaaa gaggtcacgg tgcaggactc caccaccacc atcgccaaca acctcacctc |
| 3181 caccgtccaa gtgtttacgg acgacgacta ccaactcccg tacgtcgtcg gcaacgggac |
| 3241 cgagggatgc ctgccggcct tcccccccgca ggtctttacg ctgccgcagt acggctacgc |
| 3301 gacgctgaac cgagacaacg gagacaaccc gacagagcgg agcagcttct tttgcctaga |
| 3361 gtactttccc agcaagatgc tgaggacggg caacaacttt gagtttacct acagctttga |
| 3421 agaggtgccc ttccactgca gcttcgcccc gagccagaac ctctttaagc tggccaaccc |
| 3481 gctggtggac cagtacctgt accgcttcgt gagcacctcg gccacgggcg ccatccagtt |
| 3541 ccaaaagaac ctggcgggca gatacgccaa cacctacaaa aactggttcc cggggcccat |
| 3601 gggccgaacc cagggctgga acacgagctc tggcagcagc accaacagag tcagcgtcaa |
| 3661 caacttttcc gtctcaaacc ggatgaacct ggagggggcc agctaccaag tgaaccccca |
| 3721 gcccaacggg atgacaaaca cgctccaagg cagcaaccgc tacgcgctgg aaaacaccat |
| 3781 gatcttcaac gctcaaaacg ccacgccggg aactacctcg gtgtacccag aggacaatct |
| 3841 actgctgacc agcgagagcg agactcagcc cgtcaaccgg gtggcttaca acacgggcgg |
| 3901 tcagatggcc accaacgccc agaacgccac cacggctccc acggtcggga cctacaacct |
| 3961 ccaggaagtg cttcctggca gcgtatggat ggagagggac gtgtacctcc aaggacccat |
| 4021 ctgggccaag atcccagaga cgggggcgca ctttcacccc tctccggcca tgggcggatt |
| 4081 cggactcaaa cacccgccgc ccatgatgct catcaaaaac acgccggtgc ccggcaacat |
| 4141 caccagcttc tcggacgtgc ccgtcagcag cttcatcacc cagtacagca ccgggcaggt |
| 4201 caccgtggag atggaatggg agctcaaaaa ggaaaactcc aagaggtgga acccagagat |
| 4261 ccagtacacc aacaactaca acgaccccca gtttgtggac tttgctccag acggctccgg |
| 4321 cgaatacaga accaccagag ccatcggaac ccgatacctc acccgacccc tttaacccat |
| 4381 tcatgtcgca taccctcaat aaaccgtgta ttcgtgtcag tgaaatactg cctcttgtgg |
| 4441 tcattcaatg aacatcagct tacaacatct acaaaacccc cttgcttgag agtgtggcac |
| 4501 tctccccccct gtcgcgttcg ctcgctcgct ggctcgtttg ggggggtggc agctcaaaga |
| 4561 gctgccagac gacggccctc tggccgtcgc ccccccaaac gagccagcga gcgagcgaac |
| 4621 gcgacagggg ggagag |
| |
| AAV2 (SEQ ID NO: 128) |
| 1 ttggccactc cctctctgcg cgctcgctcg ctcactgagg ccgggcgacc aaaggtcgcc |
| 61 cgacgcccgg gctttgcccg ggcggcctca gtgagcgagc gagcgcgcag agagggagtg |
| 121 gccaactcca tcactagggg ttcctggagg ggtggagtcg tgacgtgaat tacgtcatag |
| 181 ggttagggag gtcctgtatt agaggtcacg tgagtgtttt gcgacatttt gcgacaccat |
| 241 gtggtcacgc tgggtattta agcccgagtg agcacgcagg gtctccattt tgaagcggga |
| 301 ggtttgaacg cgcagccgcc atgccggggt tttacgagat tgtgattaag gtccccagcg |
| 361 accttgacga gcatctgccc ggcatttctg acagctttgt gaactgggtg gccgagaagg |
| 421 aatgggagtt gccgccagat tctgacatgg atctgaatct gattgagcag gcaccccctga |
| 481 ccgtggccga gaagctgcag cgcgactttc tgacggaatg gcgccgtgtg agtaaggccc |
| 541 cggaggccct tttctttgtg caatttgaga agggagagag ctacttccac atgcacgtgc |
| 601 tcgtggaaac caccggggtg aaatccatgg ttttgggacg tttcctgagt cagattcgcg |
| 661 aaaaactgat tcagagaatt taccgcggga tcgagccgac tttgccaaac tggttcgcgg |
| 721 tcacaaagac cagaaatggc gccggaggcg ggaacaaggt ggtggatgag tgctacatcc |
| 781 ccaattactt gctccccaaa acccagcctg agctccagtg ggcgtggact aatatggaac |
| 841 agtatttaag cgcctgtttg aatctcacgg agcgtaaacg gttggtggcg cagcatctga |
| 901 cgcacgtgtc gcagacgcag gagcagaaca aagagaatca gaatcccaat tctgatgcgc |
| 961 cggtgatcag atcaaaaact tcagccaggt acatggagct ggtcgggtgg ctcgtggaca |
| 1021 aggggattac ctcggagaag cagtggatcc aggaggacca ggcctcatac atctccttca |
| 1081 atgcggcctc caactcgcgg tcccaaatca aggctgcctt ggacaatgcg ggaaagatta |
| 1141 tgagcctgac taaaaccgcc cccgactacc tggtgggcca gcagcccgtg gaggacattt |

-continued

| Sequences |
|---|
| 1201 ccagcaatcg gatttataaa attttggaac taaacgggta cgatccccaa tatgcggctt |
| 1261 ccgtctttct gggatgggcc acgaaaaagt tcggcaagag gaacaccatc tggctgtttg |
| 1321 ggcctgcaac taccgggaag accaacatcg cggaggccat agcccacact gtgcccttct |
| 1381 acgggtgcgt aaactggacc aatgagaact ttcccttcaa cgactgtgtc gacaagatgg |
| 1441 tgatctggtg ggaggagggg aagatgaccg ccaaggtcgt ggagtcggcc aaagccattc |
| 1501 tcggaggaag caaggtgcgc gtggaccaga aatgcaagtc ctcggcccag atagacccga |
| 1561 ctcccgtgat cgtcacctcc aacaccaaca tgtgcgccgt gattgacggg aactcaacga |
| 1621 ccttcgaaca ccagcagccg ttgcaagacc ggatgttcaa atttgaactc acccgccgtc |
| 1681 tggatcatga ctttgggaag gtcaccaagc aggaagtcaa agactttttc cggtgggcaa |
| 1741 aggatcacgt ggttgaggtg gagcatgaat tctacgtcaa aaagggtgga gccaagaaaa |
| 1801 gacccgcccc cagtgacgca gatataagtg agcccaaacg ggtgcgcgag tcagttgcgc |
| 1861 agccatcgac gtcagacgcg gaagcttcga tcaactacgc agacaggtac caaaacaaat |
| 1921 gttctcgtca cgtgggcatg aatctgatgc tgtttccctg cagacaatgc gagagaatga |
| 1981 atcagaattc aaatatctgc ttcactcacg gacagaaaga ctgtttagag tgctttcccg |
| 2041 tgtcagaatc tcaacccgtt tctgtcgtca aaaaggcgta tcagaaactg tgctacattc |
| 2101 atcatatcat gggaaaggtg ccagacgctt gcactgcctg cgatctggtc aatgtggatt |
| 2161 tggatgactg catctttgaa caataaatga tttaaatcag gtatggctgc cgatggttat |
| 2221 cttccagatt ggctcgagga cactctctct gaaggaataa gacagtggtg gaagctcaaa |
| 2281 cctggcccac caccaccaaa gcccgcagag cggcataagg acgacagcag gggtcttgtg |
| 2341 cttcctgggt acaagtacct cggacccttc aacggactcg acaagggaga gccggtcaac |
| 2401 gaggcagacg ccgcggccct cgagcacgac aaagcctacg accggcagct cgacagcgga |
| 2461 gacaacccgt acctcaagta caaccacgcc gacgcggagt ttcaggagcg ccttaaagaa |
| 2521 gatacgtctt ttgggggcaa cctcggacga gcagtcttcc aggcgaaaaa gagggttctt |
| 2581 gaacctctgg gcctggttga ggaacctgtt aagacggctc cgggaaaaaa gaggccggta |
| 2641 gagcactctc ctgtggagcc agactcctcc tcgggaaccg gaaaggcggg ccagcagcct |
| 2701 gcaagaaaaa gattgaattt tggtcagact ggagacgcag actcagtacc tgacccccag |
| 2761 cctctcggac agccaccagc agccccctct ggtctgggaa ctaatacgat ggctacaggc |
| 2821 agtggcgcac caatggcaga caataacgag ggcgccgacg gagtgggtaa ttcctcggga |
| 2881 aattggcatt gcgattccac atggatgggc gacagagtca tcaccaccag cacccgaacc |
| 2941 tgggccctgc ccacctacaa caaccacctc tacaaacaaa tttccagcca atcaggagcc |
| 3001 tcgaacgaca atcactactt tggctacagc accccttggg ggtattttga cttcaacaga |
| 3061 ttccactgcc acttttcacc acgtgactgg caaagactca tcaacaacaa ctggggattc |
| 3121 cgacccaaga gactcaactt caagctcttt aacattcaag tcaaagaggt cacgcagaat |
| 3181 gacggtacga cgacgattgc caataacctt accagcacgg ttcaggtgtt tactgactcg |
| 3241 gagtaccagc tcccgtacgt cctcggctcg gcgcatcaag gatgcctccc gccgttccca |
| 3301 gcagacgtct tcatggtgcc acagtatgga tacctcaccc tgaacaacgg gagtcaggca |
| 3361 gtaggacgct cttcatttta ctgcctggag tactttcctt ctcagatgct gcgtaccgga |
| 3421 aacaacttta ccttcagcta cacttttgag gacgttcctt tccacagcag ctacgctcac |
| 3481 agccagagtc tggaccgtct catgaatcct ctcatcgacc agtacctgta ttacttgagc |
| 3541 agaacaaaca ctccaagtgg aaccaccacg cagtcaaggc ttcagttttc tcaggccgga |
| 3601 gcgagtgaca ttcgggacca gtctaggaac tggcttcctg gaccctgtta ccgccagcag |
| 3661 cgagtatcaa agacatctgc ggataacaac aacagtgaat actcgtggac tggagctacc |
| 3721 aagtaccacc tcaatggcag agactctctg gtgaatccgg gcccggccat ggcaagccac |
| 3781 aaggacgatg aagaaaagtt ttttcctcag agcggggttc tcatctttgg gaagcaaggc |
| 3841 tcagagaaaa caaatgtgga cattgaaaag gtcatgatta cagacgaaga ggaaatcagg |
| 3901 acaaccaatc ccgtggctac ggagcagtat ggttctgtat ctaccaacct ccagagaggc |
| 3961 aacagacaag cagctaccgc agatgtcaac acacaaggcg ttcttccagg catggtctgg |
| 4021 caggacagag atgtgtacct tcaggggccc atctgggcaa agattccaca cacggacgga |
| 4081 cattttcacc cctctcccct catgggtgga ttcggactta aacaccctcc tccacagatt |
| 4141 ctcatcaaga acaccccggt acctgcgaat ccttcgacca ccttcagtgc ggcaaagttt |
| 4201 gcttccttca tcacacagta ctccacggga caggtcagcg tggagatcga gtgggagctg |
| 4261 cagaaggaaa acagcaaacg ctggaatccc gaaattcagt acacttccaa ctacaacaag |
| 4321 tctgttaatg tggactttac tgtggacact aatggcgtgt attcagagcc tcgccccatt |
| 4381 ggcaccagat acctgactcg taatctgtaa ttgcttgtta atcaataaac cgtttaattc |
| 4441 gtttcagttg aactttggtc tctgcgtatt tctttcttat ctagtttcca tggctacgta |
| 4501 gataagtagc atggcgggtt aatcattaac tacaaggaac ccctagtgat ggagttggcc |
| 4561 actccctctc tgcgcgctcg ctcgctcact gaggccgggc gaccaaaggt cgcccgacgc |
| 4621 ccgggctttg cccgggcggc ctcagtgagc gagcgagcgc gcagagaggg agtggccaa |
| |
| AAV3 (SEQ ID NO: 129) |
| 1 ttggccactc cctctatgcg cactcgctcg ctcggtgggg cctggcgacc aaaggtcgcc |
| 61 agacggacgt gctttgcacg tccggcccca ccgagcgagc gagtgcgcat agagggagtg |
| 121 gccaactcca tcactagagg tatggcagtg acgtaacgcg aagcgcgcga agcgagacca |
| 181 cgcctaccag ctgcgtcagc agtcaggtga cccttttgcg acagtttgcg acaccacgtg |
| 241 gccgctgagg gtatatattc tcgagtgagc gaaccaggag ctccattttg accgcgaaat |
| 301 ttgaacgagc agcagccatg ccggggttct acgagattgt cctgaaggtc ccgagtgacc |
| 361 tggacgagcg cctgccgggc atttctaact cgtttgttaa ctgggtggcc gagaaggaat |
| 421 gggacgtgcc gccggattct gacatggatc cgaatctgat tgagcaggca cccctgaccg |
| 481 tggccgaaaa gcttcagcgc gagttcctgg tggagtggcg ccgcgtgagt aaggccccgg |
| 541 aggccctctt ttttgtccag ttcgaaaagg gggagaccta cttccacctg cacgtgctga |
| 601 ttgagaccat cggggtcaaa tccatggtgg tcggccgcta cgtgagccag attaaagaga |
| 661 agctggtgac ccgcatctac cgcggggtcg agccgcagct tccgaactgg ttcgcggtga |
| 721 ccaaaacgcg aaatggcgcc gggggcggga acaaggtggt ggacgactgc tacatcccca |
| 781 actacctgct ccccaagacc cagcccgagc tccagtgggc gtggactaac atggaccagt |
| 841 atttaagcgc ctgtttgaat ctcgcggagc gtaaacggct ggtggcgcag catctgacgc |
| 901 acgtgtcgca gacgcaggag cagaacaaag agaatcagaa ccccaattct gacgcgccgg |
| 961 tcatcaggtc aaaaacctca gccaggtaca tggagctggt cgggtggctg gtggaccgcg |

-continued

Sequences 1021 ggatcacgtc agaaaagcaa tggattcagg aggaccaggc ctcgtacatc tccttcaacg
1081 ccgcctccaa ctcgcggtcc cagatcaagg ccgcgctgga caatgcctcc aagatcatga
1141 gcctgacaaa gacggctccg gactacctgg tgggcagcaa cccgccggag gacattacca
1201 aaaatcggat ctaccaaatc ctggagctga acgggtacga tccgcagtac gcggcctccg
1261 tcttcctggg ctgggcgcaa aagaagttcg ggaagaggaa caccatctgg ctctttgggc
1321 cggccacgac gggtaaaacc aacatcgcgg aagccatcgc ccacgccgtg cccttctacg
1381 gctgcgtaaa ctggaccaat gagaactttc ccttcaacga ttgcgtcgac aagatggtga
1441 tctggtggga ggagggcaag atgacggcca aggtcgtgga gagcgccaag gccattctgg
1501 gcggaagcaa ggtgcgcgtg gaccaaaagt gcaagtcatc ggcccagatc gaacccactc
1561 ccgtgatcgt cacctccaac accaacatgt gcgccgtgat tgacgggaac agcaccacct
1621 tcgagcatca gcagccgctg caggaccgga tgtttgaatt tgaacttacc cgccgtttgg
1681 accatgactt tgggaaggtc accaaacagg aagtaaagga ctttttccgg tgggcttccg
1741 atcacgtgac tgacgtggct catgagttct acgtcagaaa gggtggagct aagaaacgcc
1801 ccgcctccaa tgacgcggat gtaagcgagc caaaacggga gtgcacgtca cttgcgcagc
1861 cgacaacgtc agacgcggaa gcaccggcgg actacgcgga caggtaccaa aacaaatgtt
1921 ctcgtcacgt gggcatgaat ctgatgcttt ttccctgtaa aacatgcgag agaatgaatc
1981 aaatttccaa tgtctgtttt acgcatggtc aaagagactg tggggaatgc ttccctggaa
2041 tgtcagaatc tcaacccgtt tctgtcgtca aaaagaagac ttatcagaaa ctgtgtccaa
2101 ttcatcatat cctgggaagg gcacccgaga ttgcctgttc ggcctgcgat ttggccaatg
2161 tggacttgga tgactgtgtt tctgagcaat aaatgactta aaccaggtat ggctgctgac
2221 ggttatcttc cagattggct cgaggacaac ctttctgaag gcattcgtga gtggtgggct
2281 ctgaaacctg gagtccctca acccaaagcg aaccaacaac accaggacaa ccgtcggggt
2341 cttgtgcttc cgggttacaa atacctcgga cccggtaacg gactcgacaa aggagagccg
2401 gtcaacgagg cggacgcggc agccctcgaa cacgacaaag cttacgacca gcagctcaag
2461 gccggtgaca acccgtacct caagtacaac cacgccgacg ccgagtttca ggagcgtctt
2521 caagaagata cgtcttttgg gggcaacctt ggcagagcag tcttccaggc caaaaagagg
2581 atccttgagc ctcttggtct ggttgaggaa gcagctaaaa cggctcctgg aaagaagggg
2641 gctgtagatc agtctcctca ggaaccggac tcatcatctg gtgttggcaa atcgggcaaa
2701 cagcctgcca gaaaaagact aaatttcggt cagactggag actcagagtc agtcccagac
2761 cctcaacctc tcggagaacc accagcagcc cccacaagtt tgggatctaa tacaatggct
2821 tcaggcggtg gcgcaccaat ggcagacaat aacgagggtg ccgatggagt gggtaattcc
2881 tcaggaaatt ggcattgcga ttcccaatgg ctgggcgaca gagtcatcac caccagcacc
2941 agaacctggg ccctgcccac ttacaacaac catctctaca agcaaatctc cagccaatca
3001 ggagcttcaa acgacaacca ctactttggc tacagcaccc cttgggggta ttttgacttt
3061 aacagattcc actgccactt ctcaccacgt gactggcagc gactcattaa caacaactgg
3121 ggattccggc ccaagaaact cagcttcaag ctcttcaaca tccaagttag aggggtcacg
3181 cagaacgatg gcacgacgac tattgccaat aaccttacca gcacggttca agtgtttacg
3241 gactcggagt atcagctccc gtacgtgctc gggtcggcgc accaaggctg tctcccgccg
3301 tttccagcgg acgtcttcat ggtccctcag tatggatacc tcaccctgaa caacggaagt
3361 caagcggtgg gacgctcatc cttttactgc ctggagtact tcccttcgca gatgctaagg
3421 actggaaata acttccaatt cagctatacc ttcgaggatg taccttttca cagcagctac
3481 gctcacagcc agagtttgga tcgcttgatg aatcctctta ttgatcagta tctgtactac
3541 ctgaacagaa cgcaaggaac aacctctgga acaaccaacc aatcacggct gctttttagc
3601 caggctgggc ctcagtctat gtctttgcag gccagaaatt ggctacctgg gccctgctac
3661 cggcaacaga gactttcaaa gactgctaac gacaacaaca acagtaactt tccttggaca
3721 gcggccagca aatatcatct caatggccgc gactcgctgg tgaatccagg accagctatg
3781 gccagtcaca aggacgatga agaaaaattt ttccctatgc acggcaatct aatatttggc
3841 aaagaaggga caacggcaag taacgcagaa ttagataatg taatgattac ggatgaagaa
3901 gagattcgta ccaccaatcc tgtggcaaca gagcagtatg gaactgtggc aaataacttg
3961 cagagctcaa atacagctcc cacgactgga actgtcaatc atcagggggc cttacctggc
4021 atggtgtggc aagatcgtga cgtgtacctt caaggaccta tctgggcaaa gattcctcac
4081 acggatggac actttcatcc ttctcctctg atgggaggct ttggactgaa acatccgcct
4141 cctcaaatca tgatcaaaaa tactccggta ccggcaaatc ctccgacgac tttcagcccg
4201 gccaagtttg cttcatttat cactcagtac tccactggac aggtcagcgt ggaaattgag
4261 tgggagctac agaaagaaaa cagcaaacgt tggaatccag agattcagta cacttccaac
4321 tacaacaagt ctgttaatgt ggactttact gtagacacta atggtgttta tagtgaacct
4381 cgccctattg gaacccggta tctcacacga aacttgtgaa tcctggttaa tcaataaacc
4441 gtttaattcg tttcagttga actttggctc ttgtgcactt ctttatcttt atcttgtttc
4501 catggctact gcgtagataa gcagcggcct gcggcgcttg cgcttcgcgg tttacaactg
4561 ctggttaata tttaactctc gccatacctc tagtgatgga gttggccact ccctctatgc
4621 gcactcgctc gctcggtggg gcctggcgac caaaggtcgc cagacggacg tgctttgcac
4681 gtccggcccc accgagcgag cgagtgcgca tagagggagt ggccaa

AAV4 (SEQ ID NO: 130)

1 ttggccactc cctctatgcg cgctcgctca ctcactcggc cctggagacc aaaggtctcc
61 agactgccgg cctctggccg gcagggccga gtgagtgagc gagcgcgcat agagggagtg
121 gccaactcca tcatctaggt ttgcccactg acgtcaatgt gacgtcctag ggttagggag
181 gtccctgtat tagcagtcac gtgagtgtcg tatttcgcgg agcgtagcgg agcgcatacc
241 aagctgccac gtcacagcca cgtggtccgt ttgcgacagt ttgcgacacc atgtggtcag
301 gagggtatat aaccgcgagt gagccagcga ggagctccat tttgcccgcg aattttgaac
361 gagcagcagc catgccgggg ttctacgaga tcgtgctgaa ggtgcccagc gacctggacg
421 agcacctgcc cggcatttct gactcttttg tgagctgggt ggccgagaag gaatgggagc
481 tgccgccgga ttctgacatg gacttgaatc tgattgagca ggcacccctg accgtggccg
541 aaaagctgca acgcgagttc ctggtcgagt ggcgccgcgt gagtaaggcc ccggaggccc
601 tcttctttgt ccagttcgag aagggggaca gctacttcca cctgcacatc ctggtggaga
661 ccgtgggcgt caaatccatg gtggtgggcc gctacgtgag ccagattaaa gagaagctgg
721 tgacccgcat ctaccgcggg gtcgagccgc agcttccgaa ctggttcgcg gtgaccaaga -continued Sequences 781 cgcgtaatgg cgccggaggc gggaacaagg tggtggacga ctgctacatc cccaactacc
841 tgctccccaa gacccagccc gagctccagt gggcgtggac taacatggac cagtatataa
901 gcgcctgttt gaatctcgcg gagcgtaaac ggctggtggc gcagcatctg acgcacgtgt
961 cgcagacgca ggagcagaac aaggaaaacc agaaccccaa ttctgacgcg ccggtcatca
1021 ggtcaaaaac ctccgccagg tacatggagc tggtcgggtg gctggtggac cgcgggatca
1081 cgtcagaaaa gcaatggatc caggaggacc aggcgtccta catctccttc aacgccgcct
1141 ccaactcgcg gtcacaaatc aaggccgcgc tggacaatgc ctccaaaatc atgagcctga
1201 caaagacggc tccggactac ctggtgggcc agaacccgcc ggaggacatt tccagcaacc
1261 gcatctaccg aatcctcgag atgaacgggt acgatccgca gtacgcggcc tccgtcttcc
1321 tgggctgggc gcaaaagaag ttcgggaaga ggaacaccat ctggctcttt gggccggcca
1381 cgacgggtaa aaccaacatc gcggaagcca tcgcccacgc cgtgcccttc tacggctgcg
1441 tgaactggac caatgagaac tttccgttca acgattgcgt cgacaagatg gtgatctggt
1501 gggaggaggg caagatgacg gccaaggtcg tagagagcgc caaggccatc ctgggcggaa
1561 gcaaggtgcg cgtggaccaa aagtgcaagt catcggccca gatcgaccca actcccgtga
1621 tcgtcacctc caacaccaac atgtgcgcgg tcatcgacgg aaactcgacc accttcgagc
1681 accaacaacc actccaggac cggatgttca agttcgagct caccaagcgc ctggagcacg
1741 actttggcaa ggtcaccaag caggaagtca aagacttttt ccggtgggcg tcagatcacg
1801 tgaccgaggt gactcacgag ttttacgtca gaaagggtgg agctagaaag aggcccgccc
1861 ccaatgacgc agatataagt gagcccaagc gggcctgtcc gtcagttgcg cagccatcga
1921 cgtcagacgc ggaagctccg gtggactacg cggacaggta ccaaaacaaa tgttctcgtc
1981 acgtgggtat gaatctgatg ctttttccct gccggcaatg cgagagaatg aatcagaatg
2041 tggacatttg cttcacgcac ggggtcatgg actgtgccga gtgcttcccc gtgtcagaat
2101 ctcaacccgt gtctgtcgtc agaaagcgga cgtatcagaa actgtgtccg attcatcaca
2161 tcatggggag ggcgcccgag gtggcctgct cggcctgcga actggccaat gtggacttgg
2221 atgactgtga catggaacaa taaatgactc aaaccagata tgactgacgg ttaccttcca
2281 gattggctag aggacaacct ctctgaaggc gttcgagagt ggtgggcgct gcaacctgga
2341 gcccctaaac ccaaggcaaa tcaacaacat caggacaacg ctcggggtct tgtgcttccg
2401 ggttacaaat acctcggacc cggcaacgga ctcgacaagg gggaacccgt caacgcagcg
2461 gacgcggcag ccctcgagca cgacaaggcc tacgaccagc agctcaaggc cggtgacaac
2521 ccctacctca agtacaacca cgccgacgcg gagttccagc agcggcttca gggcgacaca
2581 tcgtttgggg gcaacctcgg cagagcagtc ttccaggcca aaaagagggt tcttgaacct
2641 cttggtctgg ttgagcaagc gggtgagacg gctcctggaa agaagagacc gttgattgaa
2701 tccccccagc agcccgactc ctccacgggt atcggcaaaa aaggcaagca gccggctaaa
2761 aagaagctcg ttttcgaaga cgaaactgga gcaggcgacg gaccccctga gggatcaact
2821 tccggagcca tgtctgatga cagtgagatg cgtgcagcag ctggcggagc tgcagtcgag
2881 ggcggacaag gtgccgatgg agtgggtaat gcctcgggtg attggcattg cgattccacc
2941 tggtctgagg gccacgtcac gaccaccagc accagaacct gggtcttgcc cacctacaac
3001 aaccacctct acaagcgact cggagagagc ctgcagtcca acacctacaa cggattctcc
3061 accccctggg gatactttga cttcaaccgc ttccactgcc acttctcacc acgtgactgg
3121 cagcgactca tcaacaacaa ctggggcatg cgacccaaag ccatgcgggt caaaatcttc
3181 aacatccagg tcaaggaggt cacgacgtcg aacggcgaga caacggtggc taataacctt
3241 accagcacgg ttcagatctt tgcggactcg tcgtacgaac tgccgtacgt gatggatgcg
3301 ggtcaagagg gcagcctgcc tccttttccc aacgacgtct ttatggtgcc ccagtacggc
3361 tactgtggac tggtgaccgg caacacttcg cagcaacaga ctgacagaaa tgccttctac
3421 tgcctggagt actttccttc gcagatgctg cggactggca acaactttga aattacgtac
3481 agttttgaga aggtgccttt ccactcgatg tacgcgcaca gccagagcct ggaccggctg
3541 atgaaccctc tcatcgacca gtacctgtgg ggactgcaat cgaccaccac cggaaccacc
3601 ctgaatgccg ggactgccac caccaacttt accaagctgc ggcctaccaa cttttccaac
3661 tttaaaaaga actggctgcc cgggccttca atcaagcagc agggcttctc aaagactgcc
3721 aatcaaaact acaagatccc tgccaccggg tcagacagtc tcatcaaata cgagacgcac
3781 agcactctgg acggaagatg gagtgccctg acccccggac ctccaatggc cacggctgga
3841 cctgcggaca gcaagttcag caacagccag ctcatctttg cggggcctaa acagaacggc
3901 aacacggcca ccgtacccgg gactctgatc ttcacctctg aggaggagct ggcagccacc
3961 aacgccaccg atacggacat gtggggcaac ctacctggcg gtgaccagag caacagcaac
4021 ctgccgaccg tggacagact gacagccttg ggagccgtgc ctggaatggt ctggcaaaac
4081 agagacattt actaccaggg tcccatttgg gccaagattc ctcataccga tggacacttt
4141 cacccctcac cgctgattgg tgggtttggg ctgaaacacc cgcctcctca aatttttatc
4201 aagaacaccc cggtacctgc gaatcctgca acgaccttca gctctactcc ggtaaactcc
4261 ttcattactc agtacagcac tggccaggtg tcggtgcaga ttgactggga gatccagaag
4321 gagcggtcca aacgctggaa ccccgaggtc cagtttacct ccaactacgg acagcaaaac
4381 tctctgttgt gggctcccga tgcggctggg aaatacactg agcctagggc tatcggtacc
4441 cgctacctca cccaccacct gtaataacct gttaatcaat aaaccggttt attcgtttca
4501 gttgaacttt ggtctccgtg tccttcttat cttatctcgt ttccatggct actgcgtaca
4561 taagcagcgg cctgcggcgc ttgcgcttcg cggtttacaa ctgccggtta atcagtaact
4621 tctggcaaac cagatgatgg agttggccac attagctatg cgcgctcgct cactcactcg
4681 gccctggaga ccaaaggtct ccagactgcc ggcctctggc cggcagggcc gagtgagtga
4741 gcgagcgcgc atagagggag tggccaa

AAV5 (SEQ ID NO: 131)

1 ctctcccccc tgtcgcgttc gctcgctcgc tggctcgttt ggggggggtgg cagctcaaag
61 agctgccaga cgacggccct ctggccgtcg cccccccaaa cgagccagcg agcgagcgaa
121 cgcgacaggg gggagagtgc cacactctca agcaaggggg ttttgtaagc agtgatgtca
181 taatgatgta atgcttattg tcacgcgata gttaatgatt aacagtcatg tgatgtgttt
241 tatccaatag gaagaaagcg cgcgtatgag ttctcgcgag acttccgggg tataaaagac
301 cgagtgaacg agcccgccgc cattctttgc tctggactgc tagaggaccc tcgctgccat
361 ggctaccttc tatgaagtca ttgttcgcgt cccatttgac gtggaggaac atctgcctgg
421 aatttctgac agctttgtgg actgggtaac tggtcaaatt tgggagctgc ctccagagtc -continued Sequences 481 agatttaaat ttgactctgg ttgaacagcc tcagttgacg gtggctgata gaattcgccg
541 cgtgttcctg tacgagtgga acaaattttc caagcaggag tccaaattct ttgtgcagtt
601 tgaaaaggga tctgaatatt ttcatctgca cacgcttgtg gagacctccg gcatctcttc
661 catggtcctc ggccgctacg tgagtcagat tcgcgcccag ctggtgaaag tggtcttcca
721 gggaattgaa ccccagatca acgactgggt cgccatcacc aaggtaaaga agggcggagc
781 caataaggtg gtggattctg ggtatattcc cgcctacctg ctgccgaagg tccaaccgga
841 gcttcagtgg gcgtggacaa acctggacga gtataaattg gccgccctga atctggagga
901 gcgcaaacgg ctcgtcgcgc agtttctggc agaatcctcg cagcgctcgc aggaggcggc
961 ttcgcagcgt gagttctcgg ctgacccggt catcaaaagc aagacttccc agaaatacat
1021 ggcgctcgtc aactggctcg tggagcacgg catcacttcc gagaagcagt ggatccagga
1081 aaatcaggag agctacctct ccttcaactc caccggcaac tctcggagcc agatcaaggc
1141 cgcgctcgac aacgcgacca aaattatgag tctgacaaaa agcgcggtgg actacctcgt
1201 ggggagctcc gttcccgagg acatttcaaa aaacagaatc tggcaaattt ttgagatgaa
1261 tggctacgac ccggcctacg cgggatccat cctctacggc tggtgtcagc gctccttcaa
1321 caagaggaac accgtctggc tctacggacc cgccacgacc ggcaagacca acatcgcgga
1381 ggccatcgcc cacactgtgc ccttttacgg ctgcgtgaac tggaccaatg aaaactttcc
1441 ctttaatgac tgtgtggaca aaatgctcat ttggtgggag gagggaaaga tgaccaacaa
1501 ggtggttgaa tccgccaagg ccatcctggg gggctcaaag gtgcgggtcg atcagaaatg
1561 taaatcctct gttcaaattg attctacccc tgtcattgta acttccaata caaacatgtg
1621 tgtggtggtg gatgggaatt ccacgacctt tgaacaccag cagccgctgg aggaccgcat
1681 gttcaaattt gaactgacta agcggctccc gccagatttt ggcaagatta ctaagcagga
1741 agtcaaggac 111111gctt gggcaaaggt caatcaggtg ccggtgactc acgagtttaa
1801 agttcccagg gaattggcgg gaactaaagg ggcggagaaa tctctaaaac gcccactggg
1861 tgacgtcacc aatactagct ataaaagtct ggagaagcgg gccaggctct catttgttcc
1921 cgagacgcct cgcagttcag acgtgactgt tgatcccgct cctctgcgac cgctcaattg
1981 gaattcaagg tatgattgca aatgtgacta tcatgctcaa tttgacaaca tttctaacaa
2041 atgtgatgaa tgtgaatatt tgaatcgggg caaaaatgga tgtatctgtc acaatgtaac
2101 tcactgtcaa atttgtcatg ggattccccc ctgggaaaag gaaaacttgt cagattttgg
2161 ggattttgac gatgccaata aagaacagta aataaagcga gtagtcatgt cttttgttga
2221 tcaccctcca gattggttgg aagaagttgg tgaaggtctt cgcgagtttt tgggccttga
2281 agcgggccca ccgaaaccaa aacccaatca gcagcatcaa gatcaagccc gtggtcttgt
2341 gctgcctggt tataactatc tcggacccgg aaacggtctc gatcgaggag agcctgtcaa
2401 cagggcagac gaggtcgcgc gagagcacga catctcgtac aacgagcagc ttgaggcggg
2461 agacaacccc tacctcaagt acaaccacgc ggacgccgag tttcaggaga agctcgccga
2521 cgacacatcc ttcgggggaa acctcggaaa ggcagtcttt caggccaaga aaagggttct
2581 cgaacctttt ggcctggttg aagagggtgc taagacggcc cctaccggaa agcggataga
2641 cgaccacttt ccaaaaagaa agaaggctcg gaccgaagag gactccaagc cttccacctc
2701 gtcagacgcc gaagctggac ccagcggatc ccagcagctg caaatcccag cccaaccagc
2761 ctcaagtttg ggagctgata caatgtctgc gggaggtggc ggcccattgg gcgacaataa
2821 ccaaggtgcc gatggagtgg gcaatgcctc gggagattgg cattgcgatt ccacgtggat
2881 gggggacaga gtcgtcacca agtccacccg aacctgggtg ctgcccagct acaacaacca
2941 ccagtaccga gagatcaaaa gcggctccgt cgacggaagc aacgccaacg cctactttgg
3001 atacagcacc ccctgggggt actttgactt taaccgcttc cacagccact ggagcccccg
3061 agactggcaa agactcatca acaactactg gggcttcaga ccccggtccc tcagagtcaa
3121 aatcttcaac attcaagtca aagaggtcac ggtgcaggac tccaccacca ccatcgccaa
3181 caacctcacc tccaccgtcc aagtgtttac ggacgacgac taccagctgc cctacgtcgt
3241 cggcaacggg accgagggat gcctgccggc cttccctccg caggtcttta cgctgccgca
3301 gtacggttac gcgacgctga accgcgacaa cacagaaaat cccaccgaga ggagcagctt
3361 cttctgccta gagtactttc ccagcaagat gctgagaacg ggcaacaact ttgagtttac
3421 ctacaacttt gaggaggtgc ccttccactc cagcttcgct cccagtcaga acctgttcaa
3481 gctggccaac ccgctggtgg accagtactt gtaccgcttc gtgagcacaa ataacactgg
3541 cggagtccag ttcaacaaga acctggccgg gagatacgcc aacacctaca aaaactggtt
3601 cccggggccc atgggccgaa cccagggctg gaacctgggc tccggggtca accgcgccag
3661 tgtcagcgcc ttcgccacga ccaataggat ggagctcgag ggcgcgagtt accaggtgcc
3721 cccgcagccg aacggcatga ccaacaacct ccagggcagc aacacctatg ccctggagaa
3781 cactatgatc ttcaacagcc agccggcgaa cccgggcacc accgccacgt acctcgaggg
3841 caacatgctc atcaccagcg agagcgagac gcagccggtg aaccgcgtgg cgtacaacgt
3901 cggcgggcag atggccacca acaaccagag ctccaccact gcccccgcga ccggcacgta
3961 caacctccag gaaatcgtgc ccggcagcgt gtggatggag agggacgtgt acctccaagg
4021 acccatctgg gccaagatcc cagagacggg ggcgcacttt cacccctctc cggccatggg
4081 cggattcgga ctcaaacacc caccgcccat gatgctcatc aagaacacgc ctgtgcccgg
4141 aaatatcacc agcttctcgg acgtgcccgt cagcagcttc atcacccagt acagcaccgg
4201 gcaggtcacc gtggagatgg agtgggagct caagaaggaa aactccaaga ggtggaaccc
4261 agagatccag tacacaaaca actacaacga cccccagttt gtggactttg ccccggacag
4321 caccggggaa tacagaacca ccagacctat cggaacccga taccttaccc gacccccttta
4381 acccattcat gtcgcatacc ctcaataaac cgtgtattcg tgtcagtaaa atactgcctc
4441 ttgtggtcat tcaatgaata acagcttaca acatctacaa aacctccttg cttgagagtg
4501 tggcactctc ccccctgtcg cgttcgctcg ctcgctggct cgtttggggg ggtggcagct
4561 caaagagctg ccagacgacg gccctctggc cgtcgccccc ccaaacgagc cagcgagcga
4621 gcgaacgcga caggggggag ag

AAV6 (SEQ ID NO: 132)

1 ttggccactc cctctctgcg cgctcgctcg ctcactgagg ccgggcgacc aaaggtcgcc
61 cgacgcccgg gctttgcccg ggcggcctca gtgagcgagc gagcgcgcag agagggagtg
121 gccaactcca tcactagggg ttcctggagg ggtggagtcg tgacgtgaat tacgtcatag
181 ggttagggag gtcctgtatt agaggtcacg tgagtgtttt gcgacatttt gcgacaccat
241 gtggtcacgc tgggtattta agcccgagtg agcacgcagg gtctccattt tgaagcggga -continued

| Sequences |
|---|
| 301 ggtttgaacg cgcagcgcca tgccggggtt ttacgagatt gtgattaagg tccccagcga |
| 361 ccttgacgag catctgcccg gcatttctga cagctttgtg aactgggtgg ccgagaagga |
| 421 atgggagttg ccgccagatt ctgacatgga tctgaatctg attgagcagg cacccctgac |
| 481 cgtggccgag aagctgcagc gcgacttcct ggtccagtgg cgccgcgtga gtaaggcccc |
| 541 ggaggccctc ttctttgttc agttcgagaa gggcgagtcc tacttccacc tccatattct |
| 601 ggtggagacc acgggggtca aatccatggt gctgggccgc ttcctgagtc agattaggga |
| 661 caagctggtg cagaccatct accgcgggat cgagccgacc ctgcccaact ggttcgcggt |
| 721 gaccaagacg cgtaatggcg ccggaggggg gaacaaggtg gtggacgagt gctacatccc |
| 781 caactacctc ctgcccaaga ctcagcccga gctgcagtgg gcgtggacta acatggagga |
| 841 gtatataagc gcgtgtttaa acctggccga gcgcaaacgg ctcgtggcgc acgacctgac |
| 901 ccacgtcagc cagacccagg agcagaacaa ggagaatctg aaccccaatt ctgacgcgcc |
| 961 tgtcatccgg tcaaaaacct ccgcacgcta catggagctg gtcgggtggc tggtggaccg |
| 1021 gggcatcacc tccgagaagc agtggatcca ggaggaccag gcctcgtaca tctccttcaa |
| 1081 cgccgcctcc aactcgcggt cccagatcaa ggccgctctg gacaatgccg gcaagatcat |
| 1141 ggcgctgacc aaatccgcgc ccgactacct ggtaggcccc gctccgcccg ccgacattaa |
| 1201 aaccaaccgc atttaccgca tcctggagct gaacggctac gaccctgcct acgccggctc |
| 1261 cgtctttctc ggctgggccc agaaaaggtt cggaaaacgc aacaccatct ggctgtttgg |
| 1321 gccggccacc acgggcaaga ccaacatcgc ggaagccatc gcccacgccg tgcccttcta |
| 1381 cggctgcgtc aactggacca atgagaactt tcccttcaac gattgcgtcg acaagatggt |
| 1441 gatctggtgg gaggagggca agatgacggc caaggtcgtg gagtccgcca aggccattct |
| 1501 cggcggcagc aaggtgcgcg tggaccaaaa gtgcaagtcg tccgcccaga tcgatcccac |
| 1561 ccccgtgatc gtcacctcca acaccaacat gtgcgccgtg attgacggga acagcaccac |
| 1621 cttcgagcac cagcagccgt tgcaggaccg gatgttcaaa tttgaactca cccgccgtct |
| 1681 ggagcatgac tttggcaagg tgacaaagca ggaagtcaaa gagttcttcc gctgggcgca |
| 1741 ggatcacgtg accgaggtgg cgcatgagtt ctacgtcaga aagggtggag ccaacaagag |
| 1801 acccgccccc gatgacgcgg ataaaagcga gcccaagcgg gcctgcccct cagtcgcgga |
| 1861 tccatcgacg tcagacgcgg aaggagctcc ggtggacttt gccgacaggt accaaaacaa |
| 1921 atgttctcgt cacgcgggca tgcttcagat gctgtttccc tgcaaaacat gcgagagaat |
| 1981 gaatcagaat ttcaacattt gcttcacgca cgggaccaga gactgttcag aatgtttccc |
| 2041 cggcgtgtca gaatctcaac cggtcgtcag aaagaggacg tatcggaaac tctgtgccat |
| 2101 tcatcatctg ctggggcggg ctcccgagat tgcttgctcg gcctgcgatc tggtcaacgt |
| 2161 ggatctggat gactgtgttt ctgagcaata aatgacttaa accaggtatg gctgccgatg |
| 2221 gttatcttcc agattggctc gaggacaacc tctctgaggg cattcgcgag tggtgggact |
| 2281 tgaaacctgg agccccgaaa cccaaagcca accagcaaaa gcaggacgac ggccggggtc |
| 2341 tggtgcttcc tggctacaag tacctcggac ccttcaacgg actcgacaag gggggagcccg |
| 2401 tcaacgcggc ggatgcagcg gccctcgagc acgacaaggc ctacgaccag cagctcaaag |
| 2461 cgggtgacaa tccgtacctg cggtataacc acgccgacgc cgagtttcag gagcgtctgc |
| 2521 aagaagatac gtcttttggg ggcaacctcg ggcgagcagt cttccaggcc aagaagaggg |
| 2581 ttctcgaacc ttttggtctg gttgaggaag gtgctaagac ggctcctgga aagaaacgtc |
| 2641 cggtagagca gtcgccacaa gagccagact cctcctcggg cattggcaag acaggccagc |
| 2701 agcccgctaa aaagagactc aattttggtc agactggcga ctcagagtca gtccccgacc |
| 2761 cacaacctct cggagaacct ccagcaaccc ccgctgctgt gggacctact acaatggctt |
| 2821 caggcggtgg cgcaccaatg gcagacaata acgaaggcgc cgacggagtg ggtaatgcct |
| 2881 caggaaattg gcattgcgat tccacatggc tgggcgacag agtcatcacc accagcaccc |
| 2941 gaacatgggc cttgcccacc tataacaacc acctctacaa gcaaatctcc agtgcttcaa |
| 3001 cgggggccag caacgacaac cactacttcg gctacagcac cccctggggg tattttgatt |
| 3061 tcaacagatt ccactgccat ttctcaccac gtgactggca gcgactcatc aacaacaatt |
| 3121 ggggattccg gcccaagaga ctcaacttca agctcttcaa catccaagtc aaggaggtca |
| 3181 cgacgaatga tggcgtcacg accatcgcta ataaccttac cagcacggtt caagtcttct |
| 3241 cggactcgga gtaccagttg ccgtacgtcc tcggctctgc gcaccagggc tgcctccctc |
| 3301 cgttcccggc ggacgtgttc atgattccgc agtacggcta cctaacgctc aacaatggca |
| 3361 gccaggcagt gggacggtca tccttttact gcctggaata tttcccatcg cagatgctga |
| 3421 gaacgggcaa taactttacc ttcagctaca ccttcgagga cgtgcctttc cacagcagct |
| 3481 acgcgcacag ccagagcctg gaccggctga tgaatcctct catcgaccag tacctgtatt |
| 3541 acctgaacag aactcagaat cagtccggaa gtgcccaaaa caaggacttg ctgtttagcc |
| 3601 gggggtctcc agctggcatg tctgttcagc ccaaaaactg gctacctgga ccctgttacc |
| 3661 ggcagcagcg cgtttctaaa acaaaaacag acaacaacaa cagcaacttt acctggactg |
| 3721 gtgcttcaaa atataacctt aatgggcgtg aatctataat caaccctggc actgctatgg |
| 3781 cctcacacaa agacgacaaa gacaagttct ttcccatgag cggtgtcatg atttttggaa |
| 3841 aggagagcgc cggagcttca aacactgcat tggacaatgt catgatcaca gacgaagagg |
| 3901 aaatcaaagc cactaacccc gtggccaccg aaagatttgg gactgtggca gtcaatctcc |
| 3961 agagcagcag cacagaccct gcgaccggag atgtgcatgt tatgggagcc ttacctggaa |
| 4021 tggtgtggca agacagagac gtatacctgc agggtcctat ttgggccaaa attcctcaca |
| 4081 cggatggaca ctttcacccg tctcctctca tgggcggctt tggacttaag cacccgcctc |
| 4141 ctcagatcct catcaaaaac acgcctgttc ctgcgaatcc tccggcagag ttttcggcta |
| 4201 caaagtttgc ttcattcatc acccagtatt ccacaggaca agtgagcgtg gagattgaat |
| 4261 gggagctgca gaaagaaaac agcaaacgct ggaatcccga agtgcagtat acatctaact |
| 4321 atgcaaaatc tgccaacgtt gatttcactg tggacaacaa tggactttat actgagcctc |
| 4381 gccccattgg cacccgttac ctcacccgtc ccctgtaatt gtgtgttaat caataaaccg |
| 4441 gttaattcgt gtcagttgaa ctttggtctc atgtcgttat tatcttatct ggtcaccata |
| 4501 gcaaccggtt acacattaac tgcttagttg cgcttcgcga atacccctag tgatggagtt |
| 4561 gcccactccc tctatgcgcg ctcgctcgct cggtggggcc ggcagagcag agctctgccg |
| 4621 tctgcggacc tttggtccgc aggccccacc gagcgagcga gcgcgcatag agggagtggg |
| 4681 caa |

-continued

| Sequences |
|---|

```
AAV7 (SEQ ID NO: 133)
   1 ttggccactc cctctatgcg cgctcgctcg ctcggtgggg cctgcggacc aaaggtccgc
  61 agacggcaga gctctgctct gccggcccca ccgagcgagc gagcgcgcat agagggagtg
 121 gccaactcca tcactagggg taccgcgaag cgcctcccac gctgccgcgt cagcgctgac
 181 gtaaatcacg tcatagggga gtggtcctgt attagctgtc acgtgagtgc ttttgcgaca
 241 ttttgcgaca ccacgtggcc atttgaggta tatatggccg agtgagcgag caggatctcc
 301 attttgaccg cgaaatttga acgagcagca gccatgccgg gtttctacga gatcgtgatc
 361 aaggtgccga gcgacctgga cgagcacctg ccgggcattt ctgactcgtt tgtgaactgg
 421 gtggccgaga aggaatggga gctgcccccg gattctgaca tggatctgaa tctgatcgag
 481 caggcacccc tgaccgtggc cgagaagctg cagcgcgact tcctggtcca atggcgccgc
 541 gtgagtaagg ccccggaggc cctgttcttt gttcagttcg agaagggcga gagctacttc
 601 caccttcacg ttctggtgga gaccacgggg gtcaagtcca tggtgctagg ccgcttcctg
 661 agtcagattc gggagaagct ggtccagacc atctaccgcg gggtcgagcc cacgctgccc
 721 aactggttcg cggtgaccaa gacgcgtaat ggcgccggcg gggggaacaa ggtggtggac
 781 gagtgctaca tccccaacta cctcctgccc aagacccagc ccgagctgca gtgggcgtgg
 841 actaacatgg aggagtatat aagcgcgtgt ttgaacctgg ccgaacgcaa acggctcgtg
 901 gcgcagcacc tgacccacgt cagccagacg caggagcaga acaaggagaa tctgaacccc
 961 aattctgacg cgcccgtgat caggtcaaaa acctccgcgc gctacatgga gctggtcggg
1021 tggctggtgg accggggcat cacctccgag aagcagtgga tccaggagga ccaggcctcg
1081 tacatctcct tcaacgccgc ctccaactcg cggtcccaga tcaaggccgc gctggacaat
1141 gccggcaaga tcatggcgct gaccaaatcc gcgcccgact acctggtggg gccctcgctg
1201 cccgcggaca ttaaaaccaa ccgcatctac cgcatcctgg agctgaacgg gtacgatcct
1261 gcctacgccg gctccgtctt tctcggctgg gcccagaaaa agttcgggaa gcgcaacacc
1321 atctggctgt ttgggcccgc caccaccggc aagaccaaca ttgcggaagc catcgcccac
1381 gccgtgccct tctacggctg cgtcaactgg accaatgaga actttccctt caacgattgc
1441 gtcgacaaga tggtgatctg gtgggaggag ggcaagatga cggccaaggt cgtggagtcc
1501 gccaaggcca ttctcggcgg cagcaaggtg cgcgtggacc aaaagtgcaa gtcgtccgcc
1561 cagatcgacc ccacccccgt gatcgtcacc tccaacacca acatgtgcgc cgtgattgac
1621 gggaacagca ccaccttcga gcaccagcag ccgttgcagg accggatgtt caaatttgaa
1681 ctcacccgcc gtctggagca cgactttggc aaggtgacga agcaggaagt caaagagttc
1741 ttccgctggg ccagtgatca cgtgaccgag gtggcgcatg agttctacgt cagaaagggc
1801 ggagccagca aaagacccgc ccccgatgac gcggatataa gcgagcccaa gcgggcctgc
1861 ccctcagtcg cggatccatc gacgtcagac gcggaaggag ctccggtgga ctttgccgac
1921 aggtaccaaa acaaatgttc tcgtcacgcg ggcatgattc agatgctgtt tccctgcaaa
1981 acgtgcgaga gaatgaatca gaatttcaac atttgcttca cacacggggt cagagactgt
2041 ttagagtgtt tccccggcgt gtcagaatct caaccggtcg tcagaaaaaa gacgtatcgg
2101 aaactctgcg cgattcatca tctgctgggg cgggcgcccg agattgcttg ctcggcctgc
2161 gacctggtca acgtggacct ggacgactgc gtttctgagc aataaatgac ttaaaccagg
2221 tatggctgcc gatggttatc ttccagattg gctcgaggac aacctctctg agggcattcg
2281 cgagtggtgg gacctgaaac ctggagcccc gaaacccaaa gccaaccagc aaaagcagga
2341 caacggccgg ggtctggtgc ttcctggcta caagtacctc ggacccttca acggactcga
2401 caagggggag cccgtcaacg cggcggacgc agcggccctc gagcacgaca aggcctacga
2461 ccagcagctc aaagcgggtg acaatccgta cctgcggtat aaccacgccg acgccgagtt
2521 tcaggagcgt ctgcaagaag atacgtcatt tgggggcaac ctcgggcgag cagtcttcca
2581 ggccaagaag cgggttctcg aacctctcgg tctggttgag gaaggcgcta agacggctcc
2641 tgcaaagaag agaccggtag agccgtcacc tcagcgttcc cccgactcct ccacgggcat
2701 cggcaagaaa ggccagcagc ccgccagaaa gagactcaat ttcggtcaga ctggcgactc
2761 agagtcagtc cccgaccctc aacctctcgg agaacctcca gcagcgccct ctagtgtggg
2821 atctggtaca gtggctgcag gcggtggcgc accaatggca gacaataacg aaggtgccga
2881 cggagtgggt aatgcctcag gaaattggca ttgcgattcc acatggctgg gcgacagagt
2941 cattaccacc agcacccgaa cctgggccct gcccacctac aacaaccacc tctacaagca
3001 aatctccagt gaaactgcag gtagtaccaa cgacaacacc tacttcggct acagcacccc
3061 ctgggggtat tttgacttta acagattcca ctgccacttc tcaccacgtg actggcagcg
3121 actcatcaac aacaactggg gattccggcc caagaagctg cggttcaagc tcttcaacat
3181 ccaggtcaag gaggtcacga cgaatgacgg cgttacgacc atcgctaata accttaccag
3241 cacgattcag gtattctcgg actcggaata ccagctgccg tacgtcctcg gctctgcgca
3301 ccagggctgc ctgcctccgt tcccggcgga cgtcttcatg attcctcagt acggctacct
3361 gactctcaac aatggcagtc agtctgtggg acgttcctcc ttctactgcc tggagtactt
3421 cccctctcag atgctgagaa cgggcaacaa ctttgagttc agctacagct tcgaggacgt
3481 gcctttccac agcagctacg cacacagcca gagcctggac cggctgatga atcccctcat
3541 cgaccagtac ttgtactacc tggccagaac acagagtaac ccaggaggca cagctggcaa
3601 tcgggaactg cagttttacc agggcgggcc ttcaactatg gccgaacaag ccaagaattg
3661 gttacctgga ccttgcttcc ggcaacaaag agtctccaaa acgctggatc aaaacaacaa
3721 cagcaacttt gcttggactg gtgccaccaa atatcacctg aacggcagaa actcgttggt
3781 taatcccggc gtcgccatgg caactcacaa ggacgacgag gaccgctttt tcccatccag
3841 cggagtcctg atttttggaa aaactggagc aactaacaaa actacattgg aaaatgtgtt
3901 aatgacaaat gaagaagaaa ttcgtcctac taatcctgta gccacggaag aatacgggat
3961 agtcagcagc aacttacaag cggctaatac tgcagcccag acacaagttg tcaacaacca
4021 gggagcctta cctggcatgg tctggcagaa ccgggacgtg tacctgcagg gtcccatctg
4081 ggccaagatt cctcacacgg atggcaactt tcacccgtct cctttgatgg gcggctttgg
4141 acttaaacat ccgcctcctc agatcctgat caagaacact cccgttcccg ctaatcctcc
4201 ggaggtgttt actcctgcca agtttgcttc gttcatcaca cagtacagca ccggacaagt
4261 cagcgtggaa atcgagtggg agctgcagaa ggaaaacagc aagcgctgga acccggagat
4321 tcagtacacc tccaactttg aaaagcagac tggtgtggac tttgccgttg acagccaggg
4381 tgtttactct gagcctcgcc ctattggcac tcgttacctc acccgtaatc tgtaattgca
4441 tgttaatcaa taaaccggtt gattcgtttc agttgaactt tggtctcctg tgcttcttat
```

-continued

| Sequences |
|---|
| 4501 cttatcggtt tccatagcaa ctggttacac attaactgct tgggtgcgct tcacgataag |
| 4561 aacactgacg tcaccgcggt acccctagtg atggagttgg ccactccctc tatgcgcgct |
| 4621 cgctcgctcg gtggggcctg cggaccaaag gtccgcagac ggcagagctc tgctctgccg |
| 4681 gccccaccga gcgagcgagc gcgcatagag ggagtggcca a |
| |
| AAV8 (SEQ ID NO: 134) |
| 1 cagagaggga gtggccaact ccatcactag gggtagcgcg aagcgcctcc cacgctgccg |
| 61 cgtcagcgct gacgtaaatt acgtcatagg ggagtggtcc tgtattagct gtcacgtgag |
| 121 tgcttttgcg gcattttgcg acaccacgtg gccatttgag gtatatatgg ccgagtgagc |
| 181 gagcaggatc tccattttga ccgcgaaatt tgaacgagca gcagccatgc cgggcttcta |
| 241 cgagatcgtg atcaaggtgc cgagcgacct ggacgagcac ctgccgggca tttctgactc |
| 301 gtttgtgaac tgggtggccg agaaggaatg ggagctgccc ccggattctg acatggatcg |
| 361 gaatctgatc gagcaggcac ccctgaccgt ggccgagaag ctgcagcgcg acttcctggt |
| 421 ccaatggcgc cgcgtgagta aggccccgga ggccctcttc tttgttcagt tcgagaaggg |
| 481 cgagagctac tttcacctgc acgttctggt cgagaccacg gggggtcaagt ccatggtgct |
| 541 aggccgcttc ctgagtcaga ttcgggaaaa gcttggtcca gaccatctac ccgcggggtc |
| 601 gagccccacc ttgcccaact ggttcgcggt gaccaaagac gcggtaatgg cgccggcggg |
| 661 ggggaacaag gtggtggacg agtgctacat ccccaactac ctcctgccca agactcagcc |
| 721 cgagctgcag tgggcgtgga ctaacatgga ggagtatata agcgcgtgct tgaacctggc |
| 781 cgagcgcaaa cggctcgtgg cgcagcacct gacccacgtc agccagacgc aggagcagaa |
| 841 caaggagaat ctgaacccca attctgacgc gcccgtgatc aggtcaaaaa cctccgcgcg |
| 901 ctatatggag ctggtcgggt ggctggtgga ccggggcatc acctccgaga agcagtggat |
| 961 ccaggaggac caggcctcgt acatctcctt caacgccgcc tccaactcgc ggtcccagat |
| 1021 caaggccgcg ctggacaatg ccggcaagat catggcgctg accaaatccg cgcccgacta |
| 1081 cctggtgggg ccctcgctgc ccgcggacat tacccagaac cgcatctacc gcatcctcgc |
| 1141 tctcaacggc tacgaccctg cctacgccgg ctccgtcttt ctcggctggg ctcagaaaaa |
| 1201 gttcgggaaa cgcaacacca tctggctgtt tggacccgcc accaccggca agaccaacat |
| 1261 tgcggaagcc atcgcccacg ccgtgccctt ctacggctgc gtcaactgga ccaatgagaa |
| 1321 ctttcccttc aatgattgcg tcgacaagat ggtgatctgg tgggaggagg gcaagatgac |
| 1381 ggccaaggtc gtggagtccg ccaaggccat tctcggcggc agcaaggtgc gcgtggacca |
| 1441 aaagtgcaag tcgtccgccc agatcgaccc cacccccgtg atcgtcacct ccaacaccaa |
| 1501 catgtgcgcc gtgattgacg ggaacagcac caccttcgag caccagcagc ctctccagga |
| 1561 ccggatgttt aagttcgaac tcacccgccg tctggagcac gactttggca aggtgacaaa |
| 1621 gcaggaagtc aaagagttct tccgctgggc cagtgatcac gtgaccgagg tggcgcatga |
| 1681 gttttacgtc agaaagggcg gagccagcaa aagacccgcc cccgatgacg cggataaaag |
| 1741 cgagcccaag cgggcctgcc cctcagtcgc ggatccatcg acgtcagacg cggaaggagc |
| 1801 tccggtggac tttgccgaca ggtaccaaaa caaatgttct cgtcacgcgg gcatgcttca |
| 1861 gatgctgttt ccctgcaaaa cgtgcgagag aatgaatcag aatttcaaca tttgcttcac |
| 1921 acacggggtc agagactgct cagagtgttt ccccggcgtg tcagaatctc aaccggtcgt |
| 1981 cagaaagagg acgtatcgga aactctgtgc gattcatcat ctgctggggc gggctcccga |
| 2041 gattgcttgc tcggcctgcg atctggtcaa cgtggacctg gatgactgtg tttctgagca |
| 2101 ataaatgact taaaccaggt atggctgccg atggttatct tccagattgg ctcgaggaca |
| 2161 acctctctga gggcattcgc gagtggtggg cgctgaaacc tggagccccg aagcccaaag |
| 2221 ccaaccagca aaagcaggac gacggccggg gtctggtgct tcctggctac aagtacctcg |
| 2281 gacccttcaa cggactcgac aagggggagc ccgtcaacgc ggcggacgca gcggccctcg |
| 2341 agcacgacaa ggcctacgac cagcagctgc aggcgggtga caatccgtac ctgcggtata |
| 2401 accacgccga cgccgagttt caggagcgtc tgcaagaaga tacgtctttt gggggcaacc |
| 2461 tcgggcgagc agtcttccag gccaagaagc gggttctcga acctctcggt ctggttgagg |
| 2521 aaggcgctaa gacggctcct ggaaagaaga gaccggtaga gccatcaccc cagcgttctc |
| 2581 cagactcctc tacgggcatc ggcaagaaag gccaacagcc cgccagaaaa agactcaatt |
| 2641 ttggtcagac tggcgactca gagtcagttc cagaccctca acctctcgga gaacctccag |
| 2701 cagcgccctc tggtgtggga cctaatacaa tggctgcagg cggtggcgca ccaatggcag |
| 2761 acaataacga aggcgccgac ggagtgggta gttcctcggg aaattggcat tgcgattcca |
| 2821 catggctggg cgacagagtc atcaccacca gcacccgaac ctgggccctg cccacctaca |
| 2881 acaaccacct ctacaagcaa atctccaacg ggacatcggg aggagccacc aacgacaaca |
| 2941 cctacttcgg ctacagcacc ccctgggggt attttgactt taacagattc cactgccact |
| 3001 tttcaccacg tgactggcag cgactcatca acaacaactg gggattccgg cccaagagac |
| 3061 tcagcttcaa gctcttcaac atccaggtca aggaggtcac gcagaatgaa ggcaccaaga |
| 3121 ccatcgccaa taacctcacc agcaccatcc aggtgtttac ggactcggag taccagctgc |
| 3181 cgtacgttct cggctctgcc caccagggct gcctgcctcc gttcccggcg gacgtgttca |
| 3241 tgattcccca gtacggctac ctaacactca acaacggtag tcaggccgtg ggacgctcct |
| 3301 ccttctactg cctggaatac tttccttcgc agatgctgag aaccggcaac aacttccagt |
| 3361 ttacttacac cttcgaggac gtgcctttcc acagcagcta cgcccacagc cagagcttgg |
| 3421 accggctgat gaatcctctg attgaccagt acctgtacta cttgtctcgg actcaaacaa |
| 3481 caggaggcac ggcaaatacg cagactctgg gcttcagcca aggtgggcct aatacaatgg |
| 3541 ccaatcaggc aaagaactgg ctgccaggac cctgttaccg ccaacaacgc gtctcaacga |
| 3601 caaccgggca aaacaacaat agcaactttg cctggactgc tgggaccaaa taccatctga |
| 3661 atggaagaaa ttcattggct aatcctggca tcgctatggc aacacacaaa gacgacgagg |
| 3721 agcgtttttt tcccagtaac gggatcctga 11111ggcaa acaaaatgct gccagagaca |
| 3781 atgcggatta cagcgatgtc atgctcacca gcgaggaaga aatcaaaacc actaaccctg |
| 3841 tggctacaga ggaatacggt atcgtggcag ataacttgca gcagcaaaac acggctcctc |
| 3901 aaattggaac tgtcaacagc caggggggcct tacccggtat ggtctggcag aaccgggacg |
| 3961 tgtacctgca gggtcccatc tgggccaaga ttcctcacac ggacggcaac ttccacccgt |
| 4021 ctccgctgat gggcggcttt ggcctgaaac atcctccgcc tcagatcctg atcaagaaca |
| 4081 cgcctgtacc tgcggatcct ccgaccacct tcaaccagtc aaagctgaac tctttcatca |
| 4141 cgcaatacag caccggacag gtcagcgtgg aaattgaatg ggagctgcag aaggaaaaca |
| 4201 gcaagcgctg gaaccccgag atccagtaca cctccaacta ctacaaatct acaagtgtgg |

-continued

Sequences

```
4261 actttgctgt taatacagaa ggcgtgtact ctgaaccccg ccccattggc acccgttacc
4321 tcacccgtaa tctgtaattg cctgttaatc aataaaccgg ttgattcgtt tcagttgaac
4381 tttggtctct gcg

AAV9 (SEQ ID NO: 135)
   1 gcccaatacg caaaccgcct ctccccgcgc gttggccgat tcattaatgc agctggcgta
  61 atagcgaaga ggcccgcacc gatcgccctt cccaacagtt gcgcagcctg aatggcgaat
 121 ggcgattccg ttgcaatggc tggcggtaat attgttctgg atattaccag caaggccgat
 181 agtttgagtt cttctactca ggcaagtgat gttattacta atcaaagaag tattgcgaca
 241 acggttaatt tgcgtgatgg acagactctt ttactcggtg gcctcactga ttataaaaac
 301 acttctcagg attctggcgt accgttcctg tctaaaatcc ctttaatcgg cctcctgttt
 361 agctcccgct ctgattctaa cgaggaaagc acgttatacg tgctcgtcaa agcaaccata
 421 gtacgcgccc tgtagcggcg cattaagcgc ggcgggtgtg gtggttacgc gcagcgtgac
 481 cgctacactt gccagcgccc tagcgcccgc tcctttcgct ttcttccctt cctttctcgc
 541 cacgttcgcc ggctttcccc gtcaagctct aaatcggggg ctccctttag ggttccgatt
 601 tagtgcttta cggcacctcg accccaaaaa acttgattag ggtgatggtt cacgtagtgg
 661 gccatcgccc tgatagacgg tttttcgccc tttgacgttg gagtccacgt tctttaatag
 721 tggactcttg ttccaaactg gaacaacact caaccctatc tcggtctatt cttttgattt
 781 ataagggatt ttgccgattt cggcctattg gttaaaaaat gagctgattt aacaaaaatt
 841 taacgcgaat tttaacaaaa tattaacgct tacaatttaa atatttgctt atacaatctt
 901 cctgtttttg gggcttttct gattatcaac cggggtacat atgattgaca tgctagtttt
 961 acgattaccg ttcatcgccc tgcgcgctcg ctcgctcact gaggccgccc gggcaaagcc
1021 cgggcgtcgg gcgacctttg gtcgcccggc ctcagtgagc gagcgagcgc gcagagaggg
1081 agtggaattc acgcgtggat ctgaattcaa ttcacgcgtg gtacctctgg tcgttacata
1141 acttacggta aatggcccgc ctggctgacc gcccaacgac ccccgcccat tgacgtcaat
1201 aatgacgtat gttcccatag taacgccaat agggactttc cattgacgtc aatgggtgga
1261 gtatttacgg taaactgccc acttggcagt acatcaagtg tatcatatgc caagtacgcc
1321 ccctattgac gtcaatgacg gtaaatggcc cgcctggcat tatgcccagt acatgacctt
1381 atgggacttt cctacttggc agtacatcta ctcgaggcca cgttctgctt cactctcccc
1441 atctccccc cctccccacc cccaattttg tatttattta tttttaatt attttgtgca
1501 gcgatggggg cggggggggg ggggggcgc gcgccaggcg gggcggggcg gggcgagggg
1561 cggggcgggg cgaggcggag aggtgcggcg gcagccaatc agagcggcgc gctccgaaag
1621 tttcctttta tggcgaggcg gcggcggcgg cggccctata aaaagcgaag cgcgcggcgg
1681 gcgggagcgg gatcagccac cgcggtggcg gcctagagtc gacgaggaac tgaaaaacca
1741 gaaagttaac tggtaagttt agtctttttg tcttttattt caggtcccgg atccggtggt
1801 ggtgcaaatc aaagaactgc tcctcagtgg atgttgcctt tacttctagg cctgtacgga
1861 agtgttactt ctgctctaaa agctgcggaa ttgtacccgc ggccgatcca ccggtccgga
1921 attcccggga tatcgtcgac ccacgcgtcc gggccccacg ctgcgcaccc gcgggtttgc
1981 tatggcgatg agcagcggcg gcagtggtgg cggcgtcccg gagcaggagg attccgtgct
2041 gttccggcgc ggcacaggcc agagcgatga ttctgacatt tgggatgata cagcactgat
2101 aaaagcatat gataaagctg tggcttcatt taagcatgct ctaaagaatg gtgacatttg
2161 tgaaacttcg ggtaaaccaa aaaccacacc taaaagaaaa cctgctaaga agaataaaag
2221 ccaaaagaag aatactgcag cttccttaca acagtggaaa gttggggaca aatgttctgc
2281 catttggtca gaagacggtt gcatttaccc agctaccatt gcttcaattg attttaagag
2341 agaaacctgt gttgtggttt acactggata tggaaataga gaggagcaaa atctgtccga
2401 tctactttcc ccaatctgtg aagtagctaa taatatagaa cagaatgctc aagagaatga
2461 aaatgaaagc caagtttcaa cagatgaaag tgagaactcc aggtctcctg gaaataaatc
2521 agataacatc aagcccaaat ctgctccatg gaactctttt ctccctccac caccccccat
2581 gccagggcca agactgggac caggaaagcc aggtctaaaa ttcaatggcc caccaccgcc
2641 accgccacca ccaccacccc acttactatc atgctggctg cctccatttc cttctggacc
2701 accaataatt cccccaccac ctcccatatg tccagattct cttgatgatg ctgatgcttt
2761 gggaagtatg ttaatttcat ggtacatgag tggctatcat actggctatt atatgggttt
2821 tagacaaaat caaaaagaag gaaggtgctc acattcctta aattaaggag aaatgctggc
2881 atagagcagc actaaatgac accactaaag aaacgatcag acagatctag aaagcttatc
2941 gataccgtcg actagagctc gctgatcagc ctcgactgtg ccttctagtt gccagccatc
3001 tgttgtttgc ccctcccccg tgccttcctt gaccctggaa ggtgccactc ccactgtcct
3061 ttcctaataa aatgaggaaa ttgcatcgca ttgtctgagt aggtgtcatt ctattctggg
3121 gggtggggtg gggcaggaca gcaaggggga ggattgggaa gacaatagca ggcatgctgg
3181 ggagagatcg atctgaggaa cccctagtga tggagttggc cactccctct ctgcgcgctc
3241 gctcgctcac tgaggccggg cgaccaaagg tcgcccgacg cccgggcttt gcccgggcgg
3301 cctcagtgag cgagcgagcg cgcagagagg gagtggcccc cccccccccc cccccggcga
3361 ttctcttgtt tgctccagac tctcaggcaa tgacctgata gcctttgtag agacctctca
3421 aaaatagcta ccctctccgg catgaattta tcagctagaa cggttgaata tcatattgat
3481 ggtgatttga ctgtctccgg cctttctcac ccgtttgaat ctttacctac acattactca
3541 ggcattgcat ttaaaatata tgagggttct aaaaattttt atccttgcgt tgaaataaag
3601 gcttctcccg caaaagtatt acagggtcat aatgtttttg gtacaaccga tttagcttta
3661 tgctctgagg ctttattgct taattttgct aattctttgc cttgcctgta tgatttattg
3721 gatgttggaa tcgcctgatg cggtattttc tccttacgca tctgtgcggt atttcacacc
3781 gcatatggtg cactctcagt acaatctgct ctgatgccgc atagttaagc cagccccgac
3841 acccgccaac actatggtgc actctcagta caatctgctc tgatgccgca tagttaagcc
3901 agccccgaca cccgccaaca cccgctgacg cgccctgacg ggcttgtctg ctcccggcat
3961 ccgcttacag acaagctgtg accgtctccg ggagctgcat gtgtcagagg ttttcaccgt
4021 catcaccgaa acgcgcgaga cgaaagggcc tcgtgatacg cctattttta taggttaatg
4081 tcatgataat aatggtttct tagacgtcag gtggcacttt tcggggaaat gtgcgcggaa
4141 cccctatttg tttatttttc taaatacatt caaatatgta tccgctcatg agacaataac
4201 cctgataaat gcttcaataa tattgaaaaa ggaagagtat gagtattcaa catttccgtg
4261 tcgcccttat tccctttttt gcggcatttt gccttcctgt ttttgctcac ccagaaacgc
```

-continued

Sequences

```
4321 tggtgaaagt aaaagatgct gaagatcagt tgggtgcacg agtgggttac atcgaactgg
4381 atctcaacag cggtaagatc cttgagagtt ttcgccccga agaacgtttt ccaatgatga
4441 gcacttttaa agttctgcta tgtggcgcgg tattatcccg tattgacgcc gggcaagagc
4501 aactcggtcg ccgcatacac tattctcaga atgacttggt tgagtactca ccagtcacag
4561 aaaagcatct tacggatggc atgacagtaa gagaattatg cagtgctgcc ataaccatga
4621 gtgataacac tgcggccaac ttacttctga caacgatcgg aggaccgaag gagctaaccg
4681 cttttttgca caacatgggg gatcatgtaa ctcgccttga tcgttgggaa ccggagctga
4741 atgaagccat accaaacgac gagcgtgaca ccacgatgcc tgtagcaatg gcaacaacgt
4801 tgcgcaaact attaactggc gaactactta ctctagcttc ccggcaacaa ttaatagact
4861 ggatggaggc ggataaagtt gcaggaccac ttctgcgctc ggcccttccg gctggctggt
4921 ttattgctga taaatctgga gccggtgagc gtgggtctcg cggtatcatt gcagcactgg
4981 ggccagatgg taagccctcc cgtatcgtag ttatctacac gacggggagt caggcaacta
5041 tggatgaacg aaatagacag atcgctgaga taggtgcctc actgattaag cattggtaac
5101 tgtcagacca agtttactca tatatacttt agattgattt aaaacttcat ttttaattta
5161 aaaggatcta ggtgaagatc ctttttgata atctcatgac caaaatccct taacgtgagt
5221 tttcgttcca ctgagcgtca gaccccgtag aaaagatcaa aggatcttct tgagatcctt
5281 tttttctgcg cgtaatctgc tgcttgcaaa caaaaaaacc accgctacca gcggtggttt
5341 gtttgccgga tcaagagcta ccaactcttt ttccgaaggt aactggcttc agcagagcgc
5401 agataccaaa tactgttctt ctagtgtagc cgtagttagg ccaccacttc aagaactctg
5461 tagcaccgcc tacatacctc gctctgctaa tcctgttacc agtggctgct gccagtggcg
5521 ataagtcgtg tcttaccggg ttggactcaa gacgatagtt accggataag gcgcagcggt
5581 cgggctgaac ggggggttcg tgcacacagc ccagcttgga gcgaacgacc tacaccgaac
5641 tgagatacct acagcgtgag ctatgagaaa gcgccacgct tcccgaaggg agaaaggcgg
5701 acaggtatcc ggtaagcggc agggtcggaa caggagagcg cacgagggag cttccagggg
5761 gaaacgcctg gtatctttat agtcctgtcg ggtttcgcca cctctgactt gagcgtcgat
5821 ttttgtgatg ctcgtcaggg gggcggagcc tatggaaaaa cgccagcaac gcggcctttt
5881 tacggttcct ggccttttgc tggccttttg ctcacatgtt ctttcctgcg ttatcccctg
5941 attctgtgga taaccgtatt accgcctttg agtgagctga taccgctcgc cgcagccgaa
6001 cgaccgagcg cagcgagtca gtgagcgagg aagcggaaga gc
```

AAV10 (SEQ ID NO: 136)

```
   1 atgccgggct tctacgagat cgtgatcaag gtgccgagcg acctggacga gcacctgccg
  61 ggcatttctg actcgtttgt gaactgggtg gccgagaagg aatgggagct gcccccggat
 121 tctgacatgg atcggaatct gatcgagcag gcaccccctga ccgtggccga gaagctgcag
 181 cgcgacttcc tggtccactg gcgccgcgtg agtaaggccc cggaggccct cttctttgtt
 241 cagttcgaga agggcgagtc ctactttcac ctgcacgttc tggtcgagac cacgggggtc
 301 aagtccatgg tcctgggccg cttcctgagt cagatcagag acaggctggt gcagaccatc
 361 taccgcgggg tagagcccac gctgcccaac tggttcgcgg tgaccaagac gcgaaatggc
 421 gccggcgggg ggaacaaggt ggtggacgag tgctacatcc ccaactacct cctgcccaag
 481 acgcagcccg agctgcagtg ggcgtggact aacatggagg agtatataag cgcgtgtctg
 541 aacctcgcgg agcgtaaacg gctcgtggcg cagcacctga cccacgtcag ccagacgcag
 601 gagcagaaca aggagaatct gaacccgaat tctgacgcgc ccgtgatcag gtcaaaaacc
 661 tccgcgcgct acatggagct ggtcgggtgg ctggtggacc ggggcatcac ctccgagaag
 721 cagtggatcc aggaggacca ggcctcgtac atctccttca acgccgcctc caactcgcgg
 781 tcccagatca aggccgcgct ggacaatgcc ggaaagatca tggcgctgac caaatccgcg
 841 cccgactacc tggtaggccc gtccttaccc gcggacatta aggccaaccg catctaccgc
 901 atcctggagc tcaacggcta cgaccccgcc tacgccggct ccgtcttcct gggctgggcg
 961 cagaaaaagt tcggtaaaag gaatacaatt tggctgttcg ggcccgccac caccggcaag
1021 accaacatcg cggaagccat cgcccacgcc gtgcccttct acggctgcgt caactggacc
1081 aatgagaact ttcccttcaa cgattgcgtc gacaagatgg tgatctggtg ggaggagggc
1141 aagatgaccg ccaaggtcgt ggagtccgcc aaggccattc tgggcggaag caaggtgcgc
1201 gtcgaccaaa agtgcaagtc ctcggcccag atcgacccca cgcccgtgat cgtcacctcc
1261 aacaccaaca tgtgcgccgt gatcgacggg aacagcacca ccttcgagca ccagcagccc
1321 ctgcaggacc gcatgttcaa gttcgagctc acccgccgtc tggagcacga ctttggcaag
1381 gtgaccaagc aggaagtcaa agagttcttc cgctgggctc aggatcacgt gactgaggtg
1441 acgcatgagt tctacgtcag aaagggcgga gccaccaaaa gacccgcccc cagtgacgcg
1501 gatataagcg agcccaagcg ggcctgcccc tcagttgcgg agccatcgac gtcagacgcg
1561 gaagcaccgg tggactttgc ggacaggtac caaaacaaat gttctcgtca cgcgggcatg
1621 cttcagatgc tgtttccctg caagacatgc gagagaatga atcagaattt caacgtctgc
1681 ttcacgcacg ggtcagaga ctgctcagag tgcttccccg gcgcgtcaga atctcaacct
1741 gtcgtcagaa aaaagacgta tcagaaactg tgcgcgattc atcatctgct ggggcgggca
1801 cccgagattg cgtgttcggc ctgcgatctc gtcaacgtgg acttggatga ctgtgtttct
1861 gagcaataaa tgacttaaac caggtatggc tgctgacggt tatcttccag attggctcga
1921 ggacaacctc tctgagggca ttcgcgagtg gtgggacctg aaacctggag cccccaagcc
1981 caaggccaac cagcagaagc aggacgacgg ccgggggtctg gtgcttcctg gctacaagta
2041 cctcggaccc ttcaacggac tcgacaaggg ggagcccgtc aacgcggcgg acgcagcggc
2101 cctcgagcac gacaaggcct acgaccagca gctcaaagcg ggtgacaatc cgtacctgcg
2161 gtataaccac gccgacgccg agtttcagga gcgtctgcaa gaagatacgt cttttggggg
2221 caacctcggg cgagcagtct tccaggccaa gaagcgggtt ctcgaacctc tcggtctggt
2281 tgaggaagct gctaagacgg ctcctggaaa gaagagaccg gtagaaccgt cacctcagcg
2341 ttcccccgac tcctccacgg gcatcggcaa gaaaggccag cagcccgcta aaaagagact
2401 gaactttggg cagactggcg agtcagagtc agtccccgac cctcaaccaa tcggagaacc
2461 accagcaggc ccctctggtc tgggatctgg tacaatggct gcaggcggtg gcgctccaat
2521 ggcagacaat aacgaaggcg ccgacggagt gggtagttcc tcaggaaatt ggcattgcga
2581 ttccacatgg ctgggcgaca gagtcatcac caccagcacc cgaacctggg ccctgcccac
2641 ctacaacaac cacctctaca agcaaatctc caacggaca tcgggaggaa gcaccaacga
2701 caacacctac ttcggctaca gcaccccctg gggtatttt gacttcaaca gattccactg
```

-continued

Sequences 2761 ccacttctca ccacgtgact ggcagcgact catcaacaac aactggggat tccggccaaa
2821 aagactcagc ttcaagctct tcaacatcca ggtcaaggag gtcacgcaga atgaaggcac
2881 caagaccatc gccaataacc ttaccagcac gattcaggta tttacggact cggaatacca
2941 gctgccgtac gtcctcggct ccgcgcacca gggctgcctg cctccgttcc cggcggatgt
3001 cttcatgatt ccccagtacg gctacctgac actgaacaat ggaagtcaag ccgtaggccg
3061 ttcctccttc tactgcctgg aatattttcc atctcaaatg ctgcgaactg gaaacaattt
3121 tgaattcagc tacaccttcg aggacgtgcc tttccacagc agctacgcac acagccagag
3181 cttggaccga ctgatgaatc ctctcattga ccagtacctg tactacttat ccagaactca
3241 gtccacagga ggaactcaag gtacccagca attgttattt tctcaagctg ggcctgcaaa
3301 catgtcggct caggccaaga actggctgcc tggaccttgc taccggcagc agcgagtctc
3361 cacgacactg tcgcaaaaca acaacagcaa ctttgcttgg actggtgcca ccaaatatca
3421 cctgaacgga agagactctc tggtgaatcc cggtgtcgcc atggcaaccc acaaggacga
3481 cgaggaacgc ttcttcccgt cgagcggagt cctgatgttt ggaaaacagg gtgctggaag
3541 agacaatgtg gactacagca gcgttatgct aacaagcgaa gaagaaatta aaaccactaa
3601 ccctgtagcc acagaacaat acggcgtggt ggctgacaac ttgcagcaag ccaatacagg
3661 gcctattgtg ggaaatgtca acagccaagg agccttacct ggcatggtct ggcagaaccg
3721 agacgtgtac ctgcagggtc ccatctgggc caagattcct cacacggacg gcaactttca
3781 cccgtctcct ctgatgggcg gctttggact taaacacccg cctccacaga tcctgatcaa
3841 gaacacgccg gtacctgcgg atcctccaac aacgttcagc caggcgaaat tggcttcctt
3901 catcacgcag tacagcaccg gacaggtcag cgtggaaatc gagtgggagc tgcagaagga
3961 gaacagcaaa cgctggaacc cagagattca gtacacttca aactactaca aatctacaaa
4021 tgtggacttt gctgtcaata cagagggaac ttattctgag cctcgcccca ttggtactcg
4081 ttatctgaca cgtaatctgt aa AAV11 (SEQ ID NO: 137)
1 atgccgggct tctacgagat cgtgatcaag gtgccgagcg acctggacga gcacctgccg
61 ggcatttctg actcgtttgt gaactgggtg gccgagaagg aatggagct gcccccggat
121 tctgacatgg atcggaatct gatcgagcag gcacccctga ccgtggccga gaagctgcag
181 cgcgacttcc tggtccactg gcgccgcgtg agtaaggccc cggaggccct cttctttgtt
241 cagttcgaga agggcgagtc ctacttccac ctccacgttc tcgtcgagac cacgggggtc
301 aagtccatgg tcctgggccg cttcctgagt cagatcagag acaggctggt gcagaccatc
361 taccgcgggg tcgagcccac gctgcccaac tggttcgcgg tgaccaagac gcgaaatggc
421 gccggcgggg ggaacaaggt ggtggacgag tgctacatcc ccaactacct cctgcccaag
481 acccagcccg agctgcagtg ggcgtggact aacatggagg agtatataag cgcgtgtcta
541 aacctcgcgg agcgtaaacg gctcgtggcg cagcacctga cccacgtcag ccagacgcag
601 gagcagaaca aggagaatct gaacccgaat tctgacgcgc ccgtgatcag gtcaaaaacc
661 tccgcgcgct acatggagct ggtcgggtgg ctggtggacc ggggcatcac ctccgagaag
721 cagtggatcc aggaggacca ggcctcgtac atctccttca acgccgcctc caactcgcgg
781 tcccagatca aggccgcgct ggacaatgcc ggaaagatca tggcgctgac caaatccgcg
841 cccgactacc tggtaggccc gtccttaccc gcggacatta aggccaaccg catctaccgc
901 atcctggagc tcaacggcta cgacccgcc tacgccggct ccgtcttcct gggctgggcg
961 cagaaaaagt tcggtaaacg caacaccatc tggctgtttg ggcccgccac caccggcaag
1021 accaacatcg cggaagccat agcccacgcc gtgcccttct acggctgcgt gaactggacc
1081 aatgagaact ttcccttcaa cgattgcgtc gacaagatgg tgatctggtg ggaggagggc
1141 aagatgaccg ccaaggtcgt ggagtccgcc aaggccattc tgggcggaag caaggtgcgc
1201 gtggaccaaa agtgcaagtc ctcggcccag atcgacccca cgcccgtgat cgtcacctcc
1261 aacaccaaca tgtgcgccgt gatcgacggg aacagcacca ccttcgagca ccagcagccg
1321 ctgcaggacc gcatgttcaa gttcgagctc acccgccgtc tggagcacga ctttggcaag
1381 gtgaccaagc aggaagtcaa agagttcttc cgctgggctc aggatcacgt gactgaggtg
1441 gcgcatgagt tctacgtcag aaagggcgga gccaccaaaa gacccgcccc cagtgacgcg
1501 gatataagcg agcccaagcg ggcctgcccc tcagttccgg agccatcgac gtcagacgcg
1561 gaagcaccgg tggactttgc ggacaggtac caaaacaaat gttctcgtca cgcgggcatg
1621 cttcagatgc tgtttccctg caagacatgc gagagaatga atcagaattt caacgtctgc
1681 ttcacgcacg ggtcagaga ctgctcagag tgcttccccg gcgcgtcaga atctcaaccc
1741 gtcgtcagaa aaaagacgta tcagaaactg tgcgcgattc atcatctgct ggggcgggca
1801 cccgagattg cgtgttcggc ctgcgatctc gtcaacgtgg acttggatga ctgtgtttct
1861 gagcaataaa tgacttaaac caggtatggc tgctgacggt tatcttccag attggctcga
1921 ggacaacctc tctgagggca ttcgcgagtg gtgggacctg aaacctggag ccccgaagcc
1981 caaggccaac cagcagaagc aggacgacgg ccggggtctg gtgcttcctg gctacaagta
2041 cctcggaccc ttcaacggac tcgacaaggg ggagcccgtc aacgcggcgg acgcagcggc
2101 cctcgagcac gacaaggcct acgaccagca gctcaaagcg ggtgacaatc cgtacctgcg
2161 gtataaccac gccgacgccg agtttcagga gcgtctgcaa gaagatacgt cttttggggg
2221 caacctcggg cgagcagtct tccaggccaa gaagagggta ctcgaacctc tgggcctggt
2281 tgaagaaggt gctaaaacgg ctcctggaaa gaagagaccg ttagagtcac cacaagagcc
2341 cgactcctcc tcgggcatcg gcaaaaaagg caaacaacca gccagaaaga ggctcaactt
2401 tgaagaggac actggagccg gagacggacc ccctgaagga tcagatacca gcgccatgtc
2461 ttcagacatt gaaatgcgtg cagcaccggg cggaaatgct gtcgatgcgg gacaaggttc
2521 cgatggagtg ggtaatgcct cgggtgattg gcattgcgat tccacctggt ctgagggcaa
2581 ggtcacaaca acctcgacca gaacctgggt cttgcccacc tacaacaacc acttgtacct
2641 gcgtctcgga acaacatcaa gcagcaacac ctacaacgga ttctccaccc cctggggata
2701 ttttgacttc aacagattcc actgtcactt ctcaccacgt gactggcaaa gactcatcaa
2761 caacaactgg ggactacgac caaaagccat gcgcgttaaa atcttcaata tccaagttaa
2821 ggaggtcaca acgtcgaacg gcgagactac ggtcgctaat aaccttacca gcacggttca
2881 gatatttgcg gactcgtcgt atgagctccc gtacgtgatg gacgctggac aagaggggag
2941 cctgcctcct ttccccaatg acgtgttcat ggtgcctcaa tatggctact gtggcatcgt
3001 gactggcgag aatcagaacc aaacggacag aaacgctttc tactgcctgg agtattttcc
3061 ttcgcaaatg ttgagaactg gcaacaactt tgaaatggct tacaactttg agaaggtgcc -continued

| Sequences |
| --- |
| 3121 gttccactca atgtatgctc acagccagag cctggacaga ctgatgaatc cctcctgga |
| 3181 ccagtacctg tggcacttac agtcgactac ctctggagag actctgaatc aaggcaatgc |
| 3241 agcaaccaca tttggaaaaa tcaggagtgg agactttgcc ttttacagaa agaactggct |
| 3301 gcctgggcct tgtgttaaac agcagagatt ctcaaaaact gccagtcaaa attacaagat |
| 3361 tcctgccagc gggggcaacg ctctgttaaa gtatgacacc cactatacct taaacaaccg |
| 3421 ctggagcaac atcgcgcccg gacctccaat ggccacagcc ggaccttcgg atggggactt |
| 3481 cagtaacgcc cagcttatat tccctggacc atctgttacc ggaaatacaa caacttcagc |
| 3541 caacaatctg ttgtttacat cagaagaaga aattgctgcc accaacccaa gagacacgga |
| 3601 catgtttggc cagattgctg acaataatca gaatgctaca actgctccca taaccggcaa |
| 3661 cgtgactgct atgggagtgc tgcctggcat ggtgtggcaa aacagagaca tttactacca |
| 3721 agggccaatt tgggccaaga tcccacacgc ggacggacat tttcatcctt caccgctgat |
| 3781 tggtgggttt ggactgaaac acccgcctcc ccagatattc atcaagaaca ctcccgtacc |
| 3841 tgccaatcct gcgacaacct tcactgcagc cagagtggac tctttcatca cacaatacag |
| 3901 caccggccag gtcgctgttc agattgaatg ggaaattgaa aaggaacgct ccaaacgctg |
| 3961 gaatcctgaa gtgcagttta cttcaaacta tgggaaccag tcttctatgt tgtgggctcc |
| 4021 tgatacaact gggaagtata cagagccgcg ggttattggc tctcgttatt tgactaatca |
| 4081 tttgtaa |
| |
| AAV12 (SEQ ID NO: 138) |
| 1 ttgcgacagt ttgcgacacc atgtggtcac aagaggtata taaccgcgag tgagccagcg |
| 61 aggagctcca ttttgcccgc gaagtttgaa cgagcagcag ccatgccggg gttctacgag |
| 121 gtggtgatca aggtgcccag cgacctggac gagcacctgc ccggcatttc tgactccttt |
| 181 gtgaactggg tggccgagaa ggaatgggag ttgccccccgg attctgacat ggatcagaat |
| 241 ctgattgagc aggcacccct gaccgtggcc gagaagctgc agcgcgagtt cctggtggaa |
| 301 tggcgccgag tgagtaaatt tctggaggcc aagtttttttg tgcagtttga aaagggggac |
| 361 tcgtactttc atttgcatat tctgattgaa attaccggcg tgaaatccat ggtggtgggc |
| 421 cgctacgtga gtcagattag ggataaactg atccagcgca tctaccgcgg ggtcgagccc |
| 481 cagctgccca actggttcgc ggtcacaaag acccgaaatg gcgccggagg cgggaacaag |
| 541 gtggtggacg agtgctacat ccccaactac ctgctcccca aggtccagcc cgagcttcag |
| 601 tgggcgtgga ctaacatgga ggagtatata agcgcctgtt tgaacctcgc ggagcgtaaa |
| 661 cggctcgtgg cgcagcacct gacgcacgtc tcccagaccc aggagggcga caaggagaat |
| 721 ctgaacccga attctgacgc gccggtgatc cggtcaaaaa cctccgccag gtacatggag |
| 781 ctggtcgggt ggctggtgga caagggcatc acgtccgaga agcagtggat ccaggaggac |
| 841 caggcctcgt acatctcctt caacgcggcc tccaactccc ggtcgcagat caaggcggcc |
| 901 ctggacaatg cctccaaaat catgagcctc accaaaacgg ctccggacta tctcatcggg |
| 961 cagcagcccg tgggggacat taccaccaac cggatctaca aaatcctgga actgaacggg |
| 1021 tacgaccccc agtacgccgc ctccgtcttt ctcggctggg cccagaaaaa gtttggaaag |
| 1081 cgcaacacca tctggctgtt tgggcccgcc accaccggca agaccaacat cgcggaagcc |
| 1141 atcgcccacg cggtcccctt ctacggctgc gtcaactgga ccaatgagaa ctttcccttc |
| 1201 aacgactgcg tcgacaaaat ggtgatttgg tgggaggagg gcaagatgac cgccaaggtc |
| 1261 gtagagtccg ccaaggccat tctgggcggc agcaaggtgc gcgtggacca aaaatgcaag |
| 1321 gcctctgcgc agatcgaccc cacccccgtg atcgtcacct ccaacaccaa catgtgcgcc |
| 1381 gtgattgacg ggaacagcac caccttcgag caccagcagc ccctgcagga ccggatgttc |
| 1441 aagtttgaac tcacccgccg cctcgaccac gactttggca aggtcaccaa gcaggaagtc |
| 1501 aaggactttt tccggtgggc ggctgatcac gtgactgacg tggctcatga gttttacgtc |
| 1561 acaaagggtg gagctaagaa aaggcccgcc ccctctgacg aggatataag cgagcccaag |
| 1621 cggccgcgcg tgtcatttgc gcagccggag acgtcagacg cggaagctcc cggagacttc |
| 1681 gccgacaggt accaaaacaa atgttctcgt cacgcgggta tgctgcagat gctctttccc |
| 1741 tgcaagacgt gcgagagaat gaatcagaat tccaacgtct gcttcacgca cggtcagaaa |
| 1801 gattgcgggg agtgctttcc cgggtcagaa tctcaaccgg tttctgtcgt cagaaaaacg |
| 1861 tatcagaaac tgtgcatcct tcatcagctc cgggggggcac ccgagatcgc ctgctctgct |
| 1921 tgcgaccaac tcaaccccga tttggacgat tgccaatttg agcaataaat gactgaaatc |
| 1981 aggtatggct gctgacggtt atcttccaga ttggctcgag gacaacctct ctgaaggcat |
| 2041 tcgcgagtgg tgggcgctga aacctggagc tccacaaccc aaggccaacc aacagcatca |
| 2101 ggacaacggc aggggtcttg tgcttcctgg gtacaagtac ctcggaccct tcaacggact |
| 2161 cgacaaggga gagccggtca acgaggcaga cgccgcggcc ctcgagcacg acaaggccta |
| 2221 cgacaagcag ctcgagcagg gggacaaccc gtatctcaag tacaaccacg ccgacgccga |
| 2281 gttccagcag cgcttggcga ccgacacctc ttttgggggc aacctcgggc gagcagtctt |
| 2341 ccaggccaaa aagaggattc tcgagcctct gggtctggtt gaagagggcg ttaaaacggc |
| 2401 tcctggaaag aaacgcccat tagaaaagac tccaaatcgg ccgaccaacc cggactctgg |
| 2461 gaaggccccg gccaagaaaa agcaaaaaga cggcgaacca gccgactctg ctagaaggac |
| 2521 actcgacttt gaagactctg gagcaggaga cggacccccct gagggatcat cttccggaga |
| 2581 aatgtctcat gatgctgaga tgcgtgcggc gccaggcgga aatgctgtcg aggcgggaca |
| 2641 aggtgccgat ggagtgggta atgcctccgg tgattggcat tgcgattcca cctggtcaga |
| 2701 gggccgagtc accaccacca gcacccgaac ctgggtccta cccacgtaca acaaccacct |
| 2761 gtacctgcga atcggaacaa cggccaacag caacacctac aacggattct ccaccccctg |
| 2821 gggatacttt gactttaacc gcttccactg ccactttttcc ccacgcgact ggcagcgact |
| 2881 catcaacaac aactggggac tcaggccgaa atcgatgcgt gttaaaatct tcaacataca |
| 2941 ggtcaaggag gtcacgacgt caaacggcga gactacggtc gctaataacc ttaccagcac |
| 3001 ggttcagatc tttgcggatt cgacgtatga actcccatac gtgatggacg ccggtcagga |
| 3061 ggggagcttt cctccgtttc ccaacgacgt ctttatggtt ccccaatacg gatactgcgg |
| 3121 agttgtcact ggaaaaaacc agaaccagac agacagaaat gccttttact gcctggaata |
| 3181 ctttccatcc caaatgctaa gaactggcaa caattttgaa gtcagttacc aatttgaaaa |
| 3241 agttcctttc cattcaatgt acgcgcacag ccagagcctg gacagaatga tgaatccttt |
| 3301 actggatcag tacctgtggc atctgcaatc gaccactacc ggaaattccc ttaatcaagg |
| 3361 aacagctacc accacgtacg ggaaaattac cactggagac tttgcctact acaggaaaaa |
| 3421 ctggttgcct ggagcctgca ttaaacaaca aaaattttca aagaatgcca atcaaaacta |

-continued

| Sequences |
|---|
| 3481 caagattccc gccagcgggg gagacgccct tttaaagtat gacacgcata ccactctaaa |
| 3541 tgggcgatgg agtaacatgg ctcctggacc tccaatggca accgcaggtg ccggggactc |
| 3601 ggattttagc aacagccagc tgatctttgc cggacccaat ccgagcggta acacgaccac |
| 3661 atcttcaaac aatttgttgt ttacctcaga agaggagatt gccacaacaa acccacgaga |
| 3721 cacggacatg tttggacaga ttgcagataa taatcaaaat gccaccaccg cccctcacat |
| 3781 cgctaacctg gacgctatgg gaattgttcc cggaatggtc tggcaaaaca gagacatcta |
| 3841 ctaccagggc cctatttggg ccaaggtccc tcacacggac ggacactttc acccttcgcc |
| 3901 gctgatggga ggatttggac tgaaacaccc gcctccacag attttcatca aaaacacccc |
| 3961 cgtacccgcc aatcccaata ctacctttag cgctgcaagg attaattctt ttctgacgca |
| 4021 gtacagcacc ggacaagttg ccgttcagat cgactgggaa attcagaagg agcattccaa |
| 4081 acgctggaat cccgaagttc aatttacttc aaactacggc actcaaaatt ctatgctgtg |
| 4141 ggctcccgac aatgctggca actaccacga actccgggct attgggtccc gtttcctcac |

That which is claimed is:

1. A method of delivering a nucleic acid of interest to a cell, comprising contacting the cell with a substantially homogeneous population of AAV virions comprising at least two viral structural proteins from the group consisting of AAV capsid proteins VP1, VP2, and VP3, wherein the at least two viral structural proteins are sufficient to form an AAV virion that encapsidates an AAV genome, and wherein at least one of the at least two viral structural proteins present is from a single AAV serotype and is from a completely different serotype than the other viral structural protein, and wherein the VP1 is only from one serotype, the VP2 is only from one serotype, and the VP3 is only from one serotype, the AAV virion further comprising the nucleic acid within its genome, under conditions sufficient for the AAV virion to enter the cell.

2. The method of claim 1, wherein all three viral structural proteins are present.

3. The method of claim 2, wherein all three viral structural proteins are from different serotypes.

4. The method of claim 2, wherein only one of the three structural proteins is from a different serotype.

5. The method of claim 4, wherein the one viral structural protein from the different serotype is VP1.

6. The method of claim 4, wherein the one viral structural protein from the different serotype is VP2.

7. The method of claim 1, wherein none of the viral structural proteins are chimeric viral structural proteins.

8. The method of claim 1, wherein the cell is in vitro, in vivo, or ex vivo.

9. The method of claim 8, wherein the cell is selected from the group consisting of a neural cell, lung cell, retinal cell, epithelial cell, smooth muscle cell, skeletal muscle cell, cardiac muscle cell, pancreatic cell, hepatic cell, kidney cell, myocardial cell, bone cell, spleen cell, keratinocyte, fibroblast, endothelial cell, prostate cell, dendritic cell, hematopoietic cell, germ cell, progenitor cell, and a stem cell.

10. The method of claim 8, wherein the cell is within a tissue of a subject.

11. The method of claim 10, wherein the subject has a disease or disorder treatable with the expressed nucleic acid.

12. The method of claim 11, wherein the disease or disorder is hemophilia A, hemophilia B, diabetes mellitus, Gaucher disease, Fabry disease, Pompe disease, cancer, arthritis, muscle wasting, heart disease, a neurological disease or disorder, an autoimmune disease, a skeletal muscle disease, cystic fibrosis, thalassemia, phenylketonuria, low density lipoprotein (LDL) receptor deficiency, hyperammonemia, anemia, arthritis, a retinal degenerative disorder, or adenosine deaminase deficiency.

13. The method of claim 1, wherein the substantially homogeneous population of AAV virions is produced by a method comprising:

a) contacting cells, under conditions for formation of AAV virions, with a first nucleic acid sequence and a second nucleic acid sequence, wherein the AAV virion is formed from at least VP1 and VP3 viral structural proteins, wherein the first nucleic acid encodes VP1 from a first AAV serotype only but is not capable of expressing VP3 and the second nucleic acid sequence encodes VP3 from a second AAV serotype only that is different from the first AAV serotype and further is not capable of expressing VP1, and wherein the AAV virion comprises VP1 from the first serotype only and VP3 from the second serotype only, and wherein if VP2 is expressed, it is only from one serotype; and/or b) contacting cells, under conditions for formation of AAV virions, with a first nucleic acid sequence, a second nucleic acid sequence and a third nucleic acid sequence, wherein the AAV virion is formed from at least VP1 and VP3 viral structural proteins, wherein the first nucleic acid sequence encodes VP1 from a first AAV serotype only but is not capable of expressing VP3 and the second nucleic acid sequence encodes VP3 from a second AAV serotype only that is different from the first AAV serotype and further is not capable of expressing VP1, and wherein the AAV virion comprises VP1 from the first serotype only and VP3 from the second serotype only, and wherein if VP2 is expressed, it is only from one serotype, and wherein the viral structural proteins are encoded in the first nucleic acid sequence from a first AAV serotype only, that is different from the second AAV serotype and different from a third AAV serotype, the second nucleic acid sequence from the second AAV serotype only, that is different from the first and third AAV serotypes and the third nucleic acid sequence from the third AAV serotype only, that is different from the first and second AAV serotypes, and further wherein the first nucleic acid sequence has mutations in the start codons of VP2 and VP3 that prevent translation of VP2 and VP3 from an RNA transcribed from the first nucleic acid sequence, and further wherein the second nucleic acid sequence has mutations in the start codons of VP1 and VP3 that prevent translation of VP1 and VP3 from an RNA transcribed from the second nucleic acid sequence and further wherein the third nucleic acid sequence has mutations in the start codons of VP1 and VP2 that prevent translation of VP1 and VP2 from an RNA transcribed from the third nucleic acid sequence, and wherein the AAV virion comprises VP1 from the first AAV serotype only, VP2 from the second AAV serotype only, and VP3 from the third AAV serotype only;

the AAV virion further comprising the nucleic acid within its genome, under conditions sufficient for the AAV virion to enter the cell.

14. The method of claim 13, wherein the first nucleic acid sequence has mutations in the start codons of VP2 and VP3 that prevent translation of VP2 and VP3 from an RNA transcribed from the first nucleic acid sequence and further wherein the second nucleic acid sequence has mutations in the start codon of VP1 that prevent translation of VP1 from an RNA transcribed from the second nucleic acid sequence.

15. The method of claim 13, wherein VP2 of a) from only one serotype is expressed.

16. The method of claim 15, wherein VP2 of a) is from a different serotype than VP1 and a different serotype than VP3.

17. The method of claim 15, wherein VP2 of a) is from the same serotype as VP3.

18. The method of claim 13, wherein the first AAV serotype is AAV1, AAV2, AAV3, AAV4, AAVS, AAV6, AAV7, AAV8, AAV9, AAV10, AAV11, or an AAV selected from Table 1 or Table 3.

19. The method of claim 15 wherein an AAV virion is formed from VP1, VP2 and VP3 capsid proteins, wherein the viral structural proteins are encoded in the first nucleic acid sequence from a first AAV serotype only and the second nucleic acid sequence from a second AAV serotype only that is different from the first AAV serotype, and further wherein the first nucleic acid sequence has mutations in the A2 Splice Acceptor Site, and further wherein the second nucleic acid sequence has mutations in the Al Splice Acceptor Site, and wherein the AAV virion comprises VP1 from the first serotype only, and VP2 and VP3 from the second serotype only.

* * * * *

SEQUENCE LISTING

<160> NUMBER OF SEQ ID NOS: 142

<210> SEQ ID NO 1
<211> LENGTH: 6
<212> TYPE: PRT
<213> ORGANISM: Artificial
<220> FEATURE:
<223> OTHER INFORMATION: peptide

<400> SEQUENCE: 1

Arg Gly Asn Arg Gln Ala
1               5

<210> SEQ ID NO 2
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (7)..(7)
<223> OTHER INFORMATION: where Xaa is G or S

<400> SEQUENCE: 2

Asn Ser Val Arg Asp Leu Xaa
1               5

<210> SEQ ID NO 3
<211> LENGTH: 7
<212> TYPE: PRT
<213> ORGANISM: Artificial
<220> FEATURE:
<223> OTHER INFORMATION: peptide

<400> SEQUENCE: 3

Pro Arg Ser Val Thr Val Pro
1               5

<210> SEQ ID NO 4
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (6)..(6)
<223> OTHER INFORMATION: Xaa is any naturally occurring amino acid
<220> FEATURE:
<221> NAME/KEY: MISC_FEATURE
<222> LOCATION: (7)..(7)

<223> OTHER INFORMATION: Xaa is S or A

<400> SEQUENCE: 4

Asn Ser Val Ser Ser Xaa Xaa
1 5

<210> SEQ ID NO 5
<211> LENGTH: 6
<212> TYPE: PRT
<213> ORGANISM: Artificial
<220> FEATURE:
<223> OTHER INFORMATION: peptide

<400> SEQUENCE: 5

Asn Gly Arg Ala His Ala
1 5

<210> SEQ ID NO 6
<211> LENGTH: 7
<212> TYPE: PRT
<213> ORGANISM: Artificial
<220> FEATURE:
<223> OTHER INFORMATION: peptide

<400> SEQUENCE: 6

Gln Pro Glu His Ser Ser Thr
1 5

<210> SEQ ID NO 7
<211> LENGTH: 7
<212> TYPE: PRT
<213> ORGANISM: Artificial
<220> FEATURE:
<223> OTHER INFORMATION: peptide

<400> SEQUENCE: 7

Val Asn Thr Ala Asn Ser Thr
1 5

<210> SEQ ID NO 8
<211> LENGTH: 7
<212> TYPE: PRT
<213> ORGANISM: Artificial
<220> FEATURE:
<223> OTHER INFORMATION: peptide

<400> SEQUENCE: 8

His Gly Pro Met Gln Lys Ser
1 5

<210> SEQ ID NO 9
<211> LENGTH: 7
<212> TYPE: PRT
<213> ORGANISM: Artificial
<220> FEATURE:
<223> OTHER INFORMATION: peptide

<400> SEQUENCE: 9

Pro His Lys Pro Pro Leu Ala
1 5

<210> SEQ ID NO 10
<211> LENGTH: 7
<212> TYPE: PRT
<213> ORGANISM: Artificial
<220> FEATURE:
<223> OTHER INFORMATION: peptide

<400> SEQUENCE: 10

Ile Lys Asn Asn Glu Met Trp
1 5

<210> SEQ ID NO 11
<211> LENGTH: 7
<212> TYPE: PRT
<213> ORGANISM: Artificial
<220> FEATURE:
<223> OTHER INFORMATION: peptide

<400> SEQUENCE: 11

Arg Asn Leu Asp Thr Pro Met
1 5

<210> SEQ ID NO 12
<211> LENGTH: 7
<212> TYPE: PRT
<213> ORGANISM: Artificial
<220> FEATURE:
<223> OTHER INFORMATION: peptide

<400> SEQUENCE: 12

Val Asp Ser His Arg Gln Ser
1 5

<210> SEQ ID NO 13
<211> LENGTH: 7
<212> TYPE: PRT
<213> ORGANISM: Artificial
<220> FEATURE:
<223> OTHER INFORMATION: peptide

<400> SEQUENCE: 13

Tyr Asp Ser Lys Thr Lys Thr
1 5

<210> SEQ ID NO 14
<211> LENGTH: 7
<212> TYPE: PRT
<213> ORGANISM: Artificial
<220> FEATURE:
<223> OTHER INFORMATION: peptide

<400> SEQUENCE: 14

Ser Gln Leu Pro His Gln Lys
1 5

<210> SEQ ID NO 15
<211> LENGTH: 7
<212> TYPE: PRT
<213> ORGANISM: Artificial
<220> FEATURE:
<223> OTHER INFORMATION: peptide

<400> SEQUENCE: 15

Ser Thr Met Gln Gln Asn Thr
1 5

<210> SEQ ID NO 16
<211> LENGTH: 7
<212> TYPE: PRT
<213> ORGANISM: Artificial
<220> FEATURE:
<223> OTHER INFORMATION: peptide

<400> SEQUENCE: 16

Thr Glu Arg Tyr Met Thr Gln
1 5

<210> SEQ ID NO 17
<211> LENGTH: 7
<212> TYPE: PRT
<213> ORGANISM: Artificial
<220> FEATURE:
<223> OTHER INFORMATION: peptide

<400> SEQUENCE: 17

Asp Ala Ser Leu Ser Thr Ser
1 5

<210> SEQ ID NO 18
<211> LENGTH: 7
<212> TYPE: PRT
<213> ORGANISM: Artificial
<220> FEATURE:
<223> OTHER INFORMATION: peptide

<400> SEQUENCE: 18

Asp Leu Pro Asn Lys Lys Thr
1 5

<210> SEQ ID NO 19
<211> LENGTH: 7
<212> TYPE: PRT
<213> ORGANISM: Artificial
<220> FEATURE:
<223> OTHER INFORMATION: peptide

<400> SEQUENCE: 19

Asp Leu Thr Ala Ala Arg Leu
1 5

<210> SEQ ID NO 20
<211> LENGTH: 7
<212> TYPE: PRT
<213> ORGANISM: Artificial
<220> FEATURE:
<223> OTHER INFORMATION: peptide

<400> SEQUENCE: 20

Glu Pro His Gln Phe Asn Tyr
1 5

<210> SEQ ID NO 21
<211> LENGTH: 7
<212> TYPE: PRT
<213> ORGANISM: Artificial
<220> FEATURE:
<223> OTHER INFORMATION: peptide

<400> SEQUENCE: 21

Glu Pro Gln Ser Asn His Thr
1 5

<210> SEQ ID NO 22
<211> LENGTH: 7
<212> TYPE: PRT
<213> ORGANISM: Artificial
<220> FEATURE:
<223> OTHER INFORMATION: peptide

<400> SEQUENCE: 22

Met Ser Ser Trp Pro Ser Gln
1 5

<210> SEQ ID NO 23
<211> LENGTH: 7
<212> TYPE: PRT
<213> ORGANISM: Artificial
<220> FEATURE:
<223> OTHER INFORMATION: peptide

<400> SEQUENCE: 23

Asn Pro Lys His Asn Ala Thr
1 5

<210> SEQ ID NO 24
<211> LENGTH: 7
<212> TYPE: PRT
<213> ORGANISM: Artificial
<220> FEATURE:
<223> OTHER INFORMATION: peptide

<400> SEQUENCE: 24

Pro Asp Gly Met Arg Thr Thr
1 5

<210> SEQ ID NO 25
<211> LENGTH: 7
<212> TYPE: PRT
<213> ORGANISM: Artificial
<220> FEATURE:
<223> OTHER INFORMATION: peptide

<400> SEQUENCE: 25

Pro Asn Asn Asn Lys Thr Thr
1 5

<210> SEQ ID NO 26
<211> LENGTH: 7
<212> TYPE: PRT
<213> ORGANISM: Artificial
<220> FEATURE:
<223> OTHER INFORMATION: peptide

<400> SEQUENCE: 26

Gln Ser Thr Thr His Asp Ser
1 5

<210> SEQ ID NO 27
<211> LENGTH: 7
<212> TYPE: PRT
<213> ORGANISM: Artificial
<220> FEATURE:
<223> OTHER INFORMATION: peptide

<400> SEQUENCE: 27

Thr Gly Ser Lys Gln Lys Gln
1 5

<210> SEQ ID NO 28
<211> LENGTH: 7
<212> TYPE: PRT
<213> ORGANISM: Artificial
<220> FEATURE:
<223> OTHER INFORMATION: peptide

<400> SEQUENCE: 28

Ser Leu Lys His Gln Ala Leu
1 5

<210> SEQ ID NO 29
<211> LENGTH: 7
<212> TYPE: PRT
<213> ORGANISM: Artificial
<220> FEATURE:
<223> OTHER INFORMATION: peptide

<400> SEQUENCE: 29

Ser Pro Ile Asp Gly Glu Gln
1 5

<210> SEQ ID NO 30
<211> LENGTH: 8
<212> TYPE: PRT
<213> ORGANISM: Artificial
<220> FEATURE:
<223> OTHER INFORMATION: peptide

<400> SEQUENCE: 30

Trp Ile Phe Pro Trp Ile Gln Leu
1 5

<210> SEQ ID NO 31
<211> LENGTH: 9
<212> TYPE: PRT
<213> ORGANISM: Artificial
<220> FEATURE:
<223> OTHER INFORMATION: peptide

<400> SEQUENCE: 31

Cys Asp Cys Arg Gly Asp Cys Phe Cys
1 5

<210> SEQ ID NO 32
<211> LENGTH: 5
<212> TYPE: PRT
<213> ORGANISM: Artificial
<220> FEATURE:
<223> OTHER INFORMATION: peptide

<400> SEQUENCE: 32

Cys Asn Gly Arg Cys
1 5

<210> SEQ ID NO 33
<211> LENGTH: 7
<212> TYPE: PRT
<213> ORGANISM: Artificial
<220> FEATURE:
<223> OTHER INFORMATION: peptide

<400> SEQUENCE: 33

Cys Pro Arg Glu Cys Glu Ser
1 5

<210> SEQ ID NO 34
<211> LENGTH: 10
<212> TYPE: PRT
<213> ORGANISM: Artificial
<220> FEATURE:
<223> OTHER INFORMATION: peptide

<400> SEQUENCE: 34

Cys Thr Thr His Trp Gly Phe Thr Leu Cys
1               5                   10

<210> SEQ ID NO 35
<211> LENGTH: 9
<212> TYPE: PRT
<213> ORGANISM: Artificial
<220> FEATURE:
<223> OTHER INFORMATION: peptide

<400> SEQUENCE: 35

Cys Gly Arg Arg Ala Gly Gly Ser Cys
1               5

<210> SEQ ID NO 36
<211> LENGTH: 9
<212> TYPE: PRT
<213> ORGANISM: Artificial
<220> FEATURE:
<223> OTHER INFORMATION: peptide

<400> SEQUENCE: 36

Cys Lys Gly Gly Arg Ala Lys Asp Cys
1               5

<210> SEQ ID NO 37
<211> LENGTH: 9
<212> TYPE: PRT
<213> ORGANISM: Artificial
<220> FEATURE:
<223> OTHER INFORMATION: peptide

<400> SEQUENCE: 37

Cys Val Pro Glu Leu Gly His Glu Cys
1               5

<210> SEQ ID NO 38
<211> LENGTH: 9
<212> TYPE: PRT
<213> ORGANISM: Artificial
<220> FEATURE:
<223> OTHER INFORMATION: peptide

<400> SEQUENCE: 38

Cys Arg Arg Glu Thr Ala Trp Ala Lys
1               5

<210> SEQ ID NO 39
<211> LENGTH: 14
<212> TYPE: PRT
<213> ORGANISM: Artificial
<220> FEATURE:
<223> OTHER INFORMATION: peptide

<400> SEQUENCE: 39

Val Ser Trp Phe Ser His Arg Tyr Ser Pro Phe Ala Val Ser
1               5                   10

<210> SEQ ID NO 40
<211> LENGTH: 13
<212> TYPE: PRT
<213> ORGANISM: Artificial
<220> FEATURE:
<223> OTHER INFORMATION: peptide

<400> SEQUENCE: 40

Gly Tyr Arg Asp Gly Tyr Ala Gly Pro Ile Leu Tyr Asn
1               5                   10

<210> SEQ ID NO 41
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (5)..(7)
<223> OTHER INFORMATION: Xaa can be any naturally occurring amino acid

<400> SEQUENCE: 41

Xaa Xaa Xaa Tyr Xaa Xaa Xaa
1               5

<210> SEQ ID NO 42
<211> LENGTH: 4
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is E or M

<400> SEQUENCE: 42

Tyr Xaa Asn Trp
1

<210> SEQ ID NO 43
<211> LENGTH: 7
<212> TYPE: PRT
<213> ORGANISM: Artificial
<220> FEATURE:
<223> OTHER INFORMATION: peptide

<400> SEQUENCE: 43

Arg Pro Leu Pro Pro Leu Pro
1               5

<210> SEQ ID NO 44
<211> LENGTH: 7
<212> TYPE: PRT
<213> ORGANISM: Artificial
<220> FEATURE:
<223> OTHER INFORMATION: peptide

<400> SEQUENCE: 44

Ala Pro Pro Leu Pro Pro Arg
1               5

<210> SEQ ID NO 45
<211> LENGTH: 12
<212> TYPE: PRT
<213> ORGANISM: Artificial
<220> FEATURE:
<223> OTHER INFORMATION: peptide

<400> SEQUENCE: 45

Asp Val Phe Tyr Pro Tyr Pro Tyr Ala Ser Gly Ser
1 5 10

<210> SEQ ID NO 46
<211> LENGTH: 6
<212> TYPE: PRT
<213> ORGANISM: Artificial
<220> FEATURE:
<223> OTHER INFORMATION: peptide

<400> SEQUENCE: 46

Met Tyr Trp Tyr Pro Tyr
1 5

<210> SEQ ID NO 47
<211> LENGTH: 12
<212> TYPE: PRT
<213> ORGANISM: Artificial
<220> FEATURE:
<223> OTHER INFORMATION: peptide

<400> SEQUENCE: 47

Asp Ile Thr Trp Asp Gln Leu Trp Asp Leu Met Lys
1 5 10

<210> SEQ ID NO 48
<211> LENGTH: 8
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (5)..(5)
<223> OTHER INFORMATION: Xaa is G or L

<400> SEQUENCE: 48

Cys Trp Asp Asp Xaa Trp Leu Cys
1 5

<210> SEQ ID NO 49
<211> LENGTH: 14
<212> TYPE: PRT
<213> ORGANISM: Artificial
<220> FEATURE:
<223> OTHER INFORMATION: peptide

<400> SEQUENCE: 49

Glu Trp Cys Glu Tyr Leu Gly Gly Tyr Leu Arg Cys Tyr Ala
1 5 10

<210> SEQ ID NO 50
<211> LENGTH: 14
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa can be any naturally occurring amino acid

<400> SEQUENCE: 50

Tyr Xaa Cys Xaa Xaa Gly Pro Xaa Thr Trp Xaa Cys Xaa Pro
1               5                   10

<210> SEQ ID NO 51
<211> LENGTH: 14
<212> TYPE: PRT
<213> ORGANISM: Artificial
<220> FEATURE:
<223> OTHER INFORMATION: peptide

<400> SEQUENCE: 51

Ile Glu Gly Pro Thr Leu Arg Gln Trp Leu Ala Ala Arg Ala
1               5                   10

<210> SEQ ID NO 52
<211> LENGTH: 5
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Y, W, F or H

<400> SEQUENCE: 52

Leu Trp Xaa Xaa Xaa
1               5

<210> SEQ ID NO 53
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(4)
<223> OTHER INFORMATION: Xaa can be any naturally occurring amino acid

<400> SEQUENCE: 53

Xaa Phe Xaa Xaa Tyr Leu Trp
1               5

<210> SEQ ID NO 54
<211> LENGTH: 13
<212> TYPE: PRT
<213> ORGANISM: Artificial
<220> FEATURE:
<223> OTHER INFORMATION: peptide

<400> SEQUENCE: 54

Ser Ser Ile Ile Ser His Phe Arg Trp Gly Leu Cys Asp
1 5 10

<210> SEQ ID NO 55
<211> LENGTH: 13
<212> TYPE: PRT
<213> ORGANISM: Artificial
<220> FEATURE:
<223> OTHER INFORMATION: peptide

<400> SEQUENCE: 55

Met Ser Arg Pro Ala Cys Pro Pro Asn Asp Lys Tyr Glu
1 5 10

<210> SEQ ID NO 56
<211> LENGTH: 8
<212> TYPE: PRT
<213> ORGANISM: Artificial
<220> FEATURE:
<223> OTHER INFORMATION: peptide

<400> SEQUENCE: 56

Cys Leu Arg Ser Gly Arg Gly Cys
1 5

<210> SEQ ID NO 57
<211> LENGTH: 9
<212> TYPE: PRT
<213> ORGANISM: Artificial
<220> FEATURE:
<223> OTHER INFORMATION: peptide

<400> SEQUENCE: 57

Cys His Trp Met Phe Ser Pro Trp Cys
1 5

<210> SEQ ID NO 58
<211> LENGTH: 4
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 58

Trp Xaa Xaa Phe
1

<210> SEQ ID NO 59
<211> LENGTH: 8
<212> TYPE: PRT
<213> ORGANISM: Artificial
<220> FEATURE:
<223> OTHER INFORMATION: peptide

<400> SEQUENCE: 59

Cys Ser Ser Arg Leu Asp Ala Cys
1 5

<210> SEQ ID NO 60
<211> LENGTH: 7
<212> TYPE: PRT
<213> ORGANISM: Artificial

<220> FEATURE:
<223> OTHER INFORMATION: peptide

<400> SEQUENCE: 60

Cys Leu Pro Val Ala Ser Cys
1 5

<210> SEQ ID NO 61
<211> LENGTH: 13
<212> TYPE: PRT
<213> ORGANISM: Artificial
<220> FEATURE:
<223> OTHER INFORMATION: peptide

<400> SEQUENCE: 61

Cys Gly Phe Glu Cys Val Arg Gln Cys Pro Glu Arg Cys
1 5 10

<210> SEQ ID NO 62
<211> LENGTH: 13
<212> TYPE: PRT
<213> ORGANISM: Artificial
<220> FEATURE:
<223> OTHER INFORMATION: peptide

<400> SEQUENCE: 62

Cys Val Ala Leu Cys Arg Glu Ala Cys Gly Glu Gly Cys
1 5 10

<210> SEQ ID NO 63
<211> LENGTH: 9
<212> TYPE: PRT
<213> ORGANISM: Artificial
<220> FEATURE:
<223> OTHER INFORMATION: peptide

<400> SEQUENCE: 63

Ser Trp Cys Glu Pro Gly Trp Cys Arg
1 5

<210> SEQ ID NO 64
<211> LENGTH: 7
<212> TYPE: PRT
<213> ORGANISM: Artificial
<220> FEATURE:
<223> OTHER INFORMATION: peptide

<400> SEQUENCE: 64

Tyr Ser Gly Lys Trp Gly Trp
1 5

<210> SEQ ID NO 65
<211> LENGTH: 7
<212> TYPE: PRT
<213> ORGANISM: Artificial
<220> FEATURE:
<223> OTHER INFORMATION: peptide

<400> SEQUENCE: 65

Gly Leu Ser Gly Gly Arg Ser
1 5

<210> SEQ ID NO 66
<211> LENGTH: 7
<212> TYPE: PRT
<213> ORGANISM: Artificial
<220> FEATURE:

<223> OTHER INFORMATION: peptide

<400> SEQUENCE: 66

Leu Met Leu Pro Arg Ala Asp
1 5

<210> SEQ ID NO 67
<211> LENGTH: 9
<212> TYPE: PRT
<213> ORGANISM: Artificial
<220> FEATURE:
<223> OTHER INFORMATION: peptide

<400> SEQUENCE: 67

Cys Ser Cys Phe Arg Asp Val Cys Cys
1 5

<210> SEQ ID NO 68
<211> LENGTH: 9
<212> TYPE: PRT
<213> ORGANISM: Artificial
<220> FEATURE:
<223> OTHER INFORMATION: peptide

<400> SEQUENCE: 68

Cys Arg Asp Val Val Ser Val Ile Cys
1 5

<210> SEQ ID NO 69
<211> LENGTH: 6
<212> TYPE: PRT
<213> ORGANISM: Artificial
<220> FEATURE:
<223> OTHER INFORMATION: peptide

<400> SEQUENCE: 69

Met Ala Arg Ser Gly Leu
1 5

<210> SEQ ID NO 70
<211> LENGTH: 6
<212> TYPE: PRT
<213> ORGANISM: Artificial
<220> FEATURE:
<223> OTHER INFORMATION: peptide

<400> SEQUENCE: 70

Met Ala Arg Ala Lys Glu
1 5

<210> SEQ ID NO 71
<211> LENGTH: 6
<212> TYPE: PRT
<213> ORGANISM: Artificial
<220> FEATURE:
<223> OTHER INFORMATION: peptide

<400> SEQUENCE: 71

Met Ser Arg Thr Met Ser
1 5

<210> SEQ ID NO 72
<211> LENGTH: 6
<212> TYPE: PRT
<213> ORGANISM: Artificial
<220> FEATURE:
<223> OTHER INFORMATION: peptide

<400> SEQUENCE: 72

Lys Cys Cys Tyr Ser Leu
1               5

<210> SEQ ID NO 73
<211> LENGTH: 14
<212> TYPE: PRT
<213> ORGANISM: Artificial
<220> FEATURE:
<223> OTHER INFORMATION: peptide

<400> SEQUENCE: 73

Met Tyr Trp Gly Asp Ser His Trp Leu Gln Tyr Trp Tyr Glu
1               5                   10

<210> SEQ ID NO 74
<211> LENGTH: 7
<212> TYPE: PRT
<213> ORGANISM: Artificial
<220> FEATURE:
<223> OTHER INFORMATION: peptide

<400> SEQUENCE: 74

Met Gln Leu Pro Leu Ala Thr
1               5

<210> SEQ ID NO 75
<211> LENGTH: 4
<212> TYPE: PRT
<213> ORGANISM: Artificial
<220> FEATURE:
<223> OTHER INFORMATION: peptide

<400> SEQUENCE: 75

Glu Trp Leu Ser
1

<210> SEQ ID NO 76
<211> LENGTH: 4
<212> TYPE: PRT
<213> ORGANISM: Artificial
<220> FEATURE:
<223> OTHER INFORMATION: peptide

<400> SEQUENCE: 76

Ser Asn Glu Trp
1

<210> SEQ ID NO 77
<211> LENGTH: 4
<212> TYPE: PRT
<213> ORGANISM: Artificial
<220> FEATURE:
<223> OTHER INFORMATION: peptide

<400> SEQUENCE: 77

Thr Asn Tyr Leu
1

<210> SEQ ID NO 78
<211> LENGTH: 12
<212> TYPE: PRT
<213> ORGANISM: Artificial
<220> FEATURE:
<223> OTHER INFORMATION: peptide

<400> SEQUENCE: 78

Trp Asp Leu Ala Trp Met Phe Arg Leu Pro Val Gly
1 5 10

<210> SEQ ID NO 79
<211> LENGTH: 13
<212> TYPE: PRT
<213> ORGANISM: Artificial
<220> FEATURE:
<223> OTHER INFORMATION: peptide

<400> SEQUENCE: 79

Cys Thr Val Ala Leu Pro Gly Gly Tyr Val Arg Val Cys
1 5 10

<210> SEQ ID NO 80
<211> LENGTH: 13
<212> TYPE: PRT
<213> ORGANISM: Artificial
<220> FEATURE:
<223> OTHER INFORMATION: peptide

<400> SEQUENCE: 80

Cys Val Ala Tyr Cys Ile Glu His His Cys Trp Thr Cys
1 5 10

<210> SEQ ID NO 81
<211> LENGTH: 12
<212> TYPE: PRT
<213> ORGANISM: Artificial
<220> FEATURE:
<223> OTHER INFORMATION: peptide

<400> SEQUENCE: 81

Cys Val Phe Ala His Asn Tyr Asp Tyr Leu Val Cys
1 5 10

<210> SEQ ID NO 82
<211> LENGTH: 10
<212> TYPE: PRT
<213> ORGANISM: Artificial
<220> FEATURE:
<223> OTHER INFORMATION: peptide

<400> SEQUENCE: 82

Cys Val Phe Thr Ser Asn Tyr Ala Phe Cys
1 5 10

<210> SEQ ID NO 83
<211> LENGTH: 7
<212> TYPE: PRT
<213> ORGANISM: Artificial
<220> FEATURE:
<223> OTHER INFORMATION: peptide

<400> SEQUENCE: 83

Val His Ser Pro Asn Lys Lys
1 5

<210> SEQ ID NO 84
<211> LENGTH: 7
<212> TYPE: PRT
<213> ORGANISM: Artificial
<220> FEATURE:
<223> OTHER INFORMATION: peptide

<400> SEQUENCE: 84

Cys Arg Gly Asp Gly Trp Cys
1 5

<210> SEQ ID NO 85
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid

<400> SEQUENCE: 85

Xaa Arg Gly Cys Asp Xaa
1 5

<210> SEQ ID NO 86
<211> LENGTH: 4
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is S or T
<220> FEATURE:
<221> NAME/KEY: misc_feature
<222> LOCATION: (4)..(4)
<223> OTHER INFORMATION: Xaa can be any naturally occurring amino acid

<400> SEQUENCE: 86

Pro Xaa Xaa Xaa
1

<210> SEQ ID NO 87
<211> LENGTH: 11
<212> TYPE: PRT
<213> ORGANISM: Artificial
<220> FEATURE:
<223> OTHER INFORMATION: peptide

<400> SEQUENCE: 87

Ser Gly Lys Gly Pro Arg Gln Ile Thr Ala Leu
1 5 10

<210> SEQ ID NO 88
<211> LENGTH: 15
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (10)..(10)
<223> OTHER INFORMATION: Xaa is A or Q
<220> FEATURE:
<221> NAME/KEY: MISC_FEATURE
<222> LOCATION: (11)..(11)

<223> OTHER INFORMATION: Xaa is N or A
<220> FEATURE:
<221> NAME/KEY: MISC_FEATURE
<222> LOCATION: (12)..(12)
<223> OTHER INFORMATION: Xaa is L or Y
<220> FEATURE:
<221> NAME/KEY: MISC_FEATURE
<222> LOCATION: (14)..(14)
<223> OTHER INFORMATION: Xaa is N, M or R
<220> FEATURE:
<221> NAME/KEY: MISC_FEATURE
<222> LOCATION: (15)..(15)
<223> OTHER INFORMATION: Xaa is R or K

<400> SEQUENCE: 88

Ala Ala Ala Ala Ala Ala Ala Ala Ala Xaa Xaa Xaa Thr Xaa Xaa
1 5 10 15

<210> SEQ ID NO 89
<211> LENGTH: 6
<212> TYPE: PRT
<213> ORGANISM: Artificial
<220> FEATURE:
<223> OTHER INFORMATION: peptide

<400> SEQUENCE: 89

Val Tyr Met Ser Pro Phe
1 5

<210> SEQ ID NO 90
<211> LENGTH: 7
<212> TYPE: PRT
<213> ORGANISM: Artificial
<220> FEATURE:
<223> OTHER INFORMATION: peptide

<400> SEQUENCE: 90

Ala Thr Trp Leu Pro Pro Arg
1 5

<210> SEQ ID NO 91
<211> LENGTH: 12
<212> TYPE: PRT
<213> ORGANISM: Artificial
<220> FEATURE:
<223> OTHER INFORMATION: peptide

<400> SEQUENCE: 91

His Thr Met Tyr Tyr His His Tyr Gln His His Leu
1 5 10

<210> SEQ ID NO 92
<211> LENGTH: 19
<212> TYPE: PRT
<213> ORGANISM: Artificial
<220> FEATURE:
<223> OTHER INFORMATION: peptide

<400> SEQUENCE: 92

Ser Glu Val Gly Cys Arg Ala Gly Pro Leu Gln Trp Leu Cys Glu Lys
1 5 10 15

Tyr Phe Gly

<210> SEQ ID NO 93
<211> LENGTH: 18
<212> TYPE: PRT
<213> ORGANISM: Artificial
<220> FEATURE:

```
<223> OTHER INFORMATION: peptide

<400> SEQUENCE: 93

Cys Gly Leu Leu Pro Val Gly Arg Pro Asp Arg Asn Val Trp Arg Trp
1               5                   10                  15

Leu Cys


<210> SEQ ID NO 94
<211> LENGTH: 15
<212> TYPE: PRT
<213> ORGANISM: Artificial
<220> FEATURE:
<223> OTHER INFORMATION: peptide

<400> SEQUENCE: 94

Cys Lys Gly Gln Cys Asp Arg Phe Lys Gly Leu Pro Trp Glu Cys
1               5                   10                  15


<210> SEQ ID NO 95
<211> LENGTH: 5
<212> TYPE: PRT
<213> ORGANISM: Artificial
<220> FEATURE:
<223> OTHER INFORMATION: peptide

<400> SEQUENCE: 95

Ser Gly Arg Ser Ala
1               5


<210> SEQ ID NO 96
<211> LENGTH: 4
<212> TYPE: PRT
<213> ORGANISM: Artificial
<220> FEATURE:
<223> OTHER INFORMATION: peptide

<400> SEQUENCE: 96

Trp Gly Phe Pro
1


<210> SEQ ID NO 97
<211> LENGTH: 5
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Y, W, F or H

<400> SEQUENCE: 97

Leu Trp Xaa Xaa Xaa
1               5


<210> SEQ ID NO 98
<211> LENGTH: 7
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
```

<223> OTHER INFORMATION: Xaa can be any naturally occurring amino acid
<220> FEATURE:
<221> NAME/KEY: MISC_FEATURE
<222> LOCATION: (3)..(4)
<223> OTHER INFORMATION: Xaa can be any naturally occurring amino acid

<400> SEQUENCE: 98

Xaa Phe Xaa Xaa Tyr Leu Trp
1               5

<210> SEQ ID NO 99
<211> LENGTH: 17
<212> TYPE: PRT
<213> ORGANISM: Artificial
<220> FEATURE:
<223> OTHER INFORMATION: peptide

<400> SEQUENCE: 99

Ala Glu Pro Met Pro His Ser Leu Asn Phe Ser Gln Tyr Leu Trp Tyr
1               5                   10                  15

Thr

<210> SEQ ID NO 100
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: Xaa is W or F

<400> SEQUENCE: 100

Trp Ala Tyr Xaa Ser Pro
1               5

<210> SEQ ID NO 101
<211> LENGTH: 7
<212> TYPE: PRT
<213> ORGANISM: Artificial
<220> FEATURE:
<223> OTHER INFORMATION: peptide

<400> SEQUENCE: 101

Ile Glu Leu Leu Gln Ala Arg
1               5

<210> SEQ ID NO 102
<211> LENGTH: 12
<212> TYPE: PRT
<213> ORGANISM: Artificial
<220> FEATURE:
<223> OTHER INFORMATION: peptide

<400> SEQUENCE: 102

Asp Ile Thr Trp Asp Gln Leu Trp Asp Leu Met Lys
1               5                   10

<210> SEQ ID NO 103
<211> LENGTH: 16
<212> TYPE: PRT
<213> ORGANISM: Artificial
<220> FEATURE:
<223> OTHER INFORMATION: peptide

<400> SEQUENCE: 103

Ala Tyr Thr Lys Cys Ser Arg Gln Trp Arg Thr Cys Met Thr Thr His
1 5 10 15

<210> SEQ ID NO 104
<211> LENGTH: 15
<212> TYPE: PRT
<213> ORGANISM: Artificial
<220> FEATURE:
<223> OTHER INFORMATION: peptide

<400> SEQUENCE: 104

Pro Gln Asn Ser Lys Ile Pro Gly Pro Thr Phe Leu Asp Pro His
1 5 10 15

<210> SEQ ID NO 105
<211> LENGTH: 15
<212> TYPE: PRT
<213> ORGANISM: Artificial
<220> FEATURE:
<223> OTHER INFORMATION: peptide

<400> SEQUENCE: 105

Ser Met Glu Pro Ala Leu Pro Asp Trp Trp Trp Lys Met Phe Lys
1 5 10 15

<210> SEQ ID NO 106
<211> LENGTH: 16
<212> TYPE: PRT
<213> ORGANISM: Artificial
<220> FEATURE:
<223> OTHER INFORMATION: peptide

<400> SEQUENCE: 106

Ala Asn Thr Pro Cys Gly Pro Tyr Thr His Asp Cys Pro Val Lys Arg
1 5 10 15

<210> SEQ ID NO 107
<211> LENGTH: 12
<212> TYPE: PRT
<213> ORGANISM: Artificial
<220> FEATURE:
<223> OTHER INFORMATION: peptide

<400> SEQUENCE: 107

Thr Ala Cys His Gln His Val Arg Met Val Arg Pro
1 5 10

<210> SEQ ID NO 108
<211> LENGTH: 12
<212> TYPE: PRT
<213> ORGANISM: Artificial
<220> FEATURE:
<223> OTHER INFORMATION: peptide

<400> SEQUENCE: 108

Val Pro Trp Met Glu Pro Ala Tyr Gln Arg Phe Leu
1 5 10

<210> SEQ ID NO 109
<211> LENGTH: 8
<212> TYPE: PRT
<213> ORGANISM: Artificial
<220> FEATURE:
<223> OTHER INFORMATION: peptide

<400> SEQUENCE: 109

Asp Pro Arg Ala Thr Pro Gly Ser
1               5

<210> SEQ ID NO 110
<211> LENGTH: 12
<212> TYPE: PRT
<213> ORGANISM: Artificial
<220> FEATURE:
<223> OTHER INFORMATION: peptide

<400> SEQUENCE: 110

Phe Arg Pro Asn Arg Ala Gln Asp Tyr Asn Thr Asn
1               5                   10

<210> SEQ ID NO 111
<211> LENGTH: 9
<212> TYPE: PRT
<213> ORGANISM: Artificial
<220> FEATURE:
<223> OTHER INFORMATION: peptide

<400> SEQUENCE: 111

Cys Thr Lys Asn Ser Tyr Leu Met Cys
1               5

<210> SEQ ID NO 112
<211> LENGTH: 11
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa is R or Q
<220> FEATURE:
<221> NAME/KEY: MISC_FEATURE
<222> LOCATION: (3)..(3)
<223> OTHER INFORMATION: Xaa is L or R
<220> FEATURE:
<221> NAME/KEY: MISC_FEATURE
<222> LOCATION: (5)..(5)
<223> OTHER INFORMATION: Xaa is G or N
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is A or N

<400> SEQUENCE: 112

Cys Xaa Xaa Thr Xaa Xaa Xaa Gly Xaa Gly Cys
1               5                   10

<210> SEQ ID NO 113
<211> LENGTH: 9
<212> TYPE: PRT
<213> ORGANISM: Artificial
<220> FEATURE:
<223> OTHER INFORMATION: peptide

<400> SEQUENCE: 113

Cys Pro Ile Glu Asp Arg Pro Met Cys
1               5

<210> SEQ ID NO 114

<211> LENGTH: 12
<212> TYPE: PRT
<213> ORGANISM: Artificial
<220> FEATURE:
<223> OTHER INFORMATION: peptide

<400> SEQUENCE: 114

His Glu Trp Ser Tyr Leu Ala Pro Tyr Pro Trp Phe
1 5 10

<210> SEQ ID NO 115
<211> LENGTH: 9
<212> TYPE: PRT
<213> ORGANISM: Artificial
<220> FEATURE:
<223> OTHER INFORMATION: peptide

<400> SEQUENCE: 115

Met Cys Pro Lys His Pro Leu Gly Cys
1 5

<210> SEQ ID NO 116
<211> LENGTH: 15
<212> TYPE: PRT
<213> ORGANISM: Artificial
<220> FEATURE:
<223> OTHER INFORMATION: peptide

<400> SEQUENCE: 116

Arg Met Trp Pro Ser Ser Thr Val Asn Leu Ser Ala Gly Arg Arg
1 5 10 15

<210> SEQ ID NO 117
<211> LENGTH: 20
<212> TYPE: PRT
<213> ORGANISM: Artificial
<220> FEATURE:
<223> OTHER INFORMATION: peptide

<400> SEQUENCE: 117

Ser Ala Lys Thr Ala Val Ser Gln Arg Val Trp Leu Pro Ser His Arg
1 5 10 15

Gly Gly Glu Pro
20

<210> SEQ ID NO 118
<211> LENGTH: 20
<212> TYPE: PRT
<213> ORGANISM: Artificial
<220> FEATURE:
<223> OTHER INFORMATION: peptide

<400> SEQUENCE: 118

Lys Ser Arg Glu His Val Asn Asn Ser Ala Cys Pro Ser Lys Arg Ile
1 5 10 15

Thr Ala Ala Leu
20

<210> SEQ ID NO 119
<211> LENGTH: 4
<212> TYPE: PRT
<213> ORGANISM: Artificial
<220> FEATURE:
<223> OTHER INFORMATION: peptide

<400> SEQUENCE: 119

Glu Gly Phe Arg
1

<210> SEQ ID NO 120
<211> LENGTH: 6
<212> TYPE: PRT
<213> ORGANISM: Artificial
<220> FEATURE:
<223> OTHER INFORMATION: peptide

<400> SEQUENCE: 120

Ala Gly Leu Gly Val Arg
1               5

<210> SEQ ID NO 121
<211> LENGTH: 15
<212> TYPE: PRT
<213> ORGANISM: Artificial
<220> FEATURE:
<223> OTHER INFORMATION: peptide

<400> SEQUENCE: 121

Gly Thr Arg Gln Gly His Thr Met Arg Leu Gly Val Ser Asp Gly
1               5                   10                  15

<210> SEQ ID NO 122
<211> LENGTH: 15
<212> TYPE: PRT
<213> ORGANISM: Artificial
<220> FEATURE:
<223> OTHER INFORMATION: peptide

<400> SEQUENCE: 122

Ile Ala Gly Leu Ala Thr Pro Gly Trp Ser His Trp Leu Ala Leu
1               5                   10                  15

<210> SEQ ID NO 123
<211> LENGTH: 7
<212> TYPE: PRT
<213> ORGANISM: Artificial
<220> FEATURE:
<223> OTHER INFORMATION: peptide

<400> SEQUENCE: 123

Ser Met Ser Ile Ala Arg Leu
1               5

<210> SEQ ID NO 124
<211> LENGTH: 7
<212> TYPE: PRT
<213> ORGANISM: Artificial
<220> FEATURE:
<223> OTHER INFORMATION: peptide

<400> SEQUENCE: 124

His Thr Phe Glu Pro Gly Val
1               5

<210> SEQ ID NO 125
<211> LENGTH: 15
<212> TYPE: PRT
<213> ORGANISM: Artificial
<220> FEATURE:
<223> OTHER INFORMATION: peptide

<400> SEQUENCE: 125

Asn Thr Ser Leu Lys Arg Ile Ser Asn Lys Arg Ile Arg Arg Lys
1 5 10 15

<210> SEQ ID NO 126
<211> LENGTH: 15
<212> TYPE: PRT
<213> ORGANISM: Artificial
<220> FEATURE:
<223> OTHER INFORMATION: peptide

<400> SEQUENCE: 126

Leu Arg Ile Lys Arg Lys Arg Arg Lys Arg Lys Lys Thr Arg Lys
1 5 10 15

<210> SEQ ID NO 127
<211> LENGTH: 4636
<212> TYPE: DNA
<213> ORGANISM: Artificial
<220> FEATURE:
<223> OTHER INFORMATION: AAV1

<400> SEQUENCE: 127
ctctcccccc tgtcgcgttc gctcgctcgc tggctcgttt ggggggtgg cagctcaaag 60 agctgccaga cgacggccct ctggccgtcg cccccccaaa cgagccagcg agcgagcgaa 120
cgcgacaggg gggagagtgc cacactctca agcaaggagg ttttgtaagt ggtgatgtca 180
tatagttgtc acgcgatagt taatgattaa cagtcaggtg atgtgtgtta tccaatagga 240
tgaaagcgcg cgcatgagtt ctcgcgagac ttccggggta taaaggggtg agtgaacgag 300
cccgccgcca ttctctgctc tgaactgcta gaggaccctc gctgccatgg ctaccttcta 360
cgaagtcatt gttcgcgtcc catttgacgt ggaggaacat ctgcctggaa tttctgacag 420
ctttgtggac tgggtaactg gtcaaatttg ggagctgcct cccgagtcag atttgaattt 480
gactctgatt gagcagcctc agctgacggt tgctgacaga attcgccgcg tgttcctgta 540
cgagtggaac aaattttcca agcaggaatc caaattcttt gtgcagtttg aaaagggatc 600
tgaatatttt catctgcaca cgcttgtgga gacctccggc atctcttcca tggtcctagg 660
ccgctacgtg agtcagattc gcgcccagct ggtgaaagtg gtcttccagg gaatcgagcc 720
acagatcaac gactgggtcg ccatcaccaa ggtaaagaag ggcggagcca ataaggtggt 780
ggattctggg tatattcccg cctacctgct gccgaaggtc caaccggagc ttcagtgggc 840
gtggacaaac ctggacgagt ataaattggc cgccctgaac ctggaggagc gcaaacggct 900
cgtcgcgcag tttctggcag aatcctcgca gcgctcgcag gaggcggctt cgcagcgtga 960
gttctcggct gacccggtca tcaaaagcaa gacttcccag aaatacatgg cgctcgtcaa 1020
ctggctcgtg gagcacggca tcacttccga gaagcagtgg atccaggaga atcaggagag 1080
ctacctctcc ttcaactcca cgggcaactc tcggagccaa atcaaggccg cgctcgacaa 1140
cgcgaccaaa atcatgagtc tgacaaaaag cgcggtggac tacctcgtgg ggagctccgt 1200
tcccgaggac atttcaaaaa acagaatctg gcaaattttt gagatgaacg gctacgaccc 1260
ggcctacgcg ggatccatcc tctacggctg gtgtcagcgc tccttcaaca agaggaacac 1320
cgtctggctc tacggacccg ccacgaccgg caagaccaac atcgcggagg ccatcgccca 1380
cactgtgccc ttttacggct gcgtgaactg gaccaatgaa aactttccct ttaatgactg 1440
tgtggacaaa atgctcattt ggtgggagga gggaaagatg accaacaagg tggttgaatc 1500
cgccaaggcc atcctggggg gctccaaggt gcgggtcgat cagaaatgta aatcctctgt 1560

-continued

```
tcaaattgat tctacccccg tcattgtaac ttccaataca aacatgtgtg tggtggtgga   1620
tgggaattcc acgacctttg aacaccagca gccgctggag gaccgcatgt tcaaatttga   1680
actgactaag cggctcccgc cagattttgg caagattact aagcaggaag tcaaagactt   1740
ttttgcttgg gcaaaggtca atcaggtgcc ggtgactcac gagtttaaag ttcccaggga   1800
attggcggga actaaagggg cggagaaatc tctaaaacgc ccactgggtg acgtcaccaa   1860
tactagctat aaaagtccag agaagcgggc ccggctctca tttgttcccg agacgcctcg   1920
cagttcagac gtgactgtcg atcccgctcc tctgcgaccg ctcaattgga attcaaggta   1980
tgattgcaaa tgtgaccatc atgctcaatt tgacaacatt tctgacaaat gtgatgaatg   2040
tgaatatttg aatcggggca aaaatggatg tatctgtcac aatgtaactc actgtcaaat   2100
ttgtcacggg attccccccct gggagaagga aaacttgtca gattttgggg attttgacga   2160
tgccaataaa gaacagtaaa taaagcgagt agtcatgtct tttgttgatc accctccaga   2220
ttggttggaa gaagttggtg aaggtcttcg cgagtttttg ggccttgaag cgggcccacc   2280
gaaaccgaaa cccaatcagc agcatcaaga tcaagcccgt ggtcttgtgc tgcctggtta   2340
taactatctc ggacccggaa acggtctcga tcgaggagag cctgtcaaca gggcagacga   2400
ggtcgcgcga gagcacgaca tctcgtacaa cgagcagctt gaggcgggag acaaccccta   2460
cctcaagtac aaccacgcgg acgccgagtt tcaggagaag ctcgccgacg acacatcctt   2520
cgggggaaac ctcggaaagg cagtctttca ggccaagaaa agggttctcg aaccttttgg   2580
cctggttgaa gagggtgcta agacggcccc taccggaaag cggatagacg accactttcc   2640
aaaaagaaag aaggctcgga ccgaagagga ctccaagcct tccacctcgt cagacgccga   2700
agctggaccc agcggatccc agcagctgca aatcccagca caaccagcct caagtttggg   2760
agctgataca atgtctgcgg gaggtggcgg cccattgggc gacaataacc aaggtgccga   2820
tggagtgggc aatgcctcgg gagattggca ttgcgattcc acgtggatgg gggacagagt   2880
cgtcaccaag tccacccgca cctgggtgct gcccagctac aacaaccacc agtaccgaga   2940
gatcaaaagc ggctccgtcg acggaagcaa cgccaacgcc tactttggat acagcacccc   3000
ctgggggtac tttgacttta accgcttcca cagccactgg agcccccgag actggcaaag   3060
actcatcaac aactattggg gcttcagacc ccggtctctc agagtcaaaa tcttcaacat   3120
ccaagtcaaa gaggtcacgg tgcaggactc caccaccacc atcgccaaca acctcacctc   3180
caccgtccaa gtgtttacgg acgacgacta ccaactcccg tacgtcgtcg gcaacgggac   3240
cgagggatgc ctgccggcct tccccccgca ggtctttacg ctgccgcagt acggctacgc   3300
gacgctgaac cgagacaacg gagacaaccc gacagagcgg agcagcttct tttgcctaga   3360
gtactttccc agcaagatgc tgaggacggg caacaacttt gagtttacct acagctttga   3420
agaggtgccc ttccactgca gcttcgcccc gagccagaac ctctttaagc tggccaaccc   3480
gctggtggac cagtacctgt accgcttcgt gagcacctcg gccacgggcg ccatccagtt   3540
ccaaaagaac ctggcgggca gatacgccaa cacctacaaa aactggttcc cggggcccat   3600
gggccgaacc cagggctgga acacgagctc tggcagcagc accaacagag tcagcgtcaa   3660
caacttttcc gtctcaaacc ggatgaacct ggagggggcc agctaccaag tgaaccccca   3720
gcccaacggg atgacaaaca cgctccaagg cagcaaccgc tacgcgctgg aaaacaccat   3780
gatcttcaac gctcaaaacg ccacgccggg aactacctcg gtgtacccag aggacaatct   3840
actgctgacc agcgagagcg agactcagcc cgtcaaccgg gtggcttaca acacgggcgg   3900
```

tcagatggcc accaacgccc agaacgccac cacggctccc acggtcggga cctacaacct 3960
ccaggaagtg cttcctggca gcgtatggat ggagagggac gtgtacctcc aaggacccat 4020
ctgggccaag atcccagaga cgggggcgca ctttcacccc tctccggcca tgggcggatt 4080
cggactcaaa cacccgccgc ccatgatgct catcaaaaac acgccggtgc ccggcaacat 4140
caccagcttc tcggacgtgc ccgtcagcag cttcatcacc cagtacagca ccgggcaggt 4200
caccgtggag atggaatggg agctcaaaaa ggaaaactcc aagaggtgga acccagagat 4260
ccagtacacc aacaactaca acgacccccca gtttgtggac tttgctccag acggctccgg 4320
cgaatacaga accaccagag ccatcggaac ccgatacctc acccgacccc tttaacccat 4380
tcatgtcgca taccctcaat aaaccgtgta ttcgtgtcag tgaaatactg cctcttgtgg 4440
tcattcaatg aacatcagct tacaacatct acaaaacccc cttgcttgag agtgtggcac 4500
tctcccccct gtcgcgttcg ctcgctcgct ggctcgtttg ggggggtggc agctcaaaga 4560
gctgccagac gacggccctc tggccgtcgc ccccccaaac gagccagcga gcgagcgaac 4620
gcgacagggg ggagag 4636

<210> SEQ ID NO 128
<211> LENGTH: 4679
<212> TYPE: DNA
<213> ORGANISM: Artificial
<220> FEATURE:
<223> OTHER INFORMATION: AAV2

<400> SEQUENCE: 128
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctggagg ggtggagtcg tgacgtgaat tacgtcatag 180
ggttagggag gtcctgtatt agaggtcacg tgagtgtttt gcgacatttt gcgacaccat 240
gtggtcacgc tgggtattta agcccgagtg agcacgcagg gtctccattt tgaagcggga 300
ggtttgaacg cgcagccgcc atgccggggt tttacgagat tgtgattaag gtccccagcg 360
accttgacga gcatctgccc ggcatttctg acagctttgt gaactgggtg gccgagaagg 420
aatgggagtt gccgccagat tctgacatgg atctgaatct gattgagcag gcacccctga 480
ccgtggccga gaagctgcag cgcgactttc tgacggaatg gcgccgtgtg agtaaggccc 540
cggaggccct tttctttgtg caatttgaga agggagagag ctacttccac atgcacgtgc 600
tcgtggaaac caccggggtg aaatccatgg ttttgggacg tttcctgagt cagattcgcg 660
aaaaactgat tcagagaatt taccgcggga tcgagccgac tttgccaaac tggttcgcgg 720
tcacaaagac cagaaatggc gccggaggcg ggaacaaggt ggtggatgag tgctacatcc 780
ccaattactt gctccccaaa acccagcctg agctccagtg ggcgtggact aatatggaac 840
agtatttaag cgcctgtttg aatctcacgg agcgtaaacg gttggtggcg cagcatctga 900
cgcacgtgtc gcagacgcag gagcagaaca aagagaatca gaatcccaat tctgatgcgc 960
cggtgatcag atcaaaaact tcagccaggt acatggagct ggtcgggtgg ctcgtggaca 1020
aggggattac ctcggagaag cagtggatcc aggaggacca ggcctcatac atctccttca 1080
atgcggcctc caactcgcgg tcccaaatca aggctgcctt ggacaatgcg ggaaagatta 1140
tgagcctgac taaaaccgcc cccgactacc tggtgggcca gcagcccgtg gaggacattt 1200
ccagcaatcg gatttataaa attttggaac taaacgggta cgatccccaa tatgcggctt 1260
ccgtctttct gggatgggcc acgaaaaagt tcggcaagag gaacaccatc tggctgtttg 1320

-continued

```
ggcctgcaac taccgggaag accaacatcg cggaggccat agcccacact gtgcccttct   1380
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agactttttc cggtgggcaa   1740
aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt ttcaggagcg ccttaaagaa   2520
gatacgtctt ttgggggcaa cctcggacga gcagtcttcc aggcgaaaaa gagggttctt   2580
gaacctctgg gcctggttga ggaacctgtt aagacggctc cgggaaaaaa gaggccggta   2640
gagcactctc ctgtggagcc agactcctcc tcgggaaccg gaaaggcggg ccagcagcct   2700
gcaagaaaaa gattgaattt tggtcagact ggagacgcag actcagtacc tgacccccag   2760
cctctcggac agccaccagc agccccctct ggtctgggaa ctaatacgat ggctacaggc   2820
agtggcgcac caatggcaga caataacgag ggcgccgacg gagtgggtaa ttcctcggga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caagctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg gcgcatcaag gatgcctccc gccgttccca   3300
gcagacgtct tcatggtgcc acagtatgga tacctcaccc tgaacaacgg gagtcaggca   3360
gtaggacgct cttcatttta ctgcctggag tactttcctt ctcagatgct gcgtaccgga   3420
aacaacttta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggccgga   3600
gcgagtgaca ttcgggacca gtctaggaac tggcttcctg gaccctgtta ccgccagcag   3660
```

-continued

```
cgagtatcaa agacatctgc ggataacaac aacagtgaat actcgtggac tggagctacc   3720

aagtaccacc tcaatggcag agactctctg gtgaatccgg gcccggccat ggcaagccac   3780

aaggacgatg aagaaaagtt ttttcctcag agcggggttc tcatctttgg gaagcaaggc   3840

tcagagaaaa caaatgtgga cattgaaaag gtcatgatta cagacgaaga ggaaatcagg   3900

acaaccaatc ccgtggctac ggagcagtat ggttctgtat ctaccaacct ccagagaggc   3960

aacagacaag cagctaccgc agatgtcaac acacaaggcg ttcttccagg catggtctgg   4020

caggacagag atgtgtacct tcaggggccc atctgggcaa agattccaca cacggacgga   4080

cattttcacc cctctcccct catgggtgga ttcggactta aacaccctcc tccacagatt   4140

ctcatcaaga acaccccggt acctgcgaat ccttcgacca ccttcagtgc ggcaaagttt   4200

gcttccttca tcacacagta ctccacggga caggtcagcg tggagatcga gtgggagctg   4260

cagaaggaaa acagcaaacg ctggaatccc gaaattcagt acacttccaa ctacaacaag   4320

tctgttaatg tggactttac tgtggacact aatggcgtgt attcagagcc tcgccccatt   4380

ggcaccagat acctgactcg taatctgtaa ttgcttgtta atcaataaac cgtttaattc   4440

gtttcagttg aactttggtc tctgcgtatt tctttcttat ctagtttcca tggctacgta   4500

gataagtagc atggcgggtt aatcattaac tacaaggaac ccctagtgat ggagttggcc   4560

actccctctc tgcgcgctcg ctcgctcact gaggccgggc gaccaaaggt cgcccgacgc   4620

ccgggctttg cccgggcggc ctcagtgagc gagcgagcgc gcagagaggg agtggccaa    4679
```

```
<210> SEQ ID NO 129
<211> LENGTH: 4726
<212> TYPE: DNA
<213> ORGANISM: Artificial
<220> FEATURE:
<223> OTHER INFORMATION: AAV3

<400> SEQUENCE: 129
```

```
ttggccactc cctctatgcg cactcgctcg ctcggtgggg cctggcgacc aaaggtcgcc     60

agacggacgt gctttgcacg tccggcccca ccgagcgagc gagtgcgcat agagggagtg    120

gccaactcca tcactagagg tatggcagtg acgtaacgcg aagcgcgcga agcgagacca    180

cgcctaccag ctgcgtcagc agtcaggtga cccttttgcg acagtttgcg acaccacgtg    240

gccgctgagg gtatatattc tcgagtgagc gaaccaggag ctccattttg accgcgaaat    300

ttgaacgagc agcagccatg ccggggttct acgagattgt cctgaaggtc ccgagtgacc    360

tggacgagcg cctgccgggc atttctaact cgtttgttaa ctgggtggcc gagaaggaat    420

gggacgtgcc gccggattct gacatggatc cgaatctgat tgagcaggca cccctgaccg    480

tggccgaaaa gcttcagcgc gagttcctgg tggagtggcg ccgcgtgagt aaggccccgg    540

aggccctctt ttttgtccag ttcgaaaagg gggagaccta cttccacctg cacgtgctga    600

ttgagaccat cggggtcaaa tccatggtgg tcggccgcta cgtgagccag attaaagaga    660

agctggtgac ccgcatctac cgcggggtcg agccgcagct tccgaactgg ttcgcggtga    720

ccaaaacgcg aaatggcgcc gggggcggga acaaggtggt ggacgactgc tacatcccca    780

actacctgct ccccaagacc cagcccgagc tccagtgggc gtggactaac atggaccagt    840

atttaagcgc ctgtttgaat ctcgcggagc gtaaacggct ggtggcgcag catctgacgc    900

acgtgtcgca gacgcaggag cagaacaaag agaatcagaa ccccaattct gacgcgccgg    960

tcatcaggtc aaaaacctca gccaggtaca tggagctggt cgggtggctg gtggaccgcg   1020

ggatcacgtc agaaaagcaa tggattcagg aggaccaggc ctcgtacatc tccttcaacg   1080
```

```
ccgcctccaa ctcgcggtcc cagatcaagg ccgcgctgga caatgcctcc aagatcatga   1140
gcctgacaaa gacggctccg gactacctgg tgggcagcaa cccgccggag gacattacca   1200
aaaatcggat ctaccaaatc ctggagctga acgggtacga tccgcagtac gcggcctccg   1260
tcttcctggg ctgggcgcaa aagaagttcg ggaagaggaa caccatctgg ctctttgggc   1320
cggccacgac gggtaaaacc aacatcgcgg aagccatcgc ccacgccgtg cccttctacg   1380
gctgcgtaaa ctggaccaat gagaactttc ccttcaacga ttgcgtcgac aagatggtga   1440
tctggtggga ggagggcaag atgacggcca aggtcgtgga gagcgccaag gccattctgg   1500
gcggaagcaa ggtgcgcgtg gaccaaaagt gcaagtcatc ggcccagatc gaacccactc   1560
ccgtgatcgt cacctccaac accaacatgt gcgccgtgat tgacgggaac agcaccacct   1620
tcgagcatca gcagccgctg caggaccgga tgtttgaatt tgaacttacc cgccgtttgg   1680
accatgactt tgggaaggtc accaaacagg aagtaaagga ctttttccgg tgggcttccg   1740
atcacgtgac tgacgtggct catgagttct acgtcagaaa gggtggagct aagaaacgcc   1800
ccgcctccaa tgacgcggat gtaagcgagc caaaacggga gtgcacgtca cttgcgcagc   1860
cgacaacgtc agacgcggaa gcaccggcgg actacgcgga caggtaccaa aacaaatgtt   1920
ctcgtcacgt gggcatgaat ctgatgcttt ttccctgtaa aacatgcgag agaatgaatc   1980
aaatttccaa tgtctgtttt acgcatggtc aaagagactg tggggaatgc ttccctggaa   2040
tgtcagaatc tcaacccgtt tctgtcgtca aaaagaagac ttatcagaaa ctgtgtccaa   2100
ttcatcatat cctgggaagg gcacccgaga ttgcctgttc ggcctgcgat ttggccaatg   2160
tggacttgga tgactgtgtt tctgagcaat aaatgactta aaccaggtat ggctgctgac   2220
ggttatcttc cagattggct cgaggacaac ctttctgaag gcattcgtga gtggtgggct   2280
ctgaaacctg gagtccctca acccaaagcg aaccaacaac accaggacaa ccgtcggggt   2340
cttgtgcttc cgggttacaa atacctcgga cccggtaacg gactcgacaa aggagagccg   2400
gtcaacgagg cggacgcggc agccctcgaa cacgacaaag cttacgacca gcagctcaag   2460
gccggtgaca acccgtacct caagtacaac cacgccgacg ccgagtttca ggagcgtctt   2520
caagaagata cgtcttttgg gggcaacctt ggcagagcag tcttccaggc caaaaagagg   2580
atccttgagc ctcttggtct ggttgaggaa gcagctaaaa cggctcctgg aaagaagggg   2640
gctgtagatc agtctcctca ggaaccggac tcatcatctg gtgttggcaa atcgggcaaa   2700
cagcctgcca gaaaaagact aaatttcggt cagactggag actcagagtc agtcccagac   2760
cctcaacctc tcggagaacc accagcagcc cccacaagtt tgggatctaa tacaatggct   2820
tcaggcggtg gcgcaccaat ggcagacaat aacgagggtg ccgatggagt gggtaattcc   2880
tcaggaaatt ggcattgcga ttcccaatgg ctgggcgaca gagtcatcac caccagcacc   2940
agaacctggg ccctgcccac ttacaacaac catctctaca agcaaatctc cagccaatca   3000
ggagcttcaa acgacaacca ctactttggc tacagcaccc cttgggggta ttttgacttt   3060
aacagattcc actgccactt ctcaccacgt gactggcagc gactcattaa caacaactgg   3120
ggattccggc ccaagaaact cagcttcaag ctcttcaaca tccaagttag aggggtcacg   3180
cagaacgatg gcacgacgac tattgccaat aaccttacca gcacggttca agtgtttacg   3240
gactcggagt atcagctccc gtacgtgctc gggtcggcgc accaaggctg tctcccgccg   3300
tttccagcgg acgtcttcat ggtccctcag tatggatacc tcaccctgaa caacggaagt   3360
caagcggtgg gacgctcatc cttttactgc ctggagtact tcccttcgca gatgctaagg   3420
```

-continued actggaaata acttccaatt cagctatacc ttcgaggatg taccttttca cagcagctac 3480
gctcacagcc agagtttgga tcgcttgatg aatcctctta ttgatcagta tctgtactac 3540
ctgaacagaa cgcaaggaac aacctctgga acaaccaacc aatcacggct gctttttagc 3600
caggctgggc ctcagtctat gtctttgcag gccagaaatt ggctacctgg gccctgctac 3660
cggcaacaga gactttcaaa gactgctaac gacaacaaca acagtaactt tccttggaca 3720
gcggccagca aatatcatct caatggccgc gactcgctgg tgaatccagg accagctatg 3780
gccagtcaca aggacgatga agaaaaattt ttccctatgc acggcaatct aatatttggc 3840
aaagaaggga caacggcaag taacgcagaa ttagataatg taatgattac ggatgaagaa 3900
gagattcgta ccaccaatcc tgtggcaaca gagcagtatg gaactgtggc aaataacttg 3960
cagagctcaa atacagctcc cacgactgga actgtcaatc atcagggggc cttacctggc 4020
atggtgtggc aagatcgtga cgtgtacctt caaggaccta tctgggcaaa gattcctcac 4080
acggatggac actttcatcc ttctcctctg atgggaggct ttggactgaa acatccgcct 4140
cctcaaatca tgatcaaaaa tactccggta ccggcaaatc ctccgacgac tttcagcccg 4200
gccaagtttg cttcatttat cactcagtac tccactggac aggtcagcgt ggaaattgag 4260
tgggagctac agaaagaaaa cagcaaacgt tggaatccag agattcagta cacttccaac 4320
tacaacaagt ctgttaatgt ggactttact gtagacacta atggtgttta tagtgaacct 4380
cgccctattg gaacccggta tctcacacga aacttgtgaa tcctggttaa tcaataaacc 4440
gtttaattcg tttcagttga actttggctc ttgtgcactt ctttatcttt atcttgtttc 4500
catggctact gcgtagataa gcagcggcct gcggcgcttg cgcttcgcgg tttacaactg 4560
ctggttaata tttaactctc gccatacctc tagtgatgga gttggccact ccctctatgc 4620
gcactcgctc gctcggtggg gcctggcgac caaaggtcgc cagacggacg tgctttgcac 4680
gtccggcccc accgagcgag cgagtgcgca tagagggagt ggccaa 4726

<210> SEQ ID NO 130
<211> LENGTH: 4767
<212> TYPE: DNA
<213> ORGANISM: Artificial
<220> FEATURE:
<223> OTHER INFORMATION: AAV4

<400> SEQUENCE: 130
ttggccactc cctctatgcg cgctcgctca ctcactcggc cctggagacc aaaggtctcc 60
agactgccgg cctctggccg gcagggccga gtgagtgagc gagcgcgcat agagggagtg 120
gccaactcca tcatctaggt ttgcccactg acgtcaatgt gacgtcctag ggttagggag 180
gtccctgtat tagcagtcac gtgagtgtcg tatttcgcgg agcgtagcgg agcgcatacc 240
aagctgccac gtcacagcca cgtggtccgt ttgcgacagt ttgcgacacc atgtggtcag 300
gagggtatat aaccgcgagt gagccagcga ggagctccat tttgcccgcg aattttgaac 360
gagcagcagc catgccgggg ttctacgaga tcgtgctgaa ggtgcccagc gacctggacg 420
agcacctgcc cggcatttct gactcttttg tgagctgggt ggccgagaag gaatgggagc 480
tgccgccgga ttctgacatg gacttgaatc tgattgagca ggcacccctg accgtggccg 540
aaaagctgca acgcgagttc ctggtcgagt ggcgccgcgt gagtaaggcc ccggaggccc 600
tcttctttgt ccagttcgag aagggggaca gctacttcca cctgcacatc ctggtggaga 660
ccgtgggcgt caaatccatg gtggtgggcc gctacgtgag ccagattaaa gagaagctgg 720
tgacccgcat ctaccgcggg gtcgagccgc agcttccgaa ctggttcgcg gtgaccaaga 780
cgcgtaatgg cgccggaggc gggaacaagg tggtggacga ctgctacatc cccaactacc 840
tgctccccaa gacccagccc gagctccagt gggcgtggac taacatggac cagtatataa 900
gcgcctgttt gaatctcgcg gagcgtaaac ggctggtggc gcagcatctg acgcacgtgt 960
cgcagacgca ggagcagaac aaggaaaacc agaaccccaa ttctgacgcg ccggtcatca 1020
ggtcaaaaac ctccgccagg tacatggagc tggtcgggtg gctggtggac cgcgggatca 1080
cgtcagaaaa gcaatggatc caggaggacc aggcgtccta catctccttc aacgccgcct 1140
ccaactcgcg gtcacaaatc aaggccgcgc tggacaatgc ctccaaaatc atgagcctga 1200
caaagacggc tccggactac ctggtgggcc agaacccgcc ggaggacatt tccagcaacc 1260
gcatctaccg aatcctcgag atgaacgggt acgatccgca gtacgcggcc tccgtcttcc 1320
tgggctgggc gcaaaagaag ttcgggaaga ggaacaccat ctggctcttt gggccggcca 1380
cgacgggtaa aaccaacatc gcggaagcca tcgcccacgc cgtgcccttc tacggctgcg 1440
tgaactggac caatgagaac tttccgttca acgattgcgt cgacaagatg gtgatctggt 1500
gggaggaggg caagatgacg gccaaggtcg tagagagcgc caaggccatc ctgggcggaa 1560
gcaaggtgcg cgtggaccaa aagtgcaagt catcggccca gatcgaccca actcccgtga 1620
tcgtcacctc caacaccaac atgtgcgcgg tcatcgacgg aaactcgacc accttcgagc 1680
accaacaacc actccaggac cggatgttca agttcgagct caccaagcgc ctggagcacg 1740
actttggcaa ggtcaccaag caggaagtca aagacttttt ccggtgggcg tcagatcacg 1800
tgaccgaggt gactcacgag ttttacgtca gaaagggtgg agctagaaag aggcccgccc 1860
ccaatgacgc agatataagt gagcccaagc gggcctgtcc gtcagttgcg cagccatcga 1920
cgtcagacgc ggaagctccg gtggactacg cggacaggta ccaaaacaaa tgttctcgtc 1980
acgtgggtat gaatctgatg ctttttccct gccggcaatg cgagagaatg aatcagaatg 2040
tggacatttg cttcacgcac ggggtcatgg actgtgccga gtgcttcccc gtgtcagaat 2100
ctcaacccgt gtctgtcgtc agaaagcgga cgtatcagaa actgtgtccg attcatcaca 2160
tcatggggag ggcgcccgag gtggcctgct cggcctgcga actggccaat gtggacttgg 2220
atgactgtga catggaacaa taaatgactc aaaccagata tgactgacgg ttaccttcca 2280
gattggctag aggacaacct ctctgaaggc gttcgagagt ggtgggcgct gcaacctgga 2340
gcccctaaac ccaaggcaaa tcaacaacat caggacaacg ctcggggtct tgtgcttccg 2400
ggttacaaat acctcggacc cggcaacgga ctcgacaagg gggaacccgt caacgcagcg 2460
gacgcggcag ccctcgagca cgacaaggcc tacgaccagc agctcaaggc cggtgacaac 2520
ccctacctca agtacaacca cgccgacgcg gagttccagc agcggcttca gggcgacaca 2580
tcgtttgggg gcaacctcgg cagagcagtc ttccaggcca aaaagagggt tcttgaacct 2640
cttggtctgg ttgagcaagc gggtgagacg gctcctggaa agaagagacc gttgattgaa 2700
tccccccagc agcccgactc ctccacgggt atcggcaaaa aaggcaagca gccggctaaa 2760
aagaagctcg ttttcgaaga cgaaactgga gcaggcgacg gaccccctga gggatcaact 2820
tccggagcca tgtctgatga cagtgagatg cgtgcagcag ctggcggagc tgcagtcgag 2880
ggcggacaag gtgccgatgg agtgggtaat gcctcgggtg attggcattg cgattccacc 2940
tggtctgagg gccacgtcac gaccaccagc accagaacct gggtcttgcc cacctacaac 3000
aaccacctct acaagcgact cggagagagc ctgcagtcca acacctacaa cggattctcc 3060
accccctggg gatactttga cttcaaccgc ttccactgcc acttctcacc acgtgactgg 3120

-continued cagcgactca tcaacaacaa ctggggcatg cgacccaaag ccatgcgggt caaaatcttc 3180
aacatccagg tcaaggaggt cacgacgtcg aacggcgaga caacggtggc taataacctt 3240
accagcacgg ttcagatctt tgcggactcg tcgtacgaac tgccgtacgt gatggatgcg 3300
ggtcaagagg gcagcctgcc tccttttccc aacgacgtct ttatggtgcc ccagtacggc 3360
tactgtggac tggtgaccgg caacacttcg cagcaacaga ctgacagaaa tgccttctac 3420
tgcctggagt actttccttc gcagatgctg cggactggca acaactttga aattacgtac 3480
agttttgaga aggtgccttt ccactcgatg tacgcgcaca gccagagcct ggaccggctg 3540
atgaaccctc tcatcgacca gtacctgtgg ggactgcaat cgaccaccac cggaaccacc 3600
ctgaatgccg ggactgccac caccaacttt accaagctgc ggcctaccaa cttttccaac 3660
tttaaaaaga actggctgcc cgggccttca atcaagcagc agggcttctc aaagactgcc 3720
aatcaaaact acaagatccc tgccaccggg tcagacagtc tcatcaaata cgagacgcac 3780
agcactctgg acggaagatg gagtgccctg acccccggac ctccaatggc cacggctgga 3840
cctgcggaca gcaagttcag caacagccag ctcatctttg cggggcctaa acagaacggc 3900
aacacggcca ccgtacccgg gactctgatc ttcacctctg aggaggagct ggcagccacc 3960
aacgccaccg atacggacat gtggggcaac ctacctggcg gtgaccagag caacagcaac 4020
ctgccgaccg tggacagact gacagccttg ggagccgtgc ctggaatggt ctggcaaaac 4080
agagacattt actaccaggg tcccatttgg gccaagattc ctcataccga tggacacttt 4140
cacccctcac cgctgattgg tgggtttggg ctgaaacacc cgcctcctca aatttttatc 4200
aagaacaccc cggtacctgc gaatcctgca acgaccttca gctctactcc ggtaaactcc 4260
ttcattactc agtacagcac tggccaggtg tcggtgcaga ttgactggga gatccagaag 4320
gagcggtcca aacgctggaa ccccgaggtc cagtttacct ccaactacgg acagcaaaac 4380
tctctgttgt gggctcccga tgcggctggg aaatacactg agcctagggc tatcggtacc 4440
cgctacctca cccaccacct gtaataacct gttaatcaat aaaccggttt attcgtttca 4500
gttgaacttt ggtctccgtg tccttcttat cttatctcgt ttccatggct actgcgtaca 4560
taagcagcgg cctgcggcgc ttgcgcttcg cggtttacaa ctgccggtta atcagtaact 4620
tctggcaaac cagatgatgg agttggccac attagctatg cgcgctcgct cactcactcg 4680
gccctggaga ccaaaggtct ccagactgcc ggcctctggc cggcagggcc gagtgagtga 4740
gcgagcgcgc atagagggag tggccaa 4767

<210> SEQ ID NO 131
<211> LENGTH: 4642
<212> TYPE: DNA
<213> ORGANISM: Artificial
<220> FEATURE:
<223> OTHER INFORMATION: AAV5

<400> SEQUENCE: 131
ctctcccccc tgtcgcgttc gctcgctcgc tggctcgttt ggggggggtgg cagctcaaag 60 agctgccaga cgacggccct ctggccgtcg cccccccaaa cgagccagcg agcgagcgaa 120
cgcgacaggg gggagagtgc cacactctca agcaaggggg ttttgtaagc agtgatgtca 180
taatgatgta atgcttattg tcacgcgata gttaatgatt aacagtcatg tgatgtgttt 240
tatccaatag gaagaaagcg cgcgtatgag ttctcgcgag acttccgggg tataaaagac 300
cgagtgaacg agcccgccgc cattctttgc tctggactgc tagaggaccc tcgctgccat 360
ggctaccttc tatgaagtca ttgttcgcgt cccatttgac gtggaggaac atctgcctgg 420

-continued

```
aatttctgac agctttgtgg actgggtaac tggtcaaatt tgggagctgc ctccagagtc    480
agatttaaat ttgactctgg ttgaacagcc tcagttgacg gtggctgata gaattcgccg    540
cgtgttcctg tacgagtgga acaaattttc caagcaggag tccaaattct ttgtgcagtt    600
tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa ccccagatca acgactgggt cgccatcacc aaggtaaaga agggcggagc    780
caataaggtg gtggattctg ggtatattcc cgcctacctg ctgccgaagg tccaaccgga    840
gcttcagtgg gcgtggacaa acctggacga gtataaattg gccgccctga atctggagga    900
gcgcaaacgg ctcgtcgcgc agtttctggc agaatcctcg cagcgctcgc aggaggcggc    960
ttcgcagcgt gagttctcgg ctgacccggt catcaaaagc aagacttccc agaaatacat   1020
ggcgctcgtc aactggctcg tggagcacgg catcacttcc gagaagcagt ggatccagga   1080
aaatcaggag agctacctct ccttcaactc caccggcaac tctcggagcc agatcaaggc   1140
cgcgctcgac aacgcgacca aaattatgag tctgacaaaa agcgcggtgg actacctcgt   1200
ggggagctcc gttcccgagg acatttcaaa aaacagaatc tggcaaattt ttgagatgaa   1260
tggctacgac ccggcctacg cgggatccat cctctacggc tggtgtcagc gctccttcaa   1320
caagaggaac accgtctggc tctacggacc cgccacgacc ggcaagacca acatcgcgga   1380
ggccatcgcc cacactgtgc ccttttacgg ctgcgtgaac tggaccaatg aaaactttcc   1440
ctttaatgac tgtgtggaca aaatgctcat ttggtgggag gagggaaaga tgaccaacaa   1500
ggtggttgaa tccgccaagg ccatcctggg gggctcaaag gtgcgggtcg atcagaaatg   1560
taaatcctct gttcaaattg attctacccc tgtcattgta acttccaata caaacatgtg   1620
tgtggtggtg gatgggaatt ccacgacctt tgaacaccag cagccgctgg aggaccgcat   1680
gttcaaattt gaactgacta agcggctccc gccagatttt ggcaagatta ctaagcagga   1740
agtcaaggac tttttttgctt gggcaaaggt caatcaggtg ccggtgactc acgagtttaa   1800
agttcccagg gaattggcgg gaactaaagg ggcggagaaa tctctaaaac gcccactggg   1860
tgacgtcacc aatactagct ataaaagtct ggagaagcgg gccaggctct catttgttcc   1920
cgagacgcct cgcagttcag acgtgactgt tgatcccgct cctctgcgac cgctcaattg   1980
gaattcaagg tatgattgca aatgtgacta tcatgctcaa tttgacaaca tttctaacaa   2040
atgtgatgaa tgtgaatatt tgaatcgggg caaaaatgga tgtatctgtc acaatgtaac   2100
tcactgtcaa atttgtcatg ggattccccc ctgggaaaag gaaaacttgt cagattttgg   2160
ggattttgac gatgccaata aagaacagta aataaagcga gtagtcatgt cttttgttga   2220
tcaccctcca gattggttgg aagaagttgg tgaaggtctt cgcgagtttt tgggccttga   2280
agcgggccca ccgaaaccaa aacccaatca gcagcatcaa gatcaagccc gtggtcttgt   2340
gctgcctggt tataactatc tcggacccgg aaacggtctc gatcgaggag agcctgtcaa   2400
cagggcagac gaggtcgcgc gagagcacga catctcgtac aacgagcagc ttgaggcggg   2460
agacaacccc tacctcaagt acaaccacgc ggacgccgag tttcaggaga agctcgccga   2520
cgacacatcc ttcgggggaa acctcggaaa ggcagtcttt caggccaaga aaagggttct   2580
cgaacctttt ggcctggttg aagagggtgc taagacggcc cctaccggaa agcggataga   2640
cgaccacttt ccaaaaagaa agaaggctcg gaccgaagag gactccaagc cttccacctc   2700
gtcagacgcc gaagctggac ccagcggatc ccagcagctg caaatcccag cccaaccagc   2760
```

```
ctcaagtttg ggagctgata caatgtctgc gggaggtggc ggcccattgg gcgacaataa   2820

ccaaggtgcc gatggagtgg gcaatgcctc gggagattgg cattgcgatt ccacgtggat   2880

gggggacaga gtcgtcacca agtccacccg aacctgggtg ctgcccagct acaacaacca   2940

ccagtaccga gagatcaaaa gcggctccgt cgacggaagc aacgccaacg cctactttgg   3000

atacagcacc ccctgggggt actttgactt taaccgcttc cacagccact ggagcccccg   3060

agactggcaa agactcatca acaactactg gggcttcaga ccccggtccc tcagagtcaa   3120

aatcttcaac attcaagtca aagaggtcac ggtgcaggac tccaccacca ccatcgccaa   3180

caacctcacc tccaccgtcc aagtgtttac ggacgacgac taccagctgc cctacgtcgt   3240

cggcaacggg accgagggat gcctgccggc cttccctccg caggtcttta cgctgccgca   3300

gtacggttac gcgacgctga accgcgacaa cacagaaaat cccaccgaga ggagcagctt   3360

cttctgccta gagtactttc ccagcaagat gctgagaacg ggcaacaact ttgagtttac   3420

ctacaacttt gaggaggtgc ccttccactc cagcttcgct cccagtcaga acctgttcaa   3480

gctggccaac ccgctggtgg accagtactt gtaccgcttc gtgagcacaa ataacactgg   3540

cggagtccag ttcaacaaga acctggccgg gagatacgcc aacacctaca aaaactggtt   3600

cccggggccc atgggccgaa cccagggctg gaacctgggc tccggggtca accgcgccag   3660

tgtcagcgcc ttcgccacga ccaataggat ggagctcgag ggcgcgagtt accaggtgcc   3720

cccgcagccg aacggcatga ccaacaacct ccagggcagc aacacctatg ccctggagaa   3780

cactatgatc ttcaacagcc agccggcgaa cccgggcacc accgccacgt acctcgaggg   3840

caacatgctc atcaccagcg agagcgagac gcagccggtg aaccgcgtgg cgtacaacgt   3900

cggcgggcag atggccacca acaaccagag ctccaccact gcccccgcga ccggcacgta   3960

caacctccag gaaatcgtgc ccggcagcgt gtggatggag agggacgtgt acctccaagg   4020

acccatctgg gccaagatcc cagagacggg ggcgcacttt cacccctctc cggccatggg   4080

cggattcgga ctcaaacacc caccgcccat gatgctcatc aagaacacgc ctgtgcccgg   4140

aaatatcacc agcttctcgg acgtgcccgt cagcagcttc atcacccagt acagcaccgg   4200

gcaggtcacc gtggagatgg agtgggagct caagaaggaa aactccaaga ggtggaaccc   4260

agagatccag tacacaaaca actacaacga cccccagttt gtggactttg ccccggacag   4320

caccggggaa tacagaacca ccagacctat cggaacccga taccttaccc gacccccttta   4380

acccattcat gtcgcatacc ctcaataaac cgtgtattcg tgtcagtaaa atactgcctc   4440

ttgtggtcat tcaatgaata acagcttaca acatctacaa aacctccttg cttgagagtg   4500

tggcactctc ccccctgtcg cgttcgctcg ctcgctggct cgtttggggg ggtggcagct   4560

caaagagctg ccagacgacg gccctctggc cgtcgccccc ccaaacgagc cagcgagcga   4620

gcgaacgcga cagggggag ag                                             4642
```

```
<210> SEQ ID NO 132
<211> LENGTH: 4683
<212> TYPE: DNA
<213> ORGANISM: Artificial
<220> FEATURE:
<223> OTHER INFORMATION: AAV6

<400> SEQUENCE: 132

ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctggagg ggtggagtcg tgacgtgaat tacgtcatag    180
```

-continued

```
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagcgcca tgccggggtt ttacgagatt gtgattaagg tccccagcga    360
ccttgacgag catctgcccg gcatttctga cagctttgtg aactgggtgg ccgagaagga    420
atgggagttg ccgccagatt ctgacatgga tctgaatctg attgagcagg cacccctgac    480
cgtggccgag aagctgcagc gcgacttcct ggtccagtgg cgccgcgtga gtaaggcccc    540
ggaggccctc ttctttgttc agttcgagaa gggcgagtcc tacttccacc tccatattct    600
ggtggagacc acgggggtca aatccatggt gctgggccgc ttcctgagtc agattaggga    660
caagctggtg cagaccatct accgcgggat cgagccgacc ctgcccaact ggttcgcggt    720
gaccaagacg cgtaatggcg ccggaggggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aaccccaatt ctgacgcgcc    960
tgtcatccgg tcaaaaacct ccgcacgcta catggagctg gtcgggtggc tggtggaccg   1020
gggcatcacc tccgagaagc agtggatcca ggaggaccag gcctcgtaca tctccttcaa   1080
cgccgcctcc aactcgcggt cccagatcaa ggccgctctg gacaatgccg gcaagatcat   1140
ggcgctgacc aaatccgcgc ccgactacct ggtaggcccc gctccgcccg ccgacattaa   1200
aaccaaccgc atttaccgca tcctggagct gaacggctac gaccctgcct acgccggctc   1260
cgtctttctc ggctgggccc agaaaaggtt cggaaaacgc aacaccatct ggctgtttgg   1320
gccggccacc acgggcaaga ccaacatcgc ggaagccatc gcccacgccg tgcccttcta   1380
cggctgcgtc aactggacca atgagaactt tcccttcaac gattgcgtcg acaagatggt   1440
gatctggtgg gaggagggca agatgacggc caaggtcgtg gagtccgcca aggccattct   1500
cggcggcagc aaggtgcgcg tggaccaaaa gtgcaagtcg tccgcccaga tcgatcccac   1560
ccccgtgatc gtcacctcca acaccaacat gtgcgccgtg attgacggga acagcaccac   1620
cttcgagcac cagcagccgt tgcaggaccg gatgttcaaa tttgaactca cccgccgtct   1680
ggagcatgac tttggcaagg tgacaaagca ggaagtcaaa gagttcttcc gctgggcgca   1740
ggatcacgtg accgaggtgg cgcatgagtt ctacgtcaga aagggtggag ccaacaagag   1800
acccgccccc gatgacgcgg ataaaagcga gcccaagcgg gcctgcccct cagtcgcgga   1860
tccatcgacg tcagacgcgg aaggagctcc ggtggacttt gccgacaggt accaaaacaa   1920
atgttctcgt cacgcgggca tgcttcagat gctgtttccc tgcaaaacat gcgagagaat   1980
gaatcagaat ttcaacattt gcttcacgca cgggaccaga gactgttcag aatgtttccc   2040
cggcgtgtca gaatctcaac cggtcgtcag aaagaggacg tatcggaaac tctgtgccat   2100
tcatcatctg ctggggcggg ctcccgagat tgcttgctcg gcctgcgatc tggtcaacgt   2160
ggatctggat gactgtgttt ctgagcaata aatgacttaa accaggtatg gctgccgatg   2220
gttatcttcc agattggctc gaggacaacc tctctgaggg cattcgcgag tggtgggact   2280
tgaaacctgg agccccgaaa cccaaagcca accagcaaaa gcaggacgac ggccggggtc   2340
tggtgcttcc tggctacaag tacctcggac ccttcaacgg actcgacaag ggggagcccg   2400
tcaacgcggc ggatgcagcg gccctcgagc acgacaaggc ctacgaccag cagctcaaag   2460
cgggtgacaa tccgtacctg cggtataacc acgccgacgc cgagtttcag gagcgtctgc   2520
```

-continued aagaagatac gtcttttggg ggcaacctcg ggcgagcagt cttccaggcc aagaagaggg 2580
ttctcgaacc ttttggtctg gttgaggaag gtgctaagac ggctcctgga aagaaacgtc 2640
cggtagagca gtcgccacaa gagccagact cctcctcggg cattggcaag acaggccagc 2700
agcccgctaa aaagagactc aattttggtc agactggcga ctcagagtca gtccccgacc 2760
cacaacctct cggagaacct ccagcaaccc ccgctgctgt gggacctact acaatggctt 2820
caggcggtgg cgcaccaatg gcagacaata acgaaggcgc cgacggagtg ggtaatgcct 2880
caggaaattg gcattgcgat tccacatggc tgggcgacag agtcatcacc accagcaccc 2940
gaacatgggc cttgcccacc tataacaacc acctctacaa gcaaatctcc agtgcttcaa 3000
cgggggccag caacgacaac cactacttcg gctacagcac cccctggggg tattttgatt 3060
tcaacagatt ccactgccat ttctcaccac gtgactggca gcgactcatc aacaacaatt 3120
ggggattccg gcccaagaga ctcaacttca agctcttcaa catccaagtc aaggaggtca 3180
cgacgaatga tggcgtcacg accatcgcta ataaccttac cagcacggtt caagtcttct 3240
cggactcgga gtaccagttg ccgtacgtcc tcggctctgc gcaccagggc tgcctccctc 3300
cgttcccggc ggacgtgttc atgattccgc agtacggcta cctaacgctc aacaatggca 3360
gccaggcagt gggacggtca tccttttact gcctggaata tttcccatcg cagatgctga 3420
gaacgggcaa taactttacc ttcagctaca ccttcgagga cgtgcctttc cacagcagct 3480
acgcgcacag ccagagcctg gaccggctga tgaatcctct catcgaccag tacctgtatt 3540
acctgaacag aactcagaat cagtccggaa gtgcccaaaa caaggacttg ctgtttagcc 3600
gggggtctcc agctggcatg tctgttcagc ccaaaaactg gctacctgga ccctgttacc 3660
ggcagcagcg cgtttctaaa acaaaaacag acaacaacaa cagcaacttt acctggactg 3720
gtgcttcaaa atataacctt aatgggcgtg aatctataat caaccctggc actgctatgg 3780
cctcacacaa agacgacaaa gacaagttct ttcccatgag cggtgtcatg atttttggaa 3840
aggagagcgc cggagcttca aacactgcat tggacaatgt catgatcaca gacgaagagg 3900
aaatcaaagc cactaacccc gtggccaccg aaagatttgg gactgtggca gtcaatctcc 3960
agagcagcag cacagaccct gcgaccggag atgtgcatgt tatgggagcc ttacctggaa 4020
tggtgtggca agacagagac gtatacctgc agggtcctat ttgggccaaa attcctcaca 4080
cggatggaca ctttcacccg tctcctctca tgggcggctt tggacttaag cacccgcctc 4140
ctcagatcct catcaaaaac acgcctgttc ctgcgaatcc tccggcagag ttttcggcta 4200
caaagtttgc ttcattcatc acccagtatt ccacaggaca agtgagcgtg gagattgaat 4260
gggagctgca gaaagaaaac agcaaacgct ggaatcccga agtgcagtat acatctaact 4320
atgcaaaatc tgccaacgtt gatttcactg tggacaacaa tggactttat actgagcctc 4380
gccccattgg cacccgttac ctcacccgtc ccctgtaatt gtgtgttaat caataaaccg 4440
gttaattcgt gtcagttgaa ctttggtctc atgtcgttat tatcttatct ggtcaccata 4500
gcaaccggtt acacattaac tgcttagttg cgcttcgcga atacccctag tgatggagtt 4560
gcccactccc tctatgcgcg ctcgctcgct cggtggggcc ggcagagcag agctctgccg 4620
tctgcggacc tttggtccgc aggccccacc gagcgagcga gcgcgcatag agggagtggg 4680
caa 4683

<210> SEQ ID NO 133
<211> LENGTH: 4721
<212> TYPE: DNA
<213> ORGANISM: Artificial

<220> FEATURE:
<223> OTHER INFORMATION: AAV7

<400> SEQUENCE: 133
ttggccactc cctctatgcg cgctcgctcg ctcggtgggg cctgcggacc aaaggtccgc 60
agacggcaga gctctgctct gccggcccca ccgagcgagc gagcgcgcat agagggagtg 120
gccaactcca tcactagggg taccgcgaag cgcctcccac gctgccgcgt cagcgctgac 180
gtaaatcacg tcatagggga gtggtcctgt attagctgtc acgtgagtgc ttttgcgaca 240
ttttgcgaca ccacgtggcc atttgaggta tatatggccg agtgagcgag caggatctcc 300
attttgaccg cgaaatttga acgagcagca gccatgccgg gtttctacga gatcgtgatc 360
aaggtgccga gcgacctgga cgagcacctg ccgggcattt ctgactcgtt tgtgaactgg 420
gtggccgaga aggaatggga gctgcccccg gattctgaca tggatctgaa tctgatcgag 480
caggcacccc tgaccgtggc cgagaagctg cagcgcgact tcctggtcca atggcgccgc 540
gtgagtaagg ccccggaggc cctgttcttt gttcagttcg agaagggcga gagctacttc 600
caccttcacg ttctggtgga gaccacgggg gtcaagtcca tggtgctagg ccgcttcctg 660
agtcagattc gggagaagct ggtccagacc atctaccgcg gggtcgagcc cacgctgccc 720
aactggttcg cggtgaccaa gacgcgtaat ggcgccggcg gggggaacaa ggtggtggac 780
gagtgctaca tccccaacta cctcctgccc aagacccagc ccgagctgca gtgggcgtgg 840
actaacatgg aggagtatat aagcgcgtgt ttgaacctgg ccgaacgcaa acggctcgtg 900
gcgcagcacc tgacccacgt cagccagacg caggagcaga acaaggagaa tctgaacccc 960
aattctgacg cgcccgtgat caggtcaaaa acctccgcgc gctacatgga gctggtcggg 1020
tggctggtgg accggggcat cacctccgag aagcagtgga tccaggagga ccaggcctcg 1080
tacatctcct tcaacgccgc ctccaactcg cggtcccaga tcaaggccgc gctggacaat 1140
gccggcaaga tcatggcgct gaccaaatcc gcgcccgact acctggtggg gccctcgctg 1200
cccgcggaca ttaaaaccaa ccgcatctac cgcatcctgg agctgaacgg gtacgatcct 1260
gcctacgccg gctccgtctt tctcggctgg gcccagaaaa agttcgggaa gcgcaacacc 1320
atctggctgt ttgggcccgc caccaccggc aagaccaaca ttgcggaagc catcgcccac 1380
gccgtgccct tctacggctg cgtcaactgg accaatgaga actttccctt caacgattgc 1440
gtcgacaaga tggtgatctg gtgggaggag ggcaagatga cggccaaggt cgtggagtcc 1500
gccaaggcca ttctcggcgg cagcaaggtg cgcgtggacc aaaagtgcaa gtcgtccgcc 1560
cagatcgacc ccacccccgt gatcgtcacc tccaacacca acatgtgcgc cgtgattgac 1620
gggaacagca ccaccttcga gcaccagcag ccgttgcagg accggatgtt caaatttgaa 1680
ctcacccgcc gtctggagca cgactttggc aaggtgacga agcaggaagt caaagagttc 1740
ttccgctggg ccagtgatca cgtgaccgag gtggcgcatg agttctacgt cagaaagggc 1800
ggagccagca aaagacccgc ccccgatgac gcggatataa gcgagcccaa gcgggcctgc 1860
ccctcagtcg cggatccatc gacgtcagac gcggaaggag ctccggtgga ctttgccgac 1920
aggtaccaaa acaaatgttc tcgtcacgcg ggcatgattc agatgctgtt tccctgcaaa 1980
acgtgcgaga gaatgaatca gaatttcaac atttgcttca cacacggggt cagagactgt 2040
ttagagtgtt tccccggcgt gtcagaatct caaccggtcg tcagaaaaaa gacgtatcgg 2100
aaactctgcg cgattcatca tctgctgggg cgggcgcccg agattgcttg ctcggcctgc 2160
gacctggtca acgtggacct ggacgactgc gtttctgagc aataaatgac ttaaaccagg 2220

-continued

```
tatggctgcc gatggttatc ttccagattg gctcgaggac aacctctctg agggcattcg   2280
cgagtggtgg gacctgaaac ctggagcccc gaaacccaaa gccaaccagc aaaagcagga   2340
caacggccgg ggtctggtgc ttcctggcta caagtacctc ggacccttca acggactcga   2400
caagggggag cccgtcaacg cggcggacgc agcggccctc gagcacgaca aggcctacga   2460
ccagcagctc aaagcgggtg acaatccgta cctgcggtat aaccacgccg acgccgagtt   2520
tcaggagcgt ctgcaagaag atacgtcatt tgggggcaac ctcgggcgag cagtcttcca   2580
ggccaagaag cgggttctcg aacctctcgg tctggttgag gaaggcgcta agacggctcc   2640
tgcaaagaag agaccggtag agccgtcacc tcagcgttcc cccgactcct ccacgggcat   2700
cggcaagaaa ggccagcagc ccgccagaaa gagactcaat ttcggtcaga ctggcgactc   2760
agagtcagtc cccgaccctc aacctctcgg agaacctcca gcagcgccct ctagtgtggg   2820
atctggtaca gtggctgcag gcggtggcgc accaatggca gacaataacg aaggtgccga   2880
cggagtgggt aatgcctcag gaaattggca ttgcgattcc acatggctgg gcgacagagt   2940
cattaccacc agcacccgaa cctgggccct gcccacctac aacaaccacc tctacaagca   3000
aatctccagt gaaactgcag gtagtaccaa cgacaacacc tacttcggct acagcacccc   3060
ctgggggtat tttgacttta acagattcca ctgccacttc tcaccacgtg actggcagcg   3120
actcatcaac aacaactggg gattccggcc caagaagctg cggttcaagc tcttcaacat   3180
ccaggtcaag gaggtcacga cgaatgacgg cgttacgacc atcgctaata accttaccag   3240
cacgattcag gtattctcgg actcggaata ccagctgccg tacgtcctcg gctctgcgca   3300
ccagggctgc ctgcctccgt tcccggcgga cgtcttcatg attcctcagt acggctacct   3360
gactctcaac aatggcagtc agtctgtggg acgttcctcc ttctactgcc tggagtactt   3420
cccctctcag atgctgagaa cgggcaacaa ctttgagttc agctacagct tcgaggacgt   3480
gcctttccac agcagctacg cacacagcca gagcctggac cggctgatga atcccctcat   3540
cgaccagtac ttgtactacc tggccagaac acagagtaac ccaggaggca cagctggcaa   3600
tcgggaactg cagttttacc agggcgggcc ttcaactatg gccgaacaag ccaagaattg   3660
gttacctgga ccttgcttcc ggcaacaaag agtctccaaa acgctggatc aaaacaacaa   3720
cagcaacttt gcttggactg gtgccaccaa atatcacctg aacggcagaa actcgttggt   3780
taatcccggc gtcgccatgg caactcacaa ggacgacgag gaccgctttt tcccatccag   3840
cggagtcctg atttttggaa aaactggagc aactaacaaa actacattgg aaaatgtgtt   3900
aatgacaaat gaagaagaaa ttcgtcctac taatcctgta gccacggaag aatacgggat   3960
agtcagcagc aacttacaag cggctaatac tgcagcccag acacaagttg tcaacaacca   4020
gggagcctta cctggcatgg tctggcagaa ccgggacgtg tacctgcagg gtcccatctg   4080
ggccaagatt cctcacacgg atggcaactt tcacccgtct cctttgatgg gcggctttgg   4140
acttaaacat ccgcctcctc agatcctgat caagaacact cccgttcccg ctaatcctcc   4200
ggaggtgttt actcctgcca agtttgcttc gttcatcaca cagtacagca ccggacaagt   4260
cagcgtggaa atcgagtggg agctgcagaa ggaaaacagc aagcgctgga acccggagat   4320
tcagtacacc tccaactttg aaaagcagac tggtgtggac tttgccgttg acagccaggg   4380
tgtttactct gagcctcgcc ctattggcac tcgttacctc acccgtaatc tgtaattgca   4440
tgttaatcaa taaaccggtt gattcgtttc agttgaactt tggtctcctg tgcttcttat   4500
cttatcggtt tccatagcaa ctggttacac attaactgct tgggtgcgct tcacgataag   4560
aacactgacg tcaccgcggt acccctagtg atggagttgg ccactccctc tatgcgcgct   4620
```

cgctcgctcg gtggggcctg cggaccaaag gtccgcagac ggcagagctc tgctctgccg 4680
gccccaccga gcgagcgagc gcgcatagag ggagtggcca a 4721

<210> SEQ ID NO 134
<211> LENGTH: 4393
<212> TYPE: DNA
<213> ORGANISM: Artificial
<220> FEATURE:
<223> OTHER INFORMATION: AAV8

<400> SEQUENCE: 134
cagagaggga gtggccaact ccatcactag gggtagcgcg aagcgcctcc cacgctgccg 60
cgtcagcgct gacgtaaatt acgtcatagg ggagtggtcc tgtattagct gtcacgtgag 120
tgcttttgcg gcattttgcg acaccacgtg gccatttgag gtatatatgg ccgagtgagc 180
gagcaggatc tccattttga ccgcgaaatt tgaacgagca gcagccatgc cgggcttcta 240
cgagatcgtg atcaaggtgc cgagcgacct ggacgagcac ctgccgggca tttctgactc 300
gtttgtgaac tgggtggccg agaaggaatg ggagctgccc ccggattctg acatggatcg 360
gaatctgatc gagcaggcac ccctgaccgt ggccgagaag ctgcagcgcg acttcctggt 420
ccaatggcgc cgcgtgagta aggccccgga ggccctcttc tttgttcagt tcgagaaggg 480
cgagagctac tttcacctgc acgttctggt cgagaccacg gggtcaagt ccatggtgct 540 aggccgcttc ctgagtcaga ttcgggaaaa gcttggtcca gaccatctac ccgcggggtc 600
gagccccacc ttgcccaact ggttcgcggt gaccaaagac gcggtaatgg cgccggcggg 660
ggggaacaag gtggtggacg agtgctacat ccccaactac ctcctgccca agactcagcc 720
cgagctgcag tgggcgtgga ctaacatgga ggagtatata agcgcgtgct tgaacctggc 780
cgagcgcaaa cggctcgtgg cgcagcacct gacccacgtc agccagacgc aggagcagaa 840
caaggagaat ctgaacccca attctgacgc gcccgtgatc aggtcaaaaa cctccgcgcg 900
ctatatggag ctggtcgggt ggctggtgga ccggggcatc acctccgaga agcagtggat 960
ccaggaggac caggcctcgt acatctcctt caacgccgcc tccaactcgc ggtcccagat 1020
caaggccgcg ctggacaatg ccggcaagat catggcgctg accaaatccg cgcccgacta 1080
cctggtgggg ccctcgctgc ccgcggacat tacccagaac cgcatctacc gcatcctcgc 1140
tctcaacggc tacgaccctg cctacgccgg ctccgtcttt ctcggctggg ctcagaaaaa 1200
gttcgggaaa cgcaacacca tctggctgtt tggacccgcc accaccggca agaccaacat 1260
tgcggaagcc atcgcccacg ccgtgccctt ctacggctgc gtcaactgga ccaatgagaa 1320
ctttcccttc aatgattgcg tcgacaagat ggtgatctgg tgggaggagg gcaagatgac 1380
ggccaaggtc gtggagtccg ccaaggccat tctcggcggc agcaaggtgc gcgtggacca 1440
aaagtgcaag tcgtccgccc agatcgaccc cacccccgtg atcgtcacct ccaacaccaa 1500
catgtgcgcc gtgattgacg ggaacagcac caccttcgag caccagcagc ctctccagga 1560
ccggatgttt aagttcgaac tcacccgccg tctggagcac gactttggca aggtgacaaa 1620
gcaggaagtc aaagagttct tccgctgggc cagtgatcac gtgaccgagg tggcgcatga 1680
gttttacgtc agaaagggcg gagccagcaa aagacccgcc cccgatgacg cggataaaag 1740
cgagcccaag cgggcctgcc cctcagtcgc ggatccatcg acgtcagacg cggaaggagc 1800
tccggtggac tttgccgaca ggtaccaaaa caaatgttct cgtcacgcgg gcatgcttca 1860
gatgctgttt ccctgcaaaa cgtgcgagag aatgaatcag aatttcaaca tttgcttcac 1920

-continued acacggggtc agagactgct cagagtgttt ccccggcgtg tcagaatctc aaccggtcgt 1980
cagaaagagg acgtatcgga aactctgtgc gattcatcat ctgctggggc gggctcccga 2040
gattgcttgc tcggcctgcg atctggtcaa cgtggacctg gatgactgtg tttctgagca 2100
ataaatgact taaaccaggt atggctgccg atggttatct tccagattgg ctcgaggaca 2160
acctctctga gggcattcgc gagtggtggg cgctgaaacc tggagccccg aagcccaaag 2220
ccaaccagca aaagcaggac gacggccggg gtctggtgct tcctggctac aagtacctcg 2280
gacccttcaa cggactcgac aagggggagc ccgtcaacgc ggcggacgca gcggccctcg 2340
agcacgacaa ggcctacgac cagcagctgc aggcgggtga caatccgtac ctgcggtata 2400
accacgccga cgccgagttt caggagcgtc tgcaagaaga tacgtctttt gggggcaacc 2460
tcgggcgagc agtcttccag gccaagaagc gggttctcga acctctcggt ctggttgagg 2520
aaggcgctaa gacggctcct ggaaagaaga gaccggtaga gccatcaccc cagcgttctc 2580
cagactcctc tacgggcatc ggcaagaaag gccaacagcc cgccagaaaa agactcaatt 2640
ttggtcagac tggcgactca gagtcagttc cagaccctca acctctcgga gaacctccag 2700
cagcgccctc tggtgtggga cctaatacaa tggctgcagg cggtggcgca ccaatggcag 2760
acaataacga aggcgccgac ggagtgggta gttcctcggg aaattggcat tgcgattcca 2820
catggctggg cgacagagtc atcaccacca gcacccgaac ctgggccctg cccacctaca 2880
acaaccacct ctacaagcaa atctccaacg ggacatcggg aggagccacc aacgacaaca 2940
cctacttcgg ctacagcacc ccctgggggt attttgactt taacagattc cactgccact 3000
tttcaccacg tgactggcag cgactcatca acaacaactg gggattccgg cccaagagac 3060
tcagcttcaa gctcttcaac atccaggtca aggaggtcac gcagaatgaa ggcaccaaga 3120
ccatcgccaa taacctcacc agcaccatcc aggtgtttac ggactcggag taccagctgc 3180
cgtacgttct cggctctgcc caccagggct gcctgcctcc gttcccggcg gacgtgttca 3240
tgattcccca gtacggctac ctaacactca acaacggtag tcaggccgtg ggacgctcct 3300
ccttctactg cctggaatac tttccttcgc agatgctgag aaccggcaac aacttccagt 3360
ttacttacac cttcgaggac gtgcctttcc acagcagcta cgcccacagc cagagcttgg 3420
accggctgat gaatcctctg attgaccagt acctgtacta cttgtctcgg actcaaacaa 3480
caggaggcac ggcaaatacg cagactctgg gcttcagcca aggtgggcct aatacaatgg 3540
ccaatcaggc aaagaactgg ctgccaggac cctgttaccg ccaacaacgc gtctcaacga 3600
caaccgggca aaacaacaat agcaactttg cctggactgc tgggaccaaa taccatctga 3660
atggaagaaa ttcattggct aatcctggca tcgctatggc aacacacaaa gacgacgagg 3720
agcgtttttt tcccagtaac gggatcctga tttttggcaa acaaaatgct gccagagaca 3780
atgcggatta cagcgatgtc atgctcacca gcgaggaaga aatcaaaacc actaaccctg 3840
tggctacaga ggaatacggt atcgtggcag ataacttgca gcagcaaaac acggctcctc 3900
aaattggaac tgtcaacagc caggggggcct tacccggtat ggtctggcag aaccgggacg 3960
tgtacctgca gggtcccatc tgggccaaga ttcctcacac ggacggcaac ttccacccgt 4020
ctccgctgat gggcggcttt ggcctgaaac atcctccgcc tcagatcctg atcaagaaca 4080
cgcctgtacc tgcggatcct ccgaccacct tcaaccagtc aaagctgaac tctttcatca 4140
cgcaatacag caccggacag gtcagcgtgg aaattgaatg ggagctgcag aaggaaaaca 4200
gcaagcgctg gaaccccgag atccagtaca cctccaacta ctacaaatct acaagtgtgg 4260
actttgctgt taatacagaa ggcgtgtact ctgaaccccg ccccattggc acccgttacc 4320
tcacccgtaa tctgtaattg cctgttaatc aataaaccgg ttgattcgtt tcagttgaac 4380
tttggtctct gcg 4393

<210> SEQ ID NO 135
<211> LENGTH: 6042
<212> TYPE: DNA
<213> ORGANISM: Artificial
<220> FEATURE:
<223> OTHER INFORMATION: AAV9

<400> SEQUENCE: 135
gcccaatacg caaaccgcct ctccccgcgc gttggccgat tcattaatgc agctggcgta 60
atagcgaaga ggcccgcacc gatcgccctt cccaacagtt gcgcagcctg aatggcgaat 120
ggcgattccg ttgcaatggc tggcggtaat attgttctgg atattaccag caaggccgat 180
agtttgagtt cttctactca ggcaagtgat gttattacta atcaaagaag tattgcgaca 240
acggttaatt tgcgtgatgg acagactctt ttactcggtg gcctcactga ttataaaaac 300
acttctcagg attctggcgt accgttcctg tctaaaatcc ctttaatcgg cctcctgttt 360
agctcccgct ctgattctaa cgaggaaagc acgttatacg tgctcgtcaa agcaaccata 420
gtacgcgccc tgtagcggcg cattaagcgc ggcgggtgtg gtggttacgc gcagcgtgac 480
cgctacactt gccagcgccc tagcgcccgc tcctttcgct ttcttccctt cctttctcgc 540
cacgttcgcc ggctttcccc gtcaagctct aaatcggggg ctccctttag ggttccgatt 600
tagtgcttta cggcacctcg accccaaaaa acttgattag ggtgatggtt cacgtagtgg 660
gccatcgccc tgatagacgg tttttcgccc tttgacgttg gagtccacgt tctttaatag 720
tggactcttg ttccaaactg gaacaacact caaccctatc tcggtctatt cttttgattt 780
ataagggatt ttgccgattt cggcctattg gttaaaaaat gagctgattt aacaaaaatt 840
taacgcgaat tttaacaaaa tattaacgct tacaatttaa atatttgctt atacaatctt 900
cctgtttttg gggcttttct gattatcaac cggggtacat atgattgaca tgctagtttt 960
acgattaccg ttcatcgccc tgcgcgctcg ctcgctcact gaggccgccc gggcaaagcc 1020
cgggcgtcgg gcgacctttg gtcgcccggc ctcagtgagc gagcgagcgc gcagagaggg 1080
agtggaattc acgcgtggat ctgaattcaa ttcacgcgtg gtacctctgg tcgttacata 1140
acttacggta aatggcccgc ctggctgacc gcccaacgac ccccgcccat tgacgtcaat 1200
aatgacgtat gttcccatag taacgccaat agggactttc cattgacgtc aatgggtgga 1260
gtatttacgg taaactgccc acttggcagt acatcaagtg tatcatatgc caagtacgcc 1320
ccctattgac gtcaatgacg gtaaatggcc cgcctggcat tatgcccagt acatgacctt 1380
atgggacttt cctacttggc agtacatcta ctcgaggcca cgttctgctt cactctcccc 1440
atctcccccc cctccccacc cccaattttg tatttattta tttttaatt attttgtgca 1500 gcgatggggg cggggggggg gggggggcgc gcgccaggcg gggcggggcg gggcgagggg 1560
cggggcgggg cgaggcggag aggtgcggcg gcagccaatc agagcggcgc gctccgaaag 1620
tttcctttta tggcgaggcg gcggcggcgg cggccctata aaaagcgaag cgcgcggcgg 1680
gcgggagcgg gatcagccac cgcggtggcg gcctagagtc gacgaggaac tgaaaaacca 1740
gaaagttaac tggtaagttt agtctttttg tcttttattt caggtcccgg atccggtggt 1800
ggtgcaaatc aaagaactgc tcctcagtgg atgttgcctt tacttctagg cctgtacgga 1860
agtgttactt ctgctctaaa agctgcggaa ttgtacccgc ggccgatcca ccggtccgga 1920

-continued

```
attcccggga tatcgtcgac ccacgcgtcc gggccccacg ctgcgcaccc gcgggtttgc   1980
tatggcgatg agcagcggcg gcagtggtgg cggcgtcccg gagcaggagg attccgtgct   2040
gttccggcgc ggcacaggcc agagcgatga ttctgacatt tgggatgata cagcactgat   2100
aaaagcatat gataaagctg tggcttcatt taagcatgct ctaaagaatg gtgacatttg   2160
tgaaacttcg ggtaaaccaa aaaccacacc taaaagaaaa cctgctaaga agaataaaag   2220
ccaaaagaag aatactgcag cttccttaca acagtggaaa gttggggaca aatgttctgc   2280
catttggtca gaagacggtt gcatttaccc agctaccatt gcttcaattg attttaagag   2340
agaaacctgt gttgtggttt acactggata tggaaataga gaggagcaaa atctgtccga   2400
tctactttcc ccaatctgtg aagtagctaa taatatagaa cagaatgctc aagagaatga   2460
aaatgaaagc caagtttcaa cagatgaaag tgagaactcc aggtctcctg gaaataaatc   2520
agataacatc aagcccaaat ctgctccatg gaactctttt ctccctccac caccccccat   2580
gccagggcca agactgggac caggaaagcc aggtctaaaa ttcaatggcc caccaccgcc   2640
accgccacca ccaccaccc acttactatc atgctggctg cctccatttc cttctggacc    2700
accaataatt cccccaccac ctcccatatg tccagattct cttgatgatg ctgatgcttt   2760
gggaagtatg ttaatttcat ggtacatgag tggctatcat actggctatt atatgggttt   2820
tagacaaaat caaaaagaag gaaggtgctc acattcctta aattaaggag aaatgctggc   2880
atagagcagc actaaatgac accactaaag aaacgatcag acagatctag aaagcttatc   2940
gataccgtcg actagagctc gctgatcagc ctcgactgtg ccttctagtt gccagccatc   3000
tgttgtttgc ccctcccccg tgccttcctt gaccctggaa ggtgccactc ccactgtcct   3060
ttcctaataa aatgaggaaa ttgcatcgca ttgtctgagt aggtgtcatt ctattctggg   3120
gggtggggtg gggcaggaca gcaaggggga ggattgggaa gacaatagca ggcatgctgg   3180
ggagagatcg atctgaggaa cccctagtga tggagttggc cactccctct ctgcgcgctc   3240
gctcgctcac tgaggccggg cgaccaaagg tcgcccgacg cccgggcttt gcccgggcgg   3300
cctcagtgag cgagcgagcg cgcagagagg gagtggcccc cccccccccc cccccggcga   3360
ttctcttgtt tgctccagac tctcaggcaa tgacctgata gcctttgtag agacctctca   3420
aaaatagcta ccctctccgg catgaattta tcagctagaa cggttgaata tcatattgat   3480
ggtgatttga ctgtctccgg cctttctcac ccgtttgaat ctttacctac acattactca   3540
ggcattgcat ttaaaatata tgagggttct aaaaattttt atccttgcgt tgaaataaag   3600
gcttctcccg caaaagtatt acagggtcat aatgtttttg gtacaaccga tttagcttta   3660
tgctctgagg ctttattgct taattttgct aattctttgc cttgcctgta tgatttattg   3720
gatgttggaa tcgcctgatg cggtattttc tccttacgca tctgtgcggt atttcacacc   3780
gcatatggtg cactctcagt acaatctgct ctgatgccgc atagttaagc cagccccgac   3840
acccgccaac actatggtgc actctcagta caatctgctc tgatgccgca tagttaagcc   3900
agccccgaca cccgccaaca cccgctgacg cgccctgacg ggcttgtctg ctcccggcat   3960
ccgcttacag acaagctgtg accgtctccg ggagctgcat gtgtcagagg ttttcaccgt   4020
catcaccgaa acgcgcgaga cgaaagggcc tcgtgatacg cctattttta taggttaatg   4080
tcatgataat aatggtttct tagacgtcag gtggcacttt tcggggaaat gtgcgcggaa   4140
cccctatttg tttatttttc taaatacatt caaatatgta tccgctcatg agacaataac   4200
cctgataaat gcttcaataa tattgaaaaa ggaagagtat gagtattcaa catttccgtg   4260
tcgcccttat tccctttttt gcggcatttt gccttcctgt ttttgctcac ccagaaacgc   4320
```

tggtgaaagt aaaagatgct gaagatcagt tgggtgcacg agtgggttac atcgaactgg 4380
atctcaacag cggtaagatc cttgagagtt ttcgccccga agaacgtttt ccaatgatga 4440
gcacttttaa agttctgcta tgtggcgcgg tattatcccg tattgacgcc gggcaagagc 4500
aactcggtcg ccgcatacac tattctcaga atgacttggt tgagtactca ccagtcacag 4560
aaaagcatct tacggatggc atgacagtaa gagaattatg cagtgctgcc ataaccatga 4620
gtgataacac tgcggccaac ttacttctga caacgatcgg aggaccgaag gagctaaccg 4680
cttttttgca caacatgggg gatcatgtaa ctcgccttga tcgttgggaa ccggagctga 4740
atgaagccat accaaacgac gagcgtgaca ccacgatgcc tgtagcaatg gcaacaacgt 4800
tgcgcaaact attaactggc gaactactta ctctagcttc ccggcaacaa ttaatagact 4860
ggatggaggc ggataaagtt gcaggaccac ttctgcgctc ggcccttccg gctggctggt 4920
ttattgctga taaatctgga gccggtgagc gtgggtctcg cggtatcatt gcagcactgg 4980
ggccagatgg taagccctcc cgtatcgtag ttatctacac gacggggagt caggcaacta 5040
tggatgaacg aaatagacag atcgctgaga taggtgcctc actgattaag cattggtaac 5100
tgtcagacca agtttactca tatatacttt agattgattt aaaacttcat ttttaattta 5160
aaaggatcta ggtgaagatc ctttttgata atctcatgac caaaatccct taacgtgagt 5220
tttcgttcca ctgagcgtca gaccccgtag aaaagatcaa aggatcttct tgagatcctt 5280
tttttctgcg cgtaatctgc tgcttgcaaa caaaaaaacc accgctacca gcggtggttt 5340
gtttgccgga tcaagagcta ccaactcttt ttccgaaggt aactggcttc agcagagcgc 5400
agataccaaa tactgttctt ctagtgtagc cgtagttagg ccaccacttc aagaactctg 5460
tagcaccgcc tacatacctc gctctgctaa tcctgttacc agtggctgct gccagtggcg 5520
ataagtcgtg tcttaccggg ttggactcaa gacgatagtt accggataag gcgcagcggt 5580
cgggctgaac ggggggttcg tgcacacagc ccagcttgga gcgaacgacc tacaccgaac 5640
tgagatacct acagcgtgag ctatgagaaa gcgccacgct tcccgaaggg agaaaggcgg 5700
acaggtatcc ggtaagcggc agggtcggaa caggagagcg cacgagggag cttccagggg 5760
gaaacgcctg gtatctttat agtcctgtcg ggtttcgcca cctctgactt gagcgtcgat 5820
ttttgtgatg ctcgtcaggg gggcggagcc tatggaaaaa cgccagcaac gcggcctttt 5880
tacggttcct ggccttttgc tggccttttg ctcacatgtt ctttcctgcg ttatcccctg 5940
attctgtgga taaccgtatt accgcctttg agtgagctga taccgctcgc cgcagccgaa 6000
cgaccgagcg cagcgagtca gtgagcgagg aagcggaaga gc 6042

<210> SEQ ID NO 136
<211> LENGTH: 4102
<212> TYPE: DNA
<213> ORGANISM: Artificial
<220> FEATURE:
<223> OTHER INFORMATION: AAV10

<400> SEQUENCE: 136
atgccgggct tctacgagat cgtgatcaag gtgccgagcg acctggacga gcacctgccg 60
ggcatttctg actcgtttgt gaactgggtg gccgagaagg aatgggagct gcccccggat 120
tctgacatgg atcggaatct gatcgagcag gcacccctga ccgtggccga gaagctgcag 180
cgcgacttcc tggtccactg gcgccgcgtg agtaaggccc cggaggccct cttctttgtt 240
cagttcgaga agggcgagtc ctactttcac ctgcacgttc tggtcgagac cacgggggtc 300

-continued

```
aagtccatgg tcctgggccg cttcctgagt cagatcagag acaggctggt gcagaccatc    360
taccgcgggg tagagcccac gctgcccaac tggttcgcgg tgaccaagac gcgaaatggc    420
gccggcgggg ggaacaaggt ggtggacgag tgctacatcc ccaactacct cctgcccaag    480
acgcagcccg agctgcagtg ggcgtggact aacatggagg agtatataag cgcgtgtctg    540
aacctcgcgg agcgtaaacg gctcgtggcg cagcacctga cccacgtcag ccagacgcag    600
gagcagaaca aggagaatct gaacccgaat tctgacgcgc ccgtgatcag gtcaaaaacc    660
tccgcgcgct acatggagct ggtcgggtgg ctggtggacc ggggcatcac ctccgagaag    720
cagtggatcc aggaggacca ggcctcgtac atctccttca acgccgcctc caactcgcgg    780
tcccagatca aggccgcgct ggacaatgcc ggaaagatca tggcgctgac caaatccgcg    840
cccgactacc tggtaggccc gtccttaccc gcggacatta aggccaaccg catctaccgc    900
atcctggagc tcaacggcta cgacccggcc tacgccggct ccgtcttcct gggctgggcg    960
cagaaaaagt tcggtaaaag gaatacaatt tggctgttcg ggcccgccac caccggcaag   1020
accaacatcg cggaagccat cgcccacgcc gtgcccttct acggctgcgt caactggacc   1080
aatgagaact ttcccttcaa cgattgcgtc gacaagatgg tgatctggtg ggaggagggc   1140
aagatgaccg ccaaggtcgt ggagtccgcc aaggccattc tgggcggaag caaggtgcgc   1200
gtcgaccaaa agtgcaagtc ctcggcccag atcgacccca cgcccgtgat cgtcacctcc   1260
aacaccaaca tgtgcgccgt gatcgacggg aacagcacca ccttcgagca ccagcagccc   1320
ctgcaggacc gcatgttcaa gttcgagctc acccgccgtc tggagcacga ctttggcaag   1380
gtgaccaagc aggaagtcaa agagttcttc cgctgggctc aggatcacgt gactgaggtg   1440
acgcatgagt tctacgtcag aaagggcgga gccaccaaaa gacccgcccc cagtgacgcg   1500
gatataagcg agcccaagcg ggcctgcccc tcagttgcgg agccatcgac gtcagacgcg   1560
gaagcaccgg tggactttgc ggacaggtac caaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg gcgcgtcaga atctcaacct   1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataaa tgacttaaac caggtatggc tgctgacggt tatcttccag attggctcga   1920
ggacaacctc tctgagggca ttcgcgagtg gtgggacctg aaacctggag cccccaagcc   1980
caaggccaac cagcagaagc aggacgacgg ccggggtctg gtgcttcctg gctacaagta   2040
cctcggaccc ttcaacggac tcgacaaggg ggagcccgtc aacgcggcgg acgcagcggc   2100
cctcgagcac gacaaggcct acgaccagca gctcaaagcg ggtgacaatc cgtacctgcg   2160
gtataaccac gccgacgccg agtttcagga gcgtctgcaa gaagatacgt cttttggggg   2220
caacctcggg cgagcagtct tccaggccaa gaagcgggtt ctcgaacctc tcggtctggt   2280
tgaggaagct gctaagacgg ctcctggaaa gaagagaccg gtagaaccgt cacctcagcg   2340
ttcccccgac tcctccacgg gcatcggcaa gaaaggccag cagcccgcta aaaagagact   2400
gaactttggg cagactggcg agtcagagtc agtccccgac cctcaaccaa tcggagaacc   2460
accagcaggc ccctctggtc tgggatctgg tacaatggct gcaggcggtg gcgctccaat   2520
ggcagacaat aacgaaggcg ccgacggagt gggtagttcc tcaggaaatt ggcattgcga   2580
ttccacatgg ctgggcgaca gagtcatcac caccagcacc cgaacctggg ccctgcccac   2640
ctacaacaac cacctctaca agcaaatctc caacgggaca tcgggaggaa gcaccaacga   2700
```

caacacctac ttcggctaca gcaccccctg ggggtatttt gacttcaaca gattccactg 2760
ccacttctca ccacgtgact ggcagcgact catcaacaac aactggggat tccggccaaa 2820
aagactcagc ttcaagctct tcaacatcca ggtcaaggag gtcacgcaga atgaaggcac 2880
caagaccatc gccaataacc ttaccagcac gattcaggta tttacggact cggaatacca 2940
gctgccgtac gtcctcggct ccgcgcacca gggctgcctg cctccgttcc cggcggatgt 3000
cttcatgatt ccccagtacg gctacctgac actgaacaat ggaagtcaag ccgtaggccg 3060
ttcctccttc tactgcctgg aatattttcc atctcaaatg ctgcgaactg gaaacaattt 3120
tgaattcagc tacaccttcg aggacgtgcc tttccacagc agctacgcac acagccagag 3180
cttggaccga ctgatgaatc ctctcattga ccagtacctg tactacttat ccagaactca 3240
gtccacagga ggaactcaag gtacccagca attgttattt tctcaagctg ggcctgcaaa 3300
catgtcggct caggccaaga actggctgcc tggaccttgc taccggcagc agcgagtctc 3360
cacgacactg tcgcaaaaca acaacagcaa ctttgcttgg actggtgcca ccaaatatca 3420
cctgaacgga agagactctc tggtgaatcc cggtgtcgcc atggcaaccc acaaggacga 3480
cgaggaacgc ttcttcccgt cgagcggagt cctgatgttt ggaaaacagg gtgctggaag 3540
agacaatgtg gactacagca gcgttatgct aacaagcgaa gaagaaatta aaaccactaa 3600
ccctgtagcc acagaacaat acggcgtggt ggctgacaac ttgcagcaag ccaatacagg 3660
gcctattgtg ggaaatgtca acagccaagg agccttacct ggcatggtct ggcagaaccg 3720
agacgtgtac ctgcagggtc ccatctgggc caagattcct cacacggacg gcaactttca 3780
cccgtctcct ctgatgggcg gctttggact taaacacccg cctccacaga tcctgatcaa 3840
gaacacgccg gtacctgcgg atcctccaac aacgttcagc caggcgaaat tggcttcctt 3900
catcacgcag tacagcaccg gacaggtcag cgtggaaatc gagtgggagc tgcagaagga 3960
gaacagcaaa cgctggaacc cagagattca gtacacttca aactactaca aatctacaaa 4020
tgtggacttt gctgtcaata cagagggaac ttattctgag cctcgcccca ttggtactcg 4080
ttatctgaca cgtaatctgt aa 4102

<210> SEQ ID NO 137
<211> LENGTH: 4087
<212> TYPE: DNA
<213> ORGANISM: Artificial
<220> FEATURE:
<223> OTHER INFORMATION: AAV11

<400> SEQUENCE: 137
atgccgggct tctacgagat cgtgatcaag gtgccgagcg acctggacga gcacctgccg 60
ggcatttctg actcgtttgt gaactgggtg gccgagaagg aatgggagct gcccccggat 120
tctgacatgg atcggaatct gatcgagcag gcaccccctga ccgtggccga gaagctgcag 180
cgcgacttcc tggtccactg gcgccgcgtg agtaaggccc cggaggccct cttctttgtt 240
cagttcgaga agggcgagtc ctacttccac ctccacgttc tcgtcgagac cacgggggtc 300
aagtccatgg tcctgggccg cttcctgagt cagatcagag acaggctggt gcagaccatc 360
taccgcgggg tcgagcccac gctgcccaac tggttcgcgg tgaccaagac gcgaaatggc 420
gccggcgggg ggaacaaggt ggtggacgag tgctacatcc ccaactacct cctgcccaag 480
acccagcccg agctgcagtg ggcgtggact aacatggagg agtatataag cgcgtgtcta 540
aacctcgcgg agcgtaaacg gctcgtggcg cagcacctga cccacgtcag ccagacgcag 600

-continued

```
gagcagaaca aggagaatct gaacccgaat tctgacgcgc ccgtgatcag gtcaaaaacc    660
tccgcgcgct acatggagct ggtcgggtgg ctggtggacc ggggcatcac ctccgagaag    720
cagtggatcc aggaggacca ggcctcgtac atctccttca acgccgcctc caactcgcgg    780
tcccagatca aggccgcgct ggacaatgcc ggaaagatca tggcgctgac caaatccgcg    840
cccgactacc tggtaggccc gtccttaccc gcggacatta aggccaaccg catctaccgc    900
atcctggagc tcaacggcta cgaccccgcc tacgccggct ccgtcttcct gggctgggcg    960
cagaaaaagt tcggtaaacg caacaccatc tggctgtttg ggcccgccac caccggcaag   1020
accaacatcg cggaagccat agcccacgcc gtgcccttct acggctgcgt gaactggacc   1080
aatgagaact ttcccttcaa cgattgcgtc gacaagatgg tgatctggtg ggaggagggc   1140
aagatgaccg ccaaggtcgt ggagtccgcc aaggccattc tgggcggaag caaggtgcgc   1200
gtggaccaaa agtgcaagtc ctcggcccag atcgacccca cgcccgtgat cgtcacctcc   1260
aacaccaaca tgtgcgccgt gatcgacggg aacagcacca ccttcgagca ccagcagccg   1320
ctgcaggacc gcatgttcaa gttcgagctc acccgccgtc tggagcacga ctttggcaag   1380
gtgaccaagc aggaagtcaa agagttcttc cgctgggctc aggatcacgt gactgaggtg   1440
gcgcatgagt tctacgtcag aaagggcgga gccaccaaaa gacccgcccc cagtgacgcg   1500
gatataagcg agcccaagcg ggcctgcccc tcagttccgg agccatcgac gtcagacgcg   1560
gaagcaccgg tggactttgc ggacaggtac caaaacaaat gttctcgtca cgcgggcatg   1620
cttcagatgc tgtttccctg caagacatgc gagagaatga atcagaattt caacgtctgc   1680
ttcacgcacg gggtcagaga ctgctcagag tgcttccccg gcgcgtcaga atctcaaccc   1740
gtcgtcagaa aaaagacgta tcagaaactg tgcgcgattc atcatctgct ggggcgggca   1800
cccgagattg cgtgttcggc ctgcgatctc gtcaacgtgg acttggatga ctgtgtttct   1860
gagcaataaa tgacttaaac caggtatggc tgctgacggt tatcttccag attggctcga   1920
ggacaacctc tctgagggca ttcgcgagtg gtgggacctg aaacctggag ccccgaagcc   1980
caaggccaac cagcagaagc aggacgacgg ccggggtctg gtgcttcctg gctacaagta   2040
cctcggaccc ttcaacggac tcgacaaggg ggagcccgtc aacgcggcgg acgcagcggc   2100
cctcgagcac gacaaggcct acgaccagca gctcaaagcg ggtgacaatc cgtacctgcg   2160
gtataaccac gccgacgccg agtttcagga gcgtctgcaa gaagatacgt cttttggggg   2220
caacctcggg cgagcagtct tccaggccaa gaagagggta ctcgaacctc tgggcctggt   2280
tgaagaaggt gctaaaacgg ctcctggaaa gaagagaccg ttagagtcac cacaagagcc   2340
cgactcctcc tcgggcatcg gcaaaaaagg caaacaacca gccagaaaga ggctcaactt   2400
tgaagaggac actggagccg gagacggacc ccctgaagga tcagatacca gcgccatgtc   2460
ttcagacatt gaaatgcgtg cagcaccggg cggaaatgct gtcgatgcgg gacaaggttc   2520
cgatggagtg ggtaatgcct cgggtgattg gcattgcgat tccacctggt ctgagggcaa   2580
ggtcacaaca acctcgacca gaacctgggt cttgcccacc tacaacaacc acttgtacct   2640
gcgtctcgga acaacatcaa gcagcaacac ctacaacgga ttctccaccc cctggggata   2700
ttttgacttc aacagattcc actgtcactt ctcaccacgt gactggcaaa gactcatcaa   2760
caacaactgg ggactacgac caaaagccat gcgcgttaaa atcttcaata tccaagttaa   2820
ggaggtcaca acgtcgaacg gcgagactac ggtcgctaat aaccttacca gcacggttca   2880
gatatttgcg gactcgtcgt atgagctccc gtacgtgatg gacgctggac aagaggggag   2940
cctgcctcct ttccccaatg acgtgttcat ggtgcctcaa tatggctact gtggcatcgt   3000
```

```
gactggcgag aatcagaacc aaacggacag aaacgctttc tactgcctgg agtattttcc   3060

ttcgcaaatg ttgagaactg gcaacaactt tgaaatggct tacaactttg agaaggtgcc   3120

gttccactca atgtatgctc acagccagag cctggacaga ctgatgaatc ccctcctgga   3180

ccagtacctg tggcacttac agtcgactac ctctggagag actctgaatc aaggcaatgc   3240

agcaaccaca tttggaaaaa tcaggagtgg agactttgcc ttttacagaa agaactggct   3300

gcctgggcct tgtgttaaac agcagagatt ctcaaaaact gccagtcaaa attacaagat   3360

tcctgccagc gggggcaacg ctctgttaaa gtatgacacc cactatacct taaacaaccg   3420

ctggagcaac atcgcgcccg gacctccaat ggccacagcc ggaccttcgg atggggactt   3480

cagtaacgcc cagcttatat tccctggacc atctgttacc ggaaatacaa caacttcagc   3540

caacaatctg ttgtttacat cagaagaaga aattgctgcc accaacccaa gagacacgga   3600

catgtttggc cagattgctg acaataatca gaatgctaca actgctccca taaccggcaa   3660

cgtgactgct atgggagtgc tgcctggcat ggtgtggcaa aacagagaca tttactacca   3720

agggccaatt tgggccaaga tcccacacgc ggacggacat tttcatcctt caccgctgat   3780

tggtgggttt ggactgaaac acccgcctcc ccagatattc atcaagaaca ctcccgtacc   3840

tgccaatcct gcgacaacct tcactgcagc cagagtggac tctttcatca cacaatacag   3900

caccggccag gtcgctgttc agattgaatg ggaaattgaa aaggaacgct ccaaacgctg   3960

gaatcctgaa gtgcagttta cttcaaacta tgggaaccag tcttctatgt tgtgggctcc   4020

tgatacaact gggaagtata cagagccgcg ggttattggc tctcgttatt tgactaatca   4080

tttgtaa                                                             4087
```

```
<210> SEQ ID NO 138
<211> LENGTH: 4200
<212> TYPE: DNA
<213> ORGANISM: Artificial
<220> FEATURE:
<223> OTHER INFORMATION: AAV12

<400> SEQUENCE: 138
```

```
ttgcgacagt ttgcgacacc atgtggtcac aagaggtata taaccgcgag tgagccagcg     60

aggagctcca ttttgcccgc gaagtttgaa cgagcagcag ccatgccggg gttctacgag    120

gtggtgatca aggtgcccag cgacctggac gagcacctgc ccggcatttc tgactccttt    180

gtgaactggg tggccgagaa ggaatgggag ttgcccccgg attctgacat ggatcagaat    240

ctgattgagc aggcacccct gaccgtggcc gagaagctgc agcgcgagtt cctggtggaa    300

tggcgccgag tgagtaaatt tctggaggcc aagtttttg tgcagtttga aaagggggac     360

tcgtactttc atttgcatat tctgattgaa attaccggcg tgaaatccat ggtggtgggc    420

cgctacgtga gtcagattag ggataaactg atccagcgca tctaccgcgg ggtcgagccc    480

cagctgccca actggttcgc ggtcacaaag acccgaaatg gcgccggagg cgggaacaag    540

gtggtggacg agtgctacat ccccaactac ctgctcccca aggtccagcc cgagcttcag    600

tgggcgtgga ctaacatgga ggagtatata agcgcctgtt tgaacctcgc ggagcgtaaa    660

cggctcgtgg cgcagcacct gacgcacgtc tcccagaccc aggagggcga caaggagaat    720

ctgaacccga attctgacgc gccggtgatc cggtcaaaaa cctccgccag gtacatggag    780

ctggtcgggt ggctggtgga caagggcatc acgtccgaga agcagtggat ccaggaggac    840

caggcctcgt acatctcctt caacgcggcc tccaactccc ggtcgcagat caaggcggcc    900
```

-continued

```
ctggacaatg cctccaaaat catgagcctc accaaaacgg ctccggacta tctcatcggg    960
cagcagcccg tgggggacat taccaccaac cggatctaca aaatcctgga actgaacggg   1020
tacgaccccc agtacgccgc ctccgtcttt ctcggctggg cccagaaaaa gtttggaaag   1080
cgcaacacca tctggctgtt tggcccgcc  accaccggca agaccaacat cgcggaagcc   1140
atcgcccacg cggtcccctt ctacggctgc gtcaactgga ccaatgagaa ctttcccttc   1200
aacgactgcg tcgacaaaat ggtgatttgg tgggaggagg gcaagatgac cgccaaggtc   1260
gtagagtccg ccaaggccat tctgggcggc agcaaggtgc gcgtggacca aaaatgcaag   1320
gcctctgcgc agatcgaccc cacccccgtg atcgtcacct ccaacaccaa catgtgcgcc   1380
gtgattgacg ggaacagcac caccttcgag caccagcagc ccctgcagga ccggatgttc   1440
aagtttgaac tcacccgccg cctcgaccac gactttggca aggtcaccaa gcaggaagtc   1500
aaggactttt tccggtgggc ggctgatcac gtgactgacg tggctcatga gttttacgtc   1560
acaaagggtg gagctaagaa aaggcccgcc ccctctgacg aggatataag cgagcccaag   1620
cggccgcgcg tgtcatttgc gcagccggag acgtcagacg cggaagctcc cggagacttc   1680
gccgacaggt accaaaacaa atgttctcgt cacgcgggta tgctgcagat gctctttccc   1740
tgcaagacgt gcgagagaat gaatcagaat tccaacgtct gcttcacgca cggtcagaaa   1800
gattgcgggg agtgctttcc cgggtcagaa tctcaaccgg tttctgtcgt cagaaaaacg   1860
tatcagaaac tgtgcatcct tcatcagctc cgggggggcac ccgagatcgc ctgctctgct   1920
tgcgaccaac tcaaccccga tttggacgat tgccaatttg agcaataaat gactgaaatc   1980
aggtatggct gctgacggtt atcttccaga ttggctcgag gacaacctct ctgaaggcat   2040
tcgcgagtgg tgggcgctga aacctggagc tccacaaccc aaggccaacc aacagcatca   2100
ggacaacggc aggggtcttg tgcttcctgg gtacaagtac ctcggaccct tcaacggact   2160
cgacaaggga gagccggtca acgaggcaga cgccgcggcc ctcgagcacg acaaggccta   2220
cgacaagcag ctcgagcagg gggacaaccc gtatctcaag tacaaccacg ccgacgccga   2280
gttccagcag cgcttggcga ccgacacctc ttttgggggc aacctcgggc gagcagtctt   2340
ccaggccaaa aagaggattc tcgagcctct gggtctggtt gaagagggcg ttaaaacggc   2400
tcctggaaag aaacgcccat tagaaaagac tccaaatcgg ccgaccaacc cggactctgg   2460
gaaggccccg gccaagaaaa agcaaaaaga cggcgaacca gccgactctg ctagaaggac   2520
actcgacttt gaagactctg gagcaggaga cggacccccct gagggatcat cttccggaga   2580
aatgtctcat gatgctgaga tgcgtgcggc gccaggcgga aatgctgtcg aggcgggaca   2640
aggtgccgat ggagtgggta atgcctccgg tgattggcat tgcgattcca cctggtcaga   2700
gggccgagtc accaccacca gcacccgaac ctgggtccta cccacgtaca acaaccacct   2760
gtacctgcga atcggaacaa cggccaacag caacacctac aacggattct ccacccccctg   2820
gggatacttt gactttaacc gcttccactg ccacttttcc ccacgcgact ggcagcgact   2880
catcaacaac aactggggac tcaggccgaa atcgatgcgt gttaaaatct tcaacataca   2940
ggtcaaggag gtcacgacgt caaacggcga gactacggtc gctaataacc ttaccagcac   3000
ggttcagatc tttgcggatt cgacgtatga actcccatac gtgatggacg ccggtcagga   3060
ggggagcttt cctccgtttc ccaacgacgt ctttatggtt ccccaatacg gatactgcgg   3120
agttgtcact ggaaaaaacc agaaccagac agacagaaat gccttttact gcctggaata   3180
ctttccatcc caaatgctaa gaactggcaa caattttgaa gtcagttacc aatttgaaaa   3240
agttcctttc cattcaatgt acgcgcacag ccagagcctg gacagaatga tgaatccttt   3300
```

actggatcag tacctgtggc atctgcaatc gaccactacc ggaaattccc ttaatcaagg 3360
aacagctacc accacgtacg ggaaaattac cactggagac tttgcctact acaggaaaaa 3420
ctggttgcct ggagcctgca ttaaacaaca aaaattttca aagaatgcca atcaaaacta 3480
caagattccc gccagcgggg gagacgccct tttaaagtat gacacgcata ccactctaaa 3540
tgggcgatgg agtaacatgg ctcctggacc tccaatggca accgcaggtg ccggggactc 3600
ggattttagc aacagccagc tgatctttgc cggacccaat ccgagcggta acacgaccac 3660
atcttcaaac aatttgttgt ttacctcaga agaggagatt gccacaacaa acccacgaga 3720
cacggacatg tttggacaga ttgcagataa taatcaaaat gccaccaccg cccctcacat 3780
cgctaacctg gacgctatgg gaattgttcc cggaatggtc tggcaaaaca gagacatcta 3840
ctaccagggc cctatttggg ccaaggtccc tcacacggac ggacactttc acccttcgcc 3900
gctgatggga ggatttggac tgaaacaccc gcctccacag attttcatca aaaacacccc 3960
cgtacccgcc aatcccaata ctacctttag cgctgcaagg attaattctt ttctgacgca 4020
gtacagcacc ggacaagttg ccgttcagat cgactgggaa attcagaagg agcattccaa 4080
acgctggaat cccgaagttc aatttacttc aaactacggc actcaaaatt ctatgctgtg 4140
ggctcccgac aatgctggca actaccacga actccgggct attgggtccc gtttcctcac 4200

<210> SEQ ID NO 139
<211> LENGTH: 2205
<212> TYPE: DNA
<213> ORGANISM: Artificial
<220> FEATURE:
<223> OTHER INFORMATION: AAV2 VP3 only

<400> SEQUENCE: 139
ctggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttaaagaaga tacgtctttt gggggcaacc tcggacgagc agtcttccag 360
gcgaaaaaga gggttcttga acctctgggc ctggttgagg aacctgttaa ggcggctccg 420
ggaaaaaaga ggccggtaga gcactctcct gtggagccag actcctcctc gggaaccgga 480
aaggcgggcc agcagcctgc aagaaaaaga ttgaattttg gtcagactgg agacgcagac 540
tcagtacctg acccccagcc tctcggacag ccaccagcag ccccctctgg tctgggaact 600
aatacgatgg ctacaggcag tggcgcacca atggcagaca ataacgaggg cgccgacgga 660
gtgggtaatt cctcgggaaa ttggcattgc gattccacat ggatgggcga cagagtcatc 720
accaccagca cccgaacctg ggccctgccc acctacaaca accacctcta caaacaaatt 780
tccagccaat caggagcctc gaacgacaat cactactttg gctacagcac cccttggggg 840
tattttgact tcaacagatt ccactgccac ttttcaccac gtgactggca aagactcatc 900
aacaacaact ggggattccg acccaagaga ctcaacttca agctctttaa cattcaagtc 960
aaagaggtca cgcagaatga cggtacgacg acgattgcca ataaccttac cagcacggtt 1020
caggtgttta ctgactcgga gtaccagctc ccgtacgtcc tcggctcggc gcatcaagga 1080
tgcctcccgc cgttcccagc agacgtcttc atggtgccac agtatggata cctcaccctg 1140

-continued

```
aacaacggga gtcaggcagt aggacgctct tcattttact gcctggagta ctttccttct   1200
cagatgctgc gtaccggaaa caactttacc ttcagctaca cttttgagga cgttcctttc   1260
cacagcagct acgctcacag ccagagtctg gaccgtctca tgaatcctct catcgaccag   1320
tacctgtatt acttgagcag aacaaacact ccaagtggaa ccaccacgca gtcaaggctt   1380
cagttttctc aggccggagc gagtgacatt cgggaccagt ctaggaactg gcttcctgga   1440
ccctgttacc gccagcagcg agtatcaaag acatctgcgg ataacaacaa cagtgaatac   1500
tcgtggactg gagctaccaa gtaccacctc aatggcagag actctctggt gaatccgggc   1560
ccggccatgg caagccacaa ggacgatgaa gaaaagtttt ttcctcagag cggggttctc   1620
atctttggga agcaaggctc agagaaaaca aatgtggaca ttgaaaaggt catgattaca   1680
gacgaagagg aaatcaggac aaccaatccc gtggctacgg agcagtatgg ttctgtatct   1740
accaacctcc agagaggcaa cagacaagca gctaccgcag atgtcaacac acaaggcgtt   1800
cttccaggca tggtctggca ggacagagat gtgtaccttc aggggcccat ctgggcaaag   1860
attccacaca cggacggaca ttttcacccc tctcccctca tgggtggatt cggacttaaa   1920
caccctcctc cacagattct catcaagaac accccggtac ctgcgaatcc ttcgaccacc   1980
ttcagtgcgg caaagtttgc ttccttcatc acacagtact ccacgggaca ggtcagcgtg   2040
gagatcgagt gggagctgca gaaggaaaac agcaaacgct ggaatcccga aattcagtac   2100
acttccaact acaacaagtc tgttaatgtg gactttactg tggacactaa tggcgtgtat   2160
tcagagcctc gccccattgg caccagatac ctgactcgta atctg                   2205
```

<210> SEQ ID NO 140
<211> LENGTH: 2205
<212> TYPE: DNA
<213> ORGANISM: Artificial
<220> FEATURE:
<223> OTHER INFORMATION: AAV2 VP2/VP3

<400> SEQUENCE: 140

```
ctggctgccg atggttatct tccagattgg ctcgaggaca ctctctctga aggaataaga     60
cagtggtgga agctcaaacc tggcccacca ccaccaaagc ccgcagagcg gcataaggac    120
gacagcaggg gtcttgtgct tcctgggtac aagtacctcg gacccttcaa cggactcgac    180
aagggagagc cggtcaacga ggcagacgcc gcggccctcg agcacgacaa agcctacgac    240
cggcagctcg acagcggaga caacccgtac ctcaagtaca accacgccga cgcggagttt    300
caggagcgcc ttaaagaaga tacgtctttt gggggcaacc tcggacgagc agtcttccag    360
gcgaaaaaga gggttcttga acctctgggc ctggttgagg aacctgttaa gacggctccg    420
ggaaaaaaga ggccggtaga gcactctcct gtggagccag actcctcctc gggaaccgga    480
aaggcgggcc agcagcctgc aagaaaaaga ttgaattttg gtcagactgg agacgcagac    540
tcagtacctg acccccagcc tctcggacag ccaccagcag ccccctctgg tctgggaact    600
aatacgatgg ctacaggcag tggcgcacca atggcagaca ataacgaggg cgccgacgga    660
gtgggtaatt cctcgggaaa ttggcattgc gattccacat ggatgggcga cagagtcatc    720
accaccagca cccgaacctg ggccctgccc acctacaaca accacctcta caaacaaatt    780
tccagccaat caggagcctc gaacgacaat cactactttg gctacagcac cccttggggg    840
tattttgact tcaacagatt ccactgccac ttttcaccac gtgactggca aagactcatc    900
aacaacaact ggggattccg acccaagaga ctcaacttca agctctttaa cattcaagtc    960
aaagaggtca cgcagaatga cggtacgacg acgattgcca ataaccttac cagcacggtt   1020
```

caggtgttta ctgactcgga gtaccagctc ccgtacgtcc tcggctcggc gcatcaagga 1080
tgcctcccgc cgttcccagc agacgtcttc atggtgccac agtatggata cctcaccctg 1140
aacaacggga gtcaggcagt aggacgctct tcattttact gcctggagta ctttccttct 1200
cagatgctgc gtaccggaaa caactttacc ttcagctaca cttttgagga cgttcctttc 1260
cacagcagct acgctcacag ccagagtctg gaccgtctca tgaatcctct catcgaccag 1320
tacctgtatt acttgagcag aacaaacact ccaagtggaa ccaccacgca gtcaaggctt 1380
cagttttctc aggccggagc gagtgacatt cgggaccagt ctaggaactg gcttcctgga 1440
ccctgttacc gccagcagcg agtatcaaag acatctgcgg ataacaacaa cagtgaatac 1500
tcgtggactg gagctaccaa gtaccacctc aatggcagag actctctggt gaatccgggc 1560
ccggccatgg caagccacaa ggacgatgaa gaaaagtttt ttcctcagag cggggttctc 1620
atctttggga agcaaggctc agagaaaaca aatgtggaca ttgaaaaggt catgattaca 1680
gacgaagagg aaatcaggac aaccaatccc gtggctacgg agcagtatgg ttctgtatct 1740
accaacctcc agagaggcaa cagacaagca gctaccgcag atgtcaacac acaaggcgtt 1800
cttccaggca tggtctggca ggacagagat gtgtaccttc aggggcccat ctgggcaaag 1860
attccacaca cggacggaca ttttcacccc tctcccctca tgggtggatt cggacttaaa 1920
caccctcctc cacagattct catcaagaac accccggtac ctgcgaatcc ttcgaccacc 1980
ttcagtgcgg caaagtttgc ttccttcatc acacagtact ccacgggaca ggtcagcgtg 2040
gagatcgagt gggagctgca gaaggaaaac agcaaacgct ggaatcccga aattcagtac 2100
acttccaact acaacaagtc tgttaatgtg gactttactg tggacactaa tggcgtgtat 2160
tcagagcctc gccccattgg caccagatac ctgactcgta atctg 2205

<210> SEQ ID NO 141
<211> LENGTH: 2205
<212> TYPE: DNA
<213> ORGANISM: Artificial
<220> FEATURE:
<223> OTHER INFORMATION: AAV2 VP1 only

<400> SEQUENCE: 141
atggctgccg atggttatct tccagattgg ctcgaggaca ctctctctga aggaataaga 60
cagtggtgga agctcaaacc tggcccacca ccaccaaagc ccgcagagcg gcataaggac 120
gacagcaggg gtcttgtgct tcctgggtac aagtacctcg gacccttcaa cggactcgac 180
aagggagagc cggtcaacga ggcagacgcc gcggccctcg agcacgacaa agcctacgac 240
cggcagctcg acagcggaga caacccgtac ctcaagtaca accacgccga cgcggagttt 300
caggagcgcc ttaaagaaga tacgtctttt gggggcaacc tcggacgagc agtcttccag 360
gcgaaaaaga gggttcttga acctctgggc ctggttgagg aacctgttaa ggcggctccg 420
ggaaaaaaga ggccggtaga gcactctcct gtggagccag actcctcctc gggaaccgga 480
aaggcgggcc agcagcctgc aagaaaaaga ttgaattttg gtcagactgg agacgcagac 540
tcagtacctg acccccagcc tctcggacag ccaccagcag ccccctctgg tctgggaact 600
aatacgctgg ctacaggcag tggcgcacca ctggcagaca ataacgaggg cgccgacgga 660
gtgggtaatt cctcgggaaa ttggcattgc gattccacat ggctgggcga cagagtcatc 720
accaccagca cccgaacctg ggccctgccc acctacaaca accacctcta caaacaaatt 780
tccagccaat caggagcctc gaacgacaat cactactttg gctacagcac cccttggggg 840

-continued

```
tattttgact tcaacagatt ccactgccac ttttcaccac gtgactggca aagactcatc    900

aacaacaact ggggattccg acccaagaga ctcaacttca agctctttaa cattcaagtc    960

aaagaggtca cgcagaatga cggtacgacg acgattgcca ataaccttac cagcacggtt   1020

caggtgttta ctgactcgga gtaccagctc ccgtacgtcc tcggctcggc gcatcaagga   1080

tgcctcccgc cgttcccagc agacgtcttc atggtgccac agtatggata cctcaccctg   1140

aacaacggga gtcaggcagt aggacgctct tcattttact gcctggagta ctttccttct   1200

cagatgctgc gtaccggaaa caactttacc ttcagctaca cttttgagga cgttcctttc   1260

cacagcagct acgctcacag ccagagtctg gaccgtctca tgaatcctct catcgaccag   1320

tacctgtatt acttgagcag aacaaacact ccaagtggaa ccaccacgca gtcaaggctt   1380

cagttttctc aggccggagc gagtgacatt cgggaccagt ctaggaactg gcttcctgga   1440

ccctgttacc gccagcagcg agtatcaaag acatctgcgg ataacaacaa cagtgaatac   1500

tcgtggactg gagctaccaa gtaccacctc aatggcagag actctctggt gaatccgggc   1560

ccggccatgg caagccacaa ggacgatgaa gaaaagtttt ttcctcagag cggggttctc   1620

atctttggga agcaaggctc agagaaaaca aatgtggaca ttgaaaaggt catgattaca   1680

gacgaagagg aaatcaggac aaccaatccc gtggctacgg agcagtatgg ttctgtatct   1740

accaacctcc agagaggcaa cagacaagca gctaccgcag atgtcaacac acaaggcgtt   1800

cttccaggca tggtctggca ggacagagat gtgtaccttc aggggcccat ctgggcaaag   1860

attccacaca cggacggaca ttttcacccc tctcccctca tgggtggatt cggacttaaa   1920

caccctcctc cacagattct catcaagaac accccggtac ctgcgaatcc ttcgaccacc   1980

ttcagtgcgg caaagtttgc ttccttcatc acacagtact ccacgggaca ggtcagcgtg   2040

gagatcgagt gggagctgca gaaggaaaac agcaaacgct ggaatcccga aattcagtac   2100

acttccaact acaacaagtc tgttaatgtg gactttactg tggacactaa tggcgtgtat   2160

tcagagcctc gccccattgg caccagatac ctgactcgta atctg                   2205
```

<210> SEQ ID NO 142
<211> LENGTH: 2205
<212> TYPE: DNA
<213> ORGANISM: Artificial
<220> FEATURE:
<223> OTHER INFORMATION: AAV2 VP1/VP3

<400> SEQUENCE: 142

```
atggctgccg atggttatct tccagattgg ctcgaggaca ctctctctga aggaataaga     60

cagtggtgga agctcaaacc tggcccacca ccaccaaagc ccgcagagcg gcataaggac    120

gacagcaggg gtcttgtgct tcctgggtac aagtacctcg gacccttcaa cggactcgac    180

aagggagagc cggtcaacga ggcagacgcc gcggccctcg agcacgacaa agcctacgac    240

cggcagctcg acagcggaga caacccgtac ctcaagtaca accacgccga cgcggagttt    300

caggagcgcc ttaaagaaga tacgtctttt gggggcaacc tcggacgagc agtcttccag    360

gcgaaaaaga gggttcttga acctctgggc ctggttgagg aacctgttaa ggcggctccg    420

ggaaaaaaga ggccggtaga gcactctcct gtggagccag actcctcctc gggaaccgga    480

aaggcgggcc agcagcctgc aagaaaaaga ttgaattttg gtcagactgg agacgcagac    540

tcagtacctg acccccagcc tctcggacag ccaccagcag ccccctctgg tctgggaact    600

aatacgatgg ctacaggcag tggcgcacca atggcagaca ataacgaggg cgccgacgga    660

gtgggtaatt cctcgggaaa ttggcattgc gattccacat ggatgggcga cagagtcatc    720
```

-continued

```
accaccagca cccgaacctg ggccctgccc acctacaaca accacctcta caaacaaatt    780

tccagccaat caggagcctc gaacgacaat cactactttg gctacagcac cccttggggg    840

tattttgact tcaacagatt ccactgccac ttttcaccac gtgactggca aagactcatc    900

aacaacaact ggggattccg acccaagaga ctcaacttca agctctttaa cattcaagtc    960

aaagaggtca cgcagaatga cggtacgacg acgattgcca ataaccttac cagcacggtt   1020

caggtgttta ctgactcgga gtaccagctc ccgtacgtcc tcggctcggc gcatcaagga   1080

tgcctcccgc cgttcccagc agacgtcttc atggtgccac agtatggata cctcaccctg   1140

aacaacggga gtcaggcagt aggacgctct tcattttact gcctggagta ctttccttct   1200

cagatgctgc gtaccggaaa caactttacc ttcagctaca cttttgagga cgttcctttc   1260

cacagcagct acgctcacag ccagagtctg gaccgtctca tgaatcctct catcgaccag   1320

tacctgtatt acttgagcag aacaaacact ccaagtggaa ccaccacgca gtcaaggctt   1380

cagttttctc aggccggagc gagtgacatt cgggaccagt ctaggaactg gcttcctgga   1440

ccctgttacc gccagcagcg agtatcaaag acatctgcgg ataacaacaa cagtgaatac   1500

tcgtggactg gagctaccaa gtaccacctc aatggcagag actctctggt gaatccgggc   1560

ccggccatgg caagccacaa ggacgatgaa gaaaagtttt ttcctcagag cggggttctc   1620

atctttggga agcaaggctc agagaaaaca aatgtggaca ttgaaaaggt catgattaca   1680

gacgaagagg aaatcaggac aaccaatccc gtggctacgg agcagtatgg ttctgtatct   1740

accaacctcc agagaggcaa cagacaagca gctaccgcag atgtcaacac acaaggcgtt   1800

cttccaggca tggtctggca ggacagagat gtgtaccttc aggggcccat ctgggcaaag   1860

attccacaca cggacggaca ttttcacccc tctcccctca tgggtggatt cggacttaaa   1920

caccctcctc cacagattct catcaagaac accccggtac ctgcgaatcc ttcgaccacc   1980

ttcagtgcgg caaagtttgc ttccttcatc acacagtact ccacgggaca ggtcagcgtg   2040

gagatcgagt gggagctgca gaaggaaaac agcaaacgct ggaatcccga aattcagtac   2100

acttccaact acaacaagtc tgttaatgtg gactttactg tggacactaa tggcgtgtat   2160

tcagagcctc gccccattgg caccagatac ctgactcgta atctg                   2205
```

UNITED STATES PATENT AND TRADEMARK OFFICE
CERTIFICATE OF CORRECTION

PATENT NO. : 11,702,676 B2
APPLICATION NO. : 16/951004
DATED : July 18, 2023
INVENTOR(S) : Li et al.

It is certified that error appears in the above-identified patent and that said Letters Patent is hereby corrected as shown below:

On the Title Page

(56) References Cited, OTHER PUBLICATIONS, Page 3, Column 1, Hildinger et al. cite, Line 59: Please correct "6199-8203" to read --6199-6203--

(56) References Cited, OTHER PUBLICATIONS, Page 3, Column 1, Huang et al. cite, Line 62: Please correct "1062-1060" to read --1062-1069--

(56) References Cited, OTHER PUBLICATIONS, Page 4, Column 1, Lilt et al. cite, Line 27: Please correct "Lilt et al." to read --Liu et al.--

(56) References Cited, OTHER PUBLICATIONS, Page 4, Column 1, Lochrie et al. cite, Line 34: please correct "821-634" to read --821-834--

(56) References Cited, OTHER PUBLICATIONS, Page 5, Column 1, Rabinovvitz et al. cite, Line 51: Please correct "Rabinovvitz et al." to read --Rabinowitz et al.--

In the Specification

Column 1, Line 28: Please correct "AI072176" to read --AI072176--

Column 22, Line 31: Please insert a paragraph break between "(AAV2-GMN)." and "Varadi"

Column 22, Line 37: Please correct "Korbelin" to read --Körbelin--

Column 35, Line 6: Please correct "I-IGPMQKS" to read --HGPMQKS--

Column 35, Line 14: Please correct "NPKI-INAT" to read --NPKHNAT--

Column 43, Lines 49-50: Please correct "transcarbamylase, α-globin," to read --transcarbamylase, Signed and Sealed this
Twenty-sixth Day of September, 2023

Katherine Kelly Vidal
*Director of the United States Patent and Trademark Office*

β-globin, α-globin,--

Column 44, Line 1: Please correct "SERCA2A" to read --SERCA$_{2A}$--

Column 51, Line 65: Please correct "interleukin-1β" to read --interleukin-13--

Column 64, Line 65: Please insert a paragraph break between "expressed." and "19."

Column 69, Line 37: Please insert a paragraph break between "made." and "83."

Column 78, Line 18: Please insert a paragraph break between "serotype: or" and "F."

Column 83, Line 23: Please correct "helper 00(6-80" to read --helper pXX6-80--

Column 112, Line 41: Please remove the paragraph indentation beginning with "the AAV is administered"

Column 122, Line 37: Please correct "00(6-80" to read --pXX6-80--

In the Claims

Column 260, Line 32, Claim 18: Please correct "AAVS" to read --AAV5--

Column 260, Line 43, Claim 19: Please correct "Al Splice" to read --A1 Splice--